(12) United States Patent
Ramanathan et al.

(10) Patent No.: US 7,339,032 B2
(45) Date of Patent: Mar. 4, 2008

(54) HUMAN RELAXIN RECEPTOR HGPRBMY5V1

(75) Inventors: Chandra S. Ramanathan, Ringoes, NJ (US); John N. Feder, Belle Mead, NJ (US); Gabriel A. Mintier, Hightstown, NJ (US); Kelly L. Bennett, Skillman, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/486,332

(22) Filed: Jul. 13, 2006

(65) Prior Publication Data

US 2006/0257918 A1 Nov. 16, 2006

Related U.S. Application Data

(62) Division of application No. 10/994,987, filed on Nov. 22, 2004, now Pat. No. 7,189,539.

(60) Provisional application No. 60/525,021, filed on Nov. 25, 2003.

(51) Int. Cl.
*C07K 14/435* (2006.01)
*A61K 38/17* (2006.01)

(52) U.S. Cl. .................... 530/350; 514/12

(58) Field of Classification Search ............ None
See application file for complete search history.

(56) References Cited

U.S. PATENT DOCUMENTS

| | | | |
|---|---|---|---|
| 5,849,902 | A | 12/1998 | Arrow et al. |
| 6,842,846 | B2 | 1/2005 | Chen et al. |
| 2003/0027323 | A1 | 2/2003 | Feder et al. |
| 2003/0032776 | A1 | 2/2003 | Feder et al. |
| 2003/0088884 | A1 | 5/2003 | Hsu et al. |
| 2005/0079180 | A1 | 4/2005 | Kawamura et al. |

FOREIGN PATENT DOCUMENTS

| | | |
|---|---|---|
| EP | 1270724 A2 | 1/2003 |
| WO | WO 9948921 | 9/1999 |
| WO | WO 0015793 | 3/2000 |
| WO | WO 0136471 | 5/2001 |
| WO | WO 0204640 | 6/2001 |
| WO | WO 0214489 | 2/2002 |
| WO | WO02/26824 A2 | 4/2002 |
| WO | WO02/063004 A2 | 8/2002 |
| WO | WO02/102992 A2 | 12/2002 |
| WO | WO03/016487 A2 | 2/2003 |
| WO | WO03/021266 A1 | 3/2003 |
| WO | WO03/078632 A1 | 9/2003 |
| WO | WO2004/040000 A2 | 5/2004 |

OTHER PUBLICATIONS

Sudo et al., H3 relaxin is a specific ligand for LGR7 and activates the receptor by interacting with both the ectodomain and the exoloop 2. J. Biol. Chem. 278:7855-7862, 2003, Epub Dec. 27, 2002.*

Hsu, et al., "Activation of Orphan Receptors by the Hormone Relaxin", Science, vol. 295, pp. 671-674 (2002).
Hsu, et al., Science, vol. 295 (5555): 671-674 (2002).
Incyte Clone ID: 3495551.
Database WPI, Section Ch. Week 200223, Derwent Publications Ltd., London, GB; Class B04, AN 2002-179706, XP002204698, Jan. 17, 2002, Seq ID Nos. 13,14, abstract.
NCBI Entrez Accession No. gi:18677729, Hsu, S.Y. et al., Apr. 8, 2002.
NCBI Entrez Accession No. gi:18702460, Hsu, S.Y. et al., Feb. 18, 2002.
Alam, et al., "Reporter Genes: Application to the Study of Mammalian Gene Transcription", Anal. Biochem., vol. 188, pp. 245-254 (1990).
Altschul, et al., "Gapped Blast and PSI-BLAST: a new generation of protein database search programs", Nucleic Acids Res., vol. 25 (17), pp. 3389-3402 (1997).
Asatiani, et al., "Distribution and function of FSH receptor genetic variants in normal men", Andrologia, vol. 34, pp. 172-176 (2002).
Atger, et al., "Structure of the human luteinizing hormone-choriogonadotropin receptor gene: unusual promoter and 5' non-coding regions", Molec. Cell. Endocrin., vol. 111, pp. 113-123 (1995).
Babu, et al., "Structural Features and Expression of an Alternatively Spliced Growth Factor Type I Receptor for Follitropin Signaling in the Developing Ovary", Mole. Cell Biol. Res. Comm., vol. 2, pp. 21-27 (1999).
Bani, et al., "Morphological Changes Induced in Mouse Mammary Gland by Porcine and Human Relaxin", Acta Anat., vol. 119, pp. 149-154 (1984).
Bartsch, et al., "Relaxin signalling links tyrosine phosphorylation to phosphodiesterase and adenylyl cyclase activity", Molec. Human Reprod., vol. 7 (9), pp. 799-809 (2001).
Bateman, et al., "The Pfam Protein Families Database", Nucl. Acids Res., vol. 28 (1), pp. 263-266 (2000).
Baud, et al., "EMR1, an Unusual Member in the Family of Hormone Receptors with Seven Transmembrane Segments", Genomics, vol. 26, pp. 334-344 (1995).
Blache, et al., "Cloning and Tissue Distribution of a New Rat Olfactory Receptor-like (OL2)", Biochem. Biophys. Res. Comm., vol. 242, pp. 669-672 (1998).

(Continued)

*Primary Examiner*—Ruixiang Li
(74) *Attorney, Agent, or Firm*—Stephen C. D'Amico

(57) ABSTRACT

The present invention provides novel polynucleotides encoding HGPRBMY5v1 and HGPRBMY5v2 polypeptides, fragments and homologues thereof. Also provided are vectors, host cells, antibodies, and recombinant and synthetic methods for producing said polypeptides. The invention further relates to diagnostic and therapeutic methods for applying these novel HGPRBMY5v1 and HGPRBMY5v2 polypeptides to the diagnosis, treatment, and/or prevention of various diseases and/or disorders related to these polypeptides. The invention further relates to screening methods for identifying agonists and antagonists of the polynucleotides and polypeptides of the present invention.

10 Claims, 24 Drawing Sheets

OTHER PUBLICATIONS

Figure 3:
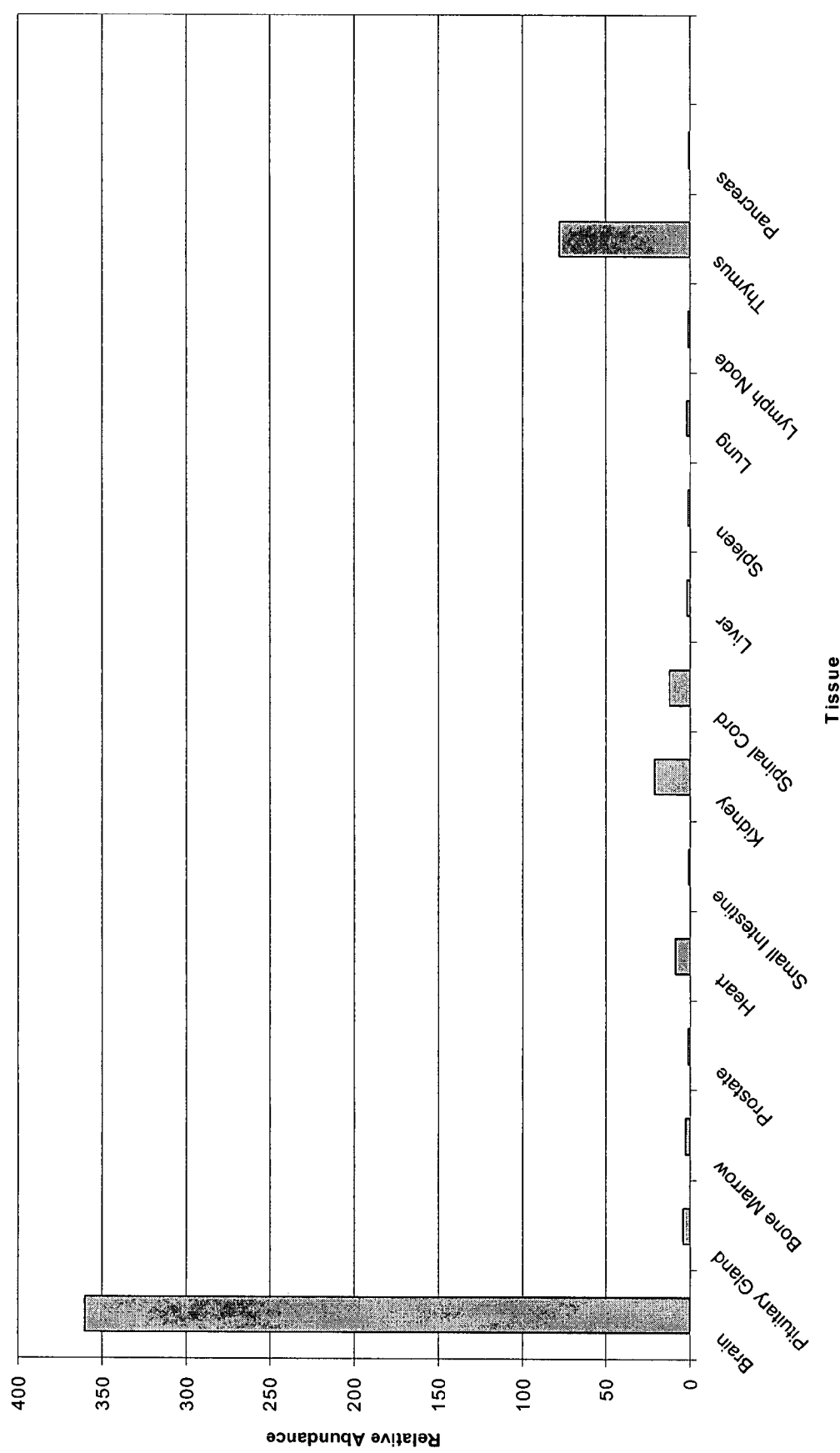

Bockmann, et all, "Cloning and Expression of a Brain-Derived TSH Receptor", Biochem. Biophys. Res. Comm. vol. 238, pp. 173-178 (1997).
Bolander, Franklyn, F., "Molecular Endocrinology", (second Ed.), Academic Press, Copyright 1994, pp. 162-176.
Boss, et al., "Induction of NFAT-mediated Transcription by $G_s$-coupled Receptors in Lymphoid and Non-lymphoid Cells", J. Biol. Chem., vol. 271 (18), pp. 10429-10432 (1995).
Bunz, et al., "Requirement for p53 and p21 to Sustain $G_2$ Arrest After DNA Damage", Science, vol. 282, pp. 1497-1501 (1998).
Cargill, et al., "Characterization of single-nucleotide polymorphisms in coding regions of human genes", Nature Genetics, vol. 22, pp. 231-238 (1999).
Chen, et al., "Constitutive receptor systems for drug discovery", J. Pharmacol. Toxicol. Meth., vol. 42, pp. 199-206 (1999).
Cheng, et al., "Hematopoietic Stem Cell Quiescence Maintained by $p21^{CIP1/wat1}$", Science, vol. 287, pp. 1804-1808 (2000).
Cocco, et al., "A Missense (T577I) Mutation in the Luteinizing Hormone Receptor Gene Associated With Familial Male-Limited Precocious Puberty", Human Mutation, vol. 7, pp. 164-166 (1996).
Cui, et al., "Identification of $Phe^{313}$ of the Ganodotropin-Releasing Hormone (GnRH) Receptor as a Site Critical for the Binding of Nonpeptide GnRH Antagonists", Molec. Endocrin., vol. 14(5), pp. 671-681 (2000).
Dayanithi, et al., "Relaxin affects the release of oxytocin and vasopressin from the neurohypophysis", Nature, vol. 325, pp. 813-816 (1987).
Dorn, et al., "Low- and high-level transgenic expression of $\beta_2$-adrenergic receptors differentially affect cardiac hypertrophy and function in $G\alpha q$-overexpressing mice", PNAS, vol. 96, pp. 6400-6405 (1999).
Draetta, Giulio F., "Mammalian $G_1$ cyclins", Curr. Opin. Cell Biol., vol. 6, pp. 842-846 (1994).
Dschietzig, et al., "Relaxin: a pregnancy hormone as central player of body fluid and circulation homeostasis", Cellular Mole. Life Sciences, vol. 60, pp. 688-700 (2003).
Chiquet-Ehrismann, et al., "Tenascin: an Extracellular Matrix Protein Involved in Tissue Interactions during Fetal Development and Oncogenesis", Cell, vol. 47, pp. 131-139 (1986).
Evans, et al., "A new point mutation in the luteinising hormone receptor gene in familial and sporadic male limited precocious puberty: genotype does not always correlate with phenotype", J. Med. Genet, vol. 33, pp. 143-147 (1996).
Failli, et al., "Relaxin up-regulates inducible nitric oxide synthase expression and nitric oxide generation in rat coronary endothelial cells", FASEB J., vol. 16, pp. 252-254 (2002).
Feng, et al., "HIV-1 Entry Cofactor: Functional cDNA Cloning of a Seven-Transmembrane, G Protein-Coupled Receptor", Science, vol. 272, pp. 872-877 (1996).
Fiering, et al., "Single cell assay of a transcription factor reveals a threshold in transcription activated by signals emanating from the T-cell antigen receptor", Genes Develop., vol. 4, pp. 1823-1834 (1990).
Frazier, et al., "Isolation of TSH and LH/CG Receptor cDNAS from Human Thyroid: Regulation by Tissue Specific Splicing", Molec. Endocrin., vol. 4, pp. 1264-1276 (1990).
George, et al., "Functional Coupling of Endogenous Serotinin ($5-HT_{1B}$) and Calcitonin (C1a) Receptors in CHO Cells to a Cyclic AMP-Responsive Luciferase Reporter Gene", J. Neurochem., vol. 69, pp. 1278-1285 (1997).
Gilman, Alfred G., "G Proteins: Transducers of Receptor-Generated Signals", Ann. Rev. Biochem, vol. 56, pp. 615-649 (1987).
Gorlov, et al., "Mutations of the Great gene cause cryptorchidism", Human Molec. Genetics, vol. 11(19), pp. 2309-2318 (2002).
Gray, et al., "CD97 is a Processed, Seven-Transmembrane, Heterodimeric Receptor Associated with Inflammation", J. Immunol., vol. 157, pp. 5438-5447 (1996).
Gromoll, et al., "Molecular Cloning of the Testicular Follicle Stimulating Hormone Receptor of the Non Human Primate Macaca Fascicularis and Identification of Multiple Transcripts in the Testis", vol. 196(3), pp. 1066-1072 (1993).

Gromoll, et al., "Characterization of the 5' flanking region of the human follicle-stimulating hormone receptor gene", Molec. Cell Endocrin., vol. 102, pp. 93-102 (1994).
Gromoll, et al., "Molecular Cloning of a Truncated Isoform of the Human Follicle Stimulating Hormone Receptor", Biochem. Biophys. Res. Comm., vol. 188(3), pp. 1077-1083 (1992).
Gromoll, et al., "A Mutation in the First Transmembrane Domain of the Lutropin Receptor Causes Male Precocious Puberty", J. Clin. Endocrin. Metab., vol. 83(2), pp. 476-480 (1998).
Gudermann, et al., "Evidence for Dual Coupling of the Murine Luteinizing Hormone Receptor to Adenylyl Cyclase and Phosphoinositide Breakdown and $Ca^{2+}$ Mobilization", J. Biol. Chem., vol. 267 (7), pp. 4479-4488 (1992).
Hawes, et al., "PHosphatidylinositor 3-Kinase Is an Early Intermediate in the $G\beta\gamma$- mediated Mitogen-activated Protein Kinase Signaling Pathway", J. Biol. Chem., vol. 271(21), pp. 12133-12136 (1996).
Heckert, et al., "Structural Organization of the Follicle-Stimulating Hormone Receptor Gene", Molec. Endocrin., vol. 6, pp. 70-80 (1992).
Hermey, et al., "Identification of a Novel Seven-Transmembrane Receptor with Homology to Glycoprotein Receptors and Its Expression in the Adult and Developing Mouse", Biochem. Biophysical Res. Comm., vol. 254, pp. 273-279 (1999).
Hofmann, et al., "A Database of Membrane Spanning Protein Segments", Biol. Chem., vol. 347, pp. 166 (1993).
Horn, et al., "The Interaction of Class B G Protein-Coupled Receptors with their Hormones", Receptors Channels, vol. 5, pp. 305-314 (1998).
Horn, et al., "G Protein-coupled receptors *in silico*", J. Mol. Med., vol. 76, pp. 464-468 (1998).
Houde, et al., "Structure of the Bovine Follicle-Stimulating Hormone Receptor Complementary DNA and Expression in Bovine Tissues", Molec. Reprod. Develop., vol. 39, pp. 127-135 (1994).
Hsu, Sheau Yu, "Cloning of Two Novel Mammalian Paralogs of Relaxin/Insulin Family Proteins and Their Expression in Testis and Kidney", Molec. Endocrin., vol. 13, pp. 2163-2174 (1999).
Hsu, et al., "The Three Subfamilies of Leucine-Rich Repeat-Containing G Protein-Coupled Receptors (LGR): Identification of LGR6 and LGR7 and the Signaling Mechanism for LGR7", Molec. Endocrin., vol. 14, pp. 1257-1271 (2000).
Hsu, et al., "Characterization of Two LGR Genes Homologous to Gonadotropin and Thyrotropin Receptors with Extracellular Leucine Leucine-Rich Repeats and a G Protein-Coupled, Seven-Transmembrane Region", Molec. Endocrin., vol. 12, pp. 1830-1845 (1998).
Huhtaniemi, et al., "The murine luteinizing hormone and follicle-stimulating hormone receptor genes: transcription initiation sites, putative promoter sequences and promoter activity", Molec. Cell. Endocrin., vol. 88, pp. 55-66 (1992).
Jia, et al., "Expression of Human Luteinizing Hormone (LH) Receptor: Interaction with LH and Chorionic Genodotropin from Human but not Equine, Rat, and Ovine Species", Molec. Endocrin., vol. 5, pp. 759-768 (1991).
Jiang, et al., "Structural predictions for the ligand-binding region of glycoprotein hormone receptors and the nature of hormone-receptor interactions", Structure, vol. 3, pp. 1341-1353 (1995).
Karttunen, et al., "Measurement of ligand-induced activation in single viable T cells using the *lacZ* reporter gene", PNAS, vol. 88, pp. 3972-3976 (1991).
Kelton, et al., The cloning of the human follicle stimulating hormone receptor and its expression in COS-7, CHO, and Y-1 Cells, Molec. Cell. Endocrin., vol. 89, pp. 141-151 (1992).
Kim, et al., "Structure and function in rhodopsin: Rhodopsin mutants with a neurtral amino acid at E134 have a partially activated conformation in the dark state", PNAS, vol. 94, pp. 14273-14278 (1997).
Khan, et al., "Cloning of Alternately Spliced mNRA Transcripts Coding For Variants of Ovine Testicular Follitropin Receptor Lacking the G Protein Coupling Domains", Biochem. Biophys. Res. Comm., vol. 190(3), pp. 888-894 (1993).

Kishimoto, et al., "Studies on the Phosphorylation of Myelin Basic Protein by Protein Kinase C and Adenosine 3':5'-Monophosphate-dependent Protein Kinase", J. Biol. Chem., vol. 260(23), pp. 12492-12499 (1985).

Kosugi, et al., "Characterization of heterogeneous mutations causing constitutive activation of the luteinizing hormone receptor in familial male precocious puberty", Human Mole. Genetics, vol. 4(2), pp. 183-188 (1995).

Kremer, et al., "Male pseudohermaphroditism due to a homozygous missense mutation of the luteinizing hormone receptor gene", Nature Genetics, vol. 9, pp. 160-164 (1995).

Kremer, et al., "Cosegregation of missense mutations of the luteinizing hormone receptor gene with familial male-limited precocious puberty", Human Molec. Genetics, vol. 2(11), pp. 1779-1783 (1993).

Kypson, et al., "Adenovirus-mediated gene transfer of the $\beta_2$-adrenergic receptor to donor hearts enhances cardiac function", Gene Ther., vol. 6, pp. 1298-1304 (1999).

Latronico, et al., "A Unique Constitutively Activating Mutation in Third Transmembrane Helix of Luteinizing Hormone Receptor Causes Sporadic Male Gonadotropin-Independent Precocious Puberty", J. Clin. Endocrin. Metab., vol. 83(7), pp. 2435-2440 (1998).

Latronico, et al., "Brief Report:Testicular and Ovarian Resistance to Luteinizing Hormone Caused by Inactivating Mutations of the Luteinizing Hormone-Receptor Gene", New Engl. J. Med., vol. 334(8), pp. 507-512 (1996).

Latronico, et al., "A Novel Mutation of the Luteinizing Hormone Receptor Gene Causing Male Gonadotropin-Independent Precocious Puberty", J. Clin. Endocrin. Metab., vol. 80(8), pp. 2490-2494 (1995).

Latronico, et al., "A Homozygous Microdeletion in Helix 7 of the Luteinizing Hormone Receptor Associated with Familial Testicular and Ovarian Resistance Is Due to Both Decreased Cell Surface Expression and Impaired Effector Activation by the Cell Surface Receptor", Molec. Endocrin., vol. 12(3), pp. 443-450 (1998).

LeDoux, Joseph E., "Emotion: Clues from the Brain", Annu. Rev. Psychol., vol. 46, pp. 209-235 (1995).

Liu, et al., "Leydig-Cell Tumors Caused by an Activating Mutation of the Gene Encoding the Luteinizing Hormone Receptor", New England J. Med., vol. 341(23), pp. 1731-1736 (1999).

Loosefelt, et al., "Cloning and Sequencing of Porcine LH-hCG Receptor cDNA: Variants Lacking Transmembrane Domain", Science, vol. 245, pp. 525-528 (1989).

Lu, et al., "The Functional Topography of Transmembrane Domain 3 of the $M_1$ Muscarinic Acetylcholine Receptor, Revealed by Scanning Mutagenesis", J. Biol. Chem., vol. 274(11), pp. 7309-7315 (1999).

Misrahi, et al., "Comparison of Immunocytochemical and Molecular Features with the Phenotype in a Case of Incomplete Male Pseudohermaphroditism Associated with a Mutation of the Luteinizing Hormone Receptor", J. Clin. Endocrin. Metab., vol. 82(7), pp. 2159-2165 (1997).

Muda, et al., "Splice variants of the relaxin and INSL3 receptors reveal unanticipated molecular complexity", Molec. Human Reprod., vol. 11(8), pp. 591-600 (2005).

Mamluk, et al., "LH Receptor mRNA and Cytochrome P450 Side-Chain Cleavage Expression in Bovine Theca and Granulosa Cells Luteinizied by LH or Forskolin", Domestic Animal Endocrin., vol. 15(2), pp. 103-114 (1998).

Martens, et al., "A Homozygous Mutation in the Luteinizing Hormone Receptor Causes Partial Leydid Cell Hypoplasia: Correlation between Receptor Activity and Phenotype", Molec. Endocrin., vol. 12(6), pp. 775-784 (1998).

Matsuoka, et al., "Identification of Novel Members of G-Protein Coupled Receptor Superfamily Expressed in Bovine Taste Tissue", Biochem. Biophys. Res. Comm., vol. 194 (1), pp. 504-511 (1993).

McDonald, et al., "Identification and Cloning of an Orphan G Protein-Coupled Receptor of the Glycoprotein Hormone Receptor Subfamily", Biochem. Biophys. Res. Comm., vol. 247, pp. 266-270 (1998).

Min, et al., "Identification of Specific Relaxin-Binding Cells in the Cervix, Mammary Glands, Nipples, Small Intestine, and Skin of Pregnant Pigs", Biol. Reprod., vol. 55, pp. 1243-1252 (1996).

Minegish, et al., "Cloning and Sequencing of Human LH/hCG Receptor cDNA", Biochem. Biophys. Res. Comm., vol. 172 (3), pp. 1049-1054 (1990).

Minegish, et al., Cloning and Sequencing of Human FSH Receptor cDNA, Biochem. Biophys. Res. Comm., vol. 175 (3), pp. 1125-1130 (1991).

Nef, et al., "Cryptochidism in mice mutant for Insl3", Nature Genetics, vol. 22, pp. 295-299 (1999).

Okada, et al., "Activation of rhodopsin: new insights from structural and biochemical studies", Trends in Biochem. Sci., vol. 26(5), pp. 318-324 (2001).

Osheroff, et al., "Autoradiographic localization of relaxin binding sites in rat brain", PNAS, vol. 88, pp. 6413-6417 (1991).

Osheroff, et al., "Relaxin binding in the rate heart atrium", PNAS, vol. 89, pp. 2384-2388 (1992).

Osuga, et al., "Derivation of Functional Antagonists Using N-Terminal Extracellular Domain of Gonadotropin and Thyrotropin Receptors", Molec. Endocrin., vol. 11(11), pp. 1659-1668 (1997).

Overbeek, et al., "Transgenic Insertion Causing Cryptochidism in Mice", Genesis, vol. 30, pp. 26-35 (2001).

Palejwala, et al., "Relaxin Positively Regulates Matrix Metalloproteinase Expression in Human Lower Uterine Segment Fibroblasts Using a Tyrosine Kinase Signaling Pathway", Endocrin., vol. 142(8), pp. 3405-3413 (2001).

Parma, et al., "Somatic mutations in the thyrotropin receptor gene cause hyperfunctioning thyroid adenomas", Nature, vol. 365, pp. 649-651 (1993).

Rees, S. et al., Chapter 8: "Reporter gene systems for the study of G protein-coupled receptor signal transduction in mammanlian cells", Signal Transduction: A Practical Approach, Second Edition, Oxford University Press, publ., Milligan, G., ed., pp. 171-221 (1999).

Remy, et al., "The porcine follitropin receptor: cDNA cloning, functional expression and chromosomal localization of the gene", Gene, vol. 163, pp. 257-261 (1995).

Richard, et al., "Cloning, sequencing and in vitro functional expression of recombinant donkey follicle-stimulating hormone receptor: a new insight into the binding specificity of gonadotrophin receptors", J. Molec. Endocrin., vol. 18, pp. 193-202 (1997).

Riken Genome Exploration Res. Group, "Functional annotation of a full-length mouse cDNA collection", Nature, vol. 409, pp. 685-690 (2001).

Rodien, et al., "Evidences for an Allelic Variant of the Human LC/CG Receptor rather than a Gene Duplication: Functional Comparison of Wild-Type and Variant Receptors", J. Clin. Endocrin. Metabol., vol. 83(12), pp. 4431-4434 (1998).

Sairam, et al., "Characterization of the 5' Flanking Region and Potential Control Elements of the Ovine Follitropin Receptor Gene", Molec. Reprod. Develop., vol. 48, pp. 480-487 (1997).

Salcedo, et al., "Human endothelial cells express CCR2 and respond to MCP-1:direct role of MCP-1 in angiogenesis and tumor progression", Blood, vol. 96(1), pp. 34-40 (2000).

Schafer, K.A., "The Cell Cycle: A Review", Vet. Pathol., vol. 35, pp. 461-478 (1998).

Selbie, et al., "G protein-coupled-receptor cross-talk:the fine-tuning of multiple receptor-signalling pathways", TIPS, vol. 19, pp. 87-93 (1998).

Shenker, et al., "A constitutively activating mutation of the luteinizing hormone receptor in familial male precocious puberty", Nature, vol. 365, pp. 652-654 (1993).

Sica, et al., "Defective Expression of the Monocyte Chemotactic Protein-1 Receptor CCR2 in Macrophages Associated with Human Ovarian Carcinoma", J. Immunol., vol. 164, pp. 733-738 (2000).

Silversides, et al., "Bovine thyrotropin receptor cDNA is characterized by full-length and truncated transcripts", J. Molec. Endocrin., vol. 18, pp. 101-112 (1997).

Sprengel, et al., "The Testicular Receptor for Follicle Stimulating Hormone:Structure and Functional Expression of Cloned cDNA", Molec. Endocrin., vol. 4, pp. 525-530 (1990).

Stavrou, et al., "A Novel Mutation of the Human Luteinizing Hormone Receptor in 46XY and 46XX Sisters", J. Clin. Endocrin. Metabol., vol. 83 (6), pp. 2091-2098 (1998).

Stein, et al., "Identification of a Point Mutation in the Thyrotropin Receptor of the hyt/hyt Hypothyroid Mouse", Molec. Endocrin., vol. 8, pp. 129-138 (1994).

St. Louis, et al., "Chronic Decrease of Blood Pressure by Rat Relaxin in Spontaneously Hypertensive Rats", Life Sciences, vol. 37, pp. 1351-1357 (1985).

Strosberg, Arthur Donny, "Structure/function relationship of proteins belonging to the family of receptors coupled to GTP-binding proteins", Eur. J. Biochem., vol. 196, pp. 1-10 (1991).

Suto, et al., "Selection of an Optimal Reporter Gene for Cell-Based High Throughput Screening Assays", J. Biomolec. Screening, vol. 2(1), pp. 7-9 (1997).

Tao, et al., "Constitutive Activation of G Protein-Coupled Receptors as a Results of Selective Substitution of a Conserved Leucine Residue in Transmembrane Helix III", Molec. Endocrin., vol. 14, pp. 1272-1282 (2000).

Thomas, et al., "Chemoreceptors expressed in taste, olfactory and male reproductive tissues", Gene, vol. 178, pp. 1-5 (1996).

Tasi-Morris, et al., "Genomic Distribution and Gonadal mRNA Expression of Two Human Luteinizing Hormone Receptor Exon 1 Sequences in Random Populations", Hum Hered, vol. 49, pp. 48-51 (1999).

Wakabayashi, et al., "The cDNA cloning and transient expression of a chicken gene encoding a follicle-stimulating hormone receptor", Gene, vol. 197, pp. 121-127 (1997).

Watson, et al., "The G-protein Linked Receptor Facts Book", Academic Press, San Diego CA, pp. 2-6 (1994).

Wess, Jürgen, "G-protein-coupled receptors: molecular mechanisms involved in receptor activation and selectively of G-protein recognition", FASEB J., vol. 11, pp. 346-354 (1997).

Whitney, M. et al., "A genome-wide functional assay of signal transduction in living mammalian cells", Nature Biotechnology, vol. 16, pp. 1329-1333 (1998).

Woodgett, et al., "Substrate specificity of protein kinase C", Eur. J. Biochem., vol. 161, pp. 177-184 (1986).

Wu, et al., Polymorphisms in the Coding Exons of the Human Luteinizing Hormone Receptor Gene, Human Mutation in Brief #124 (1997).

Yano, et al., "A New Constitutively Activating Point Mutation in the Luteinizing Hormone/Choriogonadotropin Receptor Gene in Cases of Male-Limited Precocious Puberty", J. Clin. Endocrin. Metab., vol. 80(4), pp. 1162-1168 (1995).

Yarney, et al., "Molecular Cloning, Structure, and Expression of a Testicular Follitropin Receptor with Selective Alteration in the Carboxy Terminus That Affects Signaling Function", Molec. Reprod. Develop., vol. 48, pp. 458-470 (1997).

Yarney, et al., "Molecular cloning and expression of the ovine testicular follicle stiumlating hormone receptor", Molec. Cell. Endocrin., vol. 93, pp. 219-226 (1993).

You, et al., "Characterization of the Chicken Follicle-Stimulating Hormone Receptor (cFSH-R) Complementary Deoxyribonucleic Acid, and Expression of cFSH-R Messenger Ribonucleic Acid in the Ovary", Biol. Reprod., vol. 55, pp. 1055-1062 (1996).

Yuan, et al., "Cloning and genetic characterization of an evolutionarily conserved human olfactory receptor that is differentially expressed across species", Gene, vol. 278, pp. 41-51 (2001).

Zhang, et al., "Cloning and Functional Expression of the Luteinizing Hormone Receptor Complementary Deoxyribonucleic Acid from the Marmoset Monkey Testis: Absence of Sequences Encoding Exon 10 in Other Species", Endocrin., vol. 138(6), pp. 2481-2490 (1997).

Zhao, et al., "Mice without a Functional Relaxin Gene are Unable to Deliver Milk to Their Pups", Endocrin., vol. 140(1), pp. 445-453 (1999).

Zimmerman, et al., "Targeted Disruption of the Ins13 Gene Causes Bilateral Cryptochidism", Molec. Endocrin., vol. 13, pp. 681-691 (1999).

Zlokarnik, et al., "Quantitation of Transcription and Clonal Selection of Single Living Cells with β-Lactamase as Reporter", Science, vol. 279, pp. 84-88 (1998).

NCBI Entrez Accession No. AAF48237 (gi:7292844), Adams, et al., Aug. 10, 2005.

NCBI Entrez Accession No. AAF56490 (gi:23172316), Adams, et al., Aug. 11, 2005.

NCBI Entrez Accession No. AAL73496 (gi:18483168), Gorlov, et al., Sep. 9, 2002.

NCBI Entrez Accession No. AAX85199 (gi:62529845), Muda, et al., Sep. 28, 2005.

NCBI Entrez Accession No. BAA86898 (gi:6441013), Oba, et al., Nov. 17, 1999.

NCBI Entrez Accession No. CAD28586 (gi:19578153), Paszty, et al., Mar. 19, 2002.

NCBI Entrez Accession No. CAD28588 (gi:19578157), Paszty, et al., Mar. 29, 2002.

NCBI Entrez Accession No. CAD28590 (gi:19578161), Paszty, et al., Mar. 19, 2002.

NCBI Entrez Accession No. CAD69575 (gi:28799469), Suwa, et al., Mar. 4, 2003.

NCBI Entrez Accession No. CAH73785 (gi:55662049), Phillimore, B., May 18, 2005.

NCBI Entrez Accession No. CAI17102 (gi:55957878), Pelan, S., May 18, 2005.

NCBI Entrez Accession No. NP_57018 (gi:18677729), Muda, et al., Nov. 27, 2005.

NCBI Entrez Accession No. Q8WXD0 (gi:21362625), Hsu, et al., Jan. 24, 2006.

NCBI Entrez Accession No. XP_522654 (gi:55639709), NCBI Annotation Process, Nov. 9, 2004.

Swiss-Prot Accession No. Q8WXD0, Release 41, Feb. 2003.

Swiss-Prot Accession No. Q91ZZ5, Release, 41, Feb. 2003.

Swiss-Prot Accession No. Q9HBX9, Release 41, Feb. 2003.

Swiss-Prot Accession No. Q9Z1P4, Release 41, Feb. 2003.

Ferlin, et al., "The INSL3-LGR8-GREAT Ligand-Receptor Pair in Human Cryptochidism," J. Clin. Endocrin. Metabolism, vol. 88(9), pp. 4273-4279 (2003).

Tilly, et al., "Expression of Recombinant Human Follicle-Stiumlating Hormone Receptor: Species-Specific Ligand Binding, Signal Transduction, and Identification of Multiple Ovarian Messenger Ribonucleic Acid Transcripts", Endocrinology, vol. 131(2), pp. 799-806 (1992).

* cited by examiner

FIG. 1A

```
  1  ATGCAGAAAACCAAGCAAGATGAGGACTATGAAAGAGCCATTGGATTTAGTGTCAAAATG   60
  1   M  Q  K  T  K  Q  D  E  D  Y  E  R  A  I  G  F  S  V  K  M   20

61  GATGACAGTGATTCTGATTTTGCACTGACTCAAGGTAGCATGATCACTCCTTCATGCCAA  120
 21   D  D  S  D  S  D  F  A  L  T  Q  G  S  M  I  T  P  S  C  Q   40

121  AAAGGATATTTTCCCTGTGGGAATCTTACCAAGTGCTTACCCCGAGCTTTTCACTGTGAT  180
 41   K  G  Y  F  P  C  G  N  L  T  K  C  L  P  R  A  F  H  C  D   60

181  GGCAAGGATGACTGTGGGAACGGGGCGGACGAAGAGAACTGTGGTGACACTAGTGGATGG  240
 61   G  K  D  D  C  G  N  G  A  D  E  E  N  C  G  D  T  S  G  W   80

241  GCGACCATATTTGGCACAGTGCATGGAAATGCTAACAGCGTGGCCTTAACACAGGAGTGC  300
 81   A  T  I  F  G  T  V  H  G  N  A  N  S  V  A  L  T  Q  E  C  100

301  TTTCTAAAACAGTATCCACAATGCTGTGACTGCAAAGAAACTGAATTGGAATGTGTAAAT  360
101   F  L  K  Q  Y  P  Q  C  C  D  C  K  E  T  E  L  E  C  V  N  120

361  GGTGACTTAAAGTCTGTGCCGATGATTTCTAACAATGTGACATTACTGTCTCTTAAGAAA  420
121   G  D  L  K  S  V  P  M  I  S  N  N  V  T  L  L  S  L  K  K  140

421  AACAAAATCCACAGTCTTCCAGATAAAGTTTTCATCAAATACACAAAACTTAAAAAGATA  480
141   N  K  I  H  S  L  P  D  K  V  F  I  K  Y  T  K  L  K  K  I  160

481  TTTCTTCAGCATAATTGCATTAGACACATATCCAGGAAAGCATTTTTTGGATTATGTAAT  540
161   F  L  Q  H  N  C  I  R  H  I  S  R  K  A  F  F  G  L  C  N  180

541  CTGCAAATATTATATCTCAACCACAACTGCATCACAACCCTCAGACCTGGAATATTCAAA  600
181   L  Q  I  L  Y  L  N  H  N  C  I  T  T  L  R  P  G  I  F  K  200

601  GACTTACATCAGCTAACTTGGCTAATTCTAGATGACAATCCAATAACCAGAATTTCACAG  660
201   D  L  H  Q  L  T  W  L  I  L  D  D  N  P  I  T  R  I  S  Q  220

661  CGCTTGTTTACGGGATTAAATTCCTTGTTTTTCCTGTCTATGGTTAATAACTACTTAGAA  720
221   R  L  F  T  G  L  N  S  L  F  F  L  S  M  V  N  N  Y  L  E  240

721  GCTCTTCCCAAGCAGATGTGTGCCCAAATGCCTCAACTCAACTGGGTGGATTTGGAAGGC  780
241   A  L  P  K  Q  M  C  A  Q  M  P  Q  L  N  W  V  D  L  E  G  260

781  AATAGAATAAAGTATCTCACAAATTCTACGTTTCTGTCGTGCGATTCGCTCACAGTGCTG  840
261   N  R  I  K  Y  L  T  N  S  T  F  L  S  C  D  S  L  T  V  L  280
```

FIG. 1B

```
 841  TTTCTGCCTAGAAATCAAATTGGTTTTGTTCCAGAGAAGACATTTTCTTCATTAAAAAAT   900
 281    F   L   P   R   N   Q   I   G   F   V   P   E   K   T   F   S   S   L   K   N    300

901  TTAGGAGAACTGGATCTGTCTAGCAATACGATAACGGAGCTATCACCTCACCTTTTTAAA   960
 301    L   G   E   L   D   L   S   S   N   T   I   T   E   L   S   P   H   L   F   K    320

961  GACTTGAAGCTTCTACAAAAGCTGAACCTGTCATCCAATCCTCTTATGTATCTTCACAAG  1020
 321    D   L   K   L   L   Q   K   L   N   L   S   S   N   P   L   M   Y   L   H   K    340

1021  AACCAGTTTGAAAGTCTTAAACAACTTCAGTCTCTAGACCTGGAAAGGATAGAGATTCCA  1080
 341    N   Q   F   E   S   L   K   Q   L   Q   S   L   D   L   E   R   I   E   I   P    360

1081  AATATAAACACACGAATGTTTCAACCCATGAAGAATCTTTCTCACATTTATTTCAAAAAC  1140
 361    N   I   N   T   R   M   F   Q   P   M   K   N   L   S   H   I   Y   F   K   N    380

1141  TTTCGATACTGCTCCTATGCTCCCCATGTCCGAATATGTATGCCCTTGACGGACGGCATT  1200
 381    F   R   Y   C   S   Y   A   P   H   V   R   I   C   M   P   L   T   D   G   I    400

1201  TCTTCATTTGAGGACCTCTTGGCTAACAATATCCTCAGAATATTTGTCTGGGTTATAGCT  1260
 401    S   S   F   E   D   L   L   A   N   N   I   L   R   I   F   V   W   V   I   A    420

1261  TTCATTACCTGCTTTGGAAATCTTTTTGTCATTGGCATGAGATCTTTCATTAAAGCTGAA  1320
 421    F   I   T   C   F   G   N   L   F   V   I   G   M   R   S   F   I   K   A   E    440

1321  AATACAACTCACGCTATGTCCATCAAAATCCTTTGTTGTGCTGATTGCCTGATGGGTGTT  1380
 441    N   T   T   H   A   M   S   I   K   I   L   C   C   A   D   C   L   M   G   V    460

1381  TACTTGTTCTTTGTTGGCATTTTCGATATAAAATACCGAGGGCAGTATCAGAAGTATGCC  1440
 461    Y   L   F   F   V   G   I   F   D   I   K   Y   R   G   Q   Y   Q   K   Y   A    480

1441  TTGCTGTGGATGGAGAGCGTGCAGTGCCGCCTCATGGGGTTCCTGGCCATGCTGTCCACC  1500
 481    L   L   W   M   E   S   V   Q   C   R   L   M   G   F   L   A   M   L   S   T    500

1501  GAAGTCTCTGTTCTGCTACTGACCTACTTGACTTTGGAGAAGTTCCTGGTCATTGTCTTC  1560
 501    E   V   S   V   L   L   L   T   Y   L   T   L   E   K   F   L   V   I   V   F    520

1561  CCCTTCAGTAACATTCGACCTGGAAAACGGCAGACCTCAGTCATCCTCATTTGCATCTGG  1620
 521    P   F   S   N   I   R   P   G   K   R   Q   T   S   V   I   L   I   C   I   W    540

1621  ATGGCGGGATTTTTAATAGCTGTAATTCCATTTTGGAATAAGGATTATTTTGGAAACTTT  1680
 541    M   A   G   F   L   I   A   V   I   P   F   W   N   K   D   Y   F   G   N   F    560
```

FIG. 1C

```
1681  TATGGGAAAAATGGAGTATGTTTCCCACTTTATTATGACCAAACAGAAGATATTGGAAGC  1740
 561   Y  G  K  N  G  V  C  F  P  L  Y  Y  D  Q  T  E  D  I  G  S   580

1741  AAAGGGTATTCTCTTGGAATTTTCCTAGGTGTGAACTTGCTGGCTTTTCTCATCATTGTG  1800
 581   K  G  Y  S  L  G  I  F  L  G  V  N  L  L  A  F  L  I  I  V   600

1801  TTTTCCTATATTACTATGTTCTGTTCCATTCAAAAAACCGCCTTGCAGACCACAGAAGTA  1860
 601   F  S  Y  I  T  M  F  C  S  I  Q  K  T  A  L  Q  T  T  E  V   620

1861  AGGAATTGTTTTGGAAGAGAGGTGGCTGTTGCAAATCGTTTCTTTTTTATAGTGTTCTCT  1920
 621   R  N  C  F  G  R  E  V  A  V  A  N  R  F  F  F  I  V  F  S   640

1921  GATGCCATCTGCTGGATTCCTGTATTTGTAGTTAAAATCCTTTCCCTCTTCCGGGTGGAA  1980
 641   D  A  I  C  W  I  P  V  F  V  V  K  I  L  S  L  F  R  V  E   660

1981  ATACCAGACACAATGACTTCCTGGATAGTGATTTTTTTCCTTCCAGTTAACAGTGCTTTG  2040
 661   I  P  D  T  M  T  S  W  I  V  I  F  F  L  P  V  N  S  A  L   680

2041  AATCCAATCCTCTATACTCTCACAACCAACTTTTTTAAGGACAAGTTGAAACAGCTGCTG  2100
 681   N  P  I  L  Y  T  L  T  T  N  F  F  K  D  K  L  K  Q  L  L   700

2101  CACAAACATCAGAGGAAATCAATTTTCAAAATTAAAAAAAAAAGTTTATCTACATCCATT  2160
 701   H  K  H  Q  R  K  S  I  F  K  I  K  K  K  S  L  S  T  S  I   720

2161  GTGTGGATAGAGGACTCCTCTTCCCTGAAACTTGGGGTTTTGAACAAAATAACACTTGGA  2220
 721   V  W  I  E  D  S  S  S  L  K  L  G  V  L  N  K  I  T  L  G   740

2221  GACAGTATAATGAAACCAGTTTCCTAG   2247
 741   D  S  I  M  K  P  V  S          748
```

FIG. 2A

```
                            1                                                   50
HGPRBMY5v1   (1)  ------MQKTKQDEDYERAIGFSVKMDDSDSDFALTQGSMITPSCQKGYF
HGPRBMY5     (1)  ------------------------MFFLLHFIVLINVKDFALTQGSMITPSCQKGYF
HGPRBMY5sv1  (1)  ------------------------MFFLLHFIVLINVKDFALTQGSMITPSCQKGYF
LGR5_HUMAN   (1)  ------------------------MDTSRLGVLLSLPVTLQLATGGSSPRSGVLLR
LGR5_MOUSE   (1)  ------------------------MDTSCVHMLLSLLALQLVAAGSSPGPDAIPR
LGR7_HUMAN   (1)  ------------------------MTSGSVFFYILFGKYFSHGGQDVKCSLGYF
LGR8_HUMAN   (1)  ------------------------MFLLHFIVLINVKDFALTQGSMITPSCQKGYF
LGR8_MOUSE   (1)  MIVFLVFKHLFSLRLITMWLLHVIELTEVKDFALADSMVAPLCPKGYF 51                                                  100
HGPRBMY5v1  (45)  PCGNLTKCLPRAFHCDGKDDCGNGADEENCGDTSGWATIFGTVHGNANSV
HGPRBMY5    (34)  PCGNLTKCLPRAFHCDGKDDCGNGADEENCGDTSGWATIFGTVHGNANSV
HGPRBMY5sv1 (34)  PCGNLTKCLPRAFHCDGKDDCGNGADEENCGDTSGWATIFGTVHGNANSV
LGR5_HUMAN  (33)  GCPTHCHCEPDGRMLLRVDCSDLGLSELPSNLSVFTSYLDLSMNNISQLE
LGR5_MOUSE  (33)  GCPSHCHCELDGRMLLRVDCSDLGLSELPSNLSVFTSYLDLSMNNISQLP
LGR7_HUMAN  (33)  PCGNITKCLPQLEHCNGVDDCGNQADEDNCGDNNGWSMQFDKYFASYYKM
LGR8_HUMAN  (51)  PCGNLTKCLPRAFHCDGKDDCGNGADEENCGDTSGWATIFGTVHGNANSV
LGR8_MOUSE  (34)  PCGNLTKCLPRAFHCDGVDDCGNGADEDNCGDTSGWTIFGTVHGNVNKV
```

FIG. 2B

```
                            101                                                           150
HGPRBMY5v1    (95)  A------------------LTQECFLKQYPQCCDCK----------------ETELECVNGDLKSVPMI
HGPRBMY5     (84)  A------------------LTQECFLKQYPQCCDCK----------------ETELECVNGDLKSVPMI
HGPRBMY5sv1  (84)  A------------------LTQECFLKQYPQCCDCK----------------ETELECVNGDLKSVPMI
LGR5_HUMAN   (83)  PNPLPSLRFLELRLAGNALTYIPKGAFTGLYSLKVLMLQNQLRHVPTE----
LGR5_MOUSE   (83)  ASLLHRLCFLELRLAGNALTHIPKGAFTGLHSLKVLMLQNQLRKVPEE----
LGR7_HUMAN   (83)  TSQYPFEAETPECLVGSVPVQCLCQ-----------GLELDCDETNLRAVPSV
LGR8_HUMAN   (101) A------------------LTQECFLKQYPQCCDCK----------------ETELECVNGDLKSVPMI
LGR8_MOUSE   (84)  T------------------LTQECFLSQYPQHCYCR----------------ENELECVKADLKAVPKV 151                                                           200
HGPRBMY5v1   (130) SNN-------VTLLSLKKNKIHSLPDKVFIKYTKLKKIFLQHNCIRHISRKAF
HGPRBMY5     (119) SNN-------VTLLSLKKNKIHSLPDKVFIKYTKLKKIFLQHNCIRHISRKAF
HGPRBMY5sv1  (119) SNN-------VTLLSLKKNKIHSLPDKVFIKYTKLKKIFLQHNCIRHISRKAF
LGR5_HUMAN   (133) ALQNLRSLQSLRLDANHISYVPPSCFSGLHSLRHLWLDDNALTEIPVQAF
LGR5_MOUSE   (133) ALQNLRSLQSLRLDANHISYVPPSCFSGLHSLRHLWLDDNALTDVPVQAF
LGR7_HUMAN   (125) VTAMSLQWNLIRKLPPDCFKNYHDLQKLYLQNNKITSIYAF
LGR8_HUMAN   (136) SNN-------VTLLSLKKNKIHSLPDKVFIKYTKLKKIFLQHNCIRHISRKAF
LGR8_MOUSE   (119) SSN-------VTLLSLKKNKIHRLPVKVFSRYTELRKIYLQHNCITHISRRAF
```

FIG. 2C

| | | 201 | | 250 |
|---|---|---|---|---|
| HGPRBMY5v1 | (176) | FGLCNLQILYLNHNCITT | LRPGIFKDLHQL | TWLILDDNPITRISQRLFTG |
| HGPRBMY5 | (165) | FGLCNLQILYLNHNCITT | LRPGIFKDLHQL | TWLILDDNPITRISQRLFTG |
| HGPRBMY5sv1 | (165) | FGLCNLQIL | | ILDDNPITRISQRLFTG |
| LGR5_HUMAN | (183) | RSLSALQAMTLALNKIHHIPDYAF | GNLSSLVVLHLHNNR | IHSLGKKCFDG |
| LGR5_MOUSE | (183) | RSLSALQAMTLALNKIHHIADYAF | GNLSSLVVLHLHNNR | IHSLGKKCFDG |
| LGR7_HUMAN | (171) | RGLNSLTKLYLSHNRITF | KPGVFEDLHRLEWLI | TEDNHLSRISPPTFYG |
| LGR8_HUMAN | (182) | FGLCNLQILYLNHNCITT | LRPGIFKDLHQL | TWLILDDNPITRISQRLFTG |
| LGR8_MOUSE | (165) | LGHNLQILYLISHNCITS | LRPGIFKDLHQLA | WLILDDNPITRISQKSFMG |

| | | 251 | | 300 |
|---|---|---|---|---|
| HGPRBMY5v1 | (226) | LNSLFFLSMVNNYLEALP- | KQMCAQMPQLNWVDLEGNRIKYLTNSTFLSC |
| HGPRBMY5 | (215) | LNSLFFLSMVNNYLEALP- | KQMCAQMPQLNWVDLEGNRIKYLTNSTFLSC |
| HGPRBMY5sv1 | (191) | LNSLFFLSMVNNYLEALP- | KQMCAQMPQLNWVDLEGNRIKYLTNSTFLSC |
| LGR5_HUMAN | (233) | LHSLETLDLNYNNLDEFP- | --TAIRTLSNLKELGFHSNNIRSIPEKAFVGN |
| LGR5_MOUSE | (233) | LHSLETLDLNYNNLDEFP- | --TAIKTLSNLKELGFHSNNIRSIPERAFVGN |
| LGR7_HUMAN | (221) | LNSLTLLVLMNNVLTRLPDKP | LCQHMPRLHWIDLEGNHHNLRNLTFISC |
| LGR8_HUMAN | (232) | LNSLFFLSMVNNYLEALP- | KQMCAQMPQLNWVDLEGNRIKYLTNSTFLSC |
| LGR8_MOUSE | (215) | LNSLFFLPMVGNRLEALP- | ETLCAQMPQLNWVDIANNGIKYITNSTFLIC |

FIG. 2D

```
              301                                                 350
HGPRBMY5v1  (275) DSLTVLFLPRNQIGFVPEKTFSSLKNLGELDLS----------------
HGPRBMY5    (264) DSLTVLFLPRNQIGFVPEKTFSSLKNLGELDLS----------------
HGPRBMY5sv1 (240) DSLTVLFLPRNQIGFVPEKTFSSLKNLGELDLS----------------
LGR5_HUMAN  (281) PSLITTHFYDNPIQFVGRSAFQHLPELRTLTLNGASQITEFPDLTGTANL
LGR5_MOUSE  (281) PSLITIHFYDNPIQFVGVSAFQHLPELRTLTLNGASHITEFPHLTGTATL
LGR7_HUMAN  (271) SNLTVLVMRKNKINHLNENTFAPLQKLDELDLG----------------
LGR8_HUMAN  (281) DSLTVLFLPRNQIGFVPEKTFSSLKNLGELDLS----------------
LGR8_MOUSE  (264) DSLTVLFLPRNQIGFVPEKTFSSLKNLGELDLS----------------

351                                                 400
HGPRBMY5v1  (308) --------------------------------------------------
HGPRBMY5    (297) --------------------------------------------------
HGPRBMY5sv1 (273) --------------------------------------------------
LGR5_HUMAN  (331) ESLTLTGAQISSLPQTVCNQLPNLQVLDLSYNLLEDLPSFSVCQKLQKID
LGR5_MOUSE  (331) ESLTLTGAKISSLPQAVCDQLPNLQVLDLSYNLLEDLPSLSGCQKLQKID
LGR7_HUMAN  (304) --------------------------------------------------
LGR8_HUMAN  (314) --------------------------------------------------
LGR8_MOUSE  (297) --------------------------------------------------
```

FIG. 2E

```
                    401                                                         450
HGPRBMY5v1  (308)   --SNTITELSPHLFKDLKLLQKLNLSSNPLMYLHKNQFESLKQLQSLDLE
HGPRBMY5    (297)   --SNTITELSPHLFKDLKLLQKLNLSSNPLMYLHKNQFESLKQLQSLDLE
HGPRBMY5sv1 (273)   --SNTITELSPHLFKDLKLLQKLNLSSNPLMYLHKNQFESLKQLQSLDLE
LGR5_HUMAN  (381)   LRHNEIYEIKVDTFQQLLSLRSLNLAWNKIAIIHPNAFSTLPSLIKLDLS
LGR5_MOUSE  (381)   LRHNEIYEIKGSTFQQLFNLRSLNLAWNKIAIIHPNAFSTLPSLIKLDLS
HGPRBMY5sv1 (304)   --SNKIENLPPLIFKDLKELSQLNLSYNPIQKIQANQFDYLVKLKSLSLE
LGR7_HUMAN  (314)   --SNTITELSPHLFKDLKLLQKLNLSSNPLMYLHKNQFESLKQLQSLDLE
LGR8_HUMAN  (297)   --SNMIKLPVHLFSDLHLLQKLNLSSNPLLYVHKNQFGSLKQLQSLDLE 451                                                         500
HGPRBMY5v1  (356)   RIEIPNINTRMFQPMKNLSHIYFKNFRYCS--------------------
HGPRBMY5    (345)   RIEIPNINTRMFQPMKNLSHIYFKNFRYCS--------------------
HGPRBMY5sv1 (321)   RIEIPNINTRMFQPMKNLSHIYFKNFRYCS--------------------
LGR5_HUMAN  (431)   SNLLSSFPITGLHGLTHIKLTGNHALQSLISSENFPELKVIEMPYAYQCC
LGR5_MOUSE  (431)   SNLLSSFPVTGLHGLTHLKLTGNRALQSLIPSANFPELKIIEMPSAYQCC
LGR7_HUMAN  (352)   GIEISNIQQRMFRPLMNLSHIYFKKFQYCG--------------------
LGR8_HUMAN  (362)   RIEIPNINTRMFQPMKNLSHIYFKNFRYCS--------------------
LGR8_MOUSE  (345)   RIEIPNISTGMFQPMKNLSHIYLKTFRYCS--------------------
```

FIG. 2F

```
                   501                                                      550
HGPRBMY5v1  (386)  ------------------------------------------------
HGPRBMY5    (375)  ------------------------------------------------
HGPRBMY5sv1 (351)  ------------------------------------------------
LGR5_HUMAN  (481)  AFGVCENAYKISNQWNKGDNSSMDDLHKKDAGMFQAQDERDLEDFLLDFE
LGR5_MOUSE  (481)  AFGGCENVYKISNQWNKDDGNSVDDLHKKDAGLFQVQDERDLEDFLLDFE
LGR7_HUMAN  (382)  ------------------------------------------------
LGR8_HUMAN  (392)  ------------------------------------------------
LGR8_MOUSE  (375)  ------------------------------------------------

551                                                      600
HGPRBMY5v1  (386)  ---YAPHVRICMPLTDGISSFEDLLANNILRIFVWVIAFITCFGNLFVIG
HGPRBMY5    (375)  ---YAPHVRICMPLTDGISSFEDLLANNILRIFVWVIAFITCFGNLFVIG
HGPRBMY5sv1 (351)  ---YAPHVRICMPLTDGISSFEDLLANNILRIFVWVIAFITCFGNLFVIG
LGR5_HUMAN  (531)  EDLKALHSVQCSPSPGPFKPCEHLIDGWLIRIGVWTIAVLTCNAIVTS
LGR5_MOUSE  (531)  EDLNALHSVQCSPSPGPFKPCEHLFGSWLIRIGVWTIAVLTLSCNAIVAL
LGR7_HUMAN  (382)  ---YAPHVRSCKPNTDGISSENLLASIQRVFVWVSAVTCFGNIFVIC
LGR8_HUMAN  (392)  ---YAPHVRICMPLTDGISSFEDLLANNILRIFVWVIAFITCFGNLFVIG
LGR8_MOUSE  (375)  ---YVPHVRICMPSTDGISSSEDLLANGILRVSVWVIAFITCVGNFLVIA
```

FIG. 2G

|  | | 601 | | 650 |
|---|---|---|---|---|
| HGPRBMY5v1 | (433) | MRSFIKAENTTHAMSIKILCCADCLMGVYLFFFVGIFDIKYRGQYQKYALL |
| HGPRBMY5 | (422) | MRSFIKAENTTHAMSIKILCCADCLMGVYLFFFVGIFDIKYRGQYQKYALL |
| HGPRBMY5sv1 | (398) | MRSFIKAENTTHAMSIKILCCADCLMGVYLFFFVGIFDIKYRGQYQKYALL |
| LGR5_HUMAN | (581) | TVFRSPLYISPIKLIGVIAAVNMITGVSSAVLAGVDAFTFGSFARHGAW |
| LGR5_MOUSE | (581) | TVFRTPLYISIKLIGVIAVVDILMGVSSAVLAAVDAFTFGREAQHGAW |
| LGR7_HUMAN | (429) | MRPYIRSENKLYAMSIISLCCADCLMGIYLFVIGGFDLKFRGEYNKHAQL |
| LGR8_HUMAN | (439) | MRSFIKAENTTHAMSIKILCCADCLMGVYLFFFVGIFDIKYRGQYQKYALL |
| LGR8_MOUSE | (422) | VRSLIKAENTTHAMSIKILCCADCLMGVYLFSVGVFDIKYRGQYQKYALL |

|  | | 651 | | 700 |
|---|---|---|---|---|
| HGPRBMY5v1 | (483) | WMESVQCRLMGFLAMLSTEVSVLLLTYLTLEKFLVIVFPFSNIRPG-KRQ |
| HGPRBMY5 | (472) | WMESVQCRLMGFLAMLSTEVSVLLLTYLTLEKFLVIVFPFSNIRPG-KRQ |
| HGPRBMY5sv1 | (448) | WMESVQCRLMGFLAMLSTEVSVLLLTYLTLEKFLVIVFPFSNIRPG-KRQ |
| LGR5_HUMAN | (631) | WENGVGCHVIGFLSIFASESSVFLTLAALERGFSVKYSAKFETKAPFSS |
| LGR5_MOUSE | (631) | WEDGIGCQIVGFISIFASESSIFLTLAALERGFSVKCSSKFEVKAPLFS |
| LGR7_HUMAN | (479) | WMESTHCQLVGSLAILSTEVSVLLTFLTLEKFVICIVPFRCVRPG-KCR |
| LGR8_HUMAN | (489) | WMESVQCRLMGFLAMLSTEVSVLLLTYLTLEKFLVIVFPFSNIRPG-KRQ |
| LGR8_MOUSE | (472) | WMESVPCRLLGFLATLSTEVSVLLFLTLEKFLVIVFPFSNIRLG-KRQ |

FIG. 2H

```
                   701                                                            750
HGPRBMY5v1   (532) TSVILICIWMAGFLIAVIPFWNKDYFGNFYGKNGVCFPLYYDQTEDIGSK
HGPRBMY5     (521) TSVILICIWMAGFLIAVIPFWNKDYFGNFYGKNGVCFPLYYDQTEDIGSK
HGPRBMY5sv1  (497) TSVILICIWMAGFLIAVIPFWNKDYFGNFYGKNGVCFPLYYDQTEDIGSK
LGR5_HUMAN   (681) LKVITLCALALTMAAVPLLG---G--SKYGASPICLPFGEPSTMG----
LGR5_MOUSE   (681) LRAIVLLCVLLALTIATIPLLG---G--SKYNASPICLPFGEPSTTG----
LGR7_HUMAN   (528) TITVLILIWITGFIVAFIPLSNKEFFKNYGTNGVCFPLHSEDTESIGAQ
LGR8_HUMAN   (538) TSVILICIWMAGFLIAVIPFWNKDYFGNFYGKNGVCFPLYYDQTEDIGSK
LGR8_MOUSE   (521) TAVALASIWVVGFLIAAVPFTREDYFGNFYGKNGVCFPLHYDQAEDFGSR 751                                                            800
HGPRBMY5v1   (582) GYSLGIFLGVNLLAFLIIVFSYITMFCSIQKTALQTTEVRNCFGREVAVA
HGPRBMY5     (571) GYSLGIFLGVNLLAFLIIVFSYITMFCSIQKTALQTTEVRNCFGREVAVA
HGPRBMY5sv1  (547) GYSLGIFLGVNLLAFLIIVFSYITMFCSIQKTALQTTEVRNCFGREVAVA
LGR5_HUMAN   (725) --YMVALLLNSLCFLMMTIAYTKLYCNLDKGDIEN------I--WDCSMV
LGR5_MOUSE   (725) --YMVALVLINSLCFLIMTIAYTKLYCSLEKGEIEN------L--WDCSMV
LGR7_HUMAN   (578) IYSVAIFLGINLAAFIIIVFSYIGSMFYSVHQSAITATEIRNQVKKEMILA
LGR8_HUMAN   (588) GYSLGIFLGVNLLAFLIIVFSYITMFCSIQKTALQTTEVRNCFGREVAVA
LGR8_MOUSE   (571) GYSLGIFLGVNLLAFLVIISYVTMFCSIHKTALQTAEVRSHIGKEVAVA
```

FIG. 2I

```
              801                                                               850
HGPRBMY5v1   (632)  NRFFFIVFSDAICWIPVFVVKILSLFRVEIPD-TMTSWIVIFFLPVNSAL
HGPRBMY5    (621)  NRFFFIVFSDAICWIPVFVVKILSLFRVEIPD-TMTSWIVIFFLPVNSAL
HGPRBMY5sv1 (597)  NRFFFIVFSDAICWIPVFVVKILSLFRVEIPD-TMTSWIVIFFLPVNSAL
LGR5_HUMAN  (766)  KHIALLFTNCILNCPVAFLSFSSIINLTFISPEVIKFILLVVPLPACL
LGR5_MOUSE  (766)  KHIALLFANCILYCPVAFLSFSSILNLTFISPDVIKFILLIVPLPSCL
LGR7_HUMAN  (628)  KRFFFIVFTDALCWIPTFVVKFLSLLQVEIPG-TITSWIVIFLPINSAL
LGR8_HUMAN  (638)  NRFFFIVFSDAICWIPVFVVKILSLFRVEIPD-TMTSWIVIFFLPVNSAL
LGR8_MOUSE  (621)  NRFFFIVFSDAICWIPVFVVKILSLFRVEIPG-TITSWIVVFFLPVNSAL 851                                                               900
HGPRBMY5v1   (681)  NPILYTLTNFFKDKLKQLLHKHQ-RKSIFKIKKKSLSTSIVWIEDSSSL
HGPRBMY5    (670)  NPILYTLTNFFKDKLKQLLHKHQ-RKSIFKIKKKSLSTSIVWIEDSSSL
HGPRBMY5sv1 (646)  NPILYTLTNFFKDKLKQLLHKHQ-RKSIFKIKKKSLSTSIVWIEDSSSL
LGR5_HUMAN  (816)  NPILYIFLFNPHFKEDLVSLRKQTYVWTRSKHPSLMSINSDDVEKQSCDST
LGR5_MOUSE  (816)  NPILYIVFNPHFKEDMGSIGKHTRFWMRSKHASLLSINSDDVEKRSCEST
LGR7_HUMAN  (677)  NPILYTLTTRPFKEMIHRFWYNYRQRKSMDSKGQKTYAPSFIWVEMWP--
LGR8_HUMAN  (687)  NPILYTLTNFFKDKLKQLLHKHQ-RKSIFKIKKKSLSTSIVWIEDSSSL
LGR8_MOUSE  (670)  NPILYTLTTSFFKDKLKQLLHKHR-RKPIFKVKKKSLSASIVWTDESS-L
```

FIG. 2J

```
                   901                                              942
HGPRBMY5v1   (730) KLGVLNKITLGDSIMKPVS------------------------------
HGPRBMY5     (719) KLGVLNKITLGDSIMKPVS------------------------------
HGPRBMY5sv1  (695) KLGVLNKITLGDSIMKPVS------------------------------
LGR5_HUMAN   (866) QALVTFTSSSITYDEPSSVPSPAYPVTESCHLSSVAFVPCL
LGR5_MOUSE   (866) QALVSFTHASIAYDLPSTSGASPAYPMTESCHLSSVAFVPCL
LGR7_HUMAN   (725) LQEMPPELMKPDLETYPCEMSLISQSTRLNSYS---------
LGR8_HUMAN   (736) KLGVLNKITLGDSIMKPVS------------------------------
LGR8_MOUSE   (718) KLGVLSKIALGDSIMKPVSP-----------------------------
```

FIG. 7

HGPRBMY5v1

| Protein | SWISS-PROT Accession/ International Publication Number | Identities | Similarities |
|---|---|---|---|
| Human leucine-rich repeat-containing G protein-coupled receptor 5 protein | O75473 | 18.7% | 30.3% |
| Mouse leucine-rich repeat-containing G protein-coupled receptor 5 protein | Q9Z1P4 | 18.4% | 30.2% |
| Human relaxin receptor 1 protein | Q9HBX9 | 51.0% | 63.7% |
| Human relaxin receptor 2 protein | Q8WXD0 | 95.9% | 96.0% |
| Mouse relaxin receptor 2 protein | Q91ZZ5 | 80.0% | 85.2% |
| Human HGPRBMY5 protein | WO 02/26824 | 96.7% | 96.8% |
| Human HGPRBMY5sv1 protein | WO 02/26824 | 93.4% | 93.6% |

FIG. 8A

```
  1  atgcagaaaaccaagcaagatgaggactatgaaagagccattggatttagtgtcaaaatg   60
  1  M  Q  K  T  K  Q  D  E  D  Y  E  R  A  I  G  F  S  V  K  M    20

61  gatgacagtgattctgattttgcactgactcaaggtagcatgatcactccttcatgccaa  120
 21  D  D  S  D  S  D  F  A  L  T  Q  G  S  M  I  T  P  S  C  Q    40

121  aaaggatattttcctgtgggaatcttaccaagtgcttaccccgacttttcactgtgat    180
 41  K  G  Y  F  P  C  G  N  L  T  K  C  L  P  R  A  F  H  C  D    60

181  ggcaaggatgactgtgggaacggggcggacgaagagaactgtggtgacactagtggatgg  240
 61  G  K  D  D  C  G  N  G  A  D  E  E  N  C  G  D  T  S  G  W    80

241  gcgaccatatttggcacagtgcatggaaatgctaacagcgtggccttaacacaggagtgc  300
 81  A  T  I  F  G  T  V  H  G  N  A  N  S  V  A  L  T  Q  E  C   100

301  tttctaaaacagtatccacaatgctgtgactgcaaagaaactgaattggaatgtgtaaat  360
101  F  L  K  Q  Y  P  Q  C  C  D  C  K  E  T  E  L  E  C  V  N   120

361  ggtgacttaaagtctgtgccgatgatttctaacaatgtgacattactgtctcttaagaaa  420
121  G  D  L  K  S  V  P  M  I  S  N  N  V  T  L  L  S  L  K  K   140

421  aacaaaatccacagtcttccagataaagttttcatcaaatacacaaaacttaaaaagata  480
141  N  K  I  H  S  L  P  D  K  V  F  I  K  Y  T  K  L  K  K  I   160

481  tttcttcagcataattgcattagacacatatccaggaaagcattttttggattatgtaat  540
161  F  L  Q  H  N  C  I  R  H  I  S  R  K  A  F  F  G  L  C  N   180

541  ctgcaaatattaattctagatgacaatccaataaccagaatttcacagcgcttgtttacg  600
181  L  Q  I  L  I  L  D  D  N  P  I  T  R  I  S  Q  R  L  F  T   200

601  ggattaaaattccttgtttttcctgtctatggttaataactacttagaagctcttcccaag  660
201  G  L  N  S  L  F  F  L  S  M  V  N  N  Y  L  E  A  L  P  K   220

661  cagatgtgtgcccaaatgcctcaactcaactgggtggatttggaaggcaatagaataaag  720
221  Q  M  C  A  Q  M  P  Q  L  N  W  V  D  L  E  G  N  R  I  K   240

721  tatctcacaaaattctacgtttctgtcgtgcgattcgctcacagtgctgtttctgcctaga  780
241  Y  L  T  N  S  T  F  L  S  C  D  S  L  T  V  L  F  L  P  R   260

781  aatcaaattggttttgttccagagaagacatttcttcattaaaaaatttaggagaactg  840
261  N  Q  I  G  F  V  P  E  K  T  F  S  S  L  K  N  L  G  E  L   280

841  gatctgtctagcaatacgataacggagctatcacctcaccttttaaagacttgaagctt  900
281  D  L  S  S  N  T  I  T  E  L  S  P  H  L  F  K  D  L  K  L   300

901  ctacaaaagctgaacctgtcatccaatcctcttatgtatcttcacaagaaccagtttgaa  960
301  L  Q  K  L  N  L  S  S  N  P  L  M  Y  L  H  K  N  Q  F  E   320
```

FIG. 8B

```
 961  agtcttaaacaacttcagtctctagacctggaaaggatagagattccaaatataaacaca  1020
 321  S   L   K   Q   L   Q   S   L   D   L   E   R   I   E   I   P   N   I   N   T    340

1021  cgaatgtttcaacccatgaagaatctttctcacatttatttcaaaaactttcgatactgc  1080
 341  R   M   F   Q   P   M   K   N   L   S   H   I   Y   F   K   N   F   R   Y   C    360

1081  tcctatgctccccatgtccgaatatgtatgcccttgacggacggcatttcttcatttgag  1140
 361  S   Y   A   P   H   V   R   I   C   M   P   L   T   D   G   I   S   S   F   E    380

1141  gacctcttggctaacaatatcctcagaatatttgtctggttatagctttcattacctgc   1200
 381  D   L   L   A   N   N   I   L   R   I   F   V   W   V   I   A   F   I   T   C    400

1201  tttggaaatcttttgtcattggcatgagatctttcattaaagctgaaaatacaactcac   1260
 401  F   G   N   L   F   V   I   G   M   R   S   F   I   K   A   E   N   T   T   H    420

1261  gctatgtccatcaaaatcctttgttgtgctgattgcctgatgggtgtttacttgttcttt  1320
 421  A   M   S   I   K   I   L   C   C   A   D   C   L   M   G   V   Y   L   F   F    440

1321  gttggcattttcgatataaaataccgagggcagtatcagaagtatgccttgctgtggatg  1380
 441  V   G   I   F   D   I   K   Y   R   G   Q   Y   Q   K   Y   A   L   L   W   M    460

1381  gagagcgtgcagtgccgcctcatggggttcctggccatgctgtccaccgaagtctctgtt  1440
 461  E   S   V   Q   C   R   L   M   G   F   L   A   M   L   S   T   E   V   S   V    480

1441  ctgctactgacctacttgactttggagaagttcctggtcattgtcttccccttcagtaac  1500
 481  L   L   L   T   Y   L   T   L   E   K   F   L   V   I   V   F   P   F   S   N    500

1501  attcgacctggaaaaacggcagacctcagtcatcctcatttgcatctggatggcgggattt  1560
 501  I   R   P   G   K   R   Q   T   S   V   I   L   I   C   I   W   M   A   G   F    520

1561  ttaatagctgtaattccattttggaataaggattattttggaaacttttatgggaaaaat  1620
 521  L   I   A   V   I   P   F   W   N   K   D   Y   F   G   N   F   Y   G   K   N    540

1621  ggagtatgtttcccacttttattatgaccaaacagaagatattggaagcaaagggtattct  1680
 541  G   V   C   F   P   L   Y   Y   D   Q   T   E   D   I   G   S   K   G   Y   S    560

1681  cttggaattttcctaggtgtgaacttgctggcttttctcatcattgtgttttcctatatt  1740
 561  L   G   I   F   L   G   V   N   L   L   A   F   L   I   I   V   F   S   Y   I    580

1741  actatgttctgttccattcaaaaaaccgccttgcagaccacagaagtaaggaattgtttt  1800
 581  T   M   F   C   S   I   Q   K   T   A   L   Q   T   T   E   V   R   N   C   F    600

1801  ggaagagaggtggctgttgcaaatcgtttcttttttatagtgttctctgatgccatctgc  1860
 601  G   R   E   V   A   V   A   N   R   F   F   F   I   V   F   S   D   A   I   C    620
```

FIG. 8C

```
1861  tggattcctgtatttgtagttaaaatcctttccctcttccgggtggaaataccagacaca  1920
621   W   I   P   V   F   V   V   K   I   L   S   L   F   R   V   E   I   P   D   T   640

1921  atgacttcctggatagtgattttttccttccagttaacagtgctttgaatccaatcctc  1980
641   M   T   S   W   I   V   I   F   F   L   P   V   N   S   A   L   N   P   I   L   660

1981  tatactctcacaaccaactttttaaggacaagttgaaacagctgctgcacaaacatcag  2040
661   Y   T   L   T   T   N   F   F   K   D   K   L   K   Q   L   L   H   K   H   Q   680

2041  aggaaatcaattttcaaaattaaaaaaaaaagtttatctacatccattgtgtggatagag  2100
681   R   K   S   I   F   K   I   K   K   K   S   L   S   T   S   I   V   W   I   E   700

2101  gactcctcttccctgaaacttggggttttgaacaaaataacacttggagacagtataatg  2160
701   D   S   S   S   L   K   L   G   V   L   N   K   I   T   L   G   D   S   I   M   720

2161  aaaccagtttcctag   2175
721   K   P   V   S           724
```

FIG. 9A

```
                 1                                                      50
HGPRBMY5v1   (1) MQKTKQDEDYERAIGFSVKMDDSDSDFALTQGSMITPSCQKGYFPCGNLT
HGPRBMY5v2   (1) MQKTKQDEDYERAIGFSVKMDDSDSDFALTQGSMITPSCQKGYFPCGNLT 51                                                    100
HGPRBMY5v1  (51) KCLPRAFHCDGKDDCGNGADEENCGDTSGWATIFGTVHGNANSVALTQEC
HGPRBMY5v2  (51) KCLPRAFHCDGKDDCGNGADEENCGDTSGWATIFGTVHGNANSVALTQEC 101                                                   150
HGPRBMY5v1 (101) FLKQYPQCCDCKETELECVNGDLKSVPMISNNVTLLSLKKNKIHSLPDKV
HGPRBMY5v2 (101) FLKQYPQCCDCKETELECVNGDLKSVPMISNNVTLLSLKKNKIHSLPDKV 151                                                   200
HGPRBMY5v1 (151) FIKYTKLKKIFLQHNCIRHISRKAFFGLCNLQILYLNHNCITTLRPGIFK
HGPRBMY5v2 (151) FIKYTKLKKIFLQHNCIRHISRKAFFGLCNLQIL----------------

201                                                   250
HGPRBMY5v1 (201) DLHQLTWLILDDNPITRISQRLFTGLNSLFFLSMVNNYLEALPKQMCAQM
HGPRBMY5v2 (185) -------ILDDNPITRISQRLFTGLNSLFFLSMVNNYLEALPKQMCAQM
```

FIG. 9B

```
HGPRBMY5v1 (251) PQLNWVDLEGNRIKYLTNSTFLSCDSLTVLFLPRNQIGFVPEKTFSSLKN 300
HGPRBMY5v2 (227) PQLNWVDLEGNRIKYLTNSTFLSCDSLTVLFLPRNQIGFVPEKTFSSLKN

HGPRBMY5v1 (301) LGELDLSSNTITELSPHLFKDLKLLQKLNLSSNPLMYLHKNQFESLKQLQ 350
HGPRBMY5v2 (277) LGELDLSSNTITELSPHLFKDLKLLQKLNLSSNPLMYLHKNQFESLKQLQ

HGPRBMY5v1 (351) SLDLERIEIPNINTRMFQPMKNLSHIYFKNFRYCSYAPHVRICMPLTDGI 400
HGPRBMY5v2 (327) SLDLERIEIPNINTRMFQPMKNLSHIYFKNFRYCSYAPHVRICMPLTDGI

HGPRBMY5v1 (401) SSFEDLLANNILRIFVWVIAFITCFGNLFVIGMRSFIKAENTTHAMSIKI 450
HGPRBMY5v2 (377) SSFEDLLANNILRIFVWVIAFITCFGNLFVIGMRSFIKAENTTHAMSIKI

HGPRBMY5v1 (451) LCCADCLMGVYLFFVGIFDIKYRGQYQKYALLWMESVQCRLMGFLAMLST 500
HGPRBMY5v2 (427) LCCADCLMGVYLFFVGIFDIKYRGQYQKYALLWMESVQCRLMGFLAMLST
```

FIG. 9C

```
                      501                                                  550
HGPRBMY5v1   (501)    EVSVLLLTYLTLEKFLVIVFPFSNIRPGKRQTSVILICIWMAGFLIAVIP
HGPRBMY5v2   (477)    EVSVLLLTYLTLEKFLVIVFPFSNIRPGKRQTSVILICIWMAGFLIAVIP 551                                                  600
HGPRBMY5v1   (551)    FWNKDYFGNFYGKNGVCFPLYYDQTEDIGSKGYSLGIFLGVNLLAFLIIV
HGPRBMY5v2   (527)    FWNKDYFGNFYGKNGVCFPLYYDQTEDIGSKGYSLGIFLGVNLLAFLIIV 601                                                  650
HGPRBMY5v1   (601)    FSYITMFCSIQKTALQTTEVRNCFGREVAVANRFFIVFSDAICWIPVFV
HGPRBMY5v2   (577)    FSYITMFCSIQKTALQTTEVRNCFGREVAVANRFFIVFSDAICWIPVFV 651                                                  700
HGPRBMY5v1   (651)    VKILSLFRVEIPDTMTSWIVIFFLPVNSALNPILYTLTNFFKDKLKQLL
HGPRBMY5v2   (627)    VKILSLFRVEIPDTMTSWIVIFFLPVNSALNPILYTLTNFFKDKLKQLL 701                                           748
HGPRBMY5v1   (701)    HKHQRKSIFKIKKKSLSTSIVWIEDSSSLKLGVLNKITLGDSIMKPVS
HGPRBMY5v2   (677)    HKHQRKSIFKIKKKSLSTSIVWIEDSSSLKLGVLNKITLGDSIMKPVS
```

HUMAN RELAXIN RECEPTOR HGPRBMY5V1

This application is a divisional application of non-provisional application U.S. Ser. No. 10/994,987, filed Nov. 22, 2004, now U.S. Pat. No. 7,189,539 which claims benefit to provisional application U.S. Ser. No. 60/525,021 filed Nov. 25, 2003; under 35 U.S.C. 119(e). The entire teachings of the referenced application are incorporated herein by reference.

FIELD OF THE INVENTION

The present invention provides novel polynucleotides encoding HGPRBMY5v1 and HGPRBMY5v2 polypeptides, fragments and homologues thereof. Also provided are vectors, host cells, antibodies, and recombinant and synthetic methods for producing said polypeptides. The invention further relates to diagnostic and therapeutic methods for applying these novel HGPRBMY5v1 and HGPRBMY5v2 polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Regulation of cell proliferation, differentiation, and migration is important for the formation and function of tissues. Regulatory proteins such as growth factors control these cellular processes and act as mediators in cell-cell signaling pathways. Growth factors are secreted proteins that bind to specific cell surface receptors on target cells. The bound receptors trigger intracellular signal transduction pathways which activate various downstream effectors that regulate polynucleotide expression, cell division, cell differentiation, cell motility, and other cellular processes. Some of the receptors involved in signal transduction by growth factors belong to the large superfamily of G-protein coupled receptors (GPCRs) which represent one of the largest receptor superfamilies known.

GPCRs are biologically important as their malfunction has been implicated in contributing to the onset of many diseases, which include, but are not limited to, Alzheimer's, Parkinson, diabetes, dwarfism, color blindness, retinal pigmentosa and asthma. Also, GPCRs have also been implicated in depression, schizophrenia, sleeplessness, hypertension, anxiety, stress, renal failure and in several cardiovascular, metabolic, neuro, oncology and immune disorders (F Horn, G Vriend, J. Mol. Med. 76: 464-468, 1998.). They have also been shown to play a role in HIV infection (Y Feng, C C Broder, P E Kennedy, E A Berger, Science 272:872-877, 1996).

GPCRs are integral membrane proteins characterized by the presence of seven hydrophobic transmembrane domains which together form a bundle of antiparallel alpha (a) helices. The 7 transmembrane regions are designated as TM1, TM2, TM3, TM4, TM5, TM6, and TM7. These proteins range in size from under 400 to over 1000 amino acids (Strosberg, A. D. (1991) Eur. J. Biochem. 196: 110; Coughlin, S. R. (1994) Curr. Opin. Cell Biol. 6: 191-197). The amino-terminus of a GPCR is extracellular, is of variable length, and is often glycosylated. The carboxy-terminus is cytoplasmic and generally phosphorylated. Extracellular loops of GPCRs alternate with intracellular loops and link the transmembrane domains. Cysteine disulfide bridges linking the second and third extracellular loops may interact with agonists and antagonists. The most conserved domains of GPCRs are the transmembrane domains and the first two cytoplasmic loops. The transmembrane domains account for structural and functional features of the receptor. In most G-protein coupled receptors, the bundle of a helices forms a ligand-binding pocket formed by several G-protein coupled receptor transmembrane domains.

The TM3 transmembrane domain has been implicated in signal transduction in a number of G-protein coupled receptors. Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b adrenoreceptor, phosphorylation by protein kinase A and/or specific receptor kinases mediates receptor desensitization. In fact, phosphorylation of an activated G-protein coupled receptor is a common mechanism for desensitizing signaling to a G-protein.

The extracellular N-terminal segment, or one or more of the three hydrophilic extracellular loops, have been postulated to face inward and form polar ligand binding sites which may participate in ligand binding. Ligand binding activates the receptor by inducing a conformational change in intracellular portions of the receptor. In turn, the large, third intracellular loop of the activated receptor interacts with an intracellular heterotrimeric guanine nucleotide binding (G) protein complex which mediates further intracellular signaling activities, including the activation of second messengers such as cyclic AMP (cAMP), phospholipase C, inositol triphosphate, or ion channel proteins. TM3 has been implicated in several G-protein coupled receptors as having a ligand binding site, such as the TM3 aspartate residue. TM5 serines, a TM6 asparagine and TM6 or TM7 phenylalanines or tyrosines have also been implicated in ligand binding (See, e.g., Watson, S. and S. Arkinstall (1994) The G-protein Linked Receptor Facts Book, Academic Press, San Diego Calif., pp. 2-6; Bolander, F. F. (1994) Molecular Endocrinology, Academic Press, San Diego Calif., pp. 162-176; Baldwin, J. M. (1994) Curr. Opin. Cell Biol. 6: 180-190; F Horn, R Bywater, G Krause, W Kuipers, L Oliveira, ACM Paiva, C Sander, G Vriend, Receptors and Channels, 5:305-314, 1998).

Recently, the function of many GPCRs has been shown to be enhanced upon dimerization and/or oligomerization of the activated receptor. In addition, sequestration of the activated GPCR appears to be altered upon the formation of multimeric complexes (AbdAlla, S., et al., Nature, 407:94-98 (2000)).

Structural biology has provided significant insight into the function of the various conserved residues found amongst numerous GPCRs. For example, the tripeptide Asp(Glu)-Arg-Tyr motif is important in maintaining the inactive confirmation of G-protein coupled receptors. The residues within this motif participate in the formation of several hydrogen bonds with surrounding amino acid residues that are important for maintaining the inactive state (Kim, J. M., et al., Proc. Natl. Acad. Sci. U.S.A., 94:14273-14278 (1997)). Another example relates to the conservation of two Leu (Leu76 and Leu79) residues found within helix II and two Leu residues (Leu 128 and Leu131) found within helix III of GPCRs. Mutation of the Leu128 results in a constitutively active receptor—emphasizing the importance of this residue in maintaining the ground state (Tao, Y. X., et al., Mol. Endocrinol., 14:1272-1282 (2000); and Lu. Z. L., and Hulme, E. C., J. Biol. Chem., 274:7309-7315 (1999). Additional information relative to the functional relevance of several conserved residues within GPCRs may be found by reference to Okada et al in Trends Biochem. Sci., 25:318-324 (2001).

GPCRs include receptors for sensory signal mediators (e.g., light and olfactory stimulatory molecules); adenosine, bombesin, bradykinin, endothelin, y-aminobutyric acid (GABA), hepatocyte growth factor, melanocortins, neuropeptide Y, opioid peptides, opsins, somatostatin, tachykinins, vasoactive intestinal polypeptide family, and vasopressin; biogenic amines (e.g., dopamine, epinephrine and norepinephrine, histamine, glutamate (metabotropic effect), acetylcholine (muscarinic effect), and serotonin); chemokines; lipid mediators of inflammation (e.g., prostaglandins and prostanoids, platelet activating factor, and leukotrienes); and peptide hormones (e.g., calcitonin, C5a anaphylatoxin, follicle stimulating hormone (FSH), gonadotropic-releasing hormone (GnRH), neurokinin, and thyrotropin releasing hormone (TRH), and oxytocin). GPCRs which act as receptors for stimuli that have yet to be identified are known as orphan receptors.

GPCRs are implicated in inflammation and the immune response, and include the EGF module containing, mucin-like hormone receptor (Emrl) and CD97p receptor proteins. These receptors contain between three and seven potential calcium-binding EGF-like motifs (Baud, V. et al. (1995) Genomics 26: 334-344; Gray, J. X. et al. (1996) J. Immunol. 157: 5438-5447). These GPCRs are members of the recently characterized EGF-TM7 receptors family. In addition, post-translational modification of aspartic acid or asparagine to form erythro-p-hydroxyaspartic acid or erythro-p-hydroxyasparagine has been identified in a number of proteins with domains homologous to EGF. The consensus pattern is located in the N-terminus of the EGF-like domain. Examples of such proteins are blood coagulation factors VII, IX, and X; proteins C, S, and Z; the LDL receptor; and thrombomodulin.

GPCR mutations, which may cause loss of function or constitutive activation, have been associated with numerous human diseases (Coughlin, supra). For instance, retinitis pigmentosa may arise from mutations in the rhodopsin polynucleotide. Rhodopsin is the retinal photoreceptor which is located within the discs of the eye rod cell. Parma, J. et al. (1993, Nature 365: 649-651) reported that somatic activating mutations in the thyrotropin receptor cause hyper-functioning thyroid adenomas and suggested that certain GPCRs susceptible to constitutive activation may behave as protooncopolynucleotides.

One large subfamily of GPCRs are the olfactory receptors. These receptors share the seven hydrophobic transmembrane domains of other GPCRs and function by registering G protein-mediated transduction of odorant signals. Numerous distinct olfactory receptors are required to distinguish different odors. Each olfactory sensory neuron expresses only one type of olfactory receptor, and distinct spatial zones of neurons expressing distinct receptors are found in nasal pasages. One olfactory receptor, the RAlc receptor which was isolated from a rat brain library, has been shown to be limited in expression to very distinct regions of the brain and a defined zone of the olfactory epithelium (Raming, K. et al., (1998) Receptors Channels 6: 141-151). In another example, three rat polynucleotides encoding olfactory-like receptors having typical GPCR characteristics showed expression patterns exclusively in taste, olfactory, and male reproductive tissue (Thomas, M. B. et al. (1996) Polynucleotide 178: 1-5).

Although olfactory receptors are typically associated with olfactory function and tend to localize to the olfactory bulb, there is increasing evidence that olfactory receptors and olfactory-like receptors may play more diverse roles in varying tissues (Yuan, T, T., Toy, P., McClary, J. A., Lin, R, J., Miyamoto, N, G., Kretschmer, P, J. Polynucleotide., 278(1-2):41-51, (2001); Blache, P., Gros, L., Salazar, G., Bataille, D, Biochem, Biophys, Res, Commun., 242(3):669-72, (1998); and Matsuoka, I., Mori, T., Aoki, J., Sato, T., Kurihara, K, Biochem, Biophys, Res, Commun., 194(1): 504-11, (1993)).

Relaxin is a hormone that belongs to the insulin family of structurally related molecules and was first identified as a factor in pregnany guinea pigs which was capable of lengthening the interpubic ligament of non-pregnant animals. Relaxin has a molecule weight of 6 Kd and consists of two chains, termed A and B which are covalently linked by two interchain disulfide bonds. Relaxin is important for the growth and remodeling of reproductive and other tissues during pregnancy (O. D. Sherwood, in The Physiology of Reproduction, E. Knobil, J. D. Neill, Eds. (Raven, New York, 1994), vol. 1, pp. 861-1009.). Specifically, relaxin has diverse actions in the reproductive tract and other tissues during pregnancy, which include the promotion of growth and dilation of the cervix; growth and quiescence of the uterus; growth and development of the mammary gland and nipple; and regulation of cardiovascular function.

Relaxin has also been shown to play other roles as well, including its role as a vasodilator (Bani and Bigazzi, Acta Anat 119:149-154 (1984); and St. Louis, J. and Massicotte, G., Life Sci., 37:1351-1357 (1985)); and its role in the release of vasopressin from the pituitary gland (Dayanithi, G et al., Nature 325:813-816 (1987)). Additional information specific to relaxin may be found by reference to Dshietzig et al, Cell. Mol. Life Sci. 60:688-700 (2003); which is hereby incorporated by reference herein in its entirety).

Relaxins role in elongating uterine ligaments can be understood at the molecule level based upon the elucidation that it positively regulates matric metalloproteinase expression in uterine segment fibroblasts (Palejwala, S., et al Endo., 142:3405-3413 (2001)). Additionally, relaxins role in vasodilation may be also be understood based upon its upregulation of inducible nitric oxide expression in endothelial cells (Failli, P., et al FASEB J., 16:252-254 (2001)).

Although binding sites for relaxin have been found in reproductive tissues (G. Min and O. D. Sherwood, Biol. Reprod. 55, 1243 (1996)), brain (P. L. Osheroff and H. S. Phillips, Proc. Natl. Acad. Sci. U.S.A. 88, 6413 (1991)), and heart (P. L. Osheroff, M. J. Cronin, J. A. Lofgren, Proc. Natl. Acad. Sci. U.S.A. 89, 2384 (1992)), the nature of the relaxin receptor had largely been undetermined.

Prorelaxin, the precursor form of relaxin, has a domain arrangement similar to that of insulin and insulin-like growth factor (IGF) precursors, and several relaxin and insulin-related genes have been identified, including those encoding INSL3 (or Leydig cell relaxin), INSL4, INSL5, INSL6, and relaxin 3 (S. Zimmermann, et al., Mol. Endocrinol. 13, 681 (1999); S. Y. Hsu, Mol. Endocrinol. 13, 2163 (1999); and R. A. Bathgate, et al., J. Biol. Chem. 31, 31 (2001)). The abnormal testis descent phenotype of INSL3-null mice (S. Zimmermann, et al., Mol. Endocrinol. 13, 681 (1999), and S. Nef and L. F. Parada, Nature Genet. 22, 295 (1999)) was similar to that of mice with a disruption of a G protein-coupled receptor (GPCR) encoded by the mouse GREAT gene (P. A. Overbeek, et al., Genesis 30, 26 (2001)); which had suggested that relaxin-related proteins may be ligands for GPCRs. Indeed, relaxin stimulates cAMP production in endometrial, anterior pituitary, and other cells (O. D. Sherwood, in The Physiology of Reproduction, E. Knobil, J. D. Neill, Eds. (Raven, New York, 1994), vol. 1, pp. 861-1009), an event mediated by GPCRs.

Recently, two G-protein coupled receptors, referred to as LGR7 and LGR8, were determined to represent relaxin receptors (S. Y. Hsu et al., Science, 295:671-674 (2002)). The role of both GPCRs as relaxin receptors was confirmed based upon experiments demonstrating treatment of transfected cells expressing either LGR7 or LGR8 with porcine relaxin resulted in a dose-dependent increase in cAMP production, with median effective concentrations of 1.5 and 5.0 nM, respectively. The specificity of relaxin to these receptors was tested by subjecting the same transfected cells with peptides that are structurally similar to relaxin, (insulin, IGF-I, or IGF-II) or with an unrelated peptide (glucagon). In all cases, subjecting the cells to these structurally related peptides was ineffective. These findings indicate that relaxin is a cognate ligand for these two orphan GPCRs and that it activates adenylate cyclases through Gs proteins.

Treatment of LGR7 transfected cells with relaxin and the soluble ectodomain (S. Y. Hsu et al., Science, 295:671-674 (2002)) of LGR7 (i.e., a functional LGR7 antagonist) resulted in sequesteration of relaxin and the inhibition of relaxin effects. The same results were obtained by subjecting the transfected cells with relaxin specific antibodies.

Interestingly, subcataneous administration of the LGR7 soluble ectodomain in pregant mice resulted in parturition delay by 27 hours and greatly reduced milk levels in the stomachs of living pups. Furthermore, subcataneous administration of the LGR7 soluble ectodomain in antepartum mice resulted in underdevelopment of nipples, as demonstrated by a 29% decrease in nipple size at 12 hours post parturition. These results were consistent with the nipple development deficiency phenotype observed in relaxin-null knockout mice (L. Zhao, et al., Endocrinology 140, 445 (1999)).

Characterization of the HGPRBMY5v1 and HGPRBMY5v2 polypeptides of the present invention led to the determination that they are involved in the modulation of the p21 G1/S-phase cell cycle check point protein, either directly or indirectly.

Critical transitions through the cell cycle are highly regulated by distinct protein kinase complexes, each composed of a cyclin regulatory and a cyclin-dependent kinase (cdk) catalytic subunit (for review see Draetta, Curr. Opin. Cell Biol. 6, 842-846 (1994)). These proteins regulate the cell's progression through the stages of the cell cycle and are, in turn, regulated by numerous proteins, including p53, p21, p16, and cdc25. Downstream targets of cyclin-cdk complexes include pRb and E2F. The cell cycle often is dysregulated in neoplasia due to alterations either in oncogenes that indirectly affect the cell cycle, or in tumor suppressor genes or oncogenes that directly impact cell cycle regulation, such as pRb, p53, p16, cyclin D1, or mdm-2 (for review see Schafer, Vet Pathol 1998 35, 461-478 (1998)).

P21, also known as CDNK1A (cyclin-dependent kinase inhibitor 1A), or CIP1 inhibits mainly the activity of cyclin CDK2 or CDK4 complexes. Therefore, p21 primarily blocks cell cycle progression at the G1 stage of the cell cycle. The expression of p21 is tightly controlled by the tumor suppressor protein p53, through which this protein mediates the cell cycle G1 phase arrest in response to a variety of stress stimuli. In addition, p21 protein interacts with the DNA polymerase accessory factor PCNA (proliferating cell nuclear antigen), and plays a regulatory role in S phase DNA replication and DNA damage repair.

After DNA damage, many cells appear to enter a sustained arrest in the G2 phase of the cell cycle. Bunz et al. (Science 282, 1497-1501 (1998)) demonstrated that this arrest could be sustained only when p53 was present in the cell and capable of transcriptionally activating the cyclin-dependent kinase inhibitor p21. After disruption of either the p53 or the p21 gene, gamma-radiated cells progressed into mitosis and exhibited a G2 DNA content only because of a failure of cytokinesis. Thus, p53 and p21 appear to be essential for maintaining the G2 cell cycle checkpoint in human cells.

Due to the connection between the transcriptional activity of p53 and p21 RNA expression, the readout of p21 RNA can be used to determine the effect of drugs or other insults (radiation, antisense for a specific gene, dominant negative expression) on a given cell system which contains wild type p53. Specifically, if a gene is removed using antisense products and this has an effect on the p53 activity, p21 will be upregulated and can serve therefore as an indirect marker for an influence on the cell cycle regulatory pathways and induction of cell cycle arrest.

In addition to cancer regulation of cell cycle activity has a role in numerous other systems. For example, hematopoietic stem cells are relative quiescent, while after receiving the required stimulus they undergo dramatic proliferation and inexorably move toward terminal differentiation. This is partly regulated by the presence of p21. Using p21 knockout mice Cheng et al. (Science 287, 1804-1808 (2000)) demonstrated its critical biologic importance in protecting the stem cell compartment. In the absence of p21, hematopoietic stem cell proliferation and absolute number were increased under normal homeostatic conditions. Exposing the animals to cell cycle-specific myelotoxic injury resulted in premature death due to hematopoietic cell depletion. Further, self-renewal of primitive cells was impaired in serially transplanted bone marrow from p21 –/– mice, leading to hematopoietic failure. Therefore it was concluded that p21 is the molecular switch governing the entry of stem cells into the cell cycle, and in its absence, increased cell cycling leads to stem cell exhaustion. Under conditions of stress, restricted cell cycling is crucial to prevent premature stem cell depletion and hematopoietic death. Therefore, genes involved in the downregulation of p21 expression could have a stimulatory effect and therefore be useful for the exploration of stem cell technologies.

Using the above examples, it is clear the availability of a novel cloned G-protein coupled receptor provides an opportunity for adjunct or replacement therapy, and are useful for the identification of G-protein coupled receptor agonists, or stimulators (which might stimulate and/or bias GPCR action), as well as, in the identification of G-protein coupled receptor inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of HGPRBMY5v1 and HGPRBMY5v2 polypeptides or peptides using recombinant techniques. Synthetic methods for producing the polypeptides and polynucleotides of the present invention are provided. Also provided are diagnostic methods for detecting diseases, disorders, and/or conditions related to the HGPRBMY5v1 and HGPRBMY5v2 polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the HGPRBMY5v1 protein having the amino acid sequence shown in FIGS. 1A-C (SEQ ID NO:2), respectively, or the amino acid sequence encoded by the cDNA clone, HGPRBMY5v1 (also referred to as HGPRBMY5 variant).

The present invention provides isolated nucleic acid molecules, that comprise, or alternatively consist of, a polynucleotide encoding the HGPRBMY5v2 protein having the amino acid sequence shown in FIGS. 8A-C (SEQ ID NO:82), respectively, or the amino acid sequence encoded by the cDNA clone, HGPRBMY5v2 (also referred to as HGPRBMY5 splice variant).

The present invention also relates to recombinant vectors, which include the isolated nucleic acid molecules of the present invention, and to host cells containing the recombinant vectors, as well as to methods of making such vectors and host cells, in addition to their use in the production of HGPRBMY5v1 and HGPRBMY5v2 polypeptides or peptides using recombinant techniques. Synthetic methods for producing the polypeptides and polynucleotides of the present invention are provided. Also provided are diagnostic methods for detecting diseases, disorders, and/or conditions related to the HGPRBMY5v1 and HGPRBMY5v2 polypeptides and polynucleotides, and therapeutic methods for treating such diseases, disorders, and/or conditions. The invention further relates to screening methods for identifying binding partners of the polypeptides.

The invention further provides an isolated HGPRBMY5v1 polypeptide having an amino acid sequence encoded by a polynucleotide described herein.

The invention further provides an isolated HGPRBMY5v2 polypeptide having an amino acid sequence encoded by a polynucleotide described herein.

The invention further relates to a polynucleotide encoding a polypeptide fragment of SEQ ID NO:2 and/or 82, or a polypeptide fragment encoded by the cDNA sequence included in the deposited clone, which is hybridizable to SEQ ID NO:1 and/or 81.

The invention further relates to a polynucleotide encoding a polypeptide domain of SEQ ID NO:2 and/or 82 or a polypeptide domain encoded by the cDNA sequence included in the deposited clone, which is hybridizable to SEQ ID NO:2 and/or 81.

The invention further relates to a polynucleotide encoding a polypeptide epitope of SEQ ID NO:2 and/or 82 or a polypeptide epitope encoded by the cDNA sequence included in the deposited clone, which is hybridizable to SEQ ID NO:2 and/or 81.

The invention further relates to a polynucleotide encoding a polypeptide of SEQ ID NO:2 and/or 82 or the cDNA sequence included in the deposited clone, which is hybridizable to SEQ ID NO:2 and/or 81, having biological activity.

The invention further relates to a polynucleotide which is a variant of SEQ ID NO:2 and/or 81.

The invention further relates to a polynucleotide which is an allelic variant of SEQ ID NO:2 and/or 81.

The invention further relates to a polynucleotide which encodes a species homologue of the SEQ ID NO:2 and/or 82.

The invention further relates to a polynucleotide which represents the complimentary sequence (antisense) of SEQ ID NO:2 and/or 81.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2 and/or 82, wherein the polynucleotide fragment comprises a nucleotide sequence encoding a G-protein coupled receptor.

The invention further relates to an isolated nucleic acid molecule of SEQ ID NO:2 and/or 81, wherein the polynucleotide fragment comprises a nucleotide sequence encoding the sequence identified as SEQ ID NO:2 and/or 82 or the polypeptide encoded by the cDNA sequence included in the deposited clone, which is hybridizable to SEQ ID NO:2 and/or 81.

The invention further relates to an isolated nucleic acid molecule of of SEQ ID NO:2 and/or 81, wherein the polynucleotide fragment comprises the entire nucleotide sequence of SEQ ID NO:2 and/or 81 or the cDNA sequence included in the deposited clone, which is hybridizable to SEQ ID NO:2 and/or 81.

The invention further relates to an isolated nucleic acid molecule of SEQ ID NO:2 and/or 81, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2 and/or 82 or the encoded sequence included in the deposited clone.

The invention further relates to a polypeptide fragment of SEQ ID NO:2 and/or 82 or the encoded sequence included in the deposited clone, having biological activity.

The invention further relates to a polypeptide domain of SEQ ID NO:2 and/or 82 or the encoded sequence included in the deposited clone.

The invention further relates to a polypeptide epitope of SEQ ID NO:2 and/or 82 or the encoded sequence included in the deposited clone.

The invention further relates to a full length protein of SEQ ID NO:2 and/or 82 or the encoded sequence included in the deposited clone.

The invention further relates to a variant of SEQ ID NO:2 and/or 82.

The invention further relates to an allelic variant of SEQ ID NO:2 and/or 82.

The invention further relates to a species homologue of SEQ ID NO:2 and/or 82.

The invention further relates to the isolated polypeptide of of SEQ ID NO:2 and/or 82, wherein the full length protein comprises sequential amino acid deletions from either the C-terminus or the N-terminus.

The invention further relates to an isolated antibody that binds specifically to the isolated polypeptide of SEQ ID NO:2 and/or 82.

The invention further relates to a method for preventing, treating, or ameliorating a medical condition, comprising administering to a mammalian subject a therapeutically effective amount of the polypeptide of SEQ ID NO:2 and/or 82 or the polynucleotide of SEQ ID NO:2 and/or 81.

The invention further relates to a method of diagnosing a pathological condition or a susceptibility to a pathological condition in a subject comprising the steps of (a) determining the presence or absence of a mutation in the polynucleotide of SEQ ID NO:2 and/or 81; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of of SEQ ID NO:2 and/or 82 in a biological sample; and (b) diagnosing a pathological condition or a susceptibility to a pathological condition based on the presence or amount of expression of the polypeptide.

The invention further relates to a method for identifying a binding partner to the polypeptide of SEQ ID NO:2 and/or 82 comprising the steps of (a) contacting the polypeptide of SEQ ID NO:2 and/or 82 with a binding partner; and (b) determining whether the binding partner effects an activity of the polypeptide.

The invention further relates to a polynucleotide corresponding to the cDNA sequence of SEQ ID NO:2 and/or 81.

The invention further relates to a method of identifying an activity in a biological assay, wherein the method comprises the steps of (a) expressing SEQ ID NO:2 and/or 81 in a cell, (b) isolating the supernatant; (c) detecting an activity in a biological assay; and (d) identifying the protein in the supernatant having the activity.

The invention further relates to a process for making polynucleotide sequences encoding polynucleotide products having altered activity selected from the group consisting of SEQ ID NO:2 and/or 82 activity comprising the steps of (a) shuffling a nucleotide sequence of SEQ ID NO:2 and/or 81, (b) expressing the resulting shuffled nucleotide sequences and, (c) selecting for altered activity selected from the group consisting of SEQ ID NO:2 and/or 82 activity as compared to the activity selected from the group consisting of SEQ ID NO:2 and/or 82 activity of the polynucleotide product of said unmodified nucleotide sequence.

The invention further relates to a shuffled polynucleotide sequence produced by a shuffling process, wherein said shuffled DNA molecule encodes a polynucleotide product having enhanced tolerance to an inhibitor of any one of the activities selected from the group consisting of SEQ ID NO:2 and/or 82 activity.

The invention further relates to a method for preventing, treating, or ameliorating a medical condition with the polypeptide provided as SEQ ID NO:2 and/or 82, in addition to, its encoding nucleic acid, wherein the medical condition is a reproductive disorder.

The invention further relates to a method for preventing, treating, or ameliorating a medical condition with the polypeptide provided as SEQ ID NO:2 and/or 82, in addition to, its encoding nucleic acid, wherein the medical condition is a disorder related to aberrant G-protein coupled signaling.

The invention further relates to a method for preventing, treating, or ameliorating a medical condition with the polypeptide provided as SEQ ID NO:2 and/or 82, in addition to, its encoding nucleic acid, wherein the medical condition is a cardiovascular disorder.

The invention further relates to a method for preventing, treating, or ameliorating a medical condition with the polypeptide provided as SEQ ID NO:2 and/or 82, in addition to, its encoding nucleic acid, wherein the medical condition is a cardiovascular disorder selected from the group consisting of: heart failure, atherosclerosis, and arteriosclerosis, among others disclosed herein.

The invention further relates to a method for preventing, treating, or ameliorating a medical condition with the polypeptide provided as SEQ ID NO:2 and/or 82, in addition to, its encoding nucleic acid, wherein the medical condition is a metabolic disorder.

The invention further relates to a method for preventing, treating, or ameliorating a medical condition with the polypeptide provided as SEQ ID NO:2 and/or 82, in addition to, its encoding nucleic acid, wherein the medical condition is an inflammatory disorder.

The invention further relates to a method for preventing, treating, or ameliorating a medical condition with the polypeptide provided as SEQ ID NO:2 and/or 82, in addition to, its encoding nucleic acid, wherein the medical condition is selected from the group consisting of: pregnancy disorders, embryonic implantation disorders, lactation disorders, mammary development disorders, nipple development disorders, uterine development disorders during pregnancy, uterine contractile disorders, tissue softening in birth canal during pregnancy disorders; collagen solubility disorders during pregnancy, cervical collagen concentration disorders during pregnancy, disorders affecting aberrant MMP-1 (procollagenase) regulation, disorders affecting aberrant MMP-2 (gelatinase) regulation, disorders affecting aberrant MMP-3 (prostromelysin) regulation, disorders affecting aberrant TIMP-1 regulation, interpubic lengthening disorders, disorders affecting decidualization of endometrial stromal cells, prolactin induction disorders, laminin induction disorders, glycoprotein glycodelin induction disorders, cardiovascular disorders, vasodilation disorders, high blood pressure disorders, nitric oxide synthase disorders, prostacyclin disorders, relaxin-mediated VEGF regulation disorders, relaxin-mediated bFGF regulation disorders, relaxin-mediated angiogenesis regulation disorders, relaxin-mediated wound healing regulation disorders, atrial natriuretic peptide regulation disorders, ischemic myocardial in jury, ischemia reperfusion damage, ventricular arrhythmias, disorders associated with myocardial neutrophil invasion, disorders associated with lipid peroxidation, disorders associated with mast cell granule release, disorders associated with cellular calcium overload, coronary artery disease, congestice heart failure, thrombosis, embolism, stroke, disorders associated with the release of platelets from megakaryocytes, fibroids, asthma, disorders related to aberrant interferon-gamma release or function, disorders related to aberrant recruitment or hyper-recruitment of helper T-cells, disorders related to aberrant recruitment or hyper-recruitment of immunglobulin E-antibody B cells, aberrant fluid homeostasis, and/or edema.

The invention further relates to a method of identifying a compound that modulates the biological activity of HGPRBMY5v1 and/or HGPRBMY5v2, comprising the steps of, (a) combining a candidate modulator compound with HGPRBMY5v1 or HGPRBMY5v2 having the sequence set forth in SEQ ID NO:2 or 82; and (b) measuring an effect of the candidate modulator compound on the activity of HGPRBMY5v1 or HGPRBMY5v2, wherein said method optionally includes the addition of relaxin to HGPRBMY5v1 or HGPRBMY5v2 either before or after addition of said candidate modulator compound.

The invention further relates to a method of identifying an antagonist compound that modulates the biological activity of HGPRBMY5v1 and/or HGPRBMY5v2, comprising the steps of, (a) combining a candidate modulator compound with HGPRBMY5v1 or HGPRBMY5v2 having the sequence set forth in SEQ ID NO:2 or 82 subsequent to addition of relaxin; and (b) identifying antagonist compounds by measuring an effect of the candidate modulator compound on the activity of HGPRBMY5v1 or HGPRBMY5v2, wherein said identified antagonist compound decreases relaxin dependent HGPRBMY5v1 or HGPRBMY5v2 activity.

The invention further relates to a method of identifying an agonist compound that modulates the biological activity of HGPRBMY5v1 and/or HGPRBMY5v2, comprising the steps of, (a) combining a candidate modulator compound with HGPRBMY5v1 or HGPRBMY5v2 having the sequence set forth in SEQ ID NO:2 or 82 subsequent to addition of relaxin; and (b) identifying agonist compounds by measuring an effect of the candidate modulator compound on the activity of HGPRBMY5v1 or HGPRBMY5v2, wherein said identified agonist compound increases relaxin dependent HGPRBMY5v1 or HGPRBMY5v2 activity.

The invention further relates to a method of identifying a compound that modulates the biological activity of a GPCR, comprising the steps of, (a) combining a candidate modulator compound with a host cell expressing HGPRBMY5v1 or HGPRBMY5v2 having the sequence as set forth in SEQ ID NO:2 or 82; and, (b) measuring an effect of the candidate modulator compound on the activity of the expressed HGPRBMY5v1 or HGPRBMY5v2.

The invention further relates to a method of identifying a compound that modulates the biological activity of a GPCR, comprising the steps of, (a) combining a candidate modulator compound with a host cell expressing HGPRBMY5v1 or HGPRBMY5v2 having the sequence as set forth in SEQ ID NO:2 or 82; and, (b) measuring an effect of the candidate modulator compound on the activity of the expressed HGPRBMY5v1 or HGPRBMY5v2, wherein said method optionally includes the addition of relaxin to HGPRBMY5v1 either before or after addition of said candidate modulator compound.

The invention further relates to a method of identifying an antagonist compound that modulates the biological activity of a GPCR, comprising the steps of, (a) combining a candidate modulator compound with a host cell expressing HGPRBMY5v1 or HGPRBMY5v2 having the sequence as set forth in SEQ ID NO:2 or 82 subsequent to addition of relaxin; and, (b) measuring an effect of the candidate modulator compound on the activity of the expressed HGPRBMY5v1 or HGPRBMY5v2, wherein said identified antagonist compound decreases relaxin dependent HGPRBMY5v1 or HGPRBMY5v2 activity.

The invention further relates to a method of identifying an agonist compound that modulates the biological activity of a GPCR, comprising the steps of, (a) combining a candidate modulator compound with a host cell expressing HGPRBMY5v1 or HGPRBMY5v2 having the sequence as set forth in SEQ ID NO:2 or 82 subsequent to addition of relaxin; and, (b) measuring an effect of the candidate modulator compound on the activity of the expressed HGPRBMY5v1 or HGPRBMY5v2, wherein said identified agonist compound increases relaxin dependent HGPRBMY5v1 or HGPRBMY5v2 activity.

The invention further relates to a method of identifying a compound that modulates the biological activity of HGPRBMY5v1 or HGPRBMY5v2, comprising the steps of, (a) combining a candidate modulator compound with a host cell containing a vector described herein, wherein HGPRBMY5v1 or HGPRBMY5v2 is expressed by the cell; and, (b) measuring an effect of the candidate modulator compound on the activity of the expressed HGPRBMY5v1 or HGPRBMY5v2.

The invention further relates to a method of identifying a compound that modulates the biological activity of HGPRBMY5v1 or HGPRBMY5v2, comprising the steps of, (a) combining a candidate modulator compound with a host cell containing a vector described herein, wherein HGPRBMY5v1 or HGPRBMY5v2 is expressed by the cell; and, (b) measuring an effect of the candidate modulator compound on the activity of the expressed HGPRBMY5v1 or HGPRBMY5v2, wherein said method optionally includes the addition of relaxin to HGPRBMY5v1 or HGPRBMY5v2 either before or after addition of said candidate modulator compound.

The invention further relates to a method of identifying an antagonist compound that modulates the biological activity of HGPRBMY5v1 or HGPRBMY5v2, comprising the steps of, (a) combining a candidate modulator compound with a host cell containing a vector described herein, wherein HGPRBMY5v1 or HGPRBMY5v2 is expressed by the cell, subsequent to addition of relaxin, and, (b) measuring an effect of the candidate modulator compound on the activity of the expressed HGPRBMY5v1 or HGPRBMY5v2, wherein said identified antagonist compound decreases relaxin dependent HGPRBMY5v1 or HGPRBMY5v2 activity.

The invention further relates to a method of identifying an agonist compound that modulates the biological activity of HGPRBMY5v1 or HGPRBMY5v2, comprising the steps of, (a) combining a candidate modulator compound with a host cell containing a vector described herein, wherein HGPRBMY5v1 or HGPRBMY5v2 is expressed by the cell, subsequent to addition of relaxin, and, (b) measuring an effect of the candidate modulator compound on the activity of the expressed HGPRBMY5v1 or HGPRBMY5v2, wherein said identified agonist compound increases relaxin dependent HGPRBMY5v1 or HGPRBMY5v2 activity.

The invention further relates to a method of screening for a compound that is capable of modulating the biological activity of HGPRBMY5v1 or HGPRBMY5v2, comprising the steps of: (a) providing a host cell described herein; (b) determining the biological activity of HGPRBMY5v1 or HGPRBMY5v2 in the absence of a modulator compound; (c) contacting the cell with the modulator compound; and (d) determining the biological activity of HGPRBMY5v1 or HGPRBMY5v2 in the presence of the modulator compound; wherein a difference between the activity of HGPRBMY5v1 or HGPRBMY5v2 in the presence of the modulator compound and in the absence of the modulator compound indicates a modulating effect of the compound.

The invention further relates to a method of screening for a compound that is capable of modulating the biological activity of HGPRBMY5v1 or HGPRBMY5v2, comprising the steps of: (a) providing a host cell described herein; (b) determining the biological activity of HGPRBMY5v1 or HGPRBMY5v2 in the absence of a modulator compound; (c) contacting the cell with the modulator compound; and (d) determining the biological activity of HGPRBMY5v1 or HGPRBMY5v2 in the presence of the modulator compound; wherein a difference between the activity of HGPRBMY5v1 or HGPRBMY5v2 in the presence of the modulator compound and in the absence of the modulator compound indicates a modulating effect of the compound, wherein said method optionally includes the addition of relaxin to HGPRBMY5v1 or HGPRBMY5v2 either before or after addition of said candidate modulator compound.

As used herein the terms "modulate" or "modulates" refer to an increase or decrease in the amount, quality or effect of a particular activity, DNA, RNA, or protein of HGPRBMY5v1 and/or HGPRBMY5v2.

The invention further relates to a compound that modulates the biological activity of human HGPRBMY5v1 and/or HGPRBMY5v2 as identified by the methods described herein.

The invention further relates to a method for preventing, treating, or ameliorating a medical condition with the polypeptide provided as SEQ ID NO:2 and/or SEQ ID NO:82, in addition to, its encoding nucleic acid, or a modulator thereof, wherein the medical condition is a disorder associated with aberrant p21 expression or activity.

The invention further relates to a method for preventing, treating, or ameliorating a medical condition with the polypeptide provided as SEQ ID NO:2 and/or SEQ ID NO:82, in addition to, its encoding nucleic acid, or a modulator thereof, wherein the medical condition is a cell cycle defect, disorders related to aberrant phosphorylation, disorders related to aberrant signal transduction, proliferating disorders, and/or cancers.

The invention further relates to a method for preventing, treating, or ameliorating a medical condition with the polypeptide provided as SEQ ID NO:2 and/or SEQ ID NO:82, in addition to, its encoding nucleic acid, or a modulator thereof, wherein the medical condition is a disorder associated with aberrant cell cycle regulation.

The invention further relates to a method of increasing, or alternatively decreasing, the number of cells in the G1 phase of the cell cycle comprising the step of administering an antagonist, or alternatively an agonist, of HGPRBMY5v1 and/or HGPRBMY5v2.

The invention further relates to a method of increasing, or alternatively decreasing, the number of cells in the G2 phase of the cell cycle comprising the step of administering an antagonist, or alternatively an agonist, of HGPRBMY5v1 and/or HGPRBMY5v2.

The invention further relates to a method of decreasing, or alternatively increasing, the number of cells that progress to the S phase of the cell cycle comprising the step of administering an antagonist, or alternatively an agonist, of HGPRBMY5v1 and/or HGPRBMY5v2.

The invention further relates to a method of increasing, or alternatively decreasing, the number of cells that progress to the M phase of the cell cycle comprising the step of administering an antagonist, or alternatively an agonist, of HGPRBMY5v1 and/or HGPRBMY5v2.

The invention further relates to a method of inducing, or alternatively inhibiting, cells into G1 and/or G2 phase arrest comprising the step of administering an antagonist, or alternatively an agonist, of HGPRBMY5v1 and/or HGPRBMY5v2.

The invention also relates to an antisense compound 8 to 30 nucleotides in length that specifically hybridizes to a nucleic acid molecule encoding the human HGPRBMY5v1 and/or HGPRBMY5v2 polypeptide of the present invention, wherein wherein said antisense compound inhibits the expression of the human HGPRBMY5v1 and/or HGPRBMY5v2 polypeptide.

The invention further relates to a method of inhibiting the expression of the human HGPRBMY5v1 and/or HGPRBMY5v2 polypeptide of the present invention in human cells or tissues comprising contacting said cells or tissues in vitro, or in vivo, with an antisense compound of the present invention so that expression of the HGPRBMY5v1 and/or HGPRBMY5v2 polypeptide is inhibited.

The invention further relates to a method of increasing, or alternatively decreasing, the expression of p21 in human cells or tissues comprising contacting said cells or tissues in vitro, or in vivo, with an antisense compound that specifically hybridizes to a nucleic acid molecule encoding the human HGPRBMY5v1 and/or HGPRBMY5v2 polypeptide of the present invention so that expression of the HGPRBMY5v1 and/or HGPRBMY5v2 polypeptide is inhibited.

The present invention is also directed to a method of identifying a compound that modulates the biological activity of HGPRBMY5v1 and/or HGPRBMY5v2, comprising the steps of, (a) combining a candidate modulator compound with HGPRBMY5v1 and/or HGPRBMY5v2 in the presence of an antisense molecule that antagonizes the activity of the HGPRBMY5v1 and/or HGPRBMY5v2 polypeptide selected from the group consisting of SEQ ID NO:90, 91, 92, 93, 94, 95, 96, 97, 98 and/or 99, and (b) identifying candidate compounds that reverse the antagonizing effect of the peptide.

The present invention is also directed to a method of identifying a compound that modulates the biological activity of HGPRBMY5v1, comprising the steps of, (a) combining a candidate modulator compound with HGPRBMY5v1 in the presence of a small molecule that antagonizes the activity of the HGPRBMY5v1 polypeptide selected from the group consisting of SEQ ID NO: 90, 91, 92, 93, 94, 95, 96, 97, 98 and/or 99, and (b) identifying candidate compounds that reverse the antagonizing effect of the peptide.

The present invention is also directed to a method of identifying a compound that modulates the biological activity of HGPRBMY5v1, comprising the steps of, (a) combining a candidate modulator compound with HGPRBMY5v1 in the presence of a small molecule that agonizes the activity of the HGPRBMY5v1 polypeptide selected from the group consisting of SEQ ID NO: 90, 91, 92, 93, 94, 95, 96, 97, 98 and/or 99, and (b) identifying candidate compounds that reverse the agonizing effect of the peptide.

BRIEF DESCRIPTION OF THE FIGURES/DRAWINGS

FIGS. 1A-C show the polynucleotide sequence (SEQ ID NO:1) and deduced amino acid sequence (SEQ ID NO:2) of the novel human G-protein coupled receptor, HGPRBMY5v1 of the present invention. The standard one-letter abbreviation for amino acids is used to illustrate the deduced amino acid sequence. The polynucleotide sequence contains a sequence of 2247 nucleotides (SEQ ID NO:1), encoding a polypeptide of 748 amino acids (SEQ ID NO:2). An analysis of the HGPRBMY5v1 polypeptide determined that it comprised the following features: seven transmembrane domains (TM1 to TM7) located from about amino acid 414 to about amino acid 433 (TM1; SEQ ID NO:3); from about amino acid 450 to about amino acid 468 (TM2; SEQ ID NO:4); from about amino acid 491 to about amino acid 512 (TM3; SEQ ID NO:5); from about amino acid 534 to about amino acid 552 (TM4; SEQ ID NO:6); from about amino acid 585 to about amino acid 608 (TM5; SEQ ID NO:7); from about amino acid 634 to about amino acid 657 (TM6; SEQ ID NO:8); and/or from about amino acid 669 to about amino acid 688 (TM7; SEQ ID NO:9), of SEQ ID NO:2, denoted by double underlining; and seven leucine-rich repeat domains (LRR1 to LRR7) located from about amino acid 132 to about amino acid 155 (LRR1; SEQ ID NO:3); from about amino acid 156 to about amino acid 179 (LRR2; SEQ ID NO:4); from about amino acid 180 to about amino acid 203 (LRR3; SEQ ID NO:5); from about amino acid 204 to about amino acid 227 (LRR4; SEQ ID NO:6); from about amino acid 276 to about amino acid 299 (LRR5;

SEQ ID NO:7); from about amino acid 300 to about amino acid 323 (LRR6; SEQ ID NO:8); and/or from about amino acid 324 to about amino acid 347 (LRR6; SEQ ID NO:9), of SEQ ID NO:2 (FIGS. 1A-C), denoted by single underlining. It is anticipated that the HGPRBMY5v1, polypeptide functions as a G-protein coupled receptor as described more particularly elsewhere herein.

FIGS. 2A-J show the regions of identity and similarity between the encoded HGPRBMY5v1 polypeptide (SEQ ID NO:2) to other G-protein coupled receptors, particularly relaxin receptors, specifically, the human leucme-rich repeat-containing G protein-coupled receptor 5 protein (LGR5_HUMAN; SWISS-PROT Accession No: 075473; SEQ ID NO:10); the mouse leucine-rich repeat-containing G protein-coupled receptor 5 protein (LGR5_MOUSE SWISS-PROT Accession No: Q9Z1P4; SEQ ID NO:11); the human relaxin receptor 1 protein, also referred to as the leucine-rich repeat-containing G-protein-coupled receptor 7 (LGR7 HUMAN; SWISS-PROT Accession No: Q9HBX9; SEQ ID NO:12); the human relaxin receptor 2 protein, also referred to as the human leucine-rich repeat-containing G-protein-coupled receptor 8 (LGR8_HUMAN; SWISS-PROT Accession No: Q8WXD0; SEQ ID NO:13); the mouse relaxin receptor 2 protein, also referred to as the mouse leucine-rich repeat-containing G-protein-coupled receptor 8 (LGR8_MOUSE; SWISS-PROT Accession No: Q91ZZ5; SEQ ID NO:14); the human HGPRBMY5 protein (HGPRBMY5; International Publication No. WO 02/26824; filed Sep. 26, 2001; SEQ ID NO:15); and the human HGPRBMY5sv1 splice variant protein (HGPRBMY5sv1; International Publication No. WO 02/26824; filed Sep. 26, 2001; SEQ ID NO:16). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between HGPRBMY5v1, and the other GPCRs are noted.

FIG. 3 shows an expression profile of the novel human G-protein coupled receptor, HGPRBMY5v1. The figure illustrates the relative expression level of HGPRBMY5v1 amongst various normal mRNA tissue sources. As shown, transcripts corresponding to HGPRBMY5v1 expressed predominately in the brain; significantly in thymus, and to a lesser extent, in other tissues as shown. Expression data was obtained by measuring the steady state HGPRBMY5v1 mRNA levels by quantitative PCR using the PCR primer pair provided as SEQ ID NO:83 and 84 as described herein.

Figure 4:
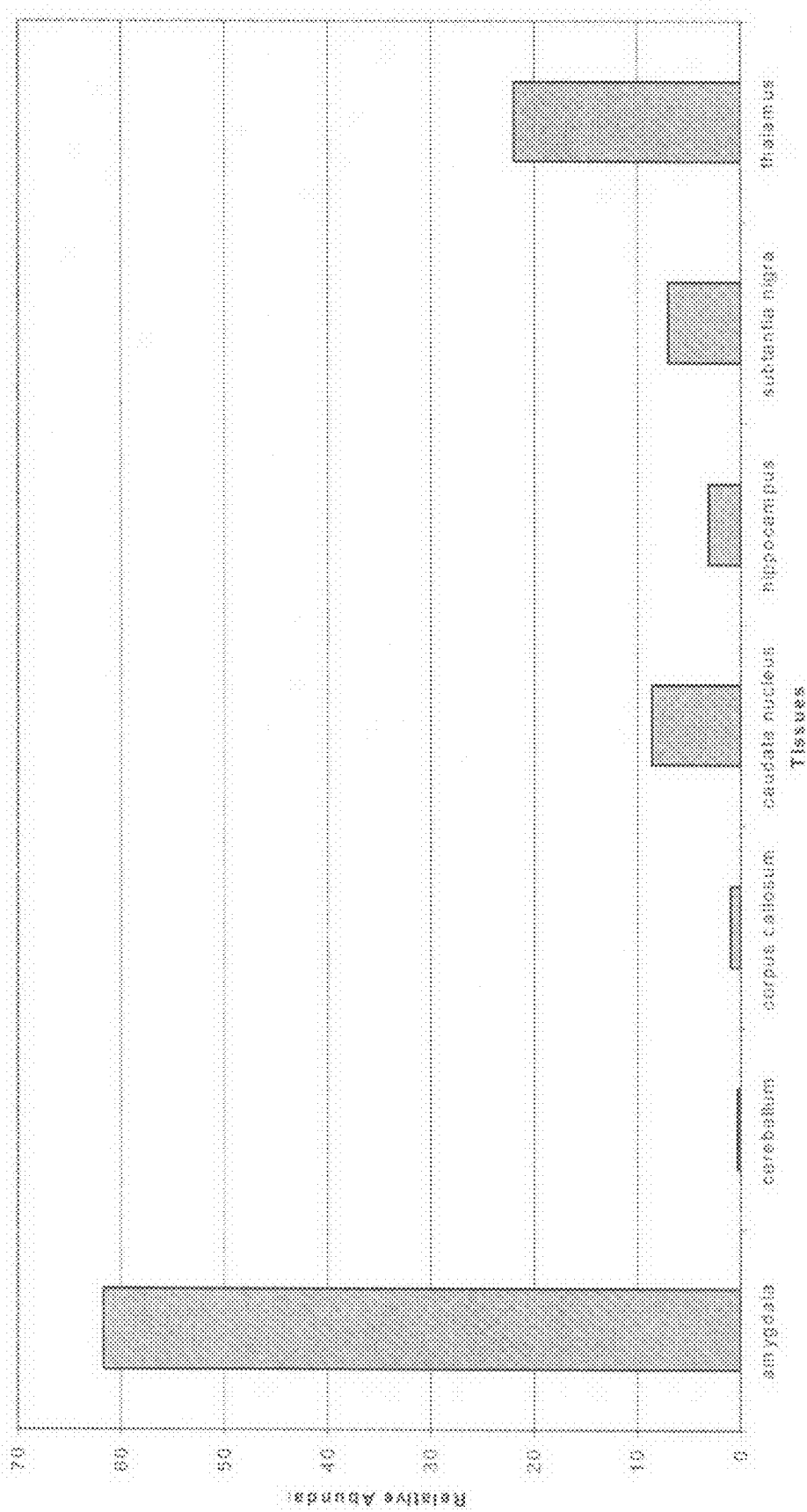

FIG. 4 shows an expression profile of the novel human G-protein coupled receptor, HGPRBMY5v1. The figure illustrates the relative expression level of HGPRBMY5v1 amongst various mRNA tissue sources isolated from brain-subregions. As shown, transcripts corresponding to HGPRBMY5v1 expressed predominately in the amygdala; significantly in the thalamus, and to a lesser extent, in other tissues as shown. Expression data was obtained by measuring the steady state HGPRBMY5v1 mRNA levels by quantitative PCR using the PCR primer pair provided as SEQ ID NO:83 and 84 as described herein.

Figure 5:
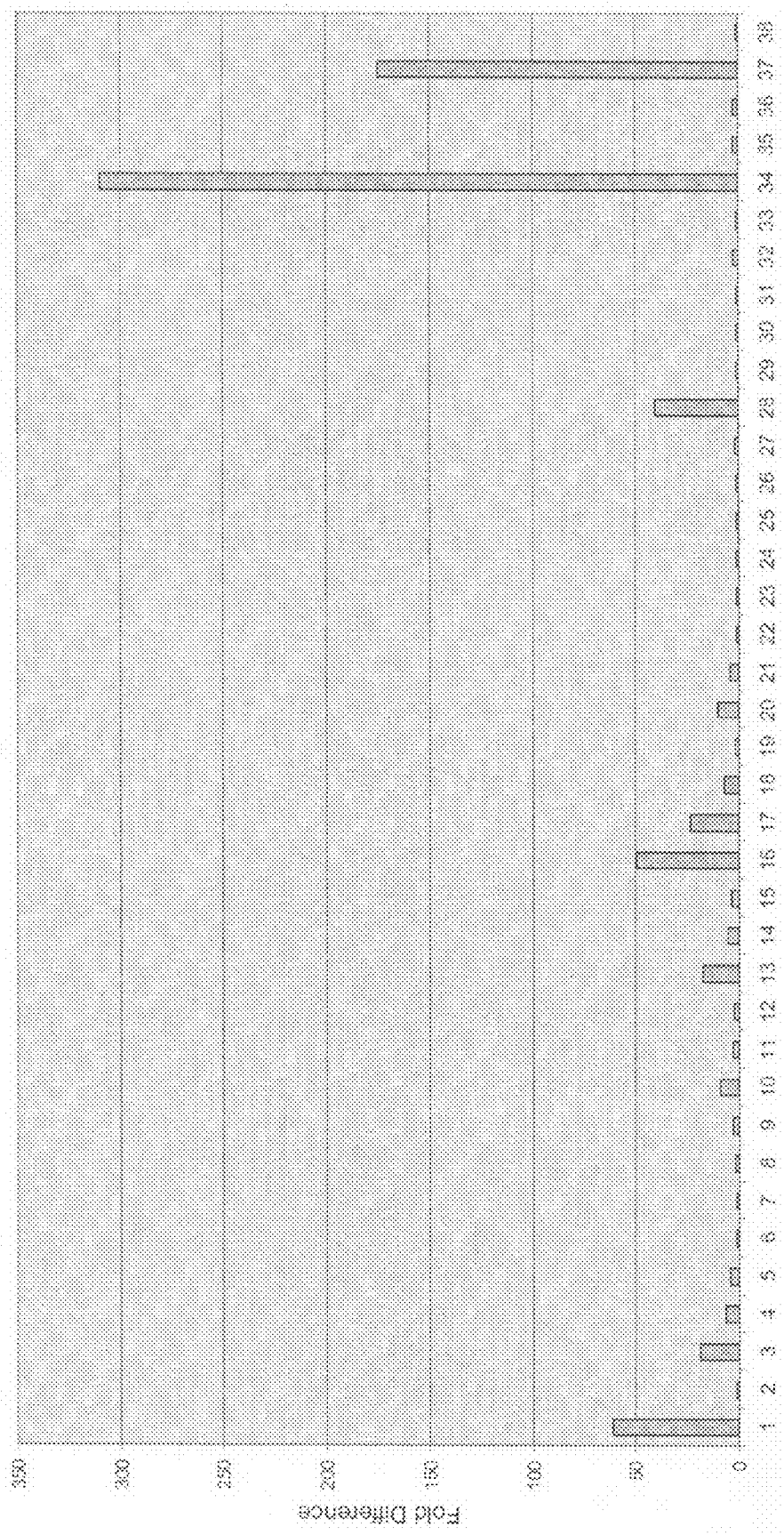

FIG. 5 shows an expanded expression profile of the novel human G-protein coupled receptor, HGPRBMY5v1. The figure illustrates the relative expression level of HGPRBMY5v1 amongst various normal mRNA tissue sources. As shown, the HGPRBMY5v1 polypeptide was expressed predominately in the nervous system, endocrine system, and male and female reproductive tracts, specifically the testis and uterus, followed by the adrenal gland and skeletal muscle. Within the brain, HGPRBMY5v1 was expressed at their highest steady state levels in putamen (see FIG. 6) and the hypothalamus. The expression in particularly relevant considering the expression in Parkinson's tissues (see FIG. 6). Expression data was obtained by measuring the steady state HGPRBMY5v1 mRNA levels by quantitative PCR using the PCR primer pair provided as SEQ ID NO:78 and 79 and Taqman probe (SEQ ID NO:80) as described in Example 6 herein.

Figure 6:
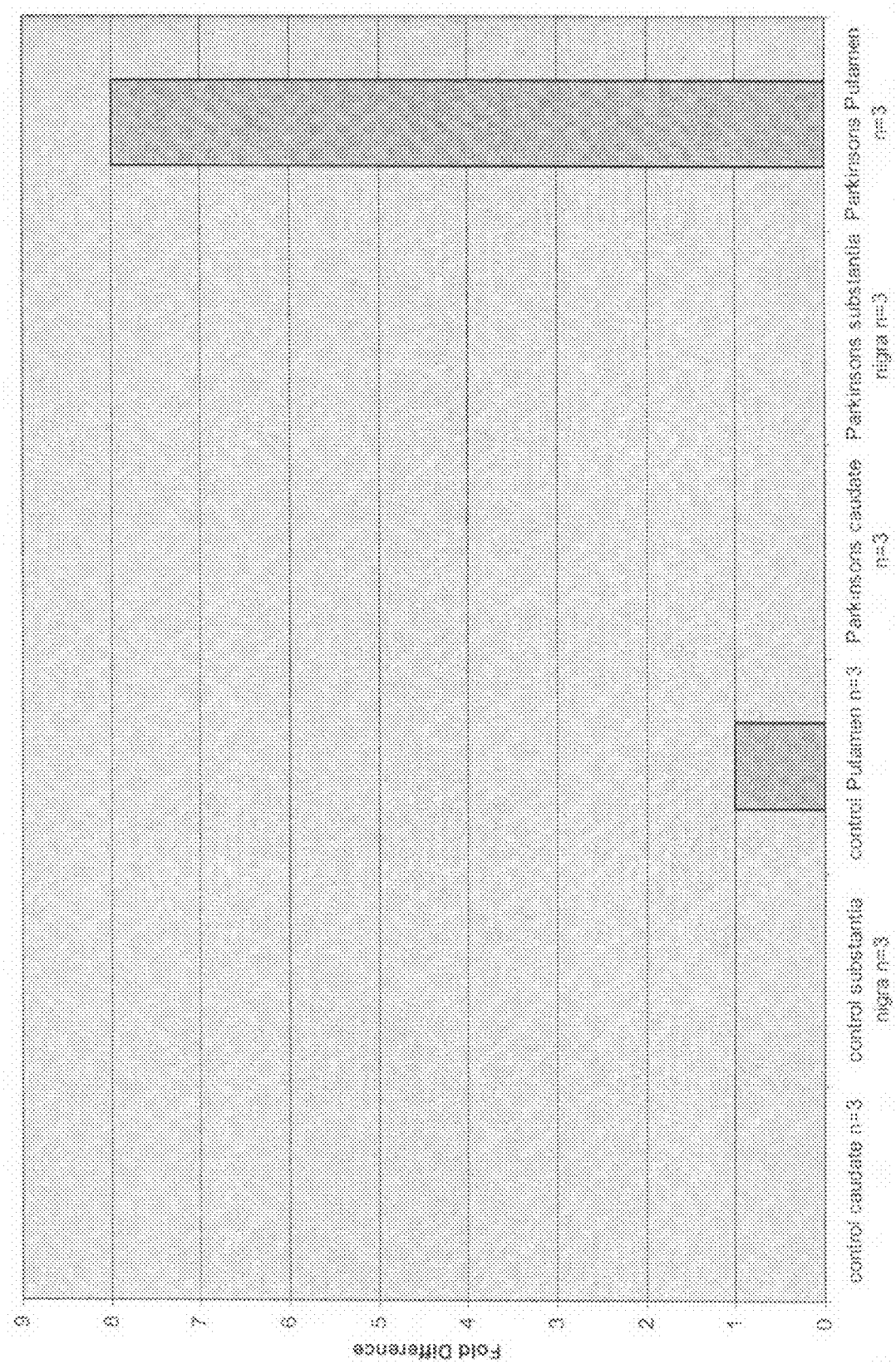

FIG. 6 shows an expanded expression profile of the novel human G-protein coupled receptor, HGPRBMY5v1, of the present invention. The figure illustrates the relative expression level of HGPRBMY5v1 amongst various mRNA tissue sources isolated from normal and diseased tissues. As shown, the HGPRBMY5v1 polypeptide was differentially expressed in Parkinson's putamen tissue compared to its respective normal putatmen tissue. Expression data was obtained by measuring the steady state HGPRBMY5v1 mRNA levels by quantitative PCR using the PCR primer pair provided as SEQ ID NO:78 and 79 and Taqman probe (SEQ ID NO:80) as described in Example 6 herein.

FIG. 7 shows a table illustrating the percent identity and percent similarity between the HGPRBMY5v1 polypeptides of the present invention with other G-protein coupled receptors, particularly relaxin receptors. The percent identity and percent similarity values were determined using the CLUSTALW algorithm using default parameters as described herein (Vector NTI suite of programs).

FIGS. 8A-C show the polynucleotide sequence (SEQ ID NO:81) and deduced amino acid sequence (SEQ ID NO:82) of the novel human G-protein coupled receptor splice variant, HGPRBMY5v2, of the present invention. The standard one-letter abbreviation for amino acids is used to illustrate the deduced amino acid sequence. The polynucleotide sequence contains a sequence of 2175 nucleotides (SEQ ID NO:81), encoding a polypeptide of 724 amino acids (SEQ ID NO:82). It is anticipated that the HGPRBMY5v2, polypeptide functions as a G-protein coupled receptor and has the same or similar activity as HGPRBMY5v1 as described more particularly elsewhere herein.

FIGS. 9A-C shows the regions of identity and similarity between the encoded HGPRBMY5v1 polypeptide (SEQ ID NO:2) and the HGPRBMY5v2 polypeptide (SEQ ID NO:82) of the present invention. The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides.

DETAILED DESCRIPTION OF THE INVENTION

The present invention may be understood more readily by reference to the following detailed description of the preferred embodiments of the invention and the Examples included herein.

The invention provides novel human sequences that encode a G-protein coupled receptor (GPCRs) with substantial homology to the relaxin family of receptors. Such receptors have been implicated in a number of diseases and/or disorders, which are known in the art or described herein.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking polynucleotide (i.e., 5' or 3' to the polynucleotide of interest in the genome). In other embodiments, the polynucleotides of the invention do not contain the coding sequence of more than 1000, 500, 250, 100, 50, 25, 20, 15, 10, 5, 4, 3, 2, or 1 genomic flanking polynucleotide(s).

As used herein, a "polynucleotide" refers to a molecule having a nucleic acid sequence contained in SEQ ID NO:1 or SEQ ID NO:81, or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1 was often generated by overlapping sequences contained in one or more clones (contig analysis).

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-C (SEQ ID NO:1), a nucleic acid molecule of the present invention encoding the HGPRBMY5v1 polypeptide may be obtained using standard cloning and screening procedures, such as those for cloning cDNAs using mRNA as starting material.

Using the information provided herein, such as the nucleotide sequence in FIGS. 8A-C (SEQ ID NO:81), a nucleic acid molecule of the present invention encoding the HGPRBMY5v2 polypeptide may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences contained in SEQ ID NO:1 and/or SEQ ID NO:81, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide" since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 polynucleotide-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:1" and "SEQ ID NO:81" refers to polynucleotide sequences while "SEQ ID NO:2" and "SEQ ID NO:82" refer to polypeptide sequences, all sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321-9, (1995); and Ann. N.Y. Acad. Sci., 7;766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify polynucleotide expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, noncoding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, polynucleotide knockout experiments, and other procedures that could use sequence information from clones to build a primer or a hybrid partner.

Polynucleotides and Polypeptides of the Invention
Features of the Polypeptide Encoded by Polynucleotide No: 1

The polypeptide of this polynucleotide provided as SEQ ID NO:2 (FIGS. 1A-C), encoded by the polynucleotide sequence according to SEQ ID NO:1 (FIGS. 1A-C), and/or encoded by the polynucleotide contained within the deposited clone, HGPRBMY5v1 (also referred to as HGPRBMY5 variant), has significant homology at the nucleotide and amino acid level to the relaxin family of G-protein coupled receptors, which include, for example, the human leucine-rich repeat-containing G protein-coupled receptor 5 protein (LGRS_HUMAN; SWISS-PROT Accession No: 075473; SEQ ID NO:10); the mouse leucine-rich repeat-containing G protein-coupled receptor 5 protein (LGR5_MOUSE; SWISS-PROT Accession No: Q9Z1P4; SEQ ID NO:11); the human relaxin receptor 1 protein, also referred to as the leucine-rich repeat-containing G-protein-coupled receptor 7 (LGR7_HUMAN; SWISS-PROT Accession No: Q9HBX9; SEQ ID NO:12); the human relaxin receptor 2 protein, also referred to as the human leucine-rich repeat-containing G-protein-coupled receptor 8 (LGR8_HUMAN; SWISS-PROT Accession No: Q8WXD0; SEQ ID NO:13); the mouse relaxin receptor 2 protein, also referred to as the mouse leucine-rich repeat-containing G-protein-coupled receptor 8 (LGR8_MOUSE; SWISS-PROT Accession No: Q91ZZ5; SEQ ID NO:14); the human HGPRBMY5 protein (HGPRBMY5; International Publication No. WO 02/26824; filed Sep. 26, 2001; SEQ ID NO:15); and the human HGPRBMY5sv1 splice variant protein (HGPRBMY5sv1; International Publication No. WO 02/26824; filed Sep. 26, 2001; SEQ ID NO:16). An alignment of the HGPRBMY5v1, polypeptide with these proteins is provided in FIGS. 2A-J.

The determined nucleotide sequence of the HGPRBMY5v1, cDNA in FIGS. 1A-C (SEQ ID NO:1) contains an open reading frame encoding a protein of about 748 amino acid residues, with a deduced molecular weight of about 85.6 kDa. The amino acid sequence of the predicted HGPRBMY5v1 polypeptide is shown in FIGS. 1A-C (SEQ ID NO:2). The HGPRBMY5v1 protein shown in FIGS. 1A-C was determined to share significant identity and similarity to relaxin G-protein coupled receptors, as shown in FIGS. 2A-J. The percent identity and similarity values between the HGPRBMY5v1 polypeptide to these known G-protein coupled receptors is provided in FIG. 7.

The HGPRBMY5v1 polypeptide was predicted to comprise seven transmembrane domains (TM1 to TM7) located from about amino acid 414 to about amino acid 433 (TM1; SEQ ID NO:3); from about amino acid 450 to about amino acid 468 (TM2; SEQ ID NO:4); from about amino acid 491 to about amino acid 512 (TM3; SEQ ID NO:5); from about amino acid 534 to about amino acid 552 (TM4; SEQ ID NO:6); from about amino acid 585 to about amino acid 608 (TM5; SEQ ID NO:7); from about amino acid 634 to about amino acid 657 (TM6; SEQ ID NO:8); and/or from about amino acid 669 to about amino acid 688 (TM6; SEQ ID NO:9), of SEQ ID NO:2 (FIGS. 1A-C). In this context, the term "about" may be construed to mean 1, 2, 3, 4, 5, 6, 7, 8, 9, or 10 amino acids beyond the N-Terminal and/or C-terminal boundary of the above referenced transmembrane domain polypeptides.

In preferred embodiments, the following transmembrane domain polypeptides are encompassed by the present invention: IFVWVIAFITCFGNLFVIGM (SEQ ID NO:3), ILCCADCLMGVYLFFVGIF (SEQ ID NO:4), LMG-FLAMLSTEVSVLLLTYLTL (SEQ ID NO:5), VILICI-WMAGFLIAVIPFW (SEQ ID NO:6), LGIFLGVN-LLAFLIIVFSYITMFC (SEQ ID NO:7), FFFIVFSDAICWIPVFVVKILSLF (SEQ ID NO:8), and/or IVIFFLPVNSALNPILYTLT (SEQ ID NO:9). Polynucleotides encoding these polypeptides are also provided. The present invention also encompasses the use of these HGPRBMY5v1 transmembrane domain polypeptides as immunogenic and/or antigenic epitopes as described elsewhere herein.

The HGPRBMY5v1 polypeptide was also predicted to comprise seven leucine-rich repeat domains (LRR1 to LRR7) located from about amino acid 132 to about amino acid 155 (LRR1; SEQ ID NO:3); from about amino acid 156 to about amino acid 179 (LRR2; SEQ ID NO:4); from about amino acid 180 to about amino acid 203 (LRR3; SEQ ID NO:5); from about amino acid 204 to about amino acid 227 (LRR4; SEQ ID NO:6); from about amino acid 276 to about amino acid 299 (LRR5; SEQ ID NO:7); from about amino acid 300 to about amino acid 323 (LRR6; SEQ ID NO:8); and/or from about amino acid 324 to about amino acid 347 (LRR6; SEQ ID NO:9), of SEQ ID NO:2 (FIGS. 1A-C). In this context, the term "about" may be construed to mean 1, 2, 3, 4, 5, 6, 7, 8, 9, or 10 amino acids beyond the N-Terminal and/or C-terminal boundary of the above referenced transmembrane domain polypeptides.

In preferred embodiments, the following leucine-rich repeat domain polypeptides are encompassed by the present invention: NVTLLSLKKNKIHSLPDKVFIKYT (SEQ ID NO:63), KLKKIFLQHNCIRHISRKAFFGLC (SEQ ID NO:64), NLQILYLNHNCITTLRPGIFKDLH (SEQ ID NO:65), QLTWLILDDNPITRISQRLFTGLN (SEQ ID NO:66), SLTVLFLPRNQIGFVPEKTFSSLK (SEQ ID NO:67), NLGELDLSSNTITELSPHLFKDLK (SEQ ID NO:68), and/or LLQKLNLSSNPLMYLHKNQFESLK (SEQ ID NO:69). Polynucleotides encoding these polypeptides are also provided. The present invention also encompasses the use of these HGPRBMY5v1 leucine-rich repeat domain polypeptides as immunogenic and/or antigenic epitopes as described elsewhere herein.

The present invention also encompasses the polypeptide sequences that intervene between each of the predicted HGPRBMY5v1 transmembrane domains. Since these regions are solvent accessible either extracellularly or intracellularly, they are particularly useful for designing antibodies specific to each region. Such antibodies may be useful as antagonists or agonists of the HGPRBMY5v1 polypeptide and may modulate its activity.

In preferred embodiments, the following inter-transmembrane domain polypeptides are encompassed by the present invention: RSFIKAENTTHAMSIK (SEQ ID NO:24), DIKYRGQYQKYALLWMESVQCR (SEQ ID NO:25), EKFLVIVFPFSNIRPGKRQTS (SEQ ID NO:26), NKDY-FGNFYGKNGVCFPLYYDQTEDIGSKGYS (SEQ ID NO:27), SIQKTALQTTEVRNCFGREVAVANR (SEQ ID NO:28), and/or RVEIPDTMTSW (SEQ ID NO:29).

In preferred embodiments, the present invention encompasses the use of N-terminal deletions, C-terminal deletions, or any combination of N-terminal and C-terminal deletions of any one or more of the HGPRBMY5v1 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., GPCR extracellular or intracellular loops) the HGPRBMY5v1 TM1 thru TM7 transmembrane domain polypeptides as antigenic and/or immunogenic epitopes.

The present invention also encompasses the ectodomain of the HGPRBMY5v1 polypeptide as determined in accordance with the teachings of Y. Osaga et al., Mol Endocrinol., 11:1659-1668 (1997); which is hereby incorporated by reference in its entirety herein). Preferably, the ectodomain of HGPRBMY5v1 is soluble. The present invention also encompasses fusion proteins of the HGPRBMY5v1 ectodomain. In particular, the present invention encompasses fusion proteins of the HGPRBMY5v1 ectodomain with the single-transmembrane domain and/or cytoplasmic domain of CD8 (about amino acid 162 of CD-8 to the end of the C terminus of CD-8), which optionally comprises a protease cleave site, particularly thrombin, among others.

The present invention encompasses polypeptide sequences comprising amino acids M1 to R413 of SEQ ID NO:2 representing the ectodomain of HGPRBMY5v1. Polynucleotides encoding this polypeptide are also provided.

The ectodomain of HGPRBMY5v1, either alone or as a fusion protein, is useful as an antagonist to HGPRBMY5v1 function, and may be useful for the treatement and/or amerlioration of disorders associated with aberrant relaxin and/or relaxin receptor function.

The HGPRBMY5v1 polypeptide was also determined to comprise several conserved cysteines which are denoted by dark shading, in addition to other identical residues, as shown in FIGS. 2A-J. Conservation of cysteines at key amino acid residues is indicative of conserved structural features, which may correlate with conservation of protein function andlor activity.

HGPRBMY5v1 is a G-protein coupled receptor that is believed to represent the physiologically relevant form of the HGPRBMY5 GPCR (SEQ ID NO:15; International Publication No. WO 02/26824; filed Sep. 26, 2001; which is hereby incorporated herein by reference in its entirety).

A protein highly homologous to HGPRBMY5 was recently deorphaned, LGR8 (SEQ ID NO:13), and determined to be one of two receptors for relaxin (Yu Hsu, S. et al, Science, 295:671-674 (2002)). In fact, the HGPRBMY5 polypeptide is identical to LGR8 with the exception of having an N-terminus that is 17 amino acids shorter than LGR8.

Likewise, HGPRBMY5v1 is a variant of HGPRBMY5 and also has a unique N-terminus portion relative to LGR8. Since HGPRBMY5v1 is a variant of the relaxin receptor, it is expected to have the same biological activity as the wild-type relaxin receptor (i.e., HGPRBMY5).

Likewise, due to the significant identity between the HGPRBMY5v1 polypeptide to the LGR8 polypeptide, the utilities referenced herein for HGRPBMY5v1 are also applicable to modulators of LGR8 and its related family members known in the art or referenced herein.

Thus, HGPRBMY5v1 is a variant of a well-known G-protein coupled receptor with well-established utility.

The present invention is also directed to a splice variant form of HGPRBMY5v1, referred to as HGPRBMY5v2. The polypeptide of this polynucleotide is provided as SEQ ID NO:82 (FIGS. 8A-C), and encoded by the polynucleotide sequence according to SEQ ID NO:81 (FIGS. 8A-C). This variant is expected to have the same or similar activity as HGPRBMY5v1. The locations of the trausmembrane domains; the leucine-rich repeat domains; the location of the ecto-domain, and other domains, including phosphorylation sites, glycosylation sites, myristolation sites, etc., are readily identifiable by comparing the amino acid alignment between HGPRBMY5v1 and HGPRBMY5v2 (see FIGS. 9A-C) with the HGPRBMY5v1 annotations described in FIGS. 1A-C and elsewhere herein. All references to HGPRBMY5v1 shall be construed to apply to HGPRBMY5v2 unless otherwise explicitly noted herein.

The present invention encompasses polypeptide sequences comprising amino acids M1 to R389 of SEQ ID NO:82 representing the ectodomain of HGPRBMY5v2. Polynucleotides encoding this polypeptide are also provided.

As referenced elsewhere herein, Relaxin mediates a number of physiological events and processes which are directly, and indirectly linked to various diseases and disorders. Since the HGPRBMY5v1 polypeptide of the present invention is believed to represent a variant relaxin receptor, it is expected that HGPRBMY5v1 polynucleotides, polypeptides, and fragments and modulators thereof are useful for treating diseases and disorders related to aberrant relaxin function, expression, and/or activity.

HGPRBMY5v1 polynucleotides, polypeptides, and fragments and modulators thereof are useful for detecting, prognosing, treating, preventing, and/or ameliorating pregnancy disorders, embryonic implantation disorders, lactation disorders, mammary development disorders, nipple development disorders, uterine development disorders during pregnancy, uterine contractile disorders, tissue softening in birth canal during pregnancy disorders; collagen solubility disorders during pregnancy, cervical collagen concentration disorders during pregnancy, disorders affecting aberrant MMP-1 (procollagenase) regulation, disorders affecting aberrant MMP-2 (gelatinase) regulation, disorders affecting aberrant MMP-3 (prostromelysin) regulation, disorders affecting aberrant TIMP-1 regulation, interpubic lengthening disorders, disorders affecting decidualization of endometrial stromal cells, prolactin induction disorders, laminin induction disorders, glycoprotein glycodelin induction disorders, cardiovascular disorders, vasodilation disorders, high blood pressure disorders, nitric oxide synthase disorders, prostacyclin disorders, relaxin-mediated VEGF regulation disorders, relaxin-mediated bFGF regulation disorders, relaxin-mediated angiogenesis regulation disorders, relaxin-mediated wound healing regulation disorders, atrial natriuretic peptide regulation disorders, ischemic myocardial in jury, ischemia reperfusion damage, ventricular arrhythmias, disorders associated with myocardial neutrophil invasion, disorders associated with lipid peroxidation, disorders associated with mast cell granule release, disorders associated with cellular calcium overload, coronary artery disease, congestice heart failure, thrombosis, embolism, stroke, disorders associated with the release of platelets from megakaryocytes, fibroids, asthma, disorders related to aberrant interferon-gamma release or function, disorders related to aberrant recruitment or hyper-recruitment of helper T-cells, disorders related to aberrant recruitment or hyper-recruitment of immunglobulin E-antibody B cells, aberrant fluid homeostasis, and/or edema.

Defects in the LGR8 polypeptide have been linked to the incidence of cryptorchidism (Genesis 30:26-35(2001)), which is a congenital malformation resulting in the failure of the testicules to descend. Cryptorchidism is one of the most common congenital defects affecting 1-3% of newborn boys Cryptorchidism is associated with increased risk of infertility and testicular cancer.

Cryptorchidism is caused by a single mutation in the LFR8 receptor that results in a threonine to proline amino acid change at amino acid position 222.

The present invention is also directed to the HGPRBMY5v1 polypeptide comprising proline at amino acid 216 of SEQ ID NO:2. Polynucleotides encoding this polypeptide are also encompassed by the present invention, including all nucleotide redundancies.

The present invention is also directed to the HGPRBMY5v2 polypeptide comprising proline at amino acid 192 of SEQ ID NO:82. Polynucleotides encoding this polypeptide are also encompassed by the present invention, including all nucleotide redundancies.

Another mutation at amino acid 647 of LGR8 has been determined to result in consitutive increases in basal cAMP levels.

The present invention is also directed to the HGPRBMY5v1 polypeptide comprising tyrosine at amino acid 641 of SEQ ID NO:2. Polynucleotides encoding this polypeptide are also encompassed by the present invention, including all nucleotide redundancies.

The present invention is also directed to the HGPRBMY5v2 polypeptide comprising tyrosine at amino acid 617 of SEQ ID NO:82. Polynucleotides encoding this polypeptide are also encompassed by the present invention, including all nucleotide redundancies.

Since the HGPRBMY5v1 polypeptide represents a minor variant form of the relaxin receptor 2 protein (LGR8_HUMAN; SWISS-PROT Accession No: Q8WXD0; SEQ ID NO:13), it is expected that the expression pattern of HGPRBMY5v1 variant is the same or similar to the relaxin receptor 2 protein since they are believed to derive from the same gene. As a consequence, the HGPRBMY5v1 polypeptide is expected to share at least some biological activity with G-protein coupled receptors, in general, and specifically with the LGR8 polypeptide, among other members of the relaxin receptor family, including LGR7, amonth others. LGR8 appears to promote growth and dilation of the cervix, growth and quiescence of the uterus, growth and development of the mammary gland and nipple, and regulation of cardiovascular function by coupling via Gs G protein mediated responses in response to relaxin exposure (Yu Hsu, S. et al, Science, 295:671-674 (2002)).

The present invention is also directed to a polypeptide sequence comprising at least 724 contiguous amino acids of SEQ ID NO:2. The present invention is also directed to a polynucleotide sequence comprising at least 2172 contigous nucleotides of SEQ ID NO:1. Such polypeptides, in addition to the polypeptides encoded by these polynucleotides, are expected to have the same or similar biological function as the full-length HGPRBMY5v1 and/or LGR8 polypeptide.

The present invention is also directed to a polypeptide sequence comprising at least 581 contiguous amino acids of SEQ ID NO:82. The present invention is also directed to a polynucleotide sequence comprising at least 1743 contigous nucleotides of SEQ ID NO:81. Such polypeptides, in addition to the polypeptides encoded by these polynucleotides, are expected to have the same or similar biological function as the full-length HGPRBMY5v1, HGPRBMY5v2, and/or LGR8 polypeptide.

The HGPRBMY5v1 polypeptide was determined to be expressed predominately in brain and significantely in thymus tissue (see FIG. 3). Within the brain, HGPRBMY5v1 was determined to be expressed in the amygdala, and significantly in the thalamus.

Consistent with the HGPRBMY5v1 expression, the relaxin receptor 2 protein was determined to be expressed in brain, kidney, muscle, testis, thyroid, uterus, peripheral blood cells, and bone marrow (Yu Hsu, S. et al, Science, 295:671-674 (2002)).

Morever, an additional analysis of HGPRBMY5v1 expression levels by TaqMan™ quantitative PCR (see FIG. 6) in disease cells and tissues indicated that the HGPRBMY5v1 polypeptide is differentially expressed in putamen tissue isolated from Parkinson's patients. The clinical manifestations of Parkinson's disease (PD), at least in early stages, reflect selective degeneration of dopamine neurons in the substantia nigra projecting through the nigrostriatal pathway to the caudal putamen with compensatory changes in these and related systems. Hence, RNA isolated from the caudate, putamen and substantia nigra were analyzed. HGPRBMY5 was observed to be highly expressed in the putamen, at a level equal to that observed in the uterus and testis. Essentially, no expression was observed in the other subregions. Furthermore, the RNA steady state level of HGPRBMY5v1 was 8 times higher in RNA isolated from the PD putamen. These data suggest that modulators of HGPRBMY5v1 function may have utility in the treatment of PD.

Characterization of the HGPRBMY5v1 and/or HGPRBMY5v2 polypeptide of the present invention using antisense oligonucleotides led to the determination that HGPRBMY5v1 and HGPRBMY5v2 are involved in the positive modulation of the p21 G1/G2 cell cycle check point modulatory protein as described in Example 7 herein.

Antisense oligonucleotides directed against the HGPRBMY5v1 and/or HGPRBMY5v2 mRNA resulted in a marked decrease in p21 expression and/or activity (see Example 7). The level of expression of p21 in response to treatment with antisense olinucleotides specific to HGPRBMY5v1 and HGPRBMY5v2 was decreased by about 50% and about 47%, respectively. A 30% reduction in p21 expression was found to be physiologically significant, and both HGPRBMY5v1 and HGPRBMY5v2 exceeded this threshold. The results were replicated in three independent experiments and determined to be statistically significant.

These results suggest that induction of HGPRBMY5v1 and/or HGPRBMY5v2 activity or expression with a modulator would induce differentiation, and stop cellular proliferation, as p21 is a cell cycle inhibitor and is known to be associated with committment down a differentiation pathway. Numerous known drugs in clinical trials (such as, for example, cdk2 inhibitors, dna methyltransferase inhibitors) also induce p21, and have been shown to have activity in patients with cancer. Thus, p21 induction is a plausable marker of anticancer potential when a target is appropriately modulated.

Downregulation of p21 is consistent with cellular proliferation since p21 is an inhibitor of the cell cycle. This data suggests it would be therapeutically beneficial to agonize HGPRBMY5v1, HGPRBMY5v2, and/or LGR8 to have a favorable effect on tumor treatment.

In preferred embodiments, HGPRBMY5v1 and/or HGPRBMY5v2 polynucleotides and polypeptides, including fragments thereof, are useful for treating, diagnosing, and/or ameliorating cell cycle defects, disorders related to aberrant phosphorylation, disorders related to aberrant signal transduction, proliferating disorders, and/or cancers.

Moreover, HGPRBMY5v1 and/or HGPRBMY5v2 polynucleotides and polypeptides, including fragments thereof, are useful for decreasing cellular proliferation, decreasing cellular proliferation in rapidly proliferating cells, increasing the number of cells in the G1 phase of the cell cycle, increasing the number of cells in the G2 phase of the cell cycle, decreasing the number of cells that progress to the S phase of the cell cycle, decreasing the number of cells that progress to the M phase of the cell cycle, modulating DNA repair, and increasing hematopoietic stem cell expansion.

In preferred embodiments, agonists directed to HGPRBMY5v1 and/or HGPRBMY5v2 are useful for decreasing cellular proliferation, decreasing cellular proliferation in rapidly proliferating cells, increasing the number of cells in the G1 phase of the cell cycle, increasing the number of cells in the G2 phase of the cell cycle, decreasing the number of cells that progress to the S phase of the cell cycle, decreasing the number of cells that progress to the M phase of the cell cycle, modulating DNA repair, and increasing hematopoietic stem cell expansion.

HGPRBMY5v1 and/or HGPRBMY5v2 polynucleotides and polypeptides, including fragments and agonists thereof, are useful for treating, preventing, or ameliorating proliferative disorders in a patient in need of treatment, such as cancer patients, particularly patients that have proliferative immune disorders such as leukemia, lymphomas, multiple myeloma, etc.

Moreover, antagonists directed against HGPRBMY5v1 and/or HGPRBMY5v2 are useful for increasing cellular proliferation, increasing cellular proliferation in rapidly proliferating cells, decreasing the number of cells in the G1 phase of the cell cycle, decreasing the number of cells in the G2 phase of the cell cycle, increasing the number of cells that progress to the S phase of the cell cycle, increasing the number of cells that progress to the M phase of the cell cycle, and releasing cells from G1 and/or G2 phase arrest. Such antagonists would be particularly useful for transforming normal cells into immortalized cell lines, stimulating hematopoietic cells to grow and divide, increasing recovery rates of cancer patients that have undergone chemotherapy or other therapeutic regimen, by boosting their immune responses, etc. In addition, such antagonists of HGPRBMY5v1 and/or HGPRBMY5v2 would also be useful for regenerating neural tissues (e.g., treatment of Parkinson's or Alzheimers patients with neural stem cells, or neural cells which have been activated by an HGPRBMY5v1 and/or HGPRBMY5v2 antagonist).

The strong homology to human G-protein coupled receptor proteins, particularly relaxin receptors, combined with the localized expression in brain tissue in addition to the differential expression in diseased brain tissue, suggests the HGPRBMY5v1 polynucleotides and polypeptides may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The HGPRBMY5v1 polynucleotides and polypeptides of the present invention, including modulators and/or fragments thereof, have uses that include detecting, prognosing, treating, preventing, and/or ameliorating neurodegenerative disorders, including, but not limited to, Parkinson's disease, diseases, disorders related to degeneration of dopamine neurons, and/or disorders related to degeneration of dopamine neurons in the substantia nigra.

The HGPRBMY5v1 polynucleotides and polypeptides of the present invention, including modulators and/or fragments thereof, have uses that include detecting, prognosing, treating, preventing, and/or ameliorating the following cardiovascular diseases and/or disorders: heart failure, atherosclerosis, and arteriosclerosis, among others disclosed herein, particularly in the "Cardiovascular Disorders" section and below.

HGPRBMY5v1 polynucleotides and polypeptides of the present invention, including modulators and/or fragments thereof, have uses that include detecting, prognosing, treating, preventing, and/or ameliorating the following additional cardiovascular disorders: myocardio infarction, congestive heart failure, arrthymias, cardiomyopathy, atherosclerosis, arterialsclerosis, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, HGPRBMY5v1 polynucleotides and polypeptides may be useful for ameliorating cardiovascular diseases and symptoms which result indirectly from various non-cardiavascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection,

*Enterococcus* infection, nonenterococcal group D streptococci infection, nonenterococcal group C streptococci infection, nonenterococcal group G streptococci infection, *Streptoccus viridans* infection, *Staphylococcus aureus* infection, coagulase-negative staphylococci infection, gram-negative Bacilli infection, Enterobacteriaceae infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

The HGPRBMY5v1 polynucleotides and polypeptides of the present invention, including modulators and/or fragments thereof, have uses that include modulating signal transduction activity, in various cells, tissues, and organisms, and particularly in mammalian brain, kidney, muscle, testis, thyroid, uterus, peripheral blood cells, bone marrow, breast, nipple, cervix, heart, and uterus.

HGPRBMY5v1 polynucleotides and polypeptides of the present invention, including modulators and/or fragments thereof, have uses that include detecting, prognosing, treating, preventing, and/or ameliorating the immune diseases and/or disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The HGPRBMY5v1 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The HGPRBMY5v1 polypeptide may be useful for modulating cytokine production, antigen presentation, or other processes, such as for boosting immune responses, etc.

Moreover, the protein may represent a factor that influences the differentiation or behavior of other blood cells, or that recruits hematopoietic cells to sites of injury. Thus, this polynucleotide product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The HGPRBMY5v1 polynucleotides and polypeptides, including fragments and modulators thereof, may have uses which include, either directly or indirectly, for inhibiting immune responses.

The HGPRBMY5v1 polynucleotides and polypeptides, including fragments and/or antagonsists thereof, may have uses which include identification of modulators of HGPRBMY5v1 function including antibodies (for detection or neutralization), naturally-occurring modulators and small molecule modulators. Antibodies to domains of the HGPRBMY5v1 protein could be used as diagnostic agents of reproductive and inflammatory conditions in patients, are useful in monitoring the activation of signal transduction pathways, and can be used as a biomarker for the involvement of G-protein couplded receptors in disease states, and in the evaluation of inhibitors of G-protein coupled receptors in vivo.

HGPRBMY5v1 polypeptides and polynucleotides have additional uses which include diagnosing diseases related to the over and/or under expression of HGPRBMY5v1 by identifying mutations in the HGPRBMY5v1 polynucleotide by using HGPRBMY5v1 sequences as probes or by determining HGPRBMY5v1 protein or mRNA expression levels. HGPRBMY5v1 polypeptides may be useful for screening compounds that affect the activity of the protein. HGPRBMY5v1 peptides can also be used for the generation of specific antibodies and as bait in yeast two hybrid screens to find proteins the specifically interact with HGPRBMY5v1 (described elsewhere herein).

In preferred embodiments, the following N-terminal HGPRBMY5v1 deletion polypeptides are encompassed by the present invention: M1-S748, Q2-S748, K3-S748, T4-S748, K5-S748, Q6-S748, D7-S748, E8-S748, D9-S748, Y10-S748, E11-S748, R12-S748, A13-S748, I14-S748, G15-S748, F16-S748, S17-S748, V18-S748, K19-S748, M20-S748, D21-S748, D22-S748, S23-S748, D24-S748, S25-S748, D26-S748, F27-S748, A28-S748, L29-S748, T30-S748, Q31-S748, G32-S748, S33-S748, M34-S748, I35-S748, T36-S748, P37-S748, S38-S748, C39-S748, Q40-S748, K41-S748, G42-S748, Y43-S748, F44-S748, P45-S748, C46-S748, G47-S748, N48-S748, L49-S748, T50-S748, K51-S748, C52-S748, L53-S748, P54-S748, R55-S748, A56-S748, F57-S748, H58-S748, C59-S748, D60-S748, G61-S748, K62-S748, D63-S748, D64-S748, C65-S748, G66-S748, N67-S748, G68-S748, A69-S748, D70-S748, E71-S748, E72-S748, N73-S748, C74-S748, G75-S748, D76-S748, T77-S748, S78-S748, G79-S748, W80-S748, A81-S748, T82-S748, I83-S748, F84-S748, G85-S748, T86-S748, V87-S748, H88-S748, G89-S748, N90-S748, A91-S748, N92-S748, S93-S748, V94-S748, A95-S748, L96-S748, T97-S748, Q98-S748, E99-S748, C100-S748, F101-S748, L102-S748, K103-S748, Q104-S748, Y105-S748, P106-S748, Q107-S748, C108-S748, C109-S748, D110-S748, C111-S748, K112-S748, E113-S748, T114-S748, E115-S748, L116-S748, E117-S748, C118-S748, V119-S748, N120-S748, G121-S748, D122-S748, L123-S748, K124-S748, S125-S748, V126-S748, P127-S748, M128-S748, I129-S748, S130-S748, N131-S748, N132-S748, V133-S748, T134-S748, L135-S748, L136-S748, S137-S748, L138-S748, K139-S748, K140-S748, N141-S748, K142-S748, I143-S748, H144-S748, S145-S748, L146-S748, P147-S748, D148-S748, K149-S748, V150-S748, F151-S748, I152-S748, K153-S748, Y154-S748, T155-S748, K156-S748, L157-S748, K158-S748, K159-S748, I160-S748, F161-S748, L162-S748, Q163-S748, H164-S748, N165-S748, C166-S748, I167-S748, R168-S748, H169-S748, I170-S748, S171-S748, R172-S748, K173-S748, A174-S748, F175-S748, F176-S748, G177-S748, L178-S748, C179-S748, N180-S748, L181-S748, Q182-S748, I183-S748, L184-S748, Y185-S748, L186-S748, N187-S748, H188-S748, N189-S748, C190-S748, I191-S748, T192-S748, T193-S748, L194-S748, R195-S748, P196-S748, G197-S748, I198-S748, F199-S748, K200-S748, D201-S748, L202-S748, H203-S748, Q204-S748, L205-S748, T206-S748, W207-S748, L208-S748, I209-S748, L210-S748, D211-S748, D212-S748, N213-S748, P214-S748, I215-S748, T216-S748, R217-S748, I218-S748, S219-S748, Q220-S748, R221-S748, L222-S748, F223-S748, T224-S748, G225-S748, L226-S748, N227-S748, S228-S748, L229-S748, F230-S748, F231-S748, L232-S748, S233-S748, M234-S748, V235-S748, N236-S748, N237-S748, Y238-S748, L239-S748, E240-S748, A241-S748, L242-S748, P243-S748, K244-S748, Q245-S748, M246-S748, C247-S748, A248-S748, Q249-S748, M250-S748, P251-S748, Q252-S748, L253-S748, N254-S748, W255-S748, V256-S748, D257-S748, L258-S748, E259-S748, G260-S748, N261-S748, R262-S748, I263-S748, K264-S748, Y265-S748, L266-S748, T267-S748, N268-S748, S269-S748, T270-S748, F271-S748, L272-S748, S273-S748, C274-S748, D275-S748, S276-S748, L277-S748, T278-S748, V279-S748, L280-S748, F281-S748, L282-S748, P283-S748, R284-S748, N285-S748, Q286-S748, I287-S748, G288-S748, F289-S748, V290-S748, P291-S748, E292-S748, K293-S748, T294-S748, F295-S748, S296-S748, S297-S748, L298-S748, K299-S748, N300-S748, L301-S748, G302-S748, E303-S748, L304-S748, D305-S748, L306-S748, S307-S748, S308-S748, N309-S748, T310-S748, I311-S748, T312-S748, E313-S748, L314-S748, S315-S748, P316-S748, H317-S748, L318-S748, F319-S748, K320-S748, D321-S748, L322-S748, K323-S748, L324-S748, L325-S748, Q326-S748, K327-S748, L328-S748, N329-S748, L330-S748, S331-S748, S332-S748, N333-S748, P334-S748, L335-S748, M336-S748, Y337-S748, L338-S748, H339-S748, K340-S748, N341-S748, Q342-S748, F343-S748, E344-S748, S345-S748, L346-S748, K347-S748, Q348-S748, L349-S748, Q350-S748, S351-S748, L352-S748, D353-S748, L354-S748, E355-S748, R356-S748, I357-S748, E358-S748, I359-S748, P360-S748, N361-S748, I362-S748, N363-S748, T364-S748, R365-S748, M366-S748, F367-S748, Q368-S748, P369-S748, M370-S748, K371-S748, N372-S748, L373-S748, S374-S748, H375-S748, I376-S748, Y377-S748, F378-S748, K379-S748, N380-S748, F381-S748, R382-S748, Y383-S748, C384-S748, S385-S748, Y386-S748, A387-S748, P388-S748, H389-S748, V390-S748, R391-S748, I392-S748, C393-S748, M394-S748, P395-S748, L396-S748, T397-S748, D398-S748, G399-S748, I400-S748, S401-S748, S402-S748, F403-S748, E404-S748, D405-S748, L406-S748, L407-S748, A408-S748, N409-S748, N410-S748, I411-S748, L412-S748, R413-S748, I414-S748, F415-S748, V416-S748, W417-S748, V418-S748, I419-S748, A420-S748, F421-S748, I422-S748, T423-S748, C424-S748, F425-S748, G426-S748, N427-S748, L428-S748, F429-S748, V430-S748, I431-S748, G432-S748, M433-S748, R434-S748, S435-S748, F436-S748, I437-S748, K438-S748, A439-S748, E440-S748, N441-S748, T442-S748, T443-S748, H444-S748, A445-S748, M446-S748, S447-S748, I448-S748, K449-S748, I450-S748, L451-S748, C452-S748, C453-S748, A454-S748, D455-S748, C456-S748, L457-S748, M458-S748, G459-S748, V460-S748, Y461-S748, L462-S748, F463-S748, F464-S748, V465-S748, G466-S748, I467-S748, F468-S748, D469-S748, I470-S748, K471-S748, Y472-S748, R473-S748, G474-S748, Q475-S748, Y476-S748, Q477-S748, K478-S748, Y479-S748, A480-S748, L481-S748, L482-S748, W483-S748, M484-S748, E485-S748, S486-S748, V487-S748, Q488-S748, C489-S748, R490-S748, L491-S748, M492-S748, G493-S748, F494-S748, L495-S748, A496-S748, M497-S748, L498-S748, S499-S748, T500-S748, E501-S748, V502-S748, S503-S748, V504-S748, L505-S748, L506-S748, L507-S748, T508-S748, Y509-S748, L510-S748, T511-S748, L512-S748, E513-S748, K514-S748, F515-S748, L516-S748, V517-S748, I518-S748, V519-S748, F520-S748, P521-S748, F522-S748, S523-S748, N524-S748, I525-S748, R526-S748, P527-S748, G528-S748, K529-S748, R530-S748, Q531-S748, T532-S748, S533-S748, V534-S748, I535-S748, L536-S748, I537-S748, C538-S748, I539-S748, W540-S748, M541-S748, A542-S748, G543-S748, F544-S748, L545-S748, I546-S748, A547-S748, V548-S748, I549-S748, P550-S748, F551-S748, W552-S748, N553-S748, K554-S748, D555-S748, Y556-S748, F557-S748, G558-S748, N559-S748, F560-S748, Y561-S748, G562-S748, K563-S748, N564-S748, G565-S748, V566-S748, C567-S748, F568-S748, P569-S748, L570-S748, Y571-S748, Y572-S748, D573-S748, Q574-S748, T575-S748, E576-S748, D577-S748, I578-S748, G579-S748, S580-S748, K581-S748, G582-S748, Y583-S748, S584-S748, L585-S748, G586-S748, I587-S748, F588-S748, L589-S748, G590-S748, V591-S748, N592-S748, L593-S748, L594-S748, A595-S748, F596-S748, L597-S748, I598-S748, I599-S748, V600-S748, F601-S748, S602-S748, Y603-S748, I604-S748, T605-S748, M606-S748, F607-S748, C608-S748, S609-S748, I610-S748, Q611-S748, K612-S748, T613-S748, A614-S748, L615-S748, Q616-S748, T617-S748, T618-S748, E619-S748, V620-S748, R621-S748, N622-S748, C623-S748, F624-S748, G625-S748, R626-S748, E627-S748, V628-S748, A629-S748, V630-S748, A631-S748, N632-S748, R633-S748, F634-S748, F635-S748, F636-S748, I637-S748, V638-S748, F639-S748, S640-S748, D641-S748, A642-S748, I643-S748, C644-S748, W645-S748, I646-S748, P647-S748, V648-S748, F649-S748, V650-S748, V651-S748, K652-S748, I653-S748, L654-S748, S655-S748, L656-S748, F657-S748, R658-S748, V659-S748, E660-S748, I661-S748, P662-S748, D663-S748, T664-S748, M665-S748, T666-S748, S667-S748, W668-S748, I669-S748, V670-S748, I671-S748, F672-S748, F673-S748, L674-S748, P675-S748, V676-S748, N677-S748, S678-S748, A679-S748, L680-S748, N681-S748, P682-S748, I683-S748, L684-S748, Y685-S748, T686-S748, L687-S748, T688-S748, T689-S748, N690-S748, F691-S748, F692-S748, K693-S748, D694-S748, K695-S748, L696-S748, K697-S748, Q698-S748, L699-S748, L700-S748, H701-S748, K702-S748, H703-S748, Q704-S748, R705-S748, K706-S748, S707-S748, I708-S748, F709-S748, K710-S748, I711-S748, K712-S748, K713-S748, K714-S748, S715-S748, L716-S748, S717-S748, T718-S748, S719-S748, I720-S748, V721-S748, W722-S748, I723-S748, E724-S748, D725-S748, S726-S748, S727-S748, S728-S748, L729-S748, K730-S748, L731-S748, G732-S748, V733-S748, L734-S748, N735-S748, K736-S748, I737-S748, T738-S748, L739-S748, G740-S748, D741-S748, and/or S742-S748 of SEQ ID NO:2. Polynucleotide sequences encoding these polypeptides are also provided. The present invention also encompasses the use of these N-terminal HGPRBMY5v1 deletion polypeptides as immunogenic and/or antigenic epitopes as described elsewhere herein.

In preferred embodiments, the following C-terminal HGPRBMY5v1 deletion polypeptides are encompassed by the present invention: M1-S748, M1-V747, M1-P746, M1-K745, M1-M744, M1-I743, M1-S742, M1-D741, M1-G740, M1-L739, M1-T738, M1-I737, M1-K736, M1-N735, M1-L734, M1-V733, M1-G732, M1-L731, M1-K730, M1-L729, M1-S728, M1-S727, M1-S726, M1-D725, M1-E724, M1-I723, M1-W722, M1-V721, M1-I720, M1-S719, M1-T718, M1-S717, M1-L716, M1-S715, M1-K714, M1-K713, M1-K712, M1-I711, M1-K710, M1-F709, M1-I708, M1-S707, M1-K706, M1-R705, M1-Q704, M1-H703, M1-K702, M1-H701, M1-L700, M1-L699, M1-Q698, M1-K697, M1-L696, M1-K695, M1-D694, M1-K693, M1-F692, M1-F691, M1-N690, M1-T689, M1-T688, M1-L687, M1-T686, M1-Y685, M1-L684, M1-I683, M1-P682, M1-N681, M1-L680, M1-A679, M1-S678, M1-N677, M1-V676, M1-P675, M1-L674, M1-F673, M1-F672, M1-I671, M1-V670, M1-I669, M1-W668, M1-S667, M1-T666, M1-M665, M1-T664, M1-D663, M1-P662, M1-I661, M1-E660, M1-V659, M1-R658, M1-F657, M1-L656, M1-S655, M1-L654, M1-I653, M1-K652, M1-V651, M1-V650, M1-F649, M1-V648, M1-P647, M1-I646, M1-W645, M1-C644, M1-I643, M1-A642, M1-D641, M1-S640, M1-F639, M1-V638, M1-I637, M1-F636, M1-F635, M1-F634, M1-R633, M1-N632, M1-A631, M1-V630, M1-A629, M1-V628, M1-E627, M1-R626, M1-G625, M1-F624, M1-C623, M1-N622, M1-R621, M1-V620, M1-E619, M1-T618, M1-T617, M1-Q616, M1-L615, M1-A614, M1-T613, M1-K612, M1-Q611, M1-I610, M1-S609, M1-C608, M1-F607, M1-M606, M1-T605, M1-I604, M1-Y603, M1-S602, M1-F601, M1-V600, M1-I599, M1-I598, M1-L597, M1-F596, M1-A595, M1-L594, M1-L593, M1-N592, M1-V591, M1-G590, M1-L589, M1-F588, M1-I587, M1-G586, M1-L585, M1-S584, M1-Y583, M1-G582, M1-K581, M1-S580, M1-G579, M1-I578, M1-D577, M1-E576, M1-T575, M1-Q574, M1-D573, M1-Y572, M1-Y571, M1-L570, M1-P569, M1-F568, M1-C567, M1-V566, M1-G565, M1-N564, M1-K563, M1-G562, M1-Y561, M1-F560, M1-N559, M1-G558, M1-F557, M1-Y556, M1-D555, M1-K554, M1-N553, M1-W552, M1-F551, M1-P550, M1-I549, M1-V548, M1-A547, M1-I546, M1-L545, M1-F544, M1-G543, M1-A542, M1-M541, M1-W540, M1-I539, M1-C538, M1-I537, M1-L536, M1-I535, M1-V534, M1-S533, M1-T532, M1-Q531, M1-R530, M1-K529, M1-G528, M1-P527, M1-R526, M1-I525, M1-N524, M1-S523, M1-F522, M1-P521, M1-F520, M1-V519, M1-I518, M1-V517, M1-L516, M1-F515, M1-K514, M1-E513, M1-L512, M1-T511, M1-L510, M1-Y509, M1-T508, M1-L507, M1-L506, M1-L505, M1-V504, M1-S503, M1-V502, M1-E501, M1-T500, M1-S499, M1-L498, M1-M497, M1-A496, M1-L495, M1-F494, M1-G493, M1-M492, M1-L491, M1-R490, M1-C489, M1-Q488, M1-V487, M1-S486, M1-E485, M1-M484, M1-W483, M1-L482, M1-L481, M1-A480, M1-Y479, M1-K478, M1-Q477, M1-Y476, M1-Q475, M1-G474, M1-R473, M1-Y472, M1-K471, M1-I470, M1-D469, M1-F468, M1-I467, M1-G466, M1-V465, M1-F464, M1-F463, M1-L462, M1-Y461, M1-V460, M1-G459, M1-M458, M1-L457, M1-C456, M1-D455, M1-A454, M1-C453, M1-C452, M1-L451, M1-I450, M1-K449, M1-I448, M1-S447, M1-M446, M1-A445, M1-H444, M1-T443, M1-T442, M1-N441, M1-E440, M1-A439, M1-K438, M1-I437, M1-F436, M1-S435, M1-R434, M1-M433, M1-G432, M1-I431, M1-V430, M1-F429, M1-L428, M1-N427, M1-G426, M1-F425, M1-C424, M1-T423, M1-I422, M1-F421, M1-A420, M1-I419, M1-V418, M1-W417, M1-V416, M1-F415, M1-I414, M1-R413, M1-L412, M1-I411, M1-N410, M1-N409, M1-A408, M1-L407, M1-L406, M1-D405, M1-E404, M1-F403, M1-S402, M1-S401, M1-I400, M1-G399, M1-D398, M1-T397, M1-L396, M1-P395, M1-M394, M1-C393, M1-I392, M1-R391, M1-V390, M1-H389, M1-P388, M1-A387, M1-Y386, M1-S385, M1-C384, M1-Y383, M1-R382, M1-F381, M1-N380, M1-K379, M1-F378, M1-Y377, M1-I376, M1-H375, M1-S374, M1-L373, M1-N372, M1-K371, M1-M370, M1-P369, M1-Q368, M1-F367, M1-M366, M1-R365, M1-T364, M1-N363, M1-I362, M1-N361, M1-P360, M1-I359, M1-E358, M1-I357, M1-R356, M1-E355, M1-L354, M1-D353, M1-L352, M1-S351, M1-Q350, M1-L349, M1-Q348, M1-K347, M1-L346, M1-S345, M1-E344, M1-F343, M1-Q342, M1-N341, M1-K340, M1-H339, M1-L338, M1-Y337, M1-M336, M1-L335, M1-P334, M1-N333, M1-S332, M1-S331, M1-L330, M1-N329, M1-L328, M1-K327, M1-Q326, M1-L325, M1-L324, M1-K323, M1-L322, M1-D321, M1-K320, M1-F319, M1-L318, M1-H317, M1-P316, M1-S315, M1-L314, M1-E313, M1-T312, M1-I311, M1-T310, M1-N309, M1-S308, M1-S307, M1-L306, M1-D305, M1-L304, M1-E303, M1-G302, M1-L301, M1-N300, M1-K299, M1-L298, M1-S297, M1-S296, M1-F295, M1-T294, M1-K293, M1-E292, M1-P291, M1-V290, M1-F289, M1-G288, M1-I287, M1-Q286, M1-N285, M1-R284, M1-P283, M1-L282, M1-F281, M1-L280, M1-V279, M1-T278, M1-L277, M1-S276, M1-D275, M1-C274, M1-S273, M1-L272, M1-F271, M1-T270, M1-S269, M1-N268, M1-T267, M1-L266, M1-Y265, M1-K264, M1-I263, M1-R262, M1-N261, M1-G260, M1-E259, M1-L258, M1-D257, M1-V256, M1-W255, M1-N254, M1-L253, M1-Q252, M1-P251, M1-M250, M1-Q249, M1-A248, M1-C247, M1-M246, M1-Q245, M1-K244, M1-P243, M1-L242, M1-A241, M1-E240, M1-L239, M1-Y238, M1-N237, M1-N236, M1-V235, M1-M234, M1-S233, M1-L232, M1-F231, M1-F230, M1-L229, M1-S228, M1-N227, M1-L226, M1-G225, M1-T224, M1-F223, M1-L222, M1-R221, M1-Q220, M1-S219, M1-I218, M1-R217, M1-T216, M1-I215, M1-P214, M1-N213, M1-D212, M1-D211, M1-L210, M1-I209, M1-L208, M1-W207, M1-T206, M1-L205, M1-Q204, M1-H203, M1-L202, M1-D201, M1-K200, M1-F199, M1-I198, M1-G197, M1-P196, M1-R195, M1-L194, M1-T193, M1-T192, M1-I191, M1-C190, M1-N189, M1-H188, M1-N187, M1-L186, M1-Y185, M1-L184, M1-I183, M1-Q182, M1-L181, M1-N180, M1-C179, M1-L178, M1-G177, M1-F176, M1-F175, M1-A174, M1-K173, M1-R172, M1-S171, M1-I170, M1-H169, M1-R168, M1-I167, M1-C166, M1-N165, M1-H164, M1-Q163, M1-L162, M1-F161, M1-I160, M1-K159, M1-K158, M1-L157, M1-K156, M1-T155, M1-Y154, M1-K153, M1-I152, M1-F151, M1-V150, M1-K149, M1-D148, M1-P147, M1-L146, M1-S145, M1-H144, M1-I143, M1-K142, M1-N141, M1-K140, M1-K139, M1-L138, M1-S137, M1-L136, M1-L135, M1-T134, M1-V133, M1-N132, M1-N131, M1-S130, M1-I129, M1-M128, M1-P127, M1-V126, M1-S125, M1-K124, M1-L123, M1-D122, M1-G121, M1-N120, M1-V119, M1-C118, M1-E117, M1-L116, M1-E115, M1-T114, M1-E113, M1-K112, M1-C111, M1-D110, M1-C109, M1-C108, M1-Q107, M1-P106, M1-Y105, M1-Q104, M1-K103, M1-L102, M1-F110, M1-C100, M1-E99, M1-Q98, M1-T97, M1-L96, M1-A95, M1-V94, M1-S93, M1-N92, M1-A91, M1-N90, M1-G89, M1-H88, M1-V87, M1-T86, M1-G85, M1-F84, M1-I83, M1-T82, M1-A81, M1-W80, M1-G79, M1-S78, M1-T77, M1-D76, M1-G75, M1-C74, M1-N73, M1-E72, M1-E71, M1-D70, M1-A69, M1-G68, M1-N67, M1-G66, M1-C65, M1-D64, M1-D63, M1-K62, M1-G61, M1-D60, M1-C59, M1-H58, M1-F57, M1-A56, M1-R55, M1-P54, M1-L53, M1-C52, M1-K51, M1-T50, M1-L49, M1-N48, M1-G47, M1-C46, M1-P45, M1-F44, M1-Y43, M1-G42, M1-K41, M1-Q40, M1-C39, M1-S38, M1-P37, M1-T36, M1-I35, M1-M34, M1-S33, M1-G32, M1-Q31, M1-T30, M1-L29, M1-A28, M1-F27, M1-D26, M1-S25, M1-D24, M1-S23, M1-D22, M1-D21, M1-M20, M1-K19, M1-V18, M1-S17, M1-F16, M1-G15, M1-I14, M1-A13, M1-R12, M1-E11, M1-Y10, M1-D9, M1-E8, and/or M1-D7 of SEQ ID NO:2. Polynucleotide sequences encoding these polypeptides are also provided. The present invention also encompasses the use of these C-terminal HGPRBMY5v1 deletion polypeptides as immunogenic and/or antigenic epitopes as described elsewhere herein.

Alternatively, preferred polypeptide sequences of the present invention may comprise polypeptide sequences corresponding to, for example, internal regions of the HGPRBMY5v1 polypeptide (e.g., any combination of both N- and C-terminal HGPRBMY5v1 polypeptide deletions) of SEQ ID NO:2. For example, internal regions could be defined by the equation: amino acid NX to amino acid CX, wherein NX refers to any N-terminal deletion polypeptide amino acid of HGPRBMY5v1 (SEQ ID NO:2), and where CX refers to any C-terminal deletion polypeptide amino acid of HGPRBMY5v1 (SEQ ID NO:2). Polynucleotides encoding these polypeptides are also provided. The present invention also encompasses the use of these polypeptides as an immunogenic and/or antigenic epitope as described elsewhere herein.

In preferred embodiments, the following N-terminal HGPRBMY5v2 deletion polypeptides are encompassed by the present invention: M1-S724, Q2-S724, K3-S724, T4-S724, K5-S724, Q6-S724, D7-S724, E8-S724, D9-S724, Y10-S724, E11-S724, R12-S724, A13-S724, I14-S724, G15-S724, F16-S724, S17-S724, V18-S724, K19-S724, M20-S724, D21-S724, D22-S724, S23-S724, D24-S724, S25-S724, D26-S724, F27-S724, A28-S724, L29-S724, T30-S724, Q31-S724, G32-S724, S33-S724, M34-S724, I35-S724, T36-S724, P37-S724, S38-S724, C39-S724, Q40-S724, K41-S724, G42-S724, Y43-S724, F44-S724, P45-S724, C46-S724, G47-S724, N48-S724, L49-S724, T50-S724, K51-S724, C52-S724, L53-S724, P54-S724, R55-S724, A56-S724, F57-S724, H58-S724, C59-S724, D60-S724, G61-S724, K62-S724, D63-S724, D64-S724, C65-S724, G66-S724, N67-S724, G68-S724, A69-S724, D70-S724, E71-S724, E72-S724, N73-S724, C74-S724, G75-S724, D76-S724, T77-S724, S78-S724, G79-S724, W80-S724, A81-S724, T82-S724, I83-S724, F84-S724, G85-S724, T86-S724, V87-S724, H88-S724, G89-S724, N90-S724, A91-S724, N92-S724, S93-S724, V94-S724, A95-S724, L96-S724, T97-S724, Q98-S724, E99-S724, C100-S724, F101-S724, L102-S724, K103-S724, Q104-S724, Y105-S724, P106-S724, Q107-S724, C108-S724, C109-S724, D110-S724, C111-S724, K112-S724, E113-S724, T114-S724, E115-S724, L116-S724, E117-S724, C118-S724, V119-S724, N120-S724, G121-S724, D122-S724, L123-S724, K124-S724, S125-S724, V126-S724, P127-S724, M128-S724, I129-S724, S130-S724, N131-S724, N132-S724, V133-S724, T134-S724, L135-S724, L136-S724, S724, S137-S724, L138-S724, K139-S724, K140-S724, N141-S724, K142-S724, I143-S724, H144-S724, S145-S724, L146-S724, P147-S724, D148-S724, K149-S724, V150-S724, F151-S724, I152-S724, K153-S724, Y154-S724, T155-S724, K156-S724, L157-S724, K158-S724, K159-S724, I160-S724, F161-S724, L162-S724, Q163-S724, H164-S724, N165-S724, C166-S724, I167-S724, R168-S724, H169-S724, I170-S724, S171-S724, R172-S724, K173-S724, A174-S724, F175-S724, F176-S724, G177-S724, L178-S724, C179-S724, N180-S724, L181-S724, Q182-S724, I183-S724, L184-S724, I185-S724, L186-S724, D187-S724, D188-S724, N189-S724, P190-S724, I191-S724, T192-S724, R193-S724, I194-S724, S195-S724, Q196-S724, R197-S724, L198-S724, F199-S724, T200-S724, G201-S724, L202-S724, N203-S724, S204-S724, L205-S724, F206-S724, F207-S724, L208-S724, S209-S724, M210-S724, V211-S724, N212-S724, N213-S724, Y214-S724, L215-S724, E216-S724, A217-S724, L218-S724, P219-S724, K220-S724, Q221-S724, M222-S724, C223-S724, A224-S724, Q225-S724, M226-S724, P227-S724, Q228-S724, L229-S724, N230-S724, W231-S724, V232-S724, D233-S724, L234-S724, E235-S724, G236-S724, N237-S724, R238-S724, I239-S724, K240-S724, Y241-S724, L242-S724, T243-S724, N244-S724, S245-S724, T246-S724, F247-S724, L248-S724, S249-S724, C250-S724, D251-S724, S252-S724, L253-S724, T254-S724, V255-S724, L256-S724, F257-S724, L258-S724, P259-S724, R260-S724, N261-S724, Q262-S724, I263-S724, G264-S724, F265-S724, V266-S724, P267-S724, E268-S724, K269-S724, T270-S724, F271-S724, S272-S724, S273-S724, L274-S724, K275-S724, N276-S724, L277-S724, G278-S724, E279-S724, L280-S724, D281-S724, L282-S724, S283-S724, S284-S724, N285-S724, T286-S724, I287-S724, T288-S724, E289-S724, L290-S724, S291-S724, P292-S724, H293-S724, L294-S724, F295-S724, K296-S724, D297-S724, L298-S724, K299-S724, L300-S724, L301-S724, Q302-S724, K303-S724, L304-S724, N305-S724, L306-S724, S307-S724, S308-S724, N309-S724, P310-S724, L311-S724, M312-S724, Y313-S724, L314-S724, H315-S724, K316-S724, N317-S724, Q318-S724, F319-S724, E320-S724, S321-S724, L322-S724, K323-S724, Q324-S724, L325-S724, Q326-S724, S327-S724, L328-S724, D329-S724, L330-S724, E331-S724, R332-S724, I333-S724, E334-S724, I335-S724, P336-S724, N337-S724, I338-S724, N339-S724, T340-S724, R341-S724, M342-S724, F343-S724, Q344-S724, P345-S724, M346-S724, K347-S724, N348-S724, L349-S724, S350-S724, H351-S724, I352-S724, Y353-S724, F354-S724, K355-S724, N356-S724, F357-S724, R358-S724, Y359-S724, C360-S724, S361-S724, Y362-S724, A363-S724, P364-S724, H365-S724, V366-S724, R367-S724, I368-S724, C369-S724, M370-S724, P371-S724, L372-S724, T373-S724, D374-S724, G375-S724, I376-S724, S377-S724, S378-S724, F379-S724, E380-S724, D381-S724, L382-S724, L383-S724, A384-S724, N385-S724, N386-S724, I387-S724, L388-S724, R389-S724, I390-S724, F391-S724, V392-S724, W393-S724, V394-S724, I395-S724, A396-S724, F397-S724, I398-S724, T399-S724, C400-S724, F401-S724, G402-S724, N403-S724, L404-S724, F405-S724, V406-S724, I407-S724, G408-S724, M409-S724, R410-S724, S411-S724, F412-S724, I413-S724, K414-S724, A415-S724, E416-S724, N417-S724, T418-S724, T419-S724, H420-S724, A421-S724, M422-S724, S423-S724, I424-S724, K425-S724, I426-S724, L427-S724, C428-S724, C429-S724, A430-S724, D431-S724, C432-S724, L433-S724, M434-S724, G435-S724, V436-S724, Y437-S724, L438-S724, F439-S724, F440-S724, V441-S724, G442-S724, I443-S724, F444-S724, D445-S724, I446-S724, K447-S724, Y448-S724, R449-S724, G450-S724, Q451-S724, Y452-S724, Q453-S724, K454-S724, Y455-S724, A456-S724, L457-S724, L458-S724, W459-S724, M460-S724, E461-S724, S462-S724, V463-S724, Q464-S724, C465-S724, R466-S724, L467-S724, M468-S724, G469-S724, F470-S724, L471-S724, A472-S724, M473-S724, L474-S724, S475-S724, T476-S724, E477-S724, V478-S724, S479-S724, V480-S724, L481-S724, L482-S724, L483-S724, T484-S724, Y485-S724, L486-S724, T487-S724, L488-S724, E489-S724, K490-S724, F491-S724, L492-S724, V493-S724, I494-S724, V495-S724, F496-S724, P497-S724, F498-S724, S499-S724, N500-S724, I501-S724, R502-S724, P503-S724, G504-S724, K505-S724, R506-S724, Q507-S724, T508-S724, S509-S724, V510-S724, I511-S724, L512-S724, I513-S724, C514-S724, I515-S724, W516-S724, M517-S724, A518-S724, G519-S724, F520-S724, L521-S724, I522-S724, A523-S724, V524-S724, I525-S724, P526-S724, F527-S724, W528-S724, N529-S724, K530-S724, D531-S724, Y532-S724, F533-S724, G534-S724, N535-S724, F536-S724, Y537-S724, G538-S724, K539-S724, N540-S724, G541-S724, V542-S724, C543-S724, F544-S724, P545-S724, L546-S724, Y547-S724, Y548-S724, D549-S724, Q550-S724, T551-S724, E552-S724, D553-S724, I554-S724, G555-S724, S556-S724, K557-S724, G558-S724, Y559-S724, S560-S724, L561-S724, G562-S724, I563-S724, F564-S724, L565-S724, G566-S724, V567-S724, N568-S724, L569-S724, L570-S724, A571-S724, F572-S724, L573-S724, I574-S724, I575-S724, V576-S724, F577-S724, S578-S724, Y579-S724, I580-S724, T581-S724, M582-S724, F583-S724, C584-S724, S585-S724, I586-S724, Q587-S724, K588-S724, T589-S724, A590-S724, L591-S724, Q592-S724, T593-S724, T594-S724, E595-S724, V596-S724, R597-S724, N598-S724, C599-S724, F600-S724, G601-S724, R602-S724, E603-S724, V604-S724, A605-S724, V606-S724, A607-S724, N608-S724, R609-S724, F610-S724, F611-S724, F612-S724, I613-S724, V614-S724, F615-S724, S616-S724, D617-S724, A618-S724, I619-S724, C620-S724, W621-S724, I622-S724, P623-S724, V624-S724, F625-S724, V626-S724, V627-S724, K628-S724, I629-S724, L630-S724, S631-S724, L632-S724, F633-S724, R634-S724, V635-S724, E636-S724, I637-S724, P638-S724, D639-S724, T640-S724, M641-S724, T642-S724, S643-S724, W644-S724, I645-S724, V646-S724, I647-S724, F648-S724, F649-S724, L650-S724, P651-S724, V652-S724, N653-S724, S654-S724, A655-S724, L656-S724, N657-S724, P658-S724, I659-S724, L660-S724, Y661-S724, T662-S724, L663-S724, T664-S724, T665-S724, N666-S724, F667-S724, F668-S724, K669-S724, D670-S724, K671-S724, L672-S724, K673-S724, Q674-S724, L675-S724, L676-S724, H677-S724, K678-S724, H679-S724, Q680-S724, R681-S724, K682-S724, S683-S724, I684-S724, F685-S724, K686-S724, I687-S724, K688-S724, K689-S724, K690-S724, S691-S724, L692-S724, S693-S724, T694-S724, S695-S724, I696-S724, V697-S724, W698-S724, I699-S724, E700-S724, D701-S724, S702-S724, S703-S724, S704-S724, L705-S724, K706-S724, L707-S724, G708-S724, V709-S724, L710-S724, N711-S724, K712-S724, I713-S724, T714-S724, L715-S724, G716-S724, D717-S724, S718-S724, and/or S718-S724 of SEQ ID NO:82. Polynucleotide sequences encoding these polypeptides are also provided. The present invention also encompasses the use of these N-terminal HGPRBMY5v2 deletion polypeptides as immunogenic and/or antigenic epitopes as described elsewhere herein.

In preferred embodiments, the following C-terminal HGPRBMY5v2 deletion polypeptides are encompassed by the present invention: M1-S724, M1-V723, M1-P722, M1-K721, M1-M720, M1-I719, M1-S718, M1-D717, M1-G716, M1-L715, M1-T714, M1-I713, M1-K712, M1-N711, M1-L710, M1-V709, M1-G708, M1-L707, M1-K706, M1-L705, M1-S704, M1-S703, M1-S702, M1-D701, M1-E700, M1-I699, M1-W698, M1-V697, M1-I696, M1-S695, M1-T694, M1-S693, M1-L692, M1-S691, M1-K690, M1-K689, M1-K688, M1-I687, M1-K686, M1-F685, M1-I684, M1-S683, M1-K682, M1-R681, M1-Q680, M1-H679, M1-K678, M1-H677, M1-L676, M1-L675, M1-Q674, M1-K673, M1-L672, M1-K671, M1-D670, M1-K669, M1-F668, M1-F667, M1-N666, M1-T665, M1-T664, M1-L663, M1-T662, M1-Y661, M1-L660, M1-I659, M1-P658, M1-N657, M1-L656, M1-A655, M1-S654, M1-N653, M1-V652, M1-P651, M1-L650, M1-F649, M1-F648, M1-I647, M1-V646, M1-I645, M1-W644, M1-S643, M1-T642, M1-M641, M1-T640, M1-D639, M1-P638, M1-I637, M1-E636, M1-V635, M1-R634, M1-F633, M1-L632, M1-S631, M1-L630, M1-I629, M1-K628, M1-V627, M1-V626, M1-F625, M1-V624, M1-P623, M1-I622, M1-W621, M1-C620, M1-I619, M1-A618, M1-D617, M1-S616, M1-F615, M1-V614, M1-I613, M1-F612, M1-F611, M1-F610, M1-R609, M1-N$_{608}$, M1-A607, M1-V606, M1-A605, M1-V604, M1-E603, M1-R602, M1-G601, M1-F600, M1-C599, M1-N598, M1-R597, M1-V596, M1-E595, M1-T594, M1-T593, M1-Q592, M1-L591, M1-A590, M1-T589, M1-K588, M1-Q587, M1-I586, M1-S585, M1-C584, M1-F583, M1-M582, M1-T581, M1-I580, M1-Y579, M1-S578, M1-F577, M1-V576, M1-I575, M1-I574, M1-L573, M1-F572, M1-A571, M1-L570, M1-L569, M1-N568, M1-V567, M1-G566, M1-L565, M1-F564, M1-I563, M1-G562, M1-L561, M1-S560, M1-Y559, M1-G558, M1-K557, M1-S556, M1-G555, M1-I554, M1-D553, M1-E552, M1-T551, M1-Q550, M1-D549, M1-Y548, M1-Y547, M1-L546, M1-P545, M1-F544, M1-C543, M1-V542, M1-G541, M1-N540, M1-K539, M1-G538, M1-Y537, M1-F536, M1-N535, M1-G534, M1-F533, M1-Y532, M1-D531, M1-K530, M1-N529, M1-W528, M1-F527, M1-P526, M1-I525, M1-V524, M1-A523, M1-I522, M1-L521, M1-F520, M1-G519, M1-A518, M1-M517, M1-W516, M1-I515, M1-C514, M1-I513, M1-L512, M1-I511, M1-V510, M1-S509, M1-T508, M1-Q507, M1-R506, M1-K505, M1-G504, M1-P503, M1-R502, M1-I501, M1-N500, M1-S499, M1-F498, M1-P497, M1-F496, M1-V495, M1-I494, M1-V493, M1-L492, M1-F491, M1-K490, M1-E489, M1-L488, M1-T487, M1-L486, M1-Y485, M1-T484, M1-L483, M1-L482, M1-L481, M1-V480, M1-S479, M1-V478, M1-E477, M1-T476, M1-S475, M1-L474, M1-M473, M1-A472, M1-L471, M1-F470, M1-G469, M1-M468, M1-L467, M1-R466, M1-C465, M1-Q464, M1-V463, M1-S462, M1-E461, M1-M460, M1-W459, M1-L458, M1-L457, M1-A456, M1-Y455, M1-K454, M1-Q453, M1-Y452, M1-Q451, M1-G450, M1-R449, M1-Y448, M1-K447, M1-I446, M1-D445, M1-F444, M1-I443, M1-G442, M1-V441, M1-F440, M1-F439, M1-L438, M1-Y437, M1-V436, M1-G435, M1-M434, M1-L433, M1-C432, M1-D431, M1-A430, M1-C429, M1-C428, M1-L427, M1-I426, M1-K425, M1-I424, M1-S423, M1-M422, M1-A421, M1-H420, M1-T419, M1-T418, M1-N417, M1-E416, M1-A415, M1-K414, M1-I413, M1-F412, M1-S411, M1-R410, M1-M409, M1-G408, M1-I407, M1-V406, M1-F405, M1-L404, M1-N403, M1-G402, M1-F401, M1-C400, M1-T399, M1-I398, M1-F397, M1-A396, M1-I395, M1-V394, M1-W393, M1-V392, M1-F391, M1-I390, M1-R389, M1-L388, M1-I387, M1-N386, M1-N385, M1-A384, M1-L383, M1-L382, M1-D381, M1-E380, M1-F379, M1-S378, M1-S377, M1-I376, M1-G375, M1-D374, M1-T373, M1-L372, M1-P371, M1-M370, M1-C369, M1-I368, M1-R367, M1-V366, M1-H365, M1-P364, M1-A363, M1-Y362, M1-S361, M1-C360, M1-Y359, M1-R358, M1-F357, M1-N356, M1-K355, M1-F354, M1-Y353, M1-I352, M1-H351, M1-S350, M1-L349, M1-N348, M1-K347, M1-M346, M1-P345, M1-Q344, M1-F343, M1-M342, M1-R341, M1-T340, M1-N339, M1-I338, M1-N337, M1-P336, M1-I335, M1-E334, M1-I333, M1-R332, M1-E331, M1-L330, M1-D329, M1-L328, M1-S327, M1-Q326, M1-L325, M1-Q324, M1-K323, M1-L322, M1-S321, M1-E320, M1-F319, M1-Q318, M1-N317, M1-K316, M1-H315, M1-L314, M1-Y313, M1-M312, M1-L311, M1-P310, M1-N309, M1-S308, M1-S307, M1-L306, M1-N305, M1-L304, M1-K303, M1-Q302, M1-L301, M1-L300, M1-K299, M1-L298, M1-D297, M1-K296, M1-F295, M1-L294, M1-H293, M1-P292, M1-S291, M1-L290, M1-E289, M1-T288, M1-I287, M1-T286, M1-N285, M1-S284, M1-S283, M1-L282, M1-D281, M1-L280, M1-E279, M1-G278, M1-L277, M1-N276, M1-K275, M1-L274, M1-S273, M1-S272, M1-F271, M1-T270, M1-K269, M1-E268, M1-P267, M1-V266, M1-F265, M1-G264, M1-I263, M1-Q262, M1-N261, M1-R260, M1-P259, M1-L258, M1-F257, M1-L256, M1-V255, M1-T254, M1-L253, M1-S252, M1-D251, M1-C250, M1-S249, M1-L248, M1-F247, M1-T246, M1-S245, M1-N244, M1-T243, M1-L242, M1-Y241, M1-K240, M1-I239, M1-R238, M1-N237, M1-G236, M1-E235, M1-L234, M1-D233, M1-V232, M1-W231, M1-N230, M1-L229, M1-Q228, M1-P227, M1-M226, M1-Q225, M1-A224, M1-C223, M1-M222, M1-Q221, M1-K220, M1-P219, M1-L218, M1-A217, M1-E216, M1-L215, M1-Y214, M1-N213, M1-N212, M1-V211, M1-M210, M1-S209, M1-L208, M1-F207, M1-F206, M1-L205, M1-S204, M1-N203, M1-L202, M1-G201, M1-T200, M1-F199, M1-L198, M1-R197, M1-Q196, M1-S195, M1-I194, M1-R193, M1-T192, M1-I191, M1-P190, M1-N189, M1-D188, M1-D187, M1-L186, M1-I185, M1-L184, M1-I183, M1-Q182, M1-L181, M1-N180, M1-C179, M1-L178, M1-G177, M1-F176, M1-F175, M1-A174, M1-K173, M1-R172, M1-S171, M1-I170, M1-H169, M1-R168, M1-I167, M1-C166, M1-N165, M1-H164, M1-Q163, M1-L162, M1-F161, M1-I160, M1-K159, M1-K158, M1-L157, M1-K156, M1-T155, M1-Y154, M1-K153, M1-I152, M1-F151, M1-V150, M1-K149, M1-D148, M1-P147, M1-L146, M1-S145, M1-H144, M1-I143, M1-K142, M1-N141, M1-K140, M1-K139, M1-L138, M1-S137, M1-L136, M1-L135, M1-T134, M1-V133, M1-N132, M1-N131, M1-S130, M1-I129, M1-M128, M1-P127, M1-V126, M1-S125, M1-K124, M1-L123, M1-D122, M1-G121, M1-N120, M1-V119, M1-C118, M1-E117, M1-L116, M1-E115, M1-T114, M1-E113, M1-K112, M1-C111, M1-D110, M1-C109, M1-C108, M1-Q107, M1-P106, M1-Y105, M1-Q104, M1-K103, M1-L102, M1-F110, M1-C100, M1-E99, M1-Q98, M1-T97, M1-L96, M1-A95, M1-V94, M1-S93, M1-N92, M1-A91, M1-N90, M1-G89, M1-H88, M1-V87, M1-T86, M1-G85, M1-F84, M1-I83, M1-T82, M1-A81, M1-W80, M1-G79, M1-S78, M1-T77, M1-D76, M1-G75, M1-C74, M1-N73, M1-E72, M1-E71, M1-D70, M1-A69, M1-G68, M1-N67, M1-G66, M1-C65, M1-D64, M1-D63, M1-K62, M1-G61, M1-D60, M1-C59, M1-H58, M1-F57, M1-A56, M1-R55, M1-P54, M1-L53, M1-C52, M1-K51, M1-T50, M1-L49, M1-N48, M1-G47, M1-C46, M1-P45, M1-F44, M1-Y43, M1-G42, M1-K41, M1-Q40, M1-C39, M1-S38, M1-P37, M1-T36, M1-I35, M1-M34, M1-S33, M1-G32, M1-Q31, M1-T30, M1-L29, M1-A28, M1-F27, M1-D26, M1-S25, M1-D24, M1-S23, M1-D22, M1-D21, M1-M20, M1-K19, M1-V18, M1-S17, M1-F16, M1-G15, M1-I14, M1-A13, M1-R12, M1-E11, M1-Y10, M1-D9, M1-E8, and/or M1-D7 of SEQ ID NO:82. Polynucleotide sequences encoding these polypeptides are also provided. The present invention also encompasses the use of these C-terminal HGPRBMY5v2 deletion polypeptides as immunogenic and/or antigenic epitopes as described elsewhere herein.

The present invention also encompasses immunogenic and/or antigenic epitopes of the HGPRBMY5v1 polypeptide.

The present invention also encompasses immunogenic and/or antigenic epitopes of the HGPRBMY5v2 polypeptide.

The HGPRBMY5v1 polypeptides of the present invention were determined to comprise several phosphorylation sites based upon the Motif algorithm (Genetics Computer Group, Inc.). The phosphorylation of such sites may regulate some biological activity of the HGPRBMY5v1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the HGPRBMY5v1 polypeptide to associate with other polypeptides, particularly relaxin and/or the INSL3 ligand for HGPRBMY5v1, or its ability to modulate certain cellular signal pathways.

The HGPRBMY5v1 polypeptide was predicted to comprise nine PKC phosphorylation sites using the Motif algorithm (Polynucleotidetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184(1986), and Kishimoto A., Nishiyama K., Nakanishi H., Uratsuji Y., Nomura H., Takeyama Y., Nishizuka Y., J. Biol. Chem. . . . 260:12492-12499(1985); which are hereby incorporated by reference herein.

In preferred embodiments, the following PKC phosphorylation site polypeptides are encompassed by the present invention: RAIGFSVKMDDSD (SEQ ID NO:30), NVTLLSLKKNKIH (SEQ ID NO:31), CIRHISRKAFFGL (SEQ ID NO:32), HNCITTLRPGIFK (SEQ ID NO:33), PITRISQRLFTGL (SEQ ID NO:34), EKTFSSLKNLGEL (SEQ ID NO:35), KNQFESLKQLQSL (SEQ ID NO:36), TTHAMSIKILCCA (SEQ ID NO:37), and/or IEDSSS-LKLGVLN (SEQ ID NO:38). Polynucleotides encoding these polypeptides are also provided. The present invention also encompasses the use of the HGPRBMY5v1 PKC phosphorylation site polypeptides as immunogenic and/or antigenic epitopes as described elsewhere herein.

The HGPRBMY5v1 polypeptide was predicted to comprise eight casein kinase II phosphorylation sites using the Motif algorithm (Polynucleotidetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation site-II domains may be found in reference to the following publication: Pinna L. A., Biochim. Biophys. Acta 1054:267-284(1990); which is hereby incorporated herein in its entirety.

In preferred embodiments, the following casein kinase II phosphorylation site polypeptide is encompassed by the present invention: MQKTKQDEDYER (SEQ ID NO:39), VKMDDSDSDFALTQ (SEQ ID NO:40), CDCK-ETELECVNGD (SEQ ID NO:41), KNKIHSLPDKVFIK (SEQ ID NO:42), DLSSNTITELSPHL (SEQ ID NO:43), LTDGISSFEDLLAN (SEQ ID NO:44), TDGISSFEDL-LANN (SEQ ID NO:45), and/or VLNKITLGDSIMKP (SEQ ID NO:46). Polynucleotides encoding these polypeptides are also provided. The present invention also encompasses the use of this casein kinase II phosphorylation site polypeptide as an immunogenic and/or antigenic epitope as described elsewhere herein.

The HGPRBMY5v1 polypeptide was predicted to comprise two cAMP- and cGMP-dependent protein kinase phosphorylation sites using the Motif algorithm (Polynucleotidetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. . . . 255:4240-4245(1980); Glass D. B., Smith S. B., J. Biol. Chem. 258:14797-14803(1983); and Glass D. B., El-Maghrabi M. R., Pilkis S. J., J. Biol. Chem. 261:2987-2993(1986); which is hereby incorporated herein in its entirety.

In preferred embodiments, the following cAMP- and cGMP-dependent protein kinase phosphorylation site polypeptide is encompassed by the present invention: NIR-PGKRQTSVILI (SEQ ID NO:47), and/or SIFKIKKK-SLSTSI (SEQ ID NO:48). Polynucleotides encoding this polypeptide are also provided. The present invention also encompasses the use of this cAMP- and cGMP-dependent protein kinase phosphorylation site polypeptide as an immunogenic and/or antigenic epitope as described elsewhere herein.

The HGPRBMY5v1 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or or [RK]-x(3)-[DE]-x (2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848(1982), and Cooper J. A., Esch F. S., Taylor S. S., Hunter T., J. Biol. Chem. 259:7835-7841(1984), which are hereby incorporated herein by reference.

In preferred embodiments, the following tyrosine phosphorylation site polypeptides are encompassed by the present invention: MQKTKQDEDYERAIG (SEQ ID NO:49). Polynucleotides encoding these polypeptides are also provided. The present invention also encompasses the use of these HGPRBMY5v1 tyrosine phosphorylation site polypeptides as immunogenic and/or antigenic epitopes as described elsewhere herein.

The HGPRBMY5v1 polypeptide has been shown to comprise six glycosylation site according to the Motif algorithm (Polynucleotidetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702(1972); Pless D. D., Lennarz W. J., Proc. Natl. Acad. Sci. U.S.A. 74:134-138(1977); Bause E., Biochem. J. 209:331-336(1983); Gavel Y., von Heijne G., Protein Eng. 3:433-442(1990); and Miletich J. P., Broze G. J. Jr., J. Biol. Chem. . . . 265:11397-11404(1990).

In preferred embodiments, the following asparagine glycosylation site polypeptides are encompassed by the present invention: YFPCGNLTKCLPRA (SEQ ID NO:50), PMISN-NVTLLSLKK (SEQ ID NO:51), IKYLTNSTFLSCDS (SEQ ID NO:52), LLQKLNLSSNPLMY (SEQ ID NO:53), FQPMKNLSHIYFKN (SEQ ID NO:54), and/or FIKAENT-THAMSIK (SEQ ID NO:55). Polynucleotides encoding these polypeptides are also provided. The present invention also encompasses the use of these HGPRBMY5v1 asparagine glycosylation site polypeptide as immunogenic and/or antigenic epitopes as described elsewhere herein.

The HGPRBMY5v1 polypeptide was predicted to comprise four N-myristoylation sites using the Motif algorithm (Polynucleotidetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA:protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99(1988); and Grand R. J. A., Biochem. J. 258:625-638(1989); which is hereby incorporated herein in its entirety.

In preferred embodiments, the following N-myristoylation site polypeptides are encompassed by the present invention: WATIFGTVHGNANSVA (SEQ ID NO:56), FGTVHGNANSVALTQE (SEQ ID NO:57), NKDYFGNFYGKNGVCF (SEQ ID NO:58), and/or KGYSLGIFLGVNLLAF (SEQ ID NO:59). Polynucleotides encoding these polypeptides are also provided. The present invention also encompasses the use of these N-myristoylation site polypeptides as immunogenic and/or antigenic epitopes as described elsewhere herein.

The HGPRBMY5v1 polypeptide has been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106:218-223(1984); and Bradbury A. F., Smyth D. G., Biosci. Rep. 7:907-916(1987).

In preferred embodiments, the following amidation site polypeptide is encompassed by the present invention: FSNIRPGKRQTSVI (SEQ ID NO:60). Polynucleotides encoding these polypeptides are also provided. The present invention also encompasses the use of this HGPRBMY5v1 amidation site polypeptide as an immunogenic and/or antigenic epitope as described elsewhere herein.

The HGPRBMY5v1 polypeptide has been shown to comprise one leucine zipper site according to the Motif algorithm (Genetics Computer Group, Inc.). Leucine zipper sites have been proposed to explain how some eukaryotic gene regulatory proteins work. The leucine zipper consists of a periodic repetition of leucine residues at every seventh position over a distance covering eight helical turns. The segments containing these periodic arrays of leucine residues seem to exist in an alpha-helical conformation. The leucine side chains extending from one alpha-helix interact with those from a similar alpha helix of a second polypeptide, facilitating dimerization; the structure formed by cooperation of these two regions forms a coiled coil. The leucine zipper pattern is present in many gene regulatory proteins, such as i.) the CCATT-box and enhancer binding protein (C/EBP); ii.) the cAMP response element (CRE) binding proteins (CREB, CRE-BP1, ATFs); iii.) the Jun/AP1 family of transcription factors; iv.) the yeast general control protein GCN4; v.) the fos oncogene, and the fos-related proteins fra-1 and fos B; vi.) the C-myc, L-myc and N-myc oncogenes; and vii.) the octamer-binding transcription factor 2 (Oct-2/OTF-2). Leucine zipper motifs have the following concensus pattern: L-x(6)-L-x(6)-L-x(6)-L, wherein 'x' represents any amino acid. Additional information relating to leucine zipper motifs may be found in reference to the following publications, which are hereby incorporated by reference herein: Landschulz W. H., Johnson P. F., McKnight S. L., Science 240:1759-1764(1988); Busch S. J., Sassone-Corsi P., Trends Genet. 6:36-40(1990); and/or O'Shea E. K., Rutkowski R., Kim P. S., Science 243:538-542(1989).

In preferred embodiments, the following leucine zipper site polypeptide is encompassed by the present invention: SVQCRLMGFLAMLSTEVSVLLLTYLTLEKFLV (SEQ ID NO:61). Polynucleotides encoding these polypeptides are also provided. The present invention also encompasses the use of this HGPRBMY5v1 leucine zipper site polypeptide as an immunogenic and/or antigenic epitope as described elsewhere herein.

The HGPRBMY5v1 polypeptide has been shown to comprise one LDL-receptor class A site domain according to the Motif algorithm (Genetics Computer Group, Inc.). Low-density lipoprotein (LDL) receptors are the major cholesterol-carrying lipoproteins of plasma. Seven successive cysteine-rich repeats of about 40 amino acids are present in the N-terminal of this multidomain membrane protein. Similar domains have been found in other extracellular and membrane proteins, which include the following: Vertebrate very low density lipoprotein (VLDL) receptor, which binds and transports VLDL; Vertebrate low-density lipoprotein receptor-related protein 1 (LRP1), which may act as a receptor for the endocytosis of extracellular ligands; Vertebrate low-density lipoprotein receptor-related protein 2 (LRP2); Complement factor I, which is responsible for cleaving the alpha-chains of C4b and C3b; Complement components C6, C7, C8 and C9; Perlecan, a large multidomain basement membrane heparan sulfate proteoglycan; Invertebrate giant extracellular hemoglobin linker chains, which allow heme-containing chains to construct giant hemoglobin; G-protein coupled receptor Grl101 of the snail *Lymnaea stagnalis*, which might directly transduce signals carried by large extracellular proteins; Vertebrate enterokinase (EC 3.4.21.9), a type II membrane protein of the intestinal brush border, which activates trypsinogen; Human autosomal dominant polycystic kidney disease protein 1 (PKD1), which is involved in adhesive protein-protein and protein-carbohydrate interactions; Vertebrate integral membrane protein DGCR2/IDD, a potential adhesion receptor; *Drosophila* serine protease nudel (EC 3.4.21.-), which is involved in the induction of dorsoventral polarity of the embryo; Avian subgroup A rous sarcoma virus receptor; and Bovine Sco-spondin, which is secreted by the subcommissural organ in embryos and is involved in the modulation of neuronal aggregation.

The LDL-receptor class A domain contains 6 disulfide-bound cysteines and a highly conserved cluster of negatively charged amino acids, of which many are clustered on one face of the module. A schematic representation of this domain is shown here:

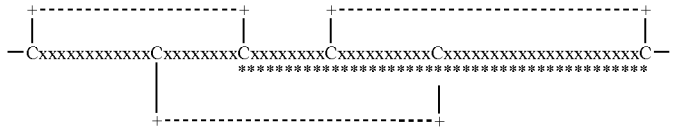

wherein, 'C'=conserved cysteine involved in a disulfide bond; 'x'=any amino acid residue; and '*'=position of the pattern.

In LDL-receptors the class A domains form the binding site for LDL and calcium. The acidic residues between the fourth and sixth cysteines are important for high-affinity binding of positively charged sequences in LDLR's ligands. The repeat has been shown to consist of a beta-hairpin structure followed by a series of beta turns. The binding of calcium seems to induce no significant conformational change.

The consensus pattern for LDL receptor class A domains is as follows: C-[VILMA]-x(5)-C-[DNH]-x(3)-[DENQHT]-C-x(3,4)-[STADE]-[DEH]-[DE]-x(1,5)-C, wherein the four C's are involved in disulfide bonds.

Additional information relating to leucine zipper motifs may be found in reference to the following publications, which are hereby incorporated by reference herein: Yamamoto T., Davis C. G., Brown M. S., Schneider W. J., Casey M. L., Goldstein J. L., Russel D. W. Cell 39:27-38(1984); Daly N. L., Scanlon M. J., Djordjevic J. T., Kroon P. A., Smith R. Proc. Natl. Acad. Sci. U.S.A. 92:6334-6338(1995); Krieger M., Herz J. Annu. Rev. Biochem. 63:601-637 (1994); Bieri S., Djordjevic J. T., Daly N. L., Smith R., Kroon P. A., Biochemistry 34:13059-13065(1995); van Driel I. R., Goldstein J. L., Suedhof T. C., Brown M. S., J. Biol. Chem. 262:17443-17449(1987); and Mahley R. W., Science 240:622-630(1988).

In preferred embodiments, the following LDL-receptor class A domain polypeptide is encompassed by the present invention: KSLEELNLSHNNLMSLPHDLFTPLHRL-ERVHL (SEQ ID NO:62). Polynucleotides encoding these polypeptides are also provided. The present invention also encompasses the use of this HGPRBMY5v1 LDL-receptor class A domain polypeptide as an immunogenic and/or antigenic epitope as described elsewhere.

The present invention encompasses the identification of compounds and drugs which stimulate HGPRBMY5v1 on the one hand (i.e., agonists) and which inhibit the function of HGPRBMY5v1 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodimenta, a polynucleotide encoding the receptor of the present invention may be employed to transfect cells to thereby express the HGPRBMY5v1 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 2233 of SEQ ID NO:1, b is an integer between 15 to 2247, where both a and b correspond to the positions of nucleotide residues shown in SEQ ID NO:1, and where b is greater than or equal to a+14.

Many polynucleotide sequences, such as EST sequences, are publicly available and accessible through sequence databases. Some of these sequences are related to SEQ ID NO:81 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 2161 of SEQ ID NO:81, b is an integer between 15 to 2175, where both a and b correspond to the positions of nucleotide residues shown in SEQ ID NO:81, and where b is greater than or equal to a+14.

TABLE I

| Polynucleotide No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | HGPRB MY5v1 (also referred to as HGPRB MY5 variant) | XXXXX Xx/Xx/Xx | N/A | 1 | 2247 | 1 | 2244 | 2 | 748 |

TABLE I-continued

| Polynucleotide No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 2. | HGPRB MY5v2 (also referred to as HGPRB MY5v1 splice variant) | XXXXX Xx/Xx/Xx | N/A | 1 | 2175 | 81 | 2172 | 82 | 724 |

Table I summarizes the information corresponding to each "Polynucleotide No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Polynucleotide No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y" although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the polynucleotides corresponding to SEQ ID NO:X, SEQ ID NO:Y, or the deposited clone. The corresponding polynucleotide can be isolated in accordance with known methods using the sequence information disclosed herein. Such methods include preparing probes or primers from the disclosed sequence and identifying or amplifying the corresponding polynucleotide from appropriate sources of genomic material.

Also provided in the present invention are species homologs, allelic variants, and/or orthologs. The skilled artisan could, using procedures well-known in the art, obtain the polynucleotide sequence corresponding to full-length polynucleotides (including, but not limited to the full-length coding region), allelic variants, splice variants, orthologs, and/or species homologues of polynucleotides corresponding to SEQ ID NO:X, SEQ ID NO:Y, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Polynucleotide 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:X, and/or a cDNA provided in ATCC Deposit No. Z:. The present invention also provides a polypeptide comprising, or alternatively consisting of, the sequence identified as SEQ ID NO:Y, and/or a polypeptide encoded by the cDNA provided in ATCC Deposit NO:Z. The present invention also provides polynucleotides encoding a polypeptide comprising, or alternatively consisting of the polypeptide sequence of SEQ ID NO:Y, and/or a polypeptide sequence encoded by the cDNA contained in ATCC Deposit No:Z.

Preferably, the present invention is directed to a polynucleotide comprising, or alternatively consisting of, the sequence identified as SEQ ID NO:X, and/or a cDNA provided in ATCC Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:X, the sequence contained in a deposit, and/or the nucleic acid sequence encoding the sequence disclosed as SEQ ID NO:Y.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE II

| Stringency Condition | Polynucleotide Hybrid± | Hybrid Length (bp)‡ | Hybridization Temperature and Buffer† | Wash Temperature and Buffer† |
| --- | --- | --- | --- | --- |
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |

TABLE II-continued

| Stringency Condition | Polynucleotide Hybrid± | Hybrid Length (bp)‡ | Hybridization Temperature and Buffer† | Wash Temperature and Buffer† |
|---|---|---|---|---|
| O | DNA:RNA | > or equal to 50 | 55° C.; 4xSSC - or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC - or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE (1xSSPE is 0.15 M NaCl, 10 mM NaH2PO4, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete. The hydridizations and washes may additionally include 5X Denhardt's reagent, .5-1.0% SDS, 100 ug/ml denatured, fragmented salmon sperm DNA, 0.5% sodium pyrophosphate, and up to 50% formamide.
*Tb - Tr: The hybridization temperature for hybrids anticipated to be less than 50 base pairs in length should be 5-10° C less than the melting temperature Tm of the hybrids there Tm is determined according to the following equations. For hybrids less than 18 base pairs in length, Tm(° C) = 2(# of A + T bases) + 4(# of G + C bases).For hybrids between 18 and 49 base pairs in length, Tm(° C) = 81.5 + 16.6($\log_{10}$[Na+]) + 0.41(%G + C) − (600/N), where N is the number of bases in the hybrid, and [Na+]is the concentration of sodium ions in the hybridization buffer ([NA+] for 1xSSC =.165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:X, the complementary strand thereto, and/or the cDNA sequence contained in the deposited clone.

The present invention also encompasses variants of the polypeptide sequence, and/or fragments therein, disclosed in SEQ ID NO:Y, a polypeptide encoded by the polynucleotide sequence in SEQ ID NO:X, and/or a polypeptide encoded by a cDNA in the deposited clone.

"Variant" refers to a polynucleotide or polypeptide differing from the polynucleotide or polypeptide of the present invention, but retaining essential properties thereof. Polynucleotiderally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a HGPRBMY5v1 and/or HGPRBMY5v2 related polypeptide having an amino acid sequence as shown in the sequence listing and described in SEQ ID NO:1 and/or 81 or the cDNA contained in ATCC deposit No:Z; (b) a nucleotide sequence encoding a mature HGPRBMY5v1 and/or HGPRBMY5v2 related polypeptide having the amino acid sequence as shown in the sequence listing and described in SEQ ID NO:1 and/or 81 or the cDNA contained in ATCC deposit No:Z; (c) a nucleotide sequence encoding a biologically active fragment of a HGPRBMY5v1 and/or HGPRBMY5v2 related polypeptide having an amino acid sequence shown in the sequence listing and described in SEQ ID NO:1 and/or 81 or the cDNA contained in ATCC deposit No:Z; (d) a nucleotide sequence encoding an antigenic fragment of a HGPRBMY5v1 and/or HGPRBMY5v2 related polypeptide having an amino acid sequence sown in the sequence listing and described in SEQ ID NO:1 and/or 81 or the cDNA contained in ATCC deposit No:Z; (e) a nucleotide sequence encoding a HGPRBMY5v1 and/or HGPRBMY5v2 related polypeptide comprising the complete amino acid sequence encoded by a human cDNA plasmid contained in SEQ ID NO:1 and/or 81 or the cDNA contained in ATCC deposit No:Z; (f) a nucleotide sequence encoding a mature HGPRBMY5v1 and/or HGPRBMY5v2 related polypeptide having an amino acid sequence encoded by a human cDNA plasmid contained in SEQ ID NO:1 and/or 81 or the cDNA contained in ATCC deposit No:Z; (g) a nucleotide sequence encoding a biologically active fragment of a HGPRBMY5v1 and/or HGPRBMY5v2 related polypeptide having an amino acid sequence encoded by a human cDNA plasmid contained in SEQ ID NO:1 and/or 81 or the cDNA contained in ATCC deposit No:Z; (h) a nucleotide sequence encoding an antigenic fragment of a HGPRBMY5v1 and/or HGPRBMY5v2 related polypeptide having an amino acid sequence encoded by a human cDNA plasmid contained in SEQ ID NO:1 and/or 81 or the cDNA contained in ATCC deposit No:Z; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 93.6%, 94%, 95%, 96%, 97%, 97.5%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a HGPRBMY5v1 and/or HGPRBMY5v2 related polypeptide having an amino acid sequence as shown in the sequence listing and described in Table I; (b) a nucleotide sequence encoding a mature HGPRBMY5v1 and/or HGPRBMY5v2 related polypeptide having the amino acid sequence as shown in the sequence listing and descried in Table I; (c) a nucleotide sequence encoding a biologically active fragment of a HGPRBMY5v1 and/or HGPRBMY5v2 related polypeptide having an amino acid sequence as shown in the sequence listing and descried in Table I; (d) a nucleotide sequence encoding an antigenic fragment of a HGPRBMY5v1 and/or HGPRBMY5v2 related polypeptide having an amino acid sequence as shown in the sequence listing and descried in Table I; (e) a nucleotide sequence encoding a HGPRBMY5v1 and/or HGPRBMY5v2 related polypeptide comprising the complete amino acid sequence encoded by a human cDNA in a cDNA plasmid contained in the ATCC Deposit and described in Table I; (f) a nucleotide sequence encoding a mature HGPRBMY5v1 and/or HGPRBMY5v2 related polypeptide having an amino acid sequence encoded by a human cDNA in a cDNA plasmid contained in the ATCC Deposit and described in Table I: (g) a nucleotide sequence encoding a biologically active fragment of a HGPRBMY5v1 and/or HGPRBMY5v2 related polypeptide having an amino acid sequence encoded by a human cDNA in a cDNA plasmid contained in the ATCC Deposit and described in Table I; (h) a nucleotide sequence encoding an antigenic fragment of a HGPRBMY5v1 and/or HGPRBMY5v2 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 93.6%, 94%, 95%, 96%, 97%, 97.5%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 96.8%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2 and/or 82, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 96.8%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2 and/or 82, a polypeptide sequence encoded by the nucleotide sequence in SEQ ID NO:1 and/or 81, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least about 80%, 85%, 90%, 91%, 92%, 93%, 93.6%, 94%, 95%, 96%, 96.8%, 97%, 97.5%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=rUB, k-tuple=1, Number of Top Diagonals=5, Gap Penalty=3, Gap Open Penalty 10, Gap Extension Penalty=0.1, Scoring Method-Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the polynucleotidetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as *E. coli*).

Naturally occurring variants are called "allelic variants" and refer to one of several alternate forms of a polynucleotide occupying a given locus on a chromosome of an organism. (Polynucleotides II, Lewin, B., ed., John Wiley & Sons, New York (1985).) These allelic variants can vary at either the polynucleotide and/or polypeptide level and are included in the present invention. Alternatively, non-naturally occurring variants may be produced by mutapolynucleotidesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. . . . 268:22105-22111 (1993)) conducted extensive mutational analysis of human cytokine IL-1a. They used random mutapolynucleotidesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses polynucleotidetic engineering to introduce amino acid changes at specific positions of a cloned polynucleotide to identify regions critical for protein function. For example, site directed mutapolynucleotidesis or alanine-scanning mutapolynucleotidesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3, 4, or 5-phenylproline, cis-3, 4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple polynucleotides with related function and assessing the relative penalty of each substitution to proper polynucleotide function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the polynucleotidetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:1 and/or 81, the sequence of the clone submitted in a deposit, and/or the cDNA encoding the polypeptide disclosed as SEQ ID NO:2 and/or 82. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1 and/or 81 or the complementary strand thereto, or is a portion of a polynucleotide sequence encoding the polypeptide of SEQ ID NO:2 and/or 82. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length" for example, is intended to include 20 or more contiguous bases from the cDNA sequence contained in a deposited clone or the nucleotide sequence shown in SEQ ID NO:1 and/or 81. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1 and/or 81, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2 and/or 82 or encoded by the cDNA contained in a deposited clone. Protein (polypeptide) fragments may be "free-standing" or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 and/or 82 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2 and/or 82, or an epitope of the polypeptide sequence encoded by a polynucleotide sequence contained in ATCC deposit No. Z or encoded by a polynucleotide that hybridizes to the complement of the sequence of SEQ ID NO:1 and/or 81 or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes" as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope" as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope" as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a polynucleotide of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the polynucleotide of interest is subcloned into a vaccinia recombination plasmid such that the open reading frame of the polynucleotide is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of polynucleotide-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 and/or 81 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutapolynucleotidesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. . . . 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S.

Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161 (4):1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9): 1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, 2$^{nd}$ ed. (1988); and Current Protocols, Chapter 2; which are hereby incorporated herein by reference in its entirety). In a preferred method, a preparation of the HGPRBMY5v1 and/or HGPRBMY5v2 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2$^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an HGPRBMY5v1 and/or HGPRBMY5v2 polypeptide or, more preferably, with a HGPRBMY5v1 and/or HGPRBMY5v2 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Polynucleotiderally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP20) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to polynucleotides encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage polynucleotide III or polynucleotide VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Polynucleotide 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Polynucleotiderally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)1 and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin polynucleotides. For example, the human heavy and light chain immunoglobulin polynucleotide complexes may be introduced randomly or by homologous recombination into mouse embryonic stem cells. Alternatively, the human variable region, constant region, and diversity region may be introduced into mouse embryonic stem cells in addition to the human heavy and light chain polynucleotides. The mouse heavy and light chain immunoglobulin polynucleotides may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transpolynucleotides harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin polynucleotides have been partially or completely inactivated. Upon challenge, human antibody production is observed, which closely resembles that seen in humans in all respects, including polynucleotide rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the HGPRBMY5v1 and/or HGPRBMY5v2 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular polynucleotide sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutapolynucleotidesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing polynucleotides from a mouse antibody molecule of appropriate antigen specificity together with polynucleotides from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo polynucleotidetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early polynucleotide promoter element from human cytomegalovirus is an effective expression system for antibodies (Foecking et al., Polynucleotide 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target polynucleotide product can be released from the GST moiety.

In an insect system, *Autographa californica* nuclear polyhedrosis virus (AcNPV) is used as a vector to express foreign polynucleotides. The virus grows in *Spodoptera frugiperda* cells. The antibody coding sequence may be cloned individually into non-essential regions (for example the polyhedrin polynucleotide) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric polynucleotide may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the polynucleotide product in the specific fashion desired. Such modifications (e.g., glycosylation) and processing (e.g., cleavage) of protein products may be important for the function of the protein. Different host cells have characteristic and specific mechanisms for the post-translational processing and modification of proteins and polynucleotide products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the polynucleotide product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) polynucleotides can be employed in tk-, hgprt- or aprt-cells, respectively. Also, antimetabolite resistance can be used as the basis of selection for the following polynucleotides: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Polynucleotide 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Polynucleotide Transfer and Expression, A Laboratory Manual, Stockton Press, NY (1990); and in Chapters 12 and 13, Dracopoli et al. (eds), Current Protocols in Human Polynucleotidetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on polynucleotide amplification for the expression of cloned polynucleotides in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker polynucleotide. Since the amplified region is associated with the antibody polynucleotide, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J. L, Analyst., 126(6):798-802, (2001); Jenkins, A, L., Yin, R., Jensen, J. L, Analyst., 126(6):798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072-3, (2001); and Quaglia, M., Chenon, K., Hall, A, J., De, Lorenzi, E., Sellergren, B, J. Am. Chem, Soc., 123(10):2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heteropolynucleotideous or homogenous phases (Zola, Monoclonal Antibodies: A Manual of Techniques, CRC Press, Inc., (1987), pp147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the polynucleotide of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Polynucleotiderally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$M, and $10^{-15}$M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the polynucleotide encoding an antibody directed against a polypeptide of the present invention, said polypeptide having the potential to elicit an allergic and/or immune response in an organism, and transforming the organism with said antibody polynucleotide such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the polynucleotide of the antibody directed against a polypeptide of the present invention, and transforming a plant with a suitable vector comprising said polynucleotide for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting polynucleotide expression of a particular polynucleotide, or polynucleotides, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Polynucleotide Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a polynucleotide gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the polynucleotide into a patient. More detail about retroviral vectors can be found in Boesen et al., Biotherapy 6:291-302 (1994), which describes the use of a retroviral vector to deliver the mdr1 polynucleotide to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene therapy 4:129-141 (1993); and Grossman and Wilson, Curr. Opin. in Polynucleotidetics and Devel. 3:110-114 (1993).

Adenoviruses are other viral vectors that can be used in gene therapy. Adenoviruses are especially attractive vehicles for delivering polynucleotides to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Polynucleotidetics and Development 3:499-503 (1993) present a review of adenovirus-based gene therapy. Bout et al., Human Gene therapy 5:3-10 (1994) demonstrated the use of adenovirus vectors to transfer polynucleotides to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a polynucleotide to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred polynucleotide. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated polynucleotide transfer, microcell-mediated polynucleotide transfer, spheroplast fusion, etc. Numerous techniques are known in the art for the introduction of foreign polynucleotides into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem . . . 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a polynucleotide gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Polynucleotiderally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Polynucleotiderally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of polynucleotide expression with a standard polynucleotide expression level, whereby an increase or decrease in the assayed polypeptide polynucleotide expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of polynucleotide expression with a standard polynucleotide expression level, whereby an increase or decrease in the assayed polypeptide polynucleotide expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein polynucleotide expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6):547-553 (1990), the Flag-peptide—i.e., the octapeptide sequence DYKDDDDK (SEQ ID NO:21), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 polynucleotide 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999;886:233-5), or HC toxin (Tonukari N J, et al., Plant Cell. 2000 February;12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and polynucleotidetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Polynucleotiderally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance polynucleotides for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratapolynucleotide Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratapolynucleotide; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase polynucleotides (AOX1) is highly active. In the presence of methanol, alcohol oxidase produced from the AOX1 polynucleotide comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "*Pichia* Protocols: Methods in Molecular Biology" D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous polynucleotidetic material (e.g., coding sequence), and/or to include polynucleotidetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, polynucleotidetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Polynucleotiderally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Polynucleotiderally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 and/or 82 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO:WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using polynucleotidetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1 and/or 81. Primers can be selected using computer analysis so that primers do not span more than one predicted exon in the genomic DNA. These primers are then used for PCR screening of somatic cell hybrids containing individual human chromosomes. Only those hybrids containing the human polynucleotide corresponding to the SEQ ID NO:1 and/or 81 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other polynucleotide mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques" Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within polynucleotide families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one polynucleotide per 20 kb, a cDNA precisely localized to a chromosomal region associated with the disease could be one of 50-500 potential causative polynucleotides.

Thus, once coinheritance is established, differences in the polynucleotide and the corresponding polynucleotide between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding polynucleotide from several normal organisms is required to distinguish the mutation from a polymorphism. If a new polymorphism is identified, this polymorphic polypeptide can be used for further linkage analysis.

Furthermore, increased or decreased expression of the polynucleotide in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured polynucleotide expression level with a standard level of polynucleotide expression level, whereby an increase or decrease in the polynucleotide expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "polynucleotide chip" or a "biological chip" as described in U.S. Pat. Nos. 5,837,832, 5,874,219, and 5,856,174. Further, such a polynucleotide chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The U.S. patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or polynucleotide chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control polynucleotide expression through triple helix formation or antisense DNA or RNA. Antisense techniques are discussed, for example, in Okano, J. Neurochem. 56: 560

(1991); "Oligodeoxynucleotides as Antisense Inhibitors of Polynucleotide Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the polynucleotide involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Polynucleotide Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal polynucleotide into an organism having a defective polynucleotide, in an effort to correct the polynucleotidetic defect. The polynucleotides disclosed in the present invention offer a means of targeting such polynucleotidetic defects in a highly accurate manner. Another goal is to insert a new polynucleotide that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct polynucleotidetic defects in certain host strains, and/or to introduce desired phenotypes in the host (e.g., introduction of a specific polymorphism within an endogenous polynucleotide corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct polynucleotidetic defects in certain host strains, and/or to introduce desired phenotypes into the host (e.g., introduction of a specific polymorphism within an endogenous polynucleotide corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "polynucleotide chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein polynucleotide expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($125I$, $121I$), carbon ($14C$), sulfur ($35S$), tritium ($3H$), indium ($112In$), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of polynucleotide expression with a standard polynucleotide expression level, whereby an increase or decrease in the assayed polypeptide polynucleotide expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncopolynucleotide or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other polynucleotidetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153: 4604-4615 (1994); Kaido, T., et al., Int. J. Cancer 60: 221-229 (1995); Ogura et al., Cancer Research 50: 5102-5106 (1990); Santodonato, et al., Human Gene therapy 7:1-10 (1996); Santodonato, et al., Gene therapy 4:1246-1255 (1997); and Zhang, et al., Cancer Gene therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratapolynucleotide; pSVK3, pBPV, pMSG and pSVL available from Pharmacia; and pEFIN1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "polynucleotide guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem., 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO:WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homopolynucleotideous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Polynucleotiderally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of polynucleotidetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO:WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO:WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14x, VT-19-17-H2, RCRE, RCRIP, GP+E-86, GP+en-vAm12, and DAN cell lines as described in Miller, Human Gene therapy, 1:5-14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutapolynucleotidesis. Furthermore, adenoviruses have been used as live enteric vaccines for many years with an excellent safety profile (Schwartzet al., Am. Rev. Respir. Dis., 109:233-238 (1974)). Finally, adenovirus mediated polynucleotide transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Polynucleotidet. Devel., 3:499-503 (1993); Rosenfeld et al., Cell, 68:143-155 (1992); Engelhardt et al., Human Polynucleotidet. Ther., 4:759-769 (1993); Yang et al., Nature Polynucleotidet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the polynucleotides deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following polynucleotides: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired polynucleotide product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO:WO 96/29411, published Sep. 26, 1996; International Publication NO:WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a polynucleotide which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "polynucleotide guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in polynucleotide expression of the foreign polynucleotide in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be polynucleotidetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinopolynucleotidemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active polynucleotide copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic polynucleotides or antigens. By "repressing expression of the oncogenic polynucleotides" is intended the suppression of the transcription of the polynucleotide, the degradation of the polynucleotide transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known polynucleotide delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus polynucleotides needed for its life cycle. Utilizing such a retroviral delivery system for polynucleotides of the present invention will target said polynucleotide and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}M$, $10^{-6}M$, $5\times10^{-7}M$, $10^{-7}M$, $5\times10^{-8}M$, $10^{-8}M$, $5\times10^{-9}M$, $10^{-9}M$, $5\times10^{-10}M$, $10^{-10}M$, $5\times10^{-11}M$, $10^{-11}M$, $5\times10^{-12}M$, $10^{-12}M$, $5\times10^{-13}M$, $10^{-13}M$, $5\times10^{-14}M$, $10^{-14}M$, $5\times10^{-15}M$, and $10^{-15}M$.

Moreover, polypeptides of the present invention may be useful in inhibiting the angiopolynucleotidesis of proliferative cells or tissues, either alone, as a protein fusion, or in combination with other polypeptides directly or indirectly, as described elsewhere herein. In a most preferred embodiment, said anti-angiopolynucleotidesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiopolynucleotidesis directly, or indirectly (See Witte L, et al., Cancer Metastasis Rev. 17(2): 155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat. Res. 400

(1-2):447-55 (1998), Med Hypotheses. 50(5):423-33 (1998), Chem. Biol. Interact. April 24;111-112:23-34 (1998), J Mol Med. 76(6):402-12 (1998), Int. J. Tissue React. 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiopolynucleotidesis Activity

The naturally occurring balance between endogenous stimulators and inhibitors of angiopolynucleotidesis is one in which inhibitory influences predominate. Rastinejad et al., Cell 56:345-355 (1989). In those rare instances in which neovascularization occurs under normal physiological conditions, such as wound healing, organ regeneration, embryonic development, and female reproductive processes, angiopolynucleotidesis is stringently regulated and spatially and temporally delimited. Under conditions of pathological angiopolynucleotidesis such as that characterizing solid tumor growth, these regulatory controls fail. Unregulated angiopolynucleotidesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., Biotech. 9:630-634 (1991); Folkman et al., N. Engl. J. Med., 333:1757-1763 (1995); Auerbach et al., J. Microvasc. Res. 29:401-411 (1985); Folkman, Advances in Cancer Research, eds. Klein and Weinhouse, Academic Press, New York, pp. 175-203 (1985); Patz, Am. J. Opthalmol. 94:715-743 (1982); and Folkman et al., Science 221:719-725 (1983). In a number of pathological conditions, the process of angiopolynucleotidesis contributes to the disease state. For example, significant data have accumulated which suggest that the growth of solid tumors is dependent on angiopolynucleotidesis. Folkman and Klagsbrun, Science 235:442-447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating, preventing, and/or diagnosing an angiopolynucleotidesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiopolynucleotidesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculopolynucleotidesis; granulations; hypertrophic scars (keloids); nonunion fractures; scleroderma; trachoma; vascular adhesions; myocardial angiopolynucleotidesis; coronary collaterals; cerebral collaterals; arteriovenous malformations; ischemic limb angiopolynucleotidesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704-710 (1978) and Gartner et al., Surv. Ophthal. 22:291-312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluopolynucleotidesis, granulations, hypertrophic scars (keloids), nonunion fractures, scleroderma, trachoma, vascular adhesions, myocardial angiopolynucleotidesis, coronary collaterals, cerebral collaterals, arteriovenous malformations, ischemic limb angiopolynucleotidesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiopolynucleotidesis as a pathologic consequence such as cat scratch disease (*Rochele minalia* quintosa), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiopolynucleotidesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited.

Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG)

(the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemialreperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507-3515 (1990)); increased sprouting of neurons may be detected by methods known in the art, such as, for example, the methods set forth in Pestronk et al. (Exp. Neurol. 70:65-82 (1980)) or Brown et al. (Ann. Rev. Neurosci. 4:17-42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria*, Mycoplasmatales, *Mycobacterium leprae, Vibrio cholerae*, Neisseriaceae (e.g., *Acinetobacter*, Gonorrhea, Menigococcal), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, *dermatocycoses*), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiopolynucleotidesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the polynucleotides encoding the putative receptors.

Moreover, the techniques of polynucleotide-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutapolynucleotidesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphopolynucleotidetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/ molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (c) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human HGPRBMY5v1 and/or HGPRBMY5v2 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a HGPRBMY5v1 and/or HGPRBMY5v2 polypeptide, or a bindable peptide fragment, of this invention, comprising providing a plurality of compounds, combining the HGPRBMY5v1 and/or HGPRBMY5v2 polypeptide, or a bindable peptide fragment, with each of a plurality of compounds for a time sufficient to allow binding under suitable conditions and detecting binding of the HGPRBMY5v1 and/or HGPRBMY5v2 polypeptide or peptide to each of the plurality of test compounds, thereby identifying the compounds that specifically bind to the HGPRBMY5v1 and/or HGPRBMY5v2 polypeptide or peptide.

Methods of identifying compounds that modulate the activity of the novel human HGPRBMY5v1 and/or HGPRBMY5v2 polypeptides and/or peptides are provided by the present invention and comprise combining a potential or candidate compound or drug modulator of calpain biological activity with an HGPRBMY5v1 and/or HGPRBMY5v2 polypeptide or peptide, for example, the HGPRBMY5v1 and/or HGPRBMY5v2 amino acid sequence as set forth in SEQ ID NO:2, and measuring an effect of the candidate compound or drug modulator on the biological activity of the HGPRBMY5v1 and/or HGPRBMY5v2 polypeptide or peptide. Such measurable effects include, for example, physical binding interaction; the ability to cleave a suitable calpain substrate; effects on native and cloned HGPRBMY5v1 and/or HGPRBMY5v2-expressing cell line; and effects of modulators or other calpain-mediated physiological measures.

Another method of identifying compounds that modulate the biological activity of the novel HGPRBMY5v1 and/or HGPRBMY5v2 polypeptides of the present invention comprises combining a potential or candidate compound or drug modulator of a calpain biological activity with a host cell that expresses the HGPRBMY5v1 and/or HGPRBMY5v2 polypeptide and measuring an effect of the candidate compound or drug modulator on the biological activity of the HGPRBMY5v1 and/or HGPRBMY5v2 polypeptide. The host cell can also be capable of being induced to express the HGPRBMY5v1 and/or HGPRBMY5v2 polypeptide, e.g., via inducible expression. Physiological effects of a given modulator candidate on the HGPRBMY5v1 and/or HGPRBMY5v2 polypeptide can also be measured. Thus, cellular assays for particular calpain modulators may be either direct measurement or quantification of the physical biological activity of the HGPRBMY5v1 and/or HGPRBMY5v2 polypeptide, or they may be measurement or quantification of a physiological effect. Such methods preferably employ a HGPRBMY5v1 and/or HGPRBMY5v2 polypeptide as described herein, or an overexpressed recombinant HGPRBMY5v1 and/or HGPRBMY5v2 polypeptide in suitable host cells containing an expression vector as described herein, wherein the HGPRBMY5v1 and/or HGPRBMY5v2 polypeptide is expressed, overexpressed, or undergoes upregulated expression.

Another aspect of the present invention embraces a method of screening for a compound that is capable of modulating the biological activity of a HGPRBMY5v1 and/or HGPRBMY5v2 polypeptide, comprising providing a host cell containing an expression vector harboring a nucleic acid sequence encoding a HGPRBMY5v1 and/or HGPRBMY5v2 polypeptide, or a functional peptide or portion thereof (e.g., SEQ ID NO:2); determining the biological activity of the expressed HGPRBMY5v1 and/or HGPRBMY5v2 polypeptide in the absence of a modulator compound; contacting the cell with the modulator compound and determining the biological activity of the expressed HGPRBMY5v1 and/or HGPRBMY5v2 polypeptide in the presence of the modulator compound. In such a method, a difference between the activity of the HGPRBMY5v1 and/or HGPRBMY5v2 polypeptide in the presence of the modulator compound and in the absence of the modulator compound indicates a modulating effect of the compound.

Essentially any chemical compound can be employed as a potential modulator or ligand in the assays according to the present invention. Compounds tested as calpain modulators can be any small chemical compound, or biological entity (e.g., protein, sugar, nucleic acid, lipid). Test compounds will typically be small chemical molecules and peptides. Polynucleotiderally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel HGPRBMY5v1 and/or HGPRBMY5v2 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487-493; and Houghton et al., 1991, *Nature*, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909-6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217-9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309-314) and PCT/US96/10287), carbohydrate libraries (e.g., Liang et al., 1996, *Science*, 274-1520-1522) and U.S. Pat. No. 5,593, 853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComPolynucleotidex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a HGPRBMY5v1 and/or HGPRBMY5v2 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a HGPRBMY5v1 and/or HGPRBMY5v2 polypeptide or peptide to measure a biological binding or ligand binding activity, the source may be a whole cell lysate that can be prepared by successive freeze-thaw cycles (e.g., one to three) in the presence of standard protease inhibitors. The HGPRBMY5v1 and/or HGPRBMY5v2 polypeptide may be partially or completely purified by standard protein purification methods, e.g., affinity chromatography using specific antibody described infra, or by ligands specific for an epitope tag engineered into the recombinant HGPRBMY5v1 and/or HGPRBMY5v2 polypeptide molecule, also as described herein. Binding activity can then be measured as described.

Compounds which are identified according to the methods provided herein, and which modulate or regulate the biological activity or physiology of the HGPRBMY5v1 and/or HGPRBMY5v2 polypeptides according to the present invention are a preferred embodiment of this invention. It is contemplated that such modulatory compounds may be employed in treatment and therapeutic methods for treating a condition that is mediated by the novel HGPRBMY5v1 and/or HGPRBMY5v2 polypeptides by administering to an individual in need of such treatment a therapeutically effective amount of the compound identified by the methods described herein.

In addition, the present invention provides methods for treating an individual in need of such treatment for a disease, disorder, or condition that is mediated by the HGPRBMY5v1 and/or HGPRBMY5v2 polypeptides of the invention, comprising administering to the individual a therapeutically effective amount of the HGPRBMY5v1 and/ or HGPRBMY5v2-modulating compound identified by a method provided herein.

Antisense and Ribozyme (Antagonists)

In specific embodiments, antagonists according to the present invention are nucleic acids corresponding to the sequences contained in SEQ ID NO:1 and/or 81, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Polynucleotide Expression, CRC Press, Boca Raton, Fla. (1988). Antisense technology can be used to control polynucleotide expression through antisense DNA or RNA, or through triple-helix formation. Antisense techniques are discussed for example, in Okano, Neurochem., 56:560 (1991); Oligodeoxynucleotides as Antisense Inhibitors of Polynucleotide Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the polynucleotide involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein polynucleotide (Brinster et al., Nature, 296:39-42 (1982)), etc.

The antisense nucleic acids of the invention comprise a sequence complementary to at least a portion of an RNA transcript of a polynucleotide of interest. However, absolute complementarity, although preferred, is not required. A sequence "complementary to at least a portion of an RNA" referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Polynucleotiderally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372: 333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO:WO88/09810, published Dec. 15, 1988) or the blood-brain barrier (see, e.g., PCT Publication NO:WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-0-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiopolynucleotidesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, *Bacteriodes*, in addition to a-hemolytic streptococci, *E. coli*, Bifobacteria, Anaerobic cocci, Eubacteria, Costridia, *lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathopolynucleotidesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the grampositive cocci (e.g., *S. aureus*, coagulase-negative staphylococci, *micrococcus*, M.sedentarius), gram-positive bacilli (e.g., *Corynebacterium* species, *C. minutissimum, Brevibacterium* species, *Propoionibacterium* species, *P. acnes*), gram-negative bacilli (e.g., Acinebacter species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, eethyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiopolynucleotidesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

F Horn, G Vriend. G protein-coupled receptors in silico. J. Mol. Med. 76: 464-468, 1998.

Y Feng, C C Broder, P E Kennedy, E A Berger. HIV-1 entry cofactor: functional cDNA cloning of a seven-transmembrane, G protein-coupled receptor. Science 272:872-877, 1996.

F Horn, R Bywater, G Krause, W Kuipers, L Oliveira, A C M Paiva, C Sander, G Vriend. The interaction of class B G protein-coupled receptors and their hormones. Receptors and Channels 5:305-314, 1998.

S F Altschul, T L Madden, A A Schaffer, J Zhang, Z Zhang, W Miller, D J Lipman. Gapped BLAST and PSI-BLAST: a new generation of protein database search programs. Nucleic Acids Res 25:3389-3402, 1997.

K Hofmann, W Stoffel. TMbase—A database of membrane spanning proteins segments. Biol. Chem. Hoppe-Seyler 347:166, 1993.

EXAMPLES

Description of the Preferred Embodiments

Example 1

Bioinformatics Analysis

G-protein coupled receptor sequences were used as probes to search the human Expressed Sequence Tag (EST) database. The search program used was gapped BLAST. The top hits from the BLAST results were searched back against the non-redundant protein and patent sequence databases. From this analysis, ESTs encoding potential GPCRs were identified based on sequence homology. An EST corresponding to the HGPRBMY5v1 GPCR was identified and the EST clone was sequenced to obtain the full-length sequence information as provided in FIGS. 1A-C (SEQ ID NO:1). The experimentally obtained sequence corresponds to a novel variant form of HGPRBMY5, HGPRBMY5v1. As described herein, HGPRBMY5v1 is a novel variant form of the LGR8, relaxin 2 receptor.

A second variant form of the LGR8, relaxin 2 receptor, was also experimentally isolated and is referred to as HGPRBMY5v2. The full-length polynucleotide and polypeptide sequences of HGPRBMY5v2 are provided in FIGS. 8A-C (SEQ ID NO:81 and SEQ ID NO:82; respectively).

The complete protein sequence of HGPRBMY5v1 was analyzed for potential transmembrane domains. TMPRED program was used for transmembrane prediction. The program predicted seven transmembrane domains and the predicted domains match with the predicted transmembrane domains of related GPCRs at the sequence level. The identified transmembrane domains are illustrated in FIGS. 1A-C, and discussed elsewhere herein.

Consistent with HGPRBMY5v1 representing a novel relaxin receptor variant, HGPRBMY5v1 was also determined to comprise 7 leucine-rich repeat domains. The identified leucine-rich repeat domains are illustrated in FIGS. 1A-C, and discussed elsewhere herein.

HGPRBMY5v1 was searched against profile hidden Markov models of GPCRs. Profile hidden Markov models (profile HMMs) are built from the Pfam alignments. The Pfam is a database of multiple alignments of protein domains or conserved protein regions. The alignments represent some evolutionary conserved structure, which has implications for the protein's function. Profile HMMs can be very useful for automatically recognizing that a new protein belongs to an existing protein family, even if the homology is weak (A. Bateman, E. Bimey, R. Durbin, S. R. Eddy, K. L. Howe, and E. L. L. Sonnhammer. *The Pfam Protein Families Database*. Nucleic Acids Research, 28:263-266, 2000). HGPRBMY5v1 matched significantly to the 7 transmembrane receptor Pfam model (rhodopsin GPCR family), at amino acids 426 to 685 of SEQ ID NO:2 (not shown). Based on sequence, structure and significant match to GPCR Pfam domain, this novel variant form has all of the elements required for a functional GPCR, and is this predicted to be a functional variant of the relaxin G-protein coupled receptor.

Example 2

Method of Constructing a Size Fractionated Brain and Testis cDNA Library

Poly A+ RNA from Clontech is treated with DNase I to remove genomic DNA contamination. The RNA is converted into double stranded cDNA using the SuperScript™ Plasmid System for cDNA Synthesis and Plasmid Cloning (Life Technologies). The cDNA is size fractionated on a TransGenomics HPLC size exclusion column (TosoHass) with dimensions of 7.8 mm×30 cm and a particle size of 10 µm. Tris buffered saline is used as the mobile phase, and the column is run at a flow rate of 0.5 ml/min. The system is calibrated using a 1 kb ladder to determine which fractions are to be pooled to obtain the largest cDNA library. Polynucleotiderally, fractions that eluted in the range of 12 to 15 minutes are used. The cDNA is precipitated, concentrated and then ligated into the Sal I/Not I sites in pSPORT. Following electroporation of the cDNA into DH12S, DNA from the resulting colonies is prepared and subjected to Sal I/Not I restriction enzyme digestion. Polynucleotiderally, the average insert size of libraries made by this procedure is greater than 3.5 Kb and the overall complexity of the library is greater than $10^7$ independent clones. The library is amplified in semi-solid agar for 2 days at 30 C. An aliquot (200 microliters) of the amplified library is inoculated into a 200 ml culture for single-stranded DNA isolation by superinfection with a fi helper phage. The single-stranded circular DNA is concentrated by ethanol precipitation, resuspended at a concentration of one microgram per microliter and used for the cDNA capture experiments.

Example 3

Method of Converting Double Stranded cDNA Libraries Into Single Strand Circular Forms I. Preparation of Culture.

LB medium (200 mL+400 ul carb) is inoculated with 0.2 to 1 ml of thawed cDNA library. The culture is incubated, shaking at 250 rpm at 37° C. for 45 min. The optical density of the culture is measured. The OD600 is preferably between 0.025 and 0.040. One mL M13K07 helper phage is added to the culture and grown for 2 hours. At that time, 500 uL Kanamycin (30 mg/mL) is added and incubation continued for 15-18 hours.

II. Preparation of Cells for Precipitation.

Cultures are poured into six 50 mL tubes. Cells are centrifuged at 10000 rpm in an HB-6 rotor for 15 minutes at 4° C. The supernatant is retrieved and cells discarded. The supernatant is filtered through a 0.2 um filter. DNase 1 (12000 units from Gibco) is added and incubated at room temperature for 90 minutes.

III. PEG Precipitation of DNA.

Fifty mL of ice-cold 40% PEG 8000, 2.5 M NaCl, 10 mM MgSO$_4$ is added to the cell pellets. The solution is mixed and distributed into 6 centrifuge tubes and covered with parafilm. The tubes are incubated on wet ice for 1 hour (or at 4° C. overnight).

Phage are pelleted at 10000 rpm in an HB-6 rotor for 20 minutes at 4° C. The supernatant is discarded and the sides of the tubes wiped dry. The pellets are resuspended in 1 mL TE, pH 8.

The resuspended pellets are placed in a 14 mL Sarstedt tube (6 mL total). SDS is added to 0.1% (60 uL of stock 10% SDS). Proteinase K (60 uL of 20 mg/mL) is then added and incubated at 42 C for 1 hour.

DNA is extracted with phenol/chloroform by first adding 1 mL of 5M NaCl followed by an equal volume of phenol/chloroform (6 mL). The mixture is vortexed and centrifuged at 5K in an HB-6 rotor for 5 minutes at 4° C. The aqueous (top) phase is transferred to a new Sarstedt tube. Extractions are repeated until no interface is visible.

The DNA is precipitated in ethanol by adding 2 volumes of 100% ethanol and precipitating overnight at −20° C. The DNA is centrifuged at 10000 rpm in HB-6 rotor for 20 minutes at 4° C. The ethanol is discarded and the pellets resuspended in 700 uL 70% ethanol. The resuspended pellets are centrifuged at 14000 rpm for 10 minutes at 4° C. The ethanol is discarded and the pellets dried by vacuum.

Oligosaccharides are then removed by resuspending the pellet in 50 uL TE, pH 8. The solutions are frozen on dry ice for 10 minutes and centrifuged at 14000 rpm for 15 minutes at 4° C. The supernatant is transferred to a new tube and the volume recorded.

The concentration of DNA is determined by measuring absorbance at 260/280. DNA is diluted 1:100 in a quartz cuvette (3 uL DNA+297 uL TE). The following equation is used to calculate DNA concentration:

$$(32 \text{ ug/mL}*\text{OD})(\text{mL}/100 \text{ uL})(100)(OD260)=\text{DNA concentration}$$

The preferred purity ratio is 1.7-2.0.

The DNA is diluted to 1 ug/uL with TB, pH 8 and stored at 4° C.

To test the quality of single-stranded DNA (ssDNA) the following reaction mixtures are prepared:

1. DNA mix per reaction
   a. 1 uL of 5 ng/uL ssDNA (1:200 dilution of VI.D.2 above)
   b. 11 uL dH2O
   c. 1.5 uL 10 uM T7 SPORT primer (fresh dilution of stock)
   d. 1.5 uL 10× Precision-Taq buffer
2. Repair mix per reaction
   a. 4 uL 5 mM dNTPs (1.25 mM each)
   b. 1.5 uL 10× Precision-Taq buffer
   c. 9.25 uL dH2O
   d. 0.25 uL Precision-Taq polymerase
   e. Preheat cocktail at 70° C. until middle of thermal cycle The DNA mixes are aliquoted into PCR tubes and thermal cycle carried out as follows:

1. 95° C., 20 sec
2. 59° C., 1 min; add 15 uL repair mix
3. 73° C., 23 min

Ethanol precipitation of the ssDNA is performed by adding 15 ug glycogen, 16 uL 7.5 M NH$_4$OAc, 125 uL 100% ethanol. The sample is centrifuged at 14000 rpm for 30 minutes at 4° C. and the pellet washed with 125 uL 70% ethanol. The ethanol is discarded and pellet dried by vacuum. The pellet is resuspended in 10 uL TB, pH 8.

The DNA is electroporated into DH10B or DH12S cells. A DNA mixture consisting of:
1. 2 uL repaired library (=1.0×10-3 ug)
2. 1 uL 1 ng/uL unrepaired library (=1.0×10-3 ug)
3. 1 uL 0.01 ug/uL pUC19 positive control DNA (=1×10-5 ug)

is aliquoted to Eppendorf tubes. Cells are thawed on ice-water. Forty uL of cells are added to each DNA aliquot by pipetting into a chilled cuvette placed between metal plates. Electroporation is carried out at 1.8 kV. Immediately following electroporation, 1 mL SOC(SOB+glucose+Mg$^{++}$) media is added to the cuvette, then transferred to a 15 mL tube. Cells are allowed to recover for 1 hr at 37° C. with shaking (225 rpm). Cells are then plated according to the following dilution scheme:

A. Dilutions of Culture
1. Serial dilutions of culture in 1:10 increments (20 uL into 180 uL LB broth)
2. Repaired dilutions
    a. 1:100
    b. 1:1K
    c. 1:10K
3. Unrepaired dilutions
    a. 1:10
    b. 1:100
4. Positive control dilutions
    a. 1:10
    b. 1:100

100 uL of each dilution is plated on small LB+carb plates and incubated at 37° C. overnight. Colonies are counted to calculate titer as follows:
1. use smallest countable dilution
2. (# of colonies)(dilution factor)(200 uL/100 uL)(1000 uL/20 uL) CFUs
3. CFUs/ug DNA used=CFU/ug % Background=(unrepaired CFU/ug/repaired CFU/ug)× 100%

Example 4

Method of Cloning the Novel Human HGPRBMY5v1 and HGPRBMY5v2 G-Protein Coupled Receptors of the Present Invention One microliter of anti-sense biotinylated oligos (or sense oligos when annealing to single stranded DNA from pSPORT2 vector), containing one hundred and fifty nanograms of 1 to 50 different 80mer oligo probes, is added to six microliters (six micrograms) of a mixture of up to 15 single-stranded covalently closed circular cDNA libraries and seven microliters of 100% formamide in a 0.5 ml PCR tube. The sequence of the 80mer oligo that may be used to clone the GPCR of the present invention is as follows:

| GPCR Clone | 80mer Cloning Oligo Sequence | |
|---|---|---|
| HGPRBMY5v1 and HGPRBMY5v2 | GTGCAAAATCAGAATCACTGTCAT CCATTTTGACACTAAATCCAATGG CTCTTTCATAGTCCTCATCTTGCT TGGTTTTC | (SEQ ID NO:70) |

The mixture is heated in a thermal cycler to 95° C. for 2 min. Fourteen microliters of 2× hybridization buffer (50% formamide, 1.5 M NaCl, 0.04 M NaPO$_4$, pH 7.2, 5 min EDTA, 0.2% SDS) is added to the heated probe/cDNA library mixture and incubated at 42° C. for 26 hours. Hybrids between the biotinylated oligo and the circular cDNA are isolated by diluting the hybridization mixture to 220 microliters solution containing 1 M NaCl, 10 mm Tris-HCl pH 7.5, 1 mM EDTA, pH 8.0 and adding 125 microliters of streptavidin magnetic beads. This solution is incubated at 42° C. for 60 min, and mixed every 5 min to re-suspend the beads. The beads are separated from the solution with a magnet and washed three times in 200 microliters of 0.1× SSPE, 0.1% SDS at 45° C.

The single stranded cDNA is released from the biotinylated oligo/streptavidin magnetic bead complex by adding 50 microliters of 0.1 N NaOH and incubating at room temperature for 10 min. Six microliters of 3 M sodium acetate is added along with 15 micrograms of glycogen and the solution ethanol precipitated with 120 microliters of 100% ethanol. The precipitated DNA is resuspended in 12 microliters of TB (10 min Tris HCl, pH 8.0), 1 mM EDTA, pH 8.0). The single-stranded cDNA is converted into double-stranded DNA in a thermal cycler by mixing 5 microliters of the captured DNA with 1.5 microliters of 10 micromolar standard SP6 primer for libraries in pSPORT 1 and 2 and 17 primer for libraries in pCMVSPORT and 1.5 microliters of 10×PCR buffer.

Sequences of primers used to repair single-stranded circular DNA isolated from the primary selection are as follows:

```
T7Sport  5'-TAATACGACTCACTATAGGG-3'   (SEQ ID NO:71)

SP6Sport 5'-ATTTAGGTGACACTATAG-3'    (SEQ ID NO:72)
```

The mixture is heated to 95° C. for 20 seconds and the temperature gradually brought down to 59° C. Fifteen microliters of a repair mix, that was preheated to 70° C. is added to the DNA (repair mix contains 4 microliters of 5 mM dNTPs (1.25 mM each), 1.5 microliters of 10× PCR buffer, 9.25 microliters of water, and 0.25 microliters of Taq polymerase). The solution incubation temperature is raised back to 73° C. and incubated for 23 mm. The repaired DNA is ethanol precipitated and resuspended in 10 microliters of TB. Electroporation is carried out using two microliters DNA per 40 microliters of E. coli DH12S cells. Three hundred and thirty three microliters are plated onto one 150-mm plate of LB agar plus 100 micrograms/milliliter of ampicillin. After overnight incubation at 37° C., the colonies from all plates are harvested by scraping into 10 ml of LB medium+50 micrograms/milliliter of ampicillin and 2 ml of sterile glycerol.

The second round of selection is initiated by making single-stranded circular DNA from the primary selected library using the method listed above. The purified single-stranded circular DNA is then assayed with polynucleotide-specific primers for each of the targeted sequences using standard PCR conditions.

The sequences of the Polynucleotide-Specific-Primer ("GSP") pairs used to identify the various targeted cDNAs in the primary selected single stranded cDNA libraries are as follows:

| GPCR Clone | GSP Oligo Sequence |
|---|---|
| HGPRBMY5v1-s | GCAGAAAACCAAGCAAGATGA (SEQ ID NO:73) |
| HGPRBMY5v1-a | TCCTTGCCATCACAGTGAAA (SEQ ID NO:74) |

The Polynucleotide-Specific-Primer ("GSP") pairs referenced for HGPRBMY5v1 (SEQ ID NO:73 and SEQ ID NO:74) may also be used for HGPRBMY5v2.

The secondary hybridization is carried out using only those 80mer biotinylated probes whose targeted sequences were positive with the GSPs. The resulting single-stranded circular DNA is converted to double strands using the antisense oligo for each target sequence as the repair primer (the sense primer is used for material captured from pSPORT2 libraries. The resulting double stranded DNA is electroporated into DH10B and the resulting colonies inoculated into 96 deep well blocks. Following overnight growth, DNA is prepared and sequentially screened for each of the targeted sequences using the GSPs. The DNA is also cut with Sal I and Not I and the inserts sized by agarose gel electrophoresis.

Those cDNA clones that were positive by PCR had the inserts sized and two clones were chosen for DNA sequencing for each polynucleotide. All of the clones had identical sequence for each respective polynucleotide.

The full-length nucleotide sequence and the encoded polypeptide for HGPRBMY5v1 are shown in FIGS. 1A-C.

Example 5

Expression Profiling of the Novel Human HGPRBMY5v1 Polypeptide

The following PCR primer pair may be used to measure the steady state levels of HGPRBMY5v1 mRNA by quantitative PCR:

| GPCR Clone | Expression Profile Oligo Sequence |
|---|---|
| HGPRBMY5v1-s | AAGCAGATGTGTGCCCAAATG (SEQ ID NO:22) |
| HGPRBMY5v1-a | GGTGAGGTGATAGTTCCGTTA (SEQ ID NO:23) TCG |
| HGPRBMY5v1.2-a | GGTGAGGTGATAGCTCCGTTA (SEQ ID NO:83) TCG |

The expression profiling oligo pairs referenced for HGPRBMY5v1 (SEQ ID NO:22, and SEQ ID NO:23 or SEQ ID NO:83) may also be used for HGPRBMY5v2.

Briefly, first strand cDNA was made from commercially available brain subregion mRNA (Clontech) and subjected to real time quantitative PCR using a PE 5700 instrument (Applied Biosystems; Foster City, Calif.) which detects the amount of DNA amplified during each cycle by the fluorescent output of SYBR green, a DNA binding dye specific for double stranded DNA. The specificity of the primer pair for its target is verified by performing a thermal denaturation profile at the end of the run which gives an indication of the number of different DNA sequences present by determining melting Tm. In the case of the HGPRBMY5 primer pair, only one DNA fragment was detected having a homogeneous melting point. Contributions of contaminating genomic DNA to the assessment of tissue abundance is controlled for by performing the PCR with first strand made with and without reverse transcriptase. In all cases, the contribution of material amplified in the no reverse transcriptase controls was negligible.

Small variations in the amount of cDNA used in each tube was determined by performing a parallel experiment using a primer pair for a gene expressed in equal amounts in all tissues, cyclophilin. These data were used to normalize the data obtained with the HGPRBMY5 primer pair. The PCR data was converted into a relative assessment of the difference in transcript abundance amongst the tissues tested and the data are presented in bar graph form (see FIG. 12).

More specifically, 5 µg poly A+RNA was diluted to 77 µl with DEPC water. The reaction mixture was made as follows, where the cocktail was enough for the number of samples and 1 extra, taking into account pipetting errors.

| COMPONENTS | VOLUME/REACTION |
|---|---|
| 10X PCR Buffer | 10 µl |
| 25 mM MgCl$_2$ | 8 µl |
| RNase-Out 40 U/µl | 2.5 µl |
| RNase-Free DNase (B-M) | 2.5 µl |
| TOTAL VOLUME | 23 µl |

The cocktail (23 µl) was then added to each sample and incubated at room temperature for 15 minutes. EDTA (250 mM; 1 µ) was added to each sample, incubated at 65° C. for 15 minutes, and then put on wet ice.

Samples were extracted with 100 µl phenol:chloroform: isoamyl alcohol. They were vortexed for 1 minute and spun at 12K rpm for 2 minutes. The top aqueous phase (90-95 µl) was removed and transferred to a new tube. For ethanol precipitation, 1 µl of glycogen (20 µg/µl), 15 µl 2M NaAcetate, and 290 µl 100% ethanol was added and precipitated at –20° C. for 1 hour. Samples were pelleted at 4° C. for 30 minutes, washed in 500 µl 70% ethanol, dried, and resuspended in 22 µl RNase-free water.

For first strand cDNA synthesis, the volume of RNA was split into 2 tubes (RT+/RT–). Oligo(dT) (1 µl) was added to each and incubated at 70° C. for 10 minutes on wet ice. The reaction mixture was made as follows, where the cocktail was enough for the number samples and 1 extra, taking into account pipetting errors.

| COMPONENTS | VOLUME/REACTION |
|---|---|
| 10X PCR Buffer | 2 µl |
| 25 mM MgCl2 | 2 µl |
| 10 mM dNTP mix | 1 µl |
| 0.1 M DTT | 2 µl |
| TOTAL VOLUME | 7 µl |

The reaction mixture (7 µl) was added to each sample and incubated at 42° C. for 5 minutes. SuperScript II RT (1 µl) was added to RT+ and 1 µl DEPC water was added to RT– samples. Samples were then incubated at 42° C. for 50 minutes. The reaction was terminated by incubating samples at 70° C. for 15 minutes and then iced. RNase H (1 µl) was added to the samples and incubated at 37° C. for 20 minutes.

Finally 79 μl water was added to obtain a final concentration of 2.5 ng/μl cDNA (assuming 100% conversion).

The number of reactions and amount of mix needed was first determined. All of the samples were run in triplicate, so sample tubes needed 3.5 reactions worth of mixture using the following formula as a guide (2×# tissue samples+1 no template control+1 for pipetting error)(3.5).

The reaction mixture consisted of the following components and volumes:

| COMPONENTS | VOL/RXN |
|---|---|
| 2X SybrGreen Master Mix | 25 μl |
| water | 23.5 μl |
| primer mix (10 uM ea.) | 0.5 μl |
| cDNA (100 ng/μl) | 1 μl |

The mixture was initially made without cDNA for enough reactions as determined above. The mix (171.5 μl) was then aliquoted into sample tubes. cDNA (3.5 μl) was added to each sample tube, mixed gently, and spun down for collection. Three 50 μl samples were aliquoted to the optical plate, where the primer and sample were set up for sample analysis. The threshold was set in Log view to intersect linear regions of amplification. The background was set in Linear view to 2-3 cycles before the amplification curve appears. The mean values for RT+ was calculated and normalized to Cyclophilin: dCt=sample mean−cyclophilin mean. The ddCt was determined by subtracting individual dcts from the highest value of dCt in the list. The relative abundance was determined by formula 2^ddCt.

For designing primers, the ideal product size range is 75-100, but 50-150 will work. The optimal melting temperature (Tm) is 60° C. for default 5700 program, but may be changed depending on the target sequence. The optimal GC content is 20-80%. The last 5 nucleotides (3' end of both primers) should have no more than 2 G/Cs. BLAST primers to ensure specific amplification. If the genomic structure of the gene is known, one can consider designing the primers to cross intron/exon boundaries.

As shown in FIG. 3, HGPRBMY5v1 was predominately expressed in the brain with significant expression observed in the thymus.

Within the brain, HGPRBMY5v1 was expressed highly in the amygdala and thalamus (see FIG. 4). The collection of brain sub-regions where HGPRBMY5v1 was expressed resembles the pathway for fear conditioning and anxiety in humans where the thalamus is the primary source of sensory stimulus to the amygdala (LeDoux, J. E., 1995, *Ann. Rev. Psychol*. 46:209-235). Agonists and antagonists of HGPRBMY5 may be useful for treating various anxiety and fear disorders as well as addiction, memory and diseases that evolve from altered appetitive motivational behavior.

Since the same primers used for determining the expression profile of HGPRBMY5v1 also hybridize with HGPRBMY5v2, the expression profile for HGPRBMY5v2 is expected to be the same as for HGRPBMY5v1.

Example 6

Method of Assessing the Expression Profile of the Novel HGPRBMY5v1 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGPRBMY5v1, the primer probe sequences were as follows:

```
                                          (SEQ ID NO:78)
Forward Primer 5'-GAAGATGACATCTGCAATGCTTTT-3'

(SEQ ID NO:79)
Reverse Primer 5'-GAGCCATTCTGCTGTGCTCTCT-3'

(SEQ ID NO:80)
TaqMan Probe   5'-TTTACCAACGGCAAGCCTTTCTGCA-3'
```

Each of these primers is specific to the 3'UTR of the HGPRBMY5v1 gene. Since HGPRBMY5v2 derives from the same gene, these primers are also useful in providing the expression profile for HGPRBMY5v2 as well.

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription reaction and Sequence Detection 100 ng of Dnase-treated total RNA was annealed to 2.5 RM of the respective gene-specific reverse primer in the presence of 5.5 mM Magnesium Chloride by heating the sample to 72° C. for 2 min and then cooling to 55° C. for 30 min. 1.25 U/μl of MuLv reverse transcriptase and 500 μM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 μM forward and reverse primers, 2.0 μM of the TaqMan probe, 500 μM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$

| Number | Tissue |
|---|---|
| 1 | adrenal-gland |
| 2 | Bladder |
| 3 | blood-vessel:renal |
| 4 | brain:amygdale |
| 5 | brain:caudate |
| 6 | brain:cerebellum |
| 7 | brain:cortex:cingulate-anterior |
| 8 | brain:cortex:cingulate-posterior |
| 9 | brain:cortex:frontal-lateral |
| 10 | brain:cortex:frontal-medial |
| 11 | brain:cortex:occipital |
| 12 | brain:cortex:parietal |
| 13 | brain:cortex:temporal |
| 14 | brain:dorsal-raphe-nucleus |
| 15 | brain:hippocampus |
| 16 | brain:hypothalamus:anterior |
| 17 | brain:hypothalamus:posterior |
| 18 | brain:locus-coeruleus |
| 19 | brain:medulla-oblongata |
| 20 | brain:nucleus-accumbens |
| 21 | brain:substantia-nigra |
| 22 | colon |
| 23 | duodenum |
| 24 | fallopian-tube |
| 25 | gallbladder |
| 26 | kidney:cortex |
| 27 | kidney:medulla |
| 28 | muscle:skeletal |
| 29 | oesophagus |
| 30 | ovary |
| 31 | pancreas |
| 32 | pineal-gland |
| 33 | pituitary-gland |
| 34 | testis |
| 35 | thyroid-gland |
| 36 | uterus:cervix |
| 37 | uterus:myometrium |
| 38 | vas-deferens |

The expanded expression profile of the HGPRBMY5v1 polypeptide in normal tissues is provided in FIG. 5 and described elsewhere herein. The identity of each tissue presented in FIG. 5 is provided in the following table.

The expanded expression profile of the HGPRBMY5v1 polypeptide in diseased tissues is provided in FIG. 6 and described elsewhere herein.

Example 7

Complementary Polynucleotides

Antisense molecules or nucleic acid sequences complementary to the HGPRBMY5v1 and/or HGPRBMY5v2 protein-encoding sequence, or any part thereof, is used to decrease or to inhibit the expression of naturally occurring HGPRBMY5v1 and/or HGPRBMY5v2. Although the use of antisense or complementary oligonucleotides comprising about 15 to 35 base-pairs is described, essentially the same procedure is used with smaller or larger nucleic acid sequence fragments. An oligonucleotide based on the coding sequence of HGPRBMY5v1 or HGPRBMY5v2 protein, as shown in FIGS. 1A-C (SEQ ID NO:1), or as shown in FIGS. 8A-C (SEQ ID NO:81); respectively, for example, is used to inhibit expression of naturally occurring HGPRBMY5v1 and/or HGPRBMY5v2. The complementary oligonucleotide is typically designed from the most unique 5' sequence and is used either to inhibit transcription by preventing promoter binding to the coding sequence, or to inhibit translation by preventing the ribosome from binding to the HGPRBMY5v1 and/or HGPRBMY5v2 protein-encoding transcript, among others. However, other regions may also be targeted.

Using an appropriate portion of the signal and 5' sequence of SEQ ID NO:1 or SEQ ID NO:81, an effective antisense oligonucleotide includes any of about 15-35 nucleotides spanning the region which translates into the signal or 5' coding sequence, among other regions, of the polypeptide as shown in FIGS. 1A-C (SEQ ID NO:2) or FIGS. 8A-C (SEQ ID NO:82). Appropriate oligonucleotides are designed using OLIGO 4.06 software and the HGPRBMY5v1 or HGPRBMY5v2 protein coding sequence (SEQ ID NO:1 or SEQ ID NO:81). Preferred oligonucleotides are deoxynucleotide, or chimeric deoxynucleotide/ribonucleotide based and are provided below. The oligonucleotides were synthesized using chemistry essentially as described in U.S. Pat. No. 5,849,902; which is hereby incorporated herein by reference in its entirety.

HGPRBMY5v1 Antisense Oligonucleotides

| ID# | Sequence | |
|---|---|---|
| 12657 | CACAGUCAUCCUUGCCAUCACAGUG | (SEQ ID NO:90) |
| 12658 | GCCAAAUAUGGUCGCCCAUCCACUA | (SEQ ID NO:91) |
| 12659 | CAAAUCCACCCAGUUGAGUUGAGGC | (SEQ ID NO:92) |
| 12660 | UCUAGGCAGAAACAGCACUGUGAGC | (SEQ ID NO:93) |
| 12661 | UGAUCAUGCUACCUUGAGUCAGUGC | (SEQ ID NO:94) |

HGPRBMY5v2 Antisense Oligonucleotides

| ID# | Sequence | |
|---|---|---|
| 12663 | UGCCAAAUAUGGUCGCCCAUCCACU | (SEQ ID NO:95) |
| 12664 | GCCUUCCAAAUCCACCCAGUUGAGU | (SEQ ID NO:96) |
| 12665 | GAUCAUGCUACCUUGAGUCAGUGCA | (SEQ ID NO:97) |
| 12666 | UAAGGCCACGCUGUUAGCAUUUCCA | (SEQ ID NO:98) |
| 12667 | UCUAGGCAGAAACAGCACUGUGAGC | (SEQ ID NO:99) |

Both HGPRBMY5v1 and HGPRBMY5v2 polypeptides have been shown to be involved in the regulation of mammalian cell cycle pathways. Subjecting cells with an effective amount of a pool of all five of the above antisense oligoncleotides (SEQ ID NOs:90 to 94 for HGPRBMY5v1 or SEQ ID NOs:95 to 99 for HGPRBMY5v2) resulted in a significant decrease in p21 expression/activity providing convincing evidence that HGPRBMY5v1 and HGPRBMY5v2 at least regulates the activity and/or expression of p21 either directly, or indirectly. Moreover, the results suggest that HGPRBMY5v1 and HGPRBMY5v2 are involved in the positive regulation of p21 activity and/or expression, either directly or indirectly. The p21 assay used is described below and was based upon the analysis of p21 activity as a downstream marker for proliferative signal transduction events.

Transfection of Post-Quiescent A549 Cells with AntiSense Oligonucleotides

Materials needed:
A549 cells maintained in DMEM with high glucose (Gibco-BRL) supplemented with 10% Fetal Bovine Serum, 2 mM L-Glutamine, and 1×penicillin/streptomycin.
Opti-MEM (Gibco-BRL)
Lipofectamine 2000 (Invitrogen)
Antisense oligomers (Sequitur)
Polystyrene tubes.
Tissue culture treated plates.
Quiescent cells were prepared as follows:
Day 0: 300,000 A549 cells were seeded in a T75 tissue culture flask in 10 ml of A549 media (as specified above), and incubated in at 37° C., 5% $CO_2$ in a humidified incubator for 48 hours.
Day 2: The T75 flasks were rocked to remove any loosely adherent cells, and the A549 growth media removed and replenished with 10 ml of fresh A549 media. The cells were cultured for six days without changing the media to create a quiescent cell population.
Day 8: Quiescent cells were plated in multi-well format and transfected with antisense oligonucleotides.
A549 cells were transfected according to the following:
1. Trypsinize T75 flask containing quiescent population of A549 cells.
2. Count the cells and seed 24-well plates with 60K quiescent A549 cells per well.
3. Allow the cells to adhere to the tissue culture plate (approximately 4 hours).
4. Transfect the cells with antisense and control oligonucleotides according to the following:
    a. A 10× stock of lipofectamine 2000 (10 ug/ml is 10×) was prepared, and diluted lipid was allowed to stand at RT for 15 minutes.
    Stock solution of lipofectamine 2000 was 1 mg/ml.
    10× solution for transfection was 10 ug/ml.
    To prepare 10× solution, dilute 10 ul of lipofectamine 2000 stock per 1 ml of Opti-MEM (serum free media).
    b. A 10× stock of each oligomer was prepared to be used in the transfection.
    Stock solutions of oligomers were at 100 uM in 20 mM HEPES, pH 7.5.
    10× concentration of oligomer was 0.25 uM.
    To prepare the 10× solutions, dilute 2.5 ul of oligomer per 1 ml of Opti-MEM.
    c. Equal volumes of the 10× lipofectamine 2000 stock and the 10× oligomer solutions were mixed well, and incubated for 15 minutes at RT to allow complexation of the oligomer and lipid. The resulting mixture was 5×.
    d. After the 15 minute complexation, 4 volumes of full growth media was added to the oligomer/lipid complexes (solution was 1×).
    e. The media was aspirated from the cells, and 0.5 ml of the 1× oligomer/lipid complexes added to each well.
    f. The cells were incubated for 16-24 hours at 37° C. in a humidified $CO_2$ incubator.
    g. Cell pellets were harvested for RNA isolation and TaqMan analysis of downstream marker genes.

TaqMan Reactions

Quantitative RT-PCR analysis was performed on total RNA preps that had been treated with DNaseI or poly A selected RNA. The Dnase treatment may be performed using methods known in the art, though preferably using a Qiagen RNeasy kit to purify the RNA samples, wherein DNAse I treatment is performed on the column.

Briefly, a master mix of reagents was prepared according to the following table:

Dnase I Treatment

| Reagent | Per r'xn (in uL) |
| --- | --- |
| 10X Buffer | 2.5 |
| Dnase I (1 unit/ul @1 unit per ug sample) | 2 |
| DEPC $H_2O$ | 0.5 |
| RNA sample @ 0.1 ug/ul (2–3 ug total) | 20 |
| Total | 25 |

Next, 5 ul of master mix was aliquoted per well of a 96-well PCR reaction plate (PE part # N801-0560). RNA samples were adjusted to 0.1 ug/ul with DEPC treated $H_2O$ (if necessary), and 20 ul was added to the aliquoted master mix for a final reaction volume of 25 ul.

The wells were capped using strip well caps (PE part # N801-0935), placed in a plate, and briefly spun in a plate centrifuge (Beckman) to collect all volume in the bottom of the tubes. Generally, a short spin up to 500 rpm in a Sorvall RT is sufficient The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT Reaction

A master mix of reagents was prepared according to the following table:

RT Reaction

| Reagent | RT Per Rx'n (in ul) | No RT Per Rx'n (in ul) |
| --- | --- | --- |
| 10X RT buffer | 5 | 2.5 |
| $MgCl_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC $H_2O$ | — | — |
| Total | 50 uL | 25 uL |

Samples were adjusted to a concentration so that 500 ng of RNA was added to each RT rx'n (10 ng for the no RT). A maximum of 19 ul can be added to the RT rx'n mixture (10.125 ul for the no RT.) Any remaining volume up to the maximum values was filled with DEPC treated H$_2$O, so that the total reaction volume was 50 ul (RT) or 25 ul (no RT).

On a 96-well PCR reaction plate (PE part # N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part # N801-0935), placed in a plate, and spin briefly in a plate centrifuge (Beckman) to collect all volume in the bottom of the tubes. Generally, a short spin up to 500 rpm in a Sorvall RT is sufficient.

For the RT-PCR reaction, the following thermal profile was used:
25° C. for 10 min
48° C. for 30 min
95° C. for 5 min
4° C. hold (for 1 hour)
Store plate @-20° C. or lower upon completion.

TaqMan Reaction (Template Comes from RT Plate)

A master mix was prepared according to the following table:

TaqMan Reaction (Per Well)

| Reagent | Per Rx'n (in ul) |
| --- | --- |
| TaqMan Master Mix | 4.17 |
| 100 uM Probe (SEQ ID NO: 102) | .025 |
| 100 uM Forward primer (SEQ ID NO: 101) | .05 |
| 100 uM Reverse primer (SEQ ID NO: 102) | .05 |
| Template | — |
| DEPC H$_2$O | 18.21 |
| Total | 22.5 |

The primers used for the RT-PCR reaction is as follows:

P21 Primer and Probes:

```
                                    (SEQ ID NO:100)
Forward Primer: CTGGAGACTCTCAGGGTCGAA (SEQ ID NO:101)
Reverse Primer: GCGCTTCCAGGACTGCA (SEQ ID NO:102)
TaqMan Probe:   ACAGATTTCTACCACTCCAAACGCCGG
```

Using a Gilson P-10 repeat pipetter, 22.5 ul of master mix was aliqouted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated H$_2$O). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part # N801-0935), placed in a plate, and spun in a centrifuge to collect all volume in the bottom of the tubes. Generally, a short spin up to 500 rpm in a Sorvall RT is sufficient.

Plates were loaded onto a PE 5700 sequence detector making sure the plate is aligned properly with the notch in the upper right hand corner. The lid was tightened down and run using the 5700 and 5700 quantitation program and the SYBR probe using the following thermal profile:
50° C. for 2 min
95° C. for 10 min
and the following for 40 cycles:
95° C. for 15 sec
60° C. for 1 min
Change the reaction volume to 25 ul.

Once the reaction was complete, a manual threshold of around 0.1 was set to minimize the background signal. Additional information relative to operation of the Gene-Amp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

Example 8

Functional Characterization of the Novel Human GPCRs, HGPRBMY5v1 and HGPRBMY5v2, of the Present Invention The use of mammalian cell reporter assays to demonstrate functional coupling of known GPCRs (G Protein Coupled Receptors) has been well documented in the literature (Gilman, 1987, Boss et al., 1996; Alam & Cook, 1990; George et al., 1997; Selbie & Hill, 1998; Rees et al., 1999). In fact, reporter assays have been successfully used for identifying novel small molecule agonists or antagonists against GPCRs as a class of drug targets (Zlokarnik et al., 1998; George et al., 1997; Boss et al., 1996; Rees et al, 2001). In such reporter assays, a promoter is regulated as a direct consequence of activation of specific signal transduction cascades following agonist binding to a GPCR (Alam & Cook 1990; Selbie & Hill, 1998; Boss et al., 1996; George et al., 1997; Gilman, 1987).

A number of response element-based reporter systems have been developed that enable the study of GPCR function. These include cAMP response element (CRE)-based reporter polynucleotides for G alpha i/o, G alpha s-coupled GPCRs, Nuclear Factor Activator of Transcription (NFAT)-based reporters for G alpha q/11-coupled receptors and MAP kinase reporter polynucleotides for use in Galpha i/o coupled receptors (Selbie & Hill, 1998; Boss et al., 1996; George et al., 1997; Gilman, 1987; Rees et al., 2001). Transcriptional response elements that regulate the expression of Beta-Lactamase within a CHO K1 cell line (Cho/NFAT-CRE: Aurora Biosciences™) (Zlokarnik et al., 1998) may be implemented to characterize the function of the orphan HGPRBMY5v1 polypeptides of the present invention. The system enables demonstration of constitutive G-protein coupling to endogenous cellular signaling components upon intracellular overexpression of orphan receptors. Overexpression has been shown to represent a physiologically relevant event. For example, it has been shown that overexpression occurs in nature during metastatic carcinomas, wherein defective expression of the monocyte chemotactic protein 1 receptor, CCR2, in macrophages is associated with the incidence of human ovarian carcinoma (Sica, et al., 2000; Salcedo et al., 2000). Indeed, it has been shown that overproduction of the Beta 2 Adrenergic Receptor in transgenic mice leads to constitutive activation of the receptor signaling pathway such that these mice exhibit increased cardiac output (Kypson et al., 1999; Dorn et al., 1999). These are only a few of the many examples demonstrating constitutive activation of GPCRs whereby many of these receptors are likely to be in the active, R*, conformation (J. Wess 1997).

Materials and Methods

DNA Constructs

The putative GPCR HGPRBMY5v1 and/or HGPRBMY5v2 cDNA may be PCR amplified using PFU™ (Stratapolynucleotide). The primers used in the PCR reaction are specific to the HGPRBMY5v1 and/or HGPRBMY5v2 polynucleotides. An appropriate 3 prime primer may be designed so as to add a Flag-tag epitope to the HGPRBMY5v1 and/or HGPRBMY5v2 polypeptides for immunocytochemistry. The product from the PCR reaction may be isolated from a 0.8% Agarose gel (Invitrogen) and purified using a Gel Extraction Kit™ from Qiagen.

The purified product may be then digested overnight along with the pcDNA3.1 Hygro™ mammalian expression vector from Invitrogen using the HindIII and BamHI restriction enzymes (New England Biolabs). These digested products are then purified using the Gel Extraction Kit™ from Qiagen and subsequently ligated to the pcDNA3.1 Hygro™ expression vector using a DNA molar ratio of 4 parts insert: 1 vector. All DNA modification enzymes are purchased from NEB. The ligation may be incubated overnight at 16 degrees Celsius, after which time, one microliter of the mix may be used to transform DH5 alpha cloning efficiency competent E. coli™ (Gibco BRL). A detailed description of the pcDNA3.1 Hygro™ mammalian expression vector is available at the Invitrogen web site (www.Invitrogen.com). The plasmid DNA from the ampicillin resistant clones are isolated using the Wizard DNA Miniprep System™ from Promega. Positive clones are then confirmed and scaled up for purification using the Qiagen Maxiprep™ plasmid DNA purification kit.

Cell Line Polynucleotideration

The pcDNA3.1hygro vector containing the orphan HGPRBMY5v1 and/or HGPRBMY5v2 cDNA are used to transfect Cho/NFAT-CRE (Aurora Biosciences) cells using Lipofectamine 2000™ according to the manufacturers specifications (Gibco BRL). Two days later, the cells are split 1:3 into selective media (DMEM 11056, 600 ug/ml Hygromycin, 200 ug/ml Zeocin, 10% FBS). All cell culture reagents are purchased from Gibco BRL-Invitrogen.

The Cho/NFAT-CRE cell lines, transiently or stably transfected with the orphan HGPRBMY5v1 and/or HGPRBMY5v2 GPCR, are analyzed using the FACS Vantage SE™ (BD), fluorescence microscopy (Nikon), and the LJL Analyst™ (Molecular Devices). In this system, changes in real-time polynucleotide expression, as a consequence of constitutive G-protein coupling of the orphan HGPRBMY5v1 and/or HGPRBMY5v2 GPCR, is examined by analyzing the fluorescence emission of the transformed cells at 447 nm and 518 nm. The changes in polynucleotide expression can be visualized using Beta-Lactamase as a reporter, that, when induced by the appropriate signaling cascade, hydrolyzes an intracellularly loaded, membrane-permeant ester, Cephalosporin-Coumarin-Fluorescein-2/Acetoxymethyl™ (CCF2/AM™ Aurora Biosciences; Zlokarnik, et al., 1998). The CCF2/AM™ substrate is a 7-hydroxycoumarin cephalosporin with a fluorescein attached through a stable thioether linkage. Induced expression of the Beta-Lactamase enzyme is readily apparent since each enzyme molecule produced is capable of changing the fluorescence of many CCF2/AM™ substrate molecules. A schematic of this cell based system is shown below.

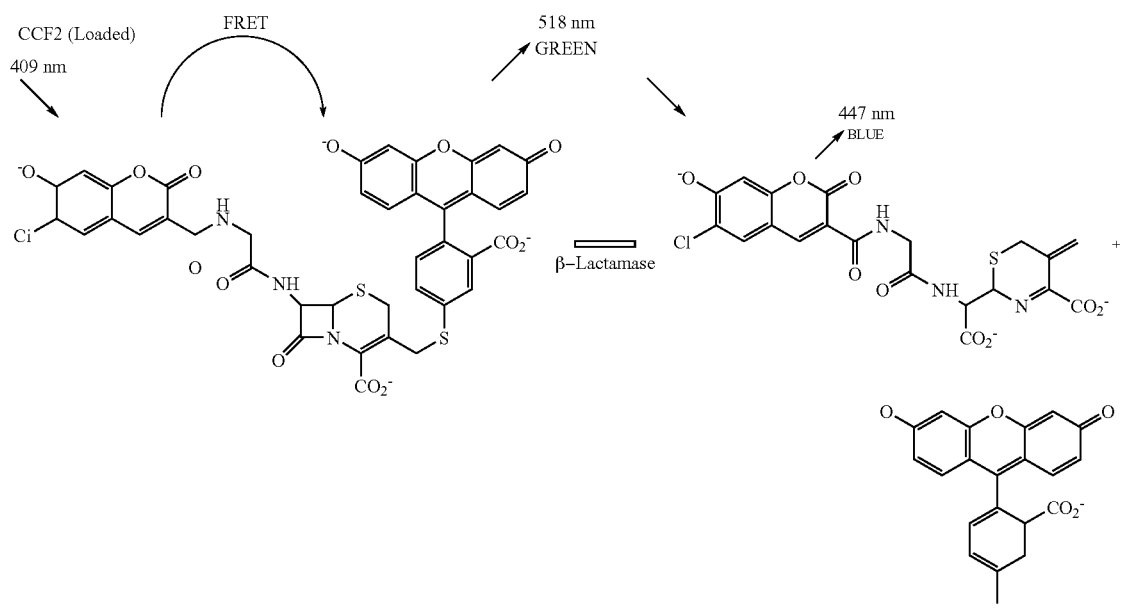

In summary, CCF2/AM™ is a membrane permeant, intracellularly-trapped, fluorescent substrate with a cephalosporin core that links a 7-hydroxycoumarin to a fluorescein. For the intact molecule, excitation of the coumarin at 409 nm results in Fluorescence Resonance Energy Transfer (FRET) to the fluorescein which emits green light at 518 nm. Production of active Beta-Lactamase results in cleavage of the Beta-Lactam ring, leading to disruption of FRET, and excitation of the coumarin only—thus giving rise to blue fluorescent emission at 447 nm.

Fluorescent emissions are detected using a Nikon-TE300 microscope equipped with an excitation filter (D405/10X-25), dichroic reflector (430DCLP), and a barrier filter for dual DAPI/FITC (510 nM) to visually capture changes in Beta-Lactamase expression. The FACS Vantage SE is equipped with a Coherent Enterprise II Argon Laser and a Coherent 302C Krypton laser. In flow cytometry, UV excitation at 351-364 nm from the Argon Laser or violet excitation at 407 nm from the Krypton laser are used. The optical filters on the FACS Vantage SE are HQ460/50m and HQ535/40m bandpass separated by a 490 dichroic mirror.

Prior to analyzing the fluorescent emissions from the cell lines as described above, the cells are loaded with the CCF2/AM substrate. A 6× CCF2/AM loading buffer may be prepared whereby 1 mM CCF2/AM (Aurora Biosciences) may be dissolved in 100% DMSO (Sigma). 12 ul of this stock solution may be added to 60 ul of 100 mg/ml Pluronic F127 (Sigma) in DMSO containing 0.1% Acetic Acid (Sigma). This solution may be added while vortexing to 1 mL of Sort Buffer (PBS minus calcium and magnesium-Gibco-25 mM HEPES-Gibco-pH 7.4, 0.1% BSA). Cells are placed in serum-free media and the 6× CCF2/AM may be added to a final concentration of 1×. The cells are then loaded at room temperature for one to two hours, and then subjected to fluorescent emission analysis as described herein. Additional details relative to the cell loading methods and/or instrument settings may be found by reference to the following publications: see Zlokarnik, et al., 1998; Whitney et al., 1998; and BD Biosciences, 1999.

Immunocytochemistry

The cell lines transfected and selected for expression of Flag-epitope tagged orphan GPCRs are analyzed by immunocytochemistry. The cells are plated at 1×10^3 in each well of a glass slide (VWR). The cells are rinsed with PBS followed by acid fixation for 30 minutes at room temperature using a mixture of 5% Glacial Acetic Acid/90% ETOH. The cells are then blocked in 2% BSA and 0.1% Triton in PBS, incubated for 2 h at room temperature or overnight at 4° C. A monoclonal anti-Flag FITC antibody may be diluted at 1:50 in blocking solution and incubated with the cells for 2 h at room temperature. Cells are then may behed three times with 0.1% Triton in PBS for five minutes. The slides are overlayed with mounting media dropwise with Biomedia-Gel Mount™ (Biomedia; Containing Anti-Quenching Agent). Cells are examined at 10× magnification using the Nikon TE300 equiped with FITC filter (535 nm).

Demonstration of Cell Surface Expression

HGPRBMY5v1 and/or HGPRBMY5v2 may be tagged at the C-terminus using the Flag epitope and inserted into the pcDNA3.1 hygro™ expression vector, as described herein. Immunocytochemistry of Cho Nfat-CRE cell lines transfected with the Flag-tagged HGPRBMY5v1 and/or HGPRBMY5v2 construct with FITC conjugated Anti Flag monoclonal antibody demonstrated that HGPRBMY5v1 and/or HGPRBMY5v2 is indeed a cell surface receptor. The immunocytochemistry also confirmed expression of the HGPRBMY5v1 and/or HGPRBMY5v2 in the Cho Nfat-CRE cell lines. Briefly, Cho Nfat-CRE cell lines are transfected with pcDNA3.1 hygro™/HGPRBMY5v1- and/or HGPRBMY5v2-Flag vector, fixed with 70% methanol, and permeablized with 0.1% TritonX100. The cells are then blocked with 1% Serum and incubated with a FITC conjugated Anti Flag monoclonal antibody at 1:50 dilution in PBS-Triton. The cells are then may behed several times with PBS-Triton, overlayed with mounting solution, and fluorescent images are captured. The control cell line, non-transfected ChoNfat CRE cell line, exhibited no detectable background fluorescence. Plasma membrane localization would be consistent with HGPRBMY5v1 and/or HGPRBMY5v2 representing a 7 transmembrane domain containing GPCR.

Screening Paradigm

The Aurora Beta-Lactamase technology provides a clear path for identifying agonists and antagonists of the HGPRBMY5v1 and/or HGPRBMY5v2 polypeptides. Cell lines that exhibit a range of constitutive coupling activity may be identified by sorting through HGPRBMY5v1 and/or HGPRBMY5v2 transfected cell lines using the FACS Vantage SE. For example, cell lines that exhibit an intermediate coupling response, using the LJL analyst, would provide the opportunity to screen, indirectly, for both agonists and antagonists of HGPRBMY5v1 and/or HGPRBMY5v2 by looking for inhibitors that block the beta lactamase response, or agonists that increase the beta lactamase response. As described herein, modulating the expression level of beta lactamase directly correlates with the level of cleaved CCR2 substrate. For example, this screening paradigm has been shown to work for the identification of modulators of a known GPCR, 5HT6, that couples through Adenylate Cyclase, in addition to, the identification of modulators of the 5HT2c GPCR, that couples through changes in $[Ca^{2+}]i$. HGPRBMY5v1 and/or HGPRBMY5v2 modulator screens may be carried out using a variety of high throughput methods known in the art, though preferably using the fully automated Aurora UHTSS system.

In preferred embodiments, the HGPRBMY5v1 and/or HGPRBMY5v2 transfected Cho Nfat-CRE cell lines of the present invention are useful for the identification of agonists and antagonists of the HGPRBMY5v1 and/or HGPRBMY5v2 polypeptides. Representative uses of these cell lines would be their inclusion in a method of identifying HGPRBMY5v1 and/or HGPRBMY5v2 agonists and antagonists. Preferably, the cell lines are useful in a method for identifying a compound that modulates the biological activity of the HGPRBMY5v1 and/or HGPRBMY5v2 polypeptides, comprising the steps of (a) combining a candidate modulator compound with a host cell expressing the HGPRBMY5v1 and/or HGPRBMY5v2 polypeptides having the sequence as set forth in SEQ ID NO:2 and/or SEQ ID NO:82; and (b) measuring an effect of the candidate modulator compound on the activity of the expressed HGPRBMY5v1 and/or HGPRBMY5v2 polypeptides. Representative vectors expressing the HGPRBMY5v1 and/or HGPRBMY5v2 polypeptides are referenced herein (e.g., pcDNA3.1 hygro™) or otherwise known in the art.

The cell lines are also useful in a method of screening for a compound that is capable of modulating the biological activity of HGPRBMY5v1 and/or HGPRBMY5v2 polypeptides, comprising the steps of: (a) determining the biological activity of the HGPRBMY5v1 and/or HGPRBMY5v2 polypeptides in the absence of a modulator compound; (b)

contacting a host cell expression the HGPRBMY5v1 and/or HGPRBMY5v2 polypeptides with the modulator compound; and (c) determining the biological activity of the HGPRBMY5v1 and/or HGPRBMY5v2 polypeptides in the presence of the modulator compound; wherein a difference between the activity of the HGPRBMY5v1 and/or HGPRBMY5v2 polypeptides in the presence of the modulator compound and in the absence of the modulator compound indicates a modulating effect of the compound. Additional uses for these cell lines are described herein or otherwise known in the art.

1. Rees, S., Brown, S., Stables, J.: Reporter polynucleotide systems for the study of G Protein Coupled Receptor signalling in mammalian cells. In Milligan G. (ed.): Signal Transduction: A practical approach. Oxford: Oxford University Press, 1999: 171-221.
2. Alam, J., Cook, J. L.: Reporter Polynucleotides: Application to the study of mammalian polynucleotide transcription. Anal. Biochem. 1990; 188: 245-254.
3. Selbie, L. A. and Hill, S. J.: G protein-coupled receptor cross-talk: The fine-tuning of multiple receptor-signaling pathways. TiPs. 1998; 19: 87-93.
4. Boss, V., Talpade, D. J., and Murphy, T. J.: Induction of NFAT mediated transcription by Gq-coupled Receptors in lympoid and non-lymphoid cells. JBC. 1996; 271: 10429-10432.
5. George, S. E., Bungay, B. J., and Naylor, L. H.: Functional coupling of endogenous serotonin (5-HT1B) and calcitonin (C1a) receptors in Cho cells to a cyclic AMP-responsive luciferase reporter polynucleotide. J. Neurochem. 1997; 69: 1278-1285.
6. Suto, C M, Igna D M: Selection of an optimal reporter for cell-based high throughput screening assays. J. Biomol. Screening. 1997; 2: 7-12.
7. Zlokarnik, G., Negulescu, P. A., Knapp, T. E., More, L., Burres, N., Feng, L., Whitney, M., Roemer, K., and Tsien, R. Y. Quantitation of transcription and clonal selection of single living cells with a B-Lactamase Reporter. Science. 1998; 279: 84-88.
8. S. Fiering et. al., Polynucleotides Dev. 4, 1823 (1990).
9. J. Karttunen and N. Shastri, PNAS 88, 3972 (1991).
10. Hawes, B. E., Luttrell. L. M., van Biesen, T., and Lefkowitz, R. J. (1996) JBC 271, 12133-12136.
11. Gilman, A. G. (1987) Annul. Rev. Biochem. 56, 615-649.
12. Maniatis et al.,
13. Salcedo, R., Ponce, M. L., Young, H. A., May beserman, K., Ward, J. M., Kleinman, H. K., Oppenheim, J. J., Murphy, W. J. Human endothelial cells express CCR2 and respond to MCP-1: direct role of MCP-1 in angiopolynucleotidesis and tumor progression. Blood. 2000; 96 (1): 34-40.
14. Sica, A., Saccani, A., Bottazzi, B., Bemasconi, S., Allavena, P., Gaetano, B., LaRossa, G., Scotton, C., Balkwill F., Mantovani, A. Defective expression of the monocyte chemotactic protein 1 receptor CCR2 in macrophages associated with human ovarian carcinoma. J. Immunology. 2000; 164: 733-8.
15. Kypson, A., Hendrickson, S., Akhter, S., Wilson, K., McDonald, P., Lilly, R., Dolber, P., Glower, D., Lefkowitz, R., Koch, W. Adenovirus-mediated polynucleotide transfer of the B2 AR to donor hearts enhances cardiac function. Gene therapy. 1999; 6: 1298-304.
16. Dorn, G. W., Tepe, N. M., Lorenz, J. N., Kock, W. J., Ligget, S. B. Low and high level transgenic expression of B2AR differentially affect cardiac hypertrophy and function in Galpha q-overexpressing mice. PNAS. 1999; 96: 6400-5.
17. J. Wess. G protein coupled receptor: molecular mechanisms involved in receptor activation and selectivity of G-protein recognition.
18. Whitney, M, Rockenstein, E, Cantin, G., Knapp, T., Zlokarnik, G., Sanders, P., Durick, K., Craig, F. F., and Negulescu, P. A. A genome-wide functional assay of signal transduction in living mammalian cells. 1998. Nature Biotech. 16: 1329-1333.
19. BD Biosciences: FACS Vantage SE Training Manual. Part Number 11-11020-00 Rev. A. August 1999.
20. Chen, G., Jaywickreme, C., Way, J., Armour S., Queen K., Watson., C., Ignar, D., Chen, W. J., Kenakin, T. Constitutive Receptor systems for drug discovery. J. Pharmacol. Toxicol. Methods 1999; 42: 199-206.

Example 9

Method of Assessing the Ability of HGPRBMY5v1 and/or HGPRBMY5v2 to Serve as a GPCR Receptor The activity of the HGPRBMY5v1 and/or HGPRBMY5v2 polypeptides may be measured using an assay based upon the property of some known GPCRs to support proliferation in vitro of fibroblasts and tumor cells under serum-free conditions (Chiquet Ehrismann, R. et al. (1986) Cell 47: 131-139). Briefly, wells in 96 well cluster plates (Falcon, Fisher Scientific, Santa Clara Calif.) are coated with HGPRBMY5v1 and/or HGPRBMY5v2 polypeptides by incubation with solutions at 50-100 Rg/ml for 15 min at ambient temperature. The coating solution is aspirated, and the wells washed with Dulbecco's medium before cells are plated. Rat fibroblast cultures or rat mammary tumor cells are prepared as described and plated at a density of 104-105 cells/ml in Dulbecco's medium supplemented with 10% fetal calf serum (FCS).

After three days the media are removed, and the cells washed three times with phosphatebuffered saline (PBS) before the addition of serum-free Dulbecco's medium containing 0.25 mg/ml bovine serum albumin (BSA, Fraction V, Sigma Chemical, St. Louis, Mo.). After 2 days the medium is aspirated, and 100 µl of [3H] thymidine (NEN) at 2 llCi/ml in fresh Dulbecco's medium containing 0.25 mg/ml BSA added. Parallel plates are fixed and stained to determine cell numbers. After 16 hr, the medium is aspirated, the cell layer washed with PBS, and the 10% trichloroacetic acid-precipitable counts in the cell layer determined by liquid scintillation counting of radioisotope (normalized to relative cell numbers; Chiquet-Ehrismann, R. et al. (1986) supra). The rates of cell proliferation and [3H] thymidine uptake are proportional to the levels of GCRP in the sample.

Alternatively, the assay for HGPRBMY5v1 and/or HGPRBMY5v2 polypeptide activity is based upon the property of CD97/Emr1 GPCR family proteins to modulate G protein-activated second messenger signal transduction pathways (e.g., cAMP; Gaudin, P. et al. (1998) J. Biol. Chem. 273: 4990-4996). A plasmid encoding the full length HGPRBMY5v1 and/or HGPRBMY5v2 polypeptide is transfected into a mammalian cell line (e.g., COS-7 or Chinese hamster ovary (CHO-K1) cell lines) using methods well-known in the art. Transfected cells are grown in 12-well trays in culture medium containing 2% FCS for 48 hours, the culture medium is discarded, then the attached cells are gently washed with PBS. The cells are then incubated in culture medium with 10% FCS or 2% FCS for 30 minutes, then the medium is removed and cells lysed by treatment with 1 M perchloric acid. The cAMP levels in the lysate are measured by radioimmunoassay using methods well-known in the art. Changes in the levels of cAMP in the lysate from 10% FCS-treated cells compared with those in 2% FCS-treated cells are proportional to the amount of the HGPRBMY5v1 and/or HGPRBMY5v2 polypeptide present in the transfected cells.

Example 10

Method of Assessing the Physiological Function of the GPRBMY5v1 Polypeptide at the Cellular Level The physiological function of the HGPRBMY5v1 and/or HGPRBMY5v2 polypeptide may be assessed by expressing the sequences encoding HGPRBMY5v1 and/or HGPRBMY5v2 at physiologically elevated levels in mammalian cell culture systems. cDNA is subcloned into a mammalian expression vector containing a strong promoter that drives high levels of cDNA expression (examples are provided elsewhere herein). Vectors of choice include pCMV SPORT (Life Technologies) and pCR3.1 (Invitrogen, Carlsbad Calif.), both of which contain the cytomegalovirus promoter. 5-10, ug of recombinant vector are transiently transfected into a human cell line, preferably of endothelial or hematopoietic origin, using either liposome formulations or electroporation. 1-2 ug of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of HGPRBMY5v1 and/or HGPRBMY5v2 polypeptides on polynucleotide expression can be assessed using highly purified populations of cells transfected with sequences encoding HGPRBMY5v1 and/or HGPRBMY5v2 and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success NY). mRNA can be purified from the cells using methods well known by those of skill in the art. Expression of mRNA encoding HGPRBMY5v1 and/or HGPRBMY5v2 polypeptides and other polynucleotides of interest can be analyzed by northern analysis or microarray techniques.

Example 11

Method of Assessing the Physiological Function of the HGPRBMY5v1 and/or HGPRBMY5v2 Polypeptides in *Xenopus* Oocytes Capped RNA transcripts from linearized plasmid templates encoding the receptor cDNAs of the invention are synthesized in vitro with RNA polymerases in accordance with standard procedures.

In vitro transcripts are suspended in water at a final concentration of 0.2 mg/ml. Ovarian lobes are removed from adult female toads, Stage V defolliculatedoocytes are obtained, and RNA transcripts (10 ng/oocyte) are injected in a 50 nl bolus using a microinjection apparatus. Two electrode voltage clamps are used to measure the currents from individual *Xenopus* oocytes in response to agonist exposure. Recordings are made in Ca2+ free Barth's medium at room temperature.

In a preferred embodiment, such a system can be used to screen known ligands and tissue/cell extracts for activating ligands. A number of GPCR ligands are known in the art and are encompassed by the present invention (see, for example, The G-Protein Linked Receptor Facts Book, referenced elsewhere herein).

Example 12

Method of Assessing the Physiological Function of the HGPRBMY5v1 and/or HGPRBMY5v2 Polypeptides Using Microphysiometric Assays Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor that is coupled to an energy utilizing intracellular signaling pathway such as the G-protein coupled receptor of the present invention.

Example 13

Method of Assessing the Physiological Function of the HGPRBMY5v1 and/or HGPRBMY5v2 Polypeptides Using Calcium and cAMP Functional Assays A well known observation in the art relates to the fact that GPCR receptors which are expressed in HEK 293 cells have been shown to be functionally couple—leading to subsequent activation of phospoholipase C (PLC) and calcium mobilization, and/or cAMP stimuation or inhibition.

Based upon the above, calcium and cAMP assays may be useful in assessing the ability of HGPRBMY5v1 and/or HGPRBMY5v2 to serve as a GPCR. Briefly, basal calcium levels in the HEK 293 cells in HGPRBMY5v1 and/or HGPRBMY5v2-transfected or vector control cells can be observed to determine whether the levels fall within a normal physiological range, 100 nM to 200 nM. HEK 293 cells expressing recombinant receptors are then loaded with fura 2 and in a single day selected GPCR ligands or tissue/cell extracts are evaluated for agonist induced calcium mobilization. Similarly, HEK 293 cells expressing recombinant HGPRBMY5v1 and/or HGPRBMY5v2 receptors are evaluated for the stimulation or inhibition of cAMP production using standard cAMP quantitation assays. Agonists presenting a calcium transient or cAMP flucuation are tested in vector control cells to determine if the response is unique to the transfected cells expressing the HGPRBMY5v1 and/or HGPRBMY5v2 receptor.

Example 14

Method of Screening for Compounds that Interact with the HGPRBMY5v1 and/or HGPRBMY5v2 Polypeptide The following assays are designed to identify compounds that bind to the HGPRBMY5v1 and/or HGPRBMY5v2 polypeptide, bind to other cellular proteins that interact with the HGPRBMY5v1 and/or HGPRBMY5v2 polypeptide, and to compounds that interfere with the interaction of the HGPRBMY5v1 and/or HGPRBMY5v2 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of HGPRBMY5v1 and/or HGPRBMY5v2 polypeptide transmembrane receptors, and members of random peptide libraries (see, e.g., Lam, K. S. et al., 1991, Nature 354:82-84; Houghton, R. et al., 1991, Nature 354:84-86), made of D-and/or L-configuration amino acids, phosphopeptides (including, but not limited to, members of random or partially degenerate phosphopeptide libraries; see, e.g., Songyang, Z., et al., 1993, Cell 72:767-778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the HGPRBMY5v1 and/or HGPRBMY5v2 polypeptide, and for ameliorating symptoms of tumor progression, for example. In instances, for example, whereby a tumor progression state or disorder results from a lower overall level of HGPRBMY5v1 and/or HGPRBMY5v2 expression, HGPRBMY5v1 and/or HGPRBMY5v2 polypeptide, and/or HGPRBMY5v1 and/or HGPRBMY5v2 polypeptide activity in a cell involved in the tumor progression state or disorder, compounds that interact with the HGPRBMY5v1 and/or HGPRBMY5v2 polypeptide can include ones which accentuate or amplify the activity of the bound HGPRBMY5v 1 and/or HGPRBMY5v2 polypeptide. Such compounds would bring about an effective increase in the level of HGPRBMY5v1 and/or HGPRBMY5v2 polypeptide activity, thus ameliorating symptoms of the tumor progression disorder or state. In instances whereby mutations within the HGPRBMY5v1 and/or HGPRBMY5v2 polypeptide cause aberrant HGPRBMY5v1 and/or HGPRBMY5v2 polypeptides to be made which have a deleterious effect that leads to tumor progression, compounds that bind HGPRBMY5v1 and/or HGPRBMY5v2 polypeptide can be identified that inhibit the activity of the bound HGPRBMY5v1 and/or HGPRBMY5v2 polypeptide. Assays for testing the effectiveness of such compounds are known in the art and discussed, elsewhere herein.

Example 15

Method of Screening, in Vitro, Compounds that Bind to the HGPRBMY5v1 and/or HGPRBMY5v2 Polypeptide In vitro systems can be designed to identify compounds capable of binding the HGPRBMY5v1 and/or HGPRBMY5v2 polypeptide of the invention. Compounds identified can be useful, for example, in modulating the activity of wild type and/or mutant HGPRBMY5v1 and/or HGPRBMY5v2 polypeptide, preferably mutant HGPRBMY5v1 and/or HGPRBMY5v2 polypeptide, can be useful in elaborating the biological function of the HGPRBMY5v1 and/or HGPRBMY5v2 polypeptide, can be utilized in screens for identifying compounds that disrupt normal HGPRBMY5v1 and/or HGPRBMY5v2 polypeptide interactions, or can in themselves disrupt such interactions.

The principle of the assays used to identify compounds that bind to the HGPRBMY5v1 and/or HGPRBMY5v2 polypeptide involves preparing a reaction mixture of the HGPRBMY5v1 and/or HGPRBMY5v2 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring HGPRBMY5v1 and/or HGPRBMY5v2 polypeptide or the test substance onto a solid phase and detecting HGPRBMY5v1 and/or HGPRBMY5v2 polypeptide/test compound complexes anchored on the solid phase at the end of the reaction. In one embodiment of such a method, the HGPRBMY5v1 and/or HGPRBMY5v2 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HGPRBMY5v1 and/or HGPRBMY5v2 polypeptide or the test compound to anchor any complexes formed in solution, and a labeled antibody specific for the other component of the possible complex to detect anchored complexes.

Another example of a screening assay to identify compounds that bind to HGPRBMY5v1 and/or HGPRBMY5v2, relates to the application of a cell membrane-based scintillation proximity assay ("SPA"). Such an assay would require the idenification of a ligand for HGPRBMY5v1 and/or HGPRBMY5v2 polypeptide. Once identified, unlabeled ligand is added to assay-ready plates that would serve as a positive control. The SPA beads and membranes are added next, and then $^{125}$I-labeled ligand is added. After an equilibration period of 2-4 hours at room temperature, the plates can be counted in a scintillation counting machine, and the percent inhibition or stimulation calculated. Such an SPA assay may be based upon a manual, automated, or semi-automated platform, and encompass 96, 384, 1536-well plates or more. Any number of SPA beads may be used as applicable to each assay. Examples of SPA beads include, for example, Leadseeker WGA PS (Amersham cat # RPNQ 0260), and SPA Beads (PVT-PEI-WGA-TypeA; Amersham cat # RPNQ0003). The utilized membranes may also be derived from a number of cell line and tissue sources depending upon the expression profile of the respective polypeptide and the adaptability of such a cell line or tissue source to the development of a SPA-based assay. Examples of membrane preparations include, for example, cell lines transformed to express the receptor to be assayed in CHO cells or HEK cells, for example. SPA-based assays are well known in the art and are encompassed by the present invention. One such assay is described in U.S. Pat. No. 4,568,649, which is incorporated herein by reference. The skilled artisan would acknowledge that certain modifications of known SPA assays may be required to adapt such assays to each respective polypeptide.

One such screening procedure involves the use of melanophores which are transfected to express the HGPRBMY5v1 and/or HGPRBMY5v2 polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor. Other screening techniques include the use of cells which express the HGPRBMY5v1 and/or HGPRBMY5v2 polypeptide (for example, transfected CHO cells) in a system which measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another screening technique involves expressing the HGPRBMY5v1 and/or HGPRBMY5v2 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists or agonists by determining inhibition of binding of labeled ligand, such as LPA, to cells which have the receptor on the surface thereof, or cell membranes containing the receptor. Such a method involves transfecting a cell (such as eukaryotic cell) with DNA encoding the HGPRBMY5v1 and/or HGPRBMY5v2 polypeptide such that the cell expresses the receptor on its surface. The cell is then contacted with a potential antagonist or agonist in the presence of a labeled form of a ligand, such as LPA. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another screening procedure involves the use of mammalian cells (CHO, HEK 293, *Xenopus* Oocytes, RBL-2H3, etc) which are transfected to express the receptor of interest. The cells are loaded with an indicator dye that produces a fluorescent signal when bound to calcium, and the cells are contacted with a test substance and a receptor agonist, such as LPA. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, *Xenopus* Oocytes, RBL-2H3, etc.) which are transfected to express the receptor of interest, and which are also transfected with a reporter polynucleotide construct that is coupled to activation of the receptor (for example, luciferase or beta-galactosidase behind an appropriate promoter). The cells are contacted with a test substance and the receptor agonist (ligand), such as LPA, and the signal produced by the reporter polynucleotide is measured after a defined period of time. The signal can be measured using a luminometer, spectrophotometer, fluorimeter, or other such instrument appropriate for the specific reporter construct used. Change of the signal generated by the ligand indicates that a compound is a potential antagonist or agonist for the receptor.

Another screening technique for antagonists or agonits involves introducing RNA encoding the HGPRBMY5v1 and/or HGPRBMY5v2 polypeptide into *Xenopus* oocytes (or CHO, HEK 293, RBL-2H3, etc.) to transiently or stably express the receptor. The receptor oocytes are then contacted with the receptor ligand, such as LPA, and a compound to be screened. Inhibition or activation of the receptor is then determined by detection of a signal, such as, cAMP, calcium, proton, or other ions.

Another method involves screening for HGPRBMY5v1 and/or HGPRBMY5v2 polypeptide inhibitors by determining inhibition or stimulation of HGPRBMY5v1 and/or HGPRBMY5v2 polypeptide-mediated cAMP and/or adenylate cyclase accumulation or diminution. Such a method involves transiently or stably transfecting a eukaryotic cell with HGPRBMY5v1 and/or HGPRBMY5v2 polypeptide receptor to express the receptor on the cell surface.

The cell is then exposed to potential antagonists or agonists in the presence of HGPRBMY5v1 and/or HGPRBMY5v2 polypeptide ligand, such as LPA. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits HGPRBMY5v1 and/or HGPRBMY5v2 polypeptide-ligand binding, the levels of HGPRBMY5v1 and/or HGPRBMY5v2 polypeptide-mediated cAMP, or adenylate cyclase activity, will be reduced or increased.

One preferred screening method involves co-transfecting HEK-293 cells with a mammalian expression plasmid encoding a G-protein coupled receptor (GPCR), such as HGPRBMY5v1 and/or HGPRBMY5v2, along with a mixture comprised of mammalian expression plasmids cDNAs encoding GU15 (Wilkie T. M. et al Proc Natl Acad Sci USA 1991 88: 10049-10053), GU16 (Amatruda T. T. et al Proc Natl Acad Sci USA 1991 8: 5587-5591, and three chimeric G-proteins refered to as Gqi5, Gqs5, and Gqo5 (Conklin B R et al Nature 1993 363: 274-276, Conklin B. R. et al Mol Pharmacol 1996 50: 885-890). Following a 24 h incubation the trasfected HEK-293 cells are plated into poly-D-lysine coated 96 well black/clear plates (Becton Dickinson, Bedford, Mass.).

The cells are assayed on FLIPR (Fluorescent Imaging Plate Reader, Molecular Devices, Sunnyvale, Calif.) for a calcium mobilization response following addition of test ligands. Upon identification of a ligand which stimulates calcium mobilization in HEK-293 cells expressing a given GPCR and the G-protein mixtures, subsequent experiments are performed to determine which, if any, G-protein is required for the functional response. HEK-293 cells are then transfected with the test GPCR, or co-transfected with the test GPCR and G015, GD16, GqiS, Gqs5, or Gqo5. If the GPCR requires the presence of one of the G-proteins for functional expression in HEK-293 cells, all subsequent experiments are performed with HEK-293 cell cotransfected with the GPCR and the G-protein which gives the best response. Alternatively, the receptor can be expressed in a different cell line, for example RBL-2H3, without additional Gproteins.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATa. Each cell type secretes a small peptide hormone that binds to a G-protein coupled receptor on opposite mating type cells which triggers a MAP kinase cascade leading to G1 arrest as a prelude to cell fusion.

Polynucleotidetic alteration of certain polynucleotides in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter polynucleotides (e.g., U.S. Pat. Nos. 5,063,154; 5,482,835; 5,691,188). Such polynucleotidetic alterations include, but are not limited to, (i) deletion of the STE2 or STE3 polynucleotide encoding the endogenous G-protein coupled pheromone receptors; (ii) deletion of the FAR1 polynucleotide encoding a protein that normally associates with cyclindependent kinases leading to cell cycle arrest; and (iii) construction of reporter polynucleotides fused to the FUS 1 polynucleotide promoter (where FUS 1 encodes a membrane-anchored glycoprotein required for cell fusion). Downstream reporter polynucleotides can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUSl-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J., Nature 384: 14-16, 1996; Manfredi et al., Mol. Cell. Biol. 16: 4700-4709,1996). This provides a rapid direct growth selection (e.g, using the FUS 1-HIS3 reporter) for surrogate peptide agonists that activate characterized or orphan receptors. Alternatively, yeast cells that functionally express human (or mammalian) G-protein coupled receptors linked to a reporter polynucleotide readout (e.g., FUS1-LacZ) can be used as a platform for high-throughput screening of known ligands, fractions of biological extracts and libraries of chemical compounds for either natural or surrogate ligands.

Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUSI-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

Example 16

Method for Identifying a Putative Ligand for the HGPRBMY5v1 and/or HGPRBMY5v2 Polypeptides Ligand binding assays provide a direct method for ascertaining receptor pharmacology and are adaptable to a high throughput format. A panel of known GPCR purified ligands may be radiolabeled to high specific activity (50-2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

A number of GPCR ligands are known in the art and are encompassed by the present invention (see, for example, The G-Protein Linked Receptor Facts Book, referenced elsewhere herein).

Alternatively, the HGPRBMY5v1 and/or HGPRBMY5v2 polypeptide of the present invention may also be functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified using methods well known in the art, some of which are described herein.

Example 17

Method of Identifying Compounds that Interfere with HGPRBMY5v1 and/or HGPRBMY5v2 Polypeptide/Cellular Product Interaction The HGPRBMY5v1 and/or HGPRBMY5v2 polypeptide of the invention can, in vivo, interact with one or more cellular or extracellular macromolecules, such as proteins. Such macromolecules include, but are not limited to, polypeptides, particularly GPCR ligands, and those products identified via screening methods described, elsewhere herein. For the purposes of this discussion, such cellular and extracellular macromolecules are referred to herein as "binding partner(s)". For the purpose of the present invention, "binding partner" may also encompass polypeptides, small molecule compounds, polysaccharides, lipids, and any other molecule or molecule type referenced herein. Compounds that disrupt such interactions can be useful in regulating the activity of the HGPRBMY5v1 and/or HGPRBMY5v2 polypeptide, especially mutant HGPRBMY5v1 and/or HGPRBMY5v2 polypeptide. Such compounds can include, but are not limited to molecules such as antibodies, peptides, and the like described in elsewhere herein.

The basic principle of the assay systems used to identify compounds that interfere with the interaction between the HGPRBMY5v1 and/or HGPRBMY5v2 polypeptide and its cellular or extracellular binding partner or partners involves preparing a reaction mixture containing the HGPRBMY5v1 and/or HGPRBMY5v2 polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of HGPRBMY5v1 and/or HGPRBMY5v2 polypeptide and its cellular or extracellular binding partner. Control reaction mixtures are incubated without the test compound or with a placebo. The formation of any complexes between the HGPRBMY5v1 and/or HGPRBMY5v2 polypeptide and the cellular or extracellular binding partner is then detected. The formation of a complex in the control reaction, but not in the reaction mixture containing the test compound, indicates that the compound interferes with the interaction of the HGPRBMY5v1 and/or HGPRBMY5v2 polypeptide and the interactive binding partner. Additionally, complex formation within reaction mixtures containing the test compound and normal HGPRBMY5v1 and/or HGPRBMY5v2 polypeptide can also be compared to complex formation within reaction mixtures containing the test compound and mutant HGPRBMY5v1 and/or HGPRBMY5v2 polypeptide. This comparison can be important in those cases wherein it is desirable to identify compounds that disrupt interactions of mutant but not normal HGPRBMY5v1 and/or HGPRBMY5v2 polypeptide.

The assay for compounds that interfere with the interaction of the HGPRBMY5v1 and/or HGPRBMY5v2 polypeptide and binding partners can be conducted in a heteropolynucleotideous or homopolynucleotideous format. Heteropolynucleotideous assays involve anchoring either the HGPRBMY5v1 and/or HGPRBMY5v2 polypeptide or the binding partner onto a solid phase and detecting complexes anchored on the solid phase at the end of the reaction. In homopolynucleotideous assays, the entire reaction is carried out in a liquid phase. In either approach, the order of addition of reactants can be varied to obtain different information about the compounds being tested. For example, test compounds that interfere with the interaction between the HGPRBMY5v1 and/or HGPRBMY5v2 polypeptide and the binding partners, e.g., by competition, can be identified by conducting the reaction in the presence of the test substance; i.e., by adding the test substance to the reaction mixture prior to or simultaneously with the HGPRBMY5v1 and/or HGPRBMY5v2 polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heteropolynucleotideous assay system, either the HGPRBMY5v1 and/or HGPRBMY5v2 polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the HGPRBMY5v1 and/or HGPRBMY5v2 polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homopolynucleotideous assay can be used. In this approach, a preformed complex of the HGPRBMY5v1 and/or HGPRBMY5v2 polypeptide and the interactive cellular or extracellular binding partner product is prepared in which either the HGPRBMY5v1 and/or HGPRBMY5v2 polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt HGPRBMY5v1 and/or HGPRBMY5v2 polypeptide-cellular or extracellular binding partner interaction can be identified.

In a particular embodiment, the HGPRBMY5v1 and/or HGPRBMY5v2 polypeptide can be prepared for immobilization using recombinant DNA techniques known in the art. For example, the HGPRBMY5v1 and/or HGPRBMY5v2 polypeptide coding region can be fused to a glutathione-S-transferase (GST) polynucleotide using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope sup.125 I, for example, by methods routinely practiced in the art. In a heteropolynucleotideous assay, e.g., the GST-HGPRBMY5v1 and/or HGPRBMY5v2 polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the HGPRBMY5v1 and/or HGPRBMY5v2 polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-HGPRBMY5v1 and/or HGPRBMY5v2 polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the HGPRBMY5v1 and/or HGPRBMY5v2 polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutapolynucleotidesis of one of the polynucleotides encoding one of the products and screening for disruption of binding in a co-immunoprecipitation assay. Compensating mutations in the polynucleotide encoding the second species in the complex can be selected. Sequence analysis of the polynucleotides encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the polynucleotide coding for the cellular or extracellular binding partner product is obtained, short polynucleotide segments can be engineered to express peptide fragments of the product, which can then be tested for binding activity and purified or synthesized.

Example 18

Isolation of a Specific Clone from the Deposited Sample

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1-10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1 and/or SEQ ID NO:81.

Particularly, a specific polynucleotide with 30-40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratapolynucleotide)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:1 and/or SEQ ID NO:81 (i.e., within the region of SEQ ID NO:1 and/or SEQ ID NO:81 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM MgCl2, 0.01% (w/v) gelatin, 20 uM each of DATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length polynucleotide). Several methods are known in the art for the identification of the 5' or 3' non-coding and/or coding portions of a polynucleotide which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7):1683-1684 (1993)).

Briefly, a specific RNA oligonucleotide is ligated to the 5' ends of a population of RNA presumably containing full-length polynucleotide RNA transcripts. A primer set containing a primer specific to the ligated RNA oligonucleotide and a primer specific to a known sequence of the polynucleotide of interest is used to PCR amplify the 5' portion of the desired full-length polynucleotide. This amplified product may then be sequenced and used to generate the full-length polynucleotide.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a polynucleotide specific oligonucleotide. The first strand synthesis reaction is used as a template for PCR amplification of the desired 5' end using a primer specific to the ligated RNA oligonucleotide and a primer specific to the known sequence of the polynucleotide of interest. The resultant product is then sequenced and analyzed to confirm that the 5' end sequence belongs to the desired polynucleotide. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255-273, (1995).

An alternative method for carrying out 5' or 3' RACE for the identification of coding or non-coding sequences is provided by Frohman, M. A., et al., Proc. Nat'l. Acad. Sci. USA, 85:8998-9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with DATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratapolynucleotide) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length polynucleotides. A second kit is available from Clontech which is a modification of a related technique, SLIC (single-stranded ligation to single-stranded cDNA), developed by Dumas et al., Nucleic Acids Res., 19:5227-32(1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Polynucleotiderating the 5' or 3' End Sequences to Obtain Full Length Polynucleotides Once a polynucleotide of interest is identified, several methods are available for the identification of the 5' or 3' portions of the polynucleotide which may not be present in the original cDNA plasmid. These methods include, but are not limited to, filter probing, clone enrichment using specific probes and protocols similar and identical to 5' and 3'RACE. While the full-length polynucleotide may be present in the library and can be identified by probing, a useful method for generating the 5' or 3' end is to use the existing sequence information from the original cDNA to generate the missing information. A method similar to 5'RACE is available for generating the missing 5' end of a desired full-length polynucleotide. (This method was published by Fromont-Racine et al., Nucleic Acids Res., 21(7): 1683-1684 (1993)). Briefly, a specific RNA oligonucleotide is ligated to the 5' ends of a population of RNA presumably 30 containing full-length polynucleotide RNA transcript and a primer set containing a primer specific to the ligated RNA oligonucleotide and a primer specific to a known sequence of the polynucleotide of interest, is used to PCR amplify the 5' portion of the desired full length polynucleotide which may then be sequenced and used to generate the full length polynucleotide. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a polynucleotide specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 19

Chromosomal Mapping of the Polynucleotides

An oligonucleotide primer set is designed according to the sequence at the 5' end of SEQ ID NO:1 and/or SEQ ID NO:81. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 20

Bacterial Expression of a Polypeptide

A polynucleotide encoding a polypeptide of the present invention is amplified using PCR oligonucleotide primers corresponding to the 5' and 3' ends of the DNA sequence, as outlined in Example 18, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The OIN culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased polynucleotide expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6× His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 21

Purification of a Polypeptide from an Inclusion Body

The following alternative method can be used to purify a polypeptide expressed in E coli when it is present in the form of inclusion bodies. Unless otherwise specified, all of the following steps are conducted at 4-10 degree C.

Upon completion of the production phase of the E. coli fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homopolynucleotideous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 22

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase polynucleotide from *E. coli* under control of a weak *Drosophila* promoter in the same orientation, followed by the polyadenylation signal of the polyhedrin polynucleotide. The inserted polynucleotides are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in Example 18, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 18. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. -1555 (1987).

The amplified fragment is isolated from a 1% agarose gel using a commercially available kit ("Polynucleotideclean" BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Polynucleotideclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratapolynucleotide Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad. Sci. USA 84:7413-7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce bluestained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 23

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed polynucleotide can also be amplified to express large amounts of the encoded protein. The DHFR (dihydrofolate reductase) marker is useful in developing cell lines that carry several hundred or even several thousand copies of the polynucleotide of interest. (See, e.g., Alt, F. W., et al., J. Biol. Chem . . . 253:1357-1370 a(1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified polynucleotide(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Polynucleotideclean" BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB11 or XL-1 Blue cells are then transformed and bacteria are identified that contain the fragment inserted into plasmid pC6 using, for instance, restriction enzyme analysis.

Chinese hamster ovary cells lacking an active DHFR polynucleotide is used for transformation. Five µg of an expression plasmid is cotransformed with 0.5 ug of the plasmid pSVneo using lipofectin (Felgner et al., supra). The plasmid pSV2-neo contains a dominant selectable marker, the neo polynucleotide from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired polynucleotide product is analyzed, for instance, by SDS-PAGE and Western blot or by reversed phase HPLC analysis.

Example 24

Method of Creating N- and C-Terminal Deletion Mutants Corresponding to the HGPRBMY5v1 and/or HGPRBMY5v2 Polypeptide of the Present Invention As described elsewhere herein, the present invention encompasses the creation of N- and C-terminal deletion mutants, in addition to any combination of N- and C-terminal deletions thereof, corresponding to the HGPRBMY5v1 and/or HGPRBMY5v2 polypeptide of the present invention. A number of methods are available to one skilled in the art for creating such mutants. Such methods may include a combination of PCR amplification and polynucleotide cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length HGPRBMY5v1 and/or HGPRBMY5v2 polypeptide sequence (as described in Example 18, for example), appropriate primers of about 15-25 nucleotides derived from the desired 5' and 3' positions of SEQ ID NO:1 and/or SEQ ID NO:81 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the L412 to S748 N-terminal deletion mutant of HGPRBMY5v1, the following primers could be used to amplify a cDNA fragment corresponding to this deletion mutant:

```
5' Primer 5'-GCAGCA GCGGCCGC CTCAGAATATTTGTCTGGGTTATAG-3'  (SEQ ID NO:75)
                    NotI 3' Primer 5'-GCAGCA GTCGAC GGAAACTGGTTTCATTATACTG-3'       (SEQ ID NO:76)
                    SalI
```

For example, in the case of the M1 to T689 C-terminal deletion mutant of HGRPBMY5v1, the following primers could be used to amplify a cDNA fragment corresponding to this deletion mutant:

```
5' Primer 5'-GCAGCA GCGGCCGC ATGCAGAAAACCAAGCAAGATGAGG-3'  (SEQ ID NO:77)
                    NotI 3' Primer 5'-GCAGCA GTCGAC GGTTGTGAGAGTATAGAGGATTGG-3'     (SEQ ID NO:1 and/or
                    SalI                                   SEQ ID NO:817)
```

In the case of the M1 to R413 C-terminal deletion mutant (HGPRBMY5v1 ectodomain), the following primers could be used to amplify a cDNA fragment corresponding to this deletion mutant:

```
5' Primer 5'-GCAGCA GCGGCCGC ATGCAGAAAACCAAGCAAGATGAGG-3'  (SEQ ID NO:1 and/or
                    NotI                                   SEQ ID NO:818)

3' Primer 5'-GCAGCA GTCGAC TCTGAGGATATTGTTAGCCAAGAGG-3'    (SEQ ID NO:1 and/or
                    SalI                                   SEQ ID NO:819)
```

For example, in the case of the L388 to S724 N-terminal deletion mutant of HGPRBMY5v2, the following primers could be used to amplify a cDNA fragment corresponding to this deletion mutant:

```
5' Primer 5'-GCAGCA GCGGCCGC CTCAGAATATTTGTCTGGGTTATAG-3'  (SEQ ID NO:84)
                   NotI 3' Primer 5'-GCAGCA GTCGAC GGAAACTGGTTTCATTATACTGTC-3'    (SEQ ID NO:85)
                   SalI
```

For example, in the case of the M1 to T665 C-terminal deletion mutant of HGRPBMY5v2, the following primers could be used to amplify a cDNA fragment corresponding to this deletion mutant:

```
5' Primer 5'-GCAGCA GCGGCCGC ATGCAGAAAACCAAGCAAGATGAGG-3'  (SEQ ID NO:86)
                   NotI 3' Primer 5'-GCAGCA GTCGAC GGTTGTGAGAGTATAGAGGATTGG-3'    (SEQ ID NO:87)
                   SalI
```

In the case of the M1 to R389 C-terminal deletion mutant (HGPRBMY5v2 ectodomain), the following primers could be used to amplify a cDNA fragment corresponding to this deletion mutant:

```
5' Primer 5'-GCAGCA GCGGCCGC ATGCAGAAAACCAAGCAAGATGAGG-3'  (SEQ ID NO:88)
                   NotI 3' Primer 5'-GCAGCA GTCGAC TCTGAGGATATTGTTAGCCAAGAGG-3'   (SEQ ID NO:89)
                   SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of HGPRBMY5v1 and/or HGPRBMY5v2), 200 uM 4dNTPs, 1 uM primers, 0.25U Taq DNA polymerase (PE), and standard Taq DNA polymerase buffer. Typical PCR cycling condition are as follows:

20-25 cycles: 45 sec, 93 degrees
  2 min, 50 degrees
  2 min, 72 degrees
1 cycle: 10 min, 72 degrees After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula: $(S+(X*3))$ to $((S+(X*3))+25)$, wherein 'S' is equal to the nucleotide position of the initiating start codon of the HGPRBMY5v1 and/or HGPRBMY5v2 polynucleotide (SEQ ID NO:1 and/or SEQ ID NO:81), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1 and/or SEQ ID NO:81. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))−25), wherein 'S' is equal to the nucleotide position of the initiating start codon of the HGPRBMY5v1 and/or HGPRBMY5v2 polynucleotide (SEQ ID NO:1 and/or SEQ ID NO:81), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1 and/or SEQ ID NO:81. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 25

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

```
Human IgG Fc region
                                         (SEQ ID NO:20)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG
```

-continued

```
ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT
```

Example 26

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using polynucleotidetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 27

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign polynucleotides, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the polynucleotide for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the polynucleotide of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling polynucleotide expression levels of a protein from a transpolynucleotide (i.e., includes stable and transient transformants) has recently been elucidated (V. M. Rivera., et al., Science, 287:826-830, (2000)). This method does not control polynucleotide expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826-830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826-830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promoter or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 28

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631-64; Rademacher et al., (1988) Annu. Rev. Biochem. 57:785-838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309-312; Helenius (1994) Mol. Biol. Of the Cell 5:253-265; Olden et al., (1978) Cell, 13:461-473; Caton et al., (1982) Cell, 37:417-427; Alexamnder and Elder (1984), Science, 226:1328-1330; and Flack et al., (1994), J. Biol. Chem., 269:14015-14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99-128; Ashwell and Harford (1982), Ann. Rev. Biochem., 51:531-54). Receptor systems have been identified that are thought to play a major role in the clearance of serum proteins through recognition of various carbohydrate structures on the glycoproteins (Stockert (1995), Physiol. Rev., 75:591-609; Kery et al., (1992), Arch. Biochem. Biophys., 298:49-55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51-53). However, studies have reported that the deletion of N-linked glycosylation sites often impairs intracellular transport and results in the intracellular accumulation of glycosylation site variants (Machamer and Rose (1988), J. Biol. Chem., 263: 5955-5960; Gallagher et al., (1992), J. Virology., 66:7136-7145; Collier et al., (1993), Biochem., 32:7818-7823; Claffey et al., (1995) Biochemica et Biophysica Acta, 1246: 1-9; Dube et al., (1988), J. Biol. Chem. 263:17516-17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinantly, in another organism (i.e., expressing a human protein in E. coli, yeast, or viral organisms; or an E. coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutapolynucleotidesis methodology known in the art and available to the skilled artisan, Preferably using PCR-directed mutapolynucleotidesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Polynucleotidetics Computer Group suite of programs) provides this function, as well.

Example 29

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased polynucleotides. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

Directed evolution is comprised of several steps. The first step is to establish a library of variants for the polynucleotide or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutapolynucleotidesis, "error-prone" PCR, chemical mutapolynucleotidesis, site-directed mutapolynucleotidesis, and other methods well known in the art (for a comprehensive listing of current mutapolynucleotidesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutapolynucleotidesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Polynucleotide, 46:145-152, (1986), and Hill, D E, et al, Methods Enzymol., 55:559-568, (1987). Both approaches have limits to the level of mutapolynucleotidesis that can be obtained. However, either approach enables the investigator to effectively control the rate of mutapolynucleotidesis. This is particularly important considering the fact that mutations beneficial to the activity of the enzyme are fairly rare. In fact, using too high a level of mutapolynucleotidesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your polynucleotide, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM MgCl2 for 10-20 min. at room temperature. The resulting fragments of 10-50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1 M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris● HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30 s, 50-55 C for 30 s, and 72 C for 30 s using 30-45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutapolynucleotidesis using the methods described by Zhao, et al. (Nucl Acid Res., 25(6):1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutapolynucleotidesis. An effect of forcing DNA polymerase to synthesize full-length polynucleotides from the small fragment DNA pool is a background mutapolynucleotidesis rate. In combination with a stringent selection method, enzymatic activity has been evolved up to 16000 fold increase over the wild-type form of the enzyme. In essence, the background mutapolynucleotidesis yielded the polynucleotidetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the polynucleotide sequence for a xenobiotic ortholog of the native protein in with the polynucleotide sequence of the novel variant polynucleotide in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the polynucleotide template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 30

Method of Determining Alterations in a Polynucleotide Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1 and/or SEQ ID NO:81. Suggested PCR conditions consist of 35 cycles at 95 degrees C. for 30 seconds; 60-120 seconds at 52-58 degrees C.; and 60-120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a polynucleotide corresponding to a polynucleotide. Genomic clones isolated according to the methods described herein are nick-translated with digoxigenindeoxy-uridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Polynucleotidet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 31

Method of Detecting Abnormal levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 32

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly (2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see, generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Polynucleotiderally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multidose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Polynucleotidentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, *haemophilus influ-*

*enzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR (zidovudine/AZT), VIDEX (didanosine/ddI), HIVID (zalcitabine/ddC), ZERIT (stavudine/d4T), EPIVIR (lamivudine/3TC), and COMBIVIR (zidovudine/lamivudine). Non-nucleoside reverse transcriptase inhibitors that may be administered in combination with the Therapeutics of the invention, include, but are not limited to, VIRAMUNE (nevirapine), RESCRIPTOR (delavirdine), and SUSTIVA (efavirenz). Protease inhibitors that may be administered in combination with the Therapeutics of the invention, include, but are not limited to, CRIXIVAN (indinavir), NORVIR (ritonavir), INVIRASE (saquinavir), and VIRACEPT (nelfmavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLOVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN (filgrastimi/G-CSF), and LEUKINE (sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE to prophylactically treat or prevent an opportunistic *Pneumocystis carinii* pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic *Mycobacterium avium* complex infection. In another specific embodiment, Therapeutics of the invention are used in any combination with RIFABUTIN, CLARITHROMYCIN, and/or AZITHROMYCIN to prophylactically treat or prevent an opportunistic *Mycobacterium tuberculosis* infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic *Toxoplasma gondii* infection. In another specific embodiment, Therapeutics of the invention are used in any combination with LEUCOVORIN and/or NEUPOGEN to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE (OKT3), SANDIMMUNE/NEORAL/SANGDYA (cyclosporin), PROGRAF (tacrolimus), CELLCEPT (mycophenolate), Azathioprine, glucorticosteroids, and RAPAMUNE (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR, IVEEGAM, SANDOGLOBULIN, GAMMAGARD S/D, and GAMIMUNE. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE (SARGRAMOSTIM) and NEUPOGEN (FILGRASTIM).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP polynucleotide significantly reduces PGP function, making it less able to force drugs out of cells. People who have two versions of the mutated polynucleotide—one inherited from each parent—have more than four times less PGP than those with two normal versions of the polynucleotide. People may also have one normal polynucleotide and one mutated one. Certain ethnic populations have increased incidence of such PGP mutations. Among individuals from Ghana, Kenya, the Sudan, as well as African Americans, frequency of the normal polynucleotide ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of therapeutic (e.g., those from african descent). Conversely, certain ethnic populations, particularly those having increased frequency of the mutated PGP (e.g., of caucasian descent, or non-african descent) may require less pharmaceutical compositions in the formulation due to an effective increase in efficacy of such compositions as a result of the increased effective absorption (e.g., less PGP activity) of said composition.

In additional embodiments, the Therapeutics of the invention are administered in combination with other therapeutic or prophylactic regimens, such as, for example, radiation therapy.

Example 33

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided herein.

Example 34

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 35

Method of Treatment using Gene Therapy-Ex Vivo

One method of gene therapy transplants fibroblasts, which are capable of expressing a polypeptide, onto a patient. Polynucleotiderally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 18 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the polynucleotide of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the polynucleotide is then added to the media and the packaging cells transduced with the vector. The packaging cells now produce infectious viral particles containing the polynucleotide (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 36

Gene Therapy Using Endogenous Polynucleotides Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO:WO 96/29411, published Sep. 26, 1996; International Publication NO:WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a polynucleotide which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC 18 plasmid.

Plasmid DNA is added to a sterile cuvette with a 0.4 cm electrode gap (Bio-Rad). The final DNA concentration is generally at least 120 pg/ml. 0.5 ml of the cell suspension (containing approximately $1.5 \times 10^6$ cells) is then added to the cuvette, and the cell suspension and DNA solutions are gently mixed. Electroporation is performed with a Polynucleotide-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 37

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other polynucleotidetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470-479 (1997); Chao et al., Pharmacol. Res. 35(6):517-522 (1997); Wolff, Neuromuscul. Disord. 7(5):314-318 (1997); Schwartz et al., Polynucleotide Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other polynucleotide therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 38

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transpolynucleotide (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated polynucleotide transfer into germ lines (Van der Putten et al., Proc. Natl. Acad. Sci., USA 82:6148-6152 (1985)), blastocysts or embryos; polynucleotide targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a polynucleotide gun (see, e.g., Ulmer et al., Science 259:1745 (1993); introducing nucleic acid constructs into embryonic pleuripotent stem cells and transferring the stem cells back into the blastocyst; and sperm-mediated polynucleotide transfer (Lavitrano et al., Cell 57:717-723 (1989); etc. For a review of such techniques, see Gordon, "Transgenic Animals" Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transpolynucleotide in all their cells, as well as animals which carry the transpolynucleotide in some, but not all their cells, i.e., mosaic animals or chimeric. The transpolynucleotide may be integrated as a single transpolynucleotide or as multiple copies such as in concatamers, e.g., head-to-head tandems or head-to-tail tandems. The transpolynucleotide may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transpolynucleotide be integrated into the chromosomal site of the endogenous polynucleotide, polynucleotide targeting is preferred. Briefly, when such a technique is to be utilized, vectors containing some nucleotide sequences homologous to the endogenous polynucleotide are designed for the purpose of integrating, via homologous recombination with chromosomal sequences, into and disrupting the function of the nucleotide sequence of the endogenous polynucleotide. The transpolynucleotide may also be selectively introduced into a particular cell type, thus inactivating the endogenous polynucleotide in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art.

Once transgenic animals have been generated, the expression of the recombinant polynucleotide may be assayed utilizing standard techniques. Initial screening may be accomplished by Southern blot analysis or PCR techniques to analyze animal tissues to verify that integration of the transpolynucleotide has taken place. The level of mRNA expression of the transpolynucleotide in the tissues of the transgenic animals may also be assessed using techniques which include, but are not limited to, Northern blot analysis of tissue samples obtained from the animal, in situ hybridization analysis, and reverse transcriptase-PCR(RT-PCR). Samples of transgenic polynucleotide-expressing tissue may also be evaluated immunocytochemically or immunohistochemically using antibodies specific for the transpolynucleotide product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transpolynucleotide at higher levels because of the effects of additive expression of each transpolynucleotide; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transpolynucleotide on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 39

Knock—Out Animals

Endogenous polynucleotide expression can also be reduced by inactivating or "knocking out" the polynucleotide and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the polynucleotide) can be used, with or without a selectable marker and/or a negative selectable marker, to transfect cells that express polypeptides of the invention in vivo. In another embodiment, techniques known in the art are used to generate knockouts in cells that contain, but do not express the polynucleotide of interest. Insertion of the DNA construct, via targeted homologous recombination, results in inactivation of the targeted polynucleotide. Such approaches are particularly suited in research and agricultural fields where modifications to embryonic stem cells can be used to generate animal offspring with an inactive targeted polynucleotide (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are polynucleotidetically engineered to express the polypeptides of the invention, or alternatively, that are polynucleotidetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are polynucleotidetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transpolynucleotide into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., polynucleotidetically engineered fibroblasts can be implanted as part of a skin graft; polynucleotidetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 40

Method of Isolating Antibody Fragments Directed Against HGPRBMY5v1 and/or HGPRBMY5v2 from a Library of scFvs Naturally occurring V-polynucleotides isolated from human PBLs are constructed into a library of antibody fragments which contain reactivities against HGPRBMY5v1 and/or HGPRBMY5v2 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to inoculate 50 ml of 2×TY-AMP-GLU, 2×108 TU of delta polynucleotide 3 helper (M13 delta polynucleotide III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta polynucleotide III is prepared as follows: M13 delta polynucleotide III helper phage does not encode polynucleotide III protein, hence the phage(mid) displaying antibody fragments have a greater avidity of binding to antigen. Infectious M13 delta polynucleotide III particles are made by growing the helper phage in cells harboring a pUC 19 derivative supplying the wild type polynucleotide III protein during phage morphopolynucleotidesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta polynucleotide 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 41

Signal Transduction Assays

The activity of GPCRs or homologues thereof, can be measured using any assay suitable for the measurement of the activity of a G protein-coupled receptor, as commonly known in the art. Signal transduction activity of a G protein-coupled receptor can be monitor by monitoring intracellular $Ca^{2+}$, cAMP, inosital 1,4,5-trisphophate ($IP_3$), or 1,2-diacylglycerol (DAG). Assays for the measurement of intracellular $Ca^{2+}$ are described in Sakurai et al. (EP 480 381). Intracellular $IP_3$ can be measured using a kit available from Amersham, Inc. (Arlington Heights, Ill.). A kit for measuring intracellular cAMP is available from Diagnostic Products, Inc. (Los Angeles, Calif.).

Activation of a G protein-coupled receptor triggers the release of $Ca^{2+}$ ions sequestered in the mitochondria, endoplasmic reticulum, and other cytoplasmic vesicles into the cytoplasm. Fluorescent dyes, e.g., fura-2, can be used to measure the concentration of free cytoplasmic $Ca^{2+}$. The ester of fura-2, which is lipophilic and can diffuse across the cell membrane, is added to the media of the host cells expressing GPCRs. Once inside the cell, the fura-2 ester is hydrolyzed by cytosolic esterases to its non-lipophilic form, and then the dye cannot diffuse back out of the cell. The non-lipophilic form of fura-2 will fluoresce when it binds to free $Ca^{2+}$. The fluorescence can be measured without lysing the cells at an excitation spectrum of 340 nm or 380 nm and at fluorescence spectrum of 500 nm (Sakurai et al., EP 480 381).

Upon activation of a G protein-coupled receptor, the rise of free cytosolic $Ca^{2+}$ concentrations is preceded by the hydrolysis of phosphatidylinositol 4,5-bisphosphate. Hydrolysis of this phospholipid by the phospholipase C yields 1,2-diacylglycerol (DAG), which remains in the membrane, and water-soluble inositol 1,4,5-trisphophate ($IP_3$). Binding of ligands or agonists will increase the concentration of DAG and $IP_3$. Thus, signal transduction activity can be measured by monitoring the concentration of these hydrolysis products.

To measure the $IP_3$ concentrations, radioactivity labeled $^3H$-inositol is added to the media of host cells expressing GPCRs. The $^3H$-inositol is taken up by the cells and incorporated into $IP_3$. The resulting inositol triphosphate is separated from the mono and di-phosphate forms and measured (Sakurai et al., EP 480 381). Alternatively, Amersham provides an inositol 1,4,5-triphosphate assay system. With this system Amersham provides tritylated inositol 1,4,5-triphosphate and a receptor capable of distinguishing the radioactive inositol from other inositol phosphates. With these reagents an effective and accurate competition assay can be performed to determine the inositol triphosphate levels.

Cyclic AMP levels can be measured according to the methods described in Gilman et al., Proc. Natl. Acad. Sci 67:305-312 (1970). In addition, a kit for assaying levels of cAMP is available from Diagnostic Products Corp. (Los Angeles, Calif.).

One skilled in the art could easily modify the exemplified studies to test the activity of polynucleotides of the invention (e.g., gene therapy), agonists, and/or antagonists of polynucleotides or polypeptides of the invention.

Example 42

GPCR Activity

Another method for screening compounds which are antagonists, and thus inhibit activation of the receptor polypeptide of the present invention is provided. This involves determining inhibition of binding of labeled ligand, such as DATP, dAMP, or UTP, to cells which have the receptor on the surface thereof, or cell membranes containing the receptor. Such a method further involves transfecting a eukaryotic cell with DNA encoding the GPCR polypeptide such that the cell expresses the receptor on its surface. The cell is then contacted with a potential antagonist in the presence of a labeled form of a ligand, such as DATP, DAMP, or UTP. The ligand can be labeled, e.g., by radioactivity, fluorescence, or any detectable label commonly known in the art. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called a binding assay. Naturally, this same technique can be used to determine agonists.

In a further screening procedure, mammalian cells, for example, but not limited to, CHO, HEK 293, Xenopus Oocytes, RBL-2H3, etc., which are transfected, are used to express the receptor of interest. The cells are loaded with an indicator dye that produces a fluorescent signal when bound to calcium, and the cells are contacted with a test substance and a receptor agonist, such as DATP, DAMP, or UTP. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

In yet another screening procedure, mammalian cells are transfected to express the receptor of interest, and are also transfected with a reporter polynucleotide construct that is coupled to activation of the receptor (for example, but not limited to luciferase or beta-galactosidase behind an appropriate promoter). The cells are contacted with a test substance and the receptor agonist (ligand), such as DATP, dAMP, or UTP, and the signal produced by the reporter polynucleotide is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another screening technique for antagonists or agonists involves introducing RNA encoding the GPCR polypeptide into cells (or CHO, HEK 293, RBL-2H3, etc.) to transiently or stably express the receptor. The receptor cells are then contacted with the receptor ligand, such as dATP, dAMP, or UTP, and a compound to be screened. Inhibition or activation of the receptor is then determined by detection of a signal, such as, cAMP, calcium, proton, or other ions.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated polypeptide selected from the group consisting of:
   (a) an isolated polypeptide comprising amino acids 1 to 748 of SEQ ID NO:2;
   (b) an isolated polypeptide comprising amino acids 2 to 748 of SEQ ID NO:2;
   (c) an isolated polypeptide comprising a polypeptide sequence encoded by nucleotides 1 to 2244 of SEQ ID NO: 1; and
   (d) an isolated polypeptide comprising a polypeptide sequence encoded by nucleotides 4 to 2244 of SEQ ID NO:1.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. The isolated polypeptide of claim 1, produced by a method comprising:
   (a) culturing an isolated recombinant host cell comprising a vector that comprises the coding region encoding the polypeptide of claim 1, under conditions such that said polypeptide is expressed; and
   (b) recovering said polypeptide.

7. The isolated polypeptide of claim 1, further comprising a heterologous polypeptide sequence.

8. The isolated polypeptide of claim 2, wherein said heterologous polypeptide is the Fc domain of immunoglobulin.

(i). In claim 6, line 1, replace "An isolated polypeptide" by The isolated polypeptide of claim 1.

9. An isolated polypeptide comprising the amino acid sequence of SEQ ID NO: 2 except that one amino acid residue in SEQ ID NO: 2 is substituted, wherein said polypeptide binds to relaxin or positively regulates the expression of p21 in a cell in which said polypeptide is expressed.

10. An isolated polypeptide comprising amino acids 1 to 724 of SEQ ID NO: 2 except that one amino acid residue in SEQ ID NO: 2 is substituted, wherein said polypeptide binds to relaxin.

* * * * *

UNITED STATES PATENT AND TRADEMARK OFFICE
CERTIFICATE OF CORRECTION

PATENT NO. : 7,339,032 B2  Page 1 of 5
APPLICATION NO. : 11/486332
DATED : March 4, 2008
INVENTOR(S) : Chandra S. Ramanathan et al.

It is certified that error appears in the above-identified patent and that said Letters Patent is hereby corrected as shown below:

Column 173, Line 10 - Table below should be deleted from Column 173, Line 10 and inserted at Column 173, Line 48 directly under the paragraph ending on Column 173, Line 48.

--

| Number | Tissue |
|---|---|
| 1 | adrenal-gland |
| 2 | Bladder |
| 3 | blood-vessel:renal |
| 4 | brain:amygdale |
| 5 | brain:caudate |
| 6 | brain:cerebellum |
| 7 | brain:cortex:cingulate-anterior |
| 8 | brain:cortex:cingulate-posterior |
| 9 | brain:cortex:frontal-lateral |
| 10 | brain:cortex:frontal-medial |
| 11 | brain:cortex:occipital |
| 12 | brain:cortex:parietal |
| 13 | brain:cortex:temporal |
| 14 | brain:dorsal-raphe-nucleus |
| 15 | brain:hippocampus |

UNITED STATES PATENT AND TRADEMARK OFFICE
CERTIFICATE OF CORRECTION

PATENT NO. : 7,339,032 B2
APPLICATION NO. : 11/486332
DATED : March 4, 2008
INVENTOR(S) : Chandra S. Ramanathan et al.

It is certified that error appears in the above-identified patent and that said Letters Patent is hereby corrected as shown below:

Column 173, Line 10 (Table) (continued)

| | |
|---|---|
| 16 | brain:hypothalamus:anterior |
| 17 | brain:hypothalamus:posterior |
| 18 | brain:locus-coeruleus |
| 19 | brain:medulla-oblongata |
| 20 | brain:nucleus-accumbens |
| 21 | brain:substantia-nigra |
| 22 | colon |
| 23 | duodenum |
| 24 | fallopian-tube |
| 25 | gallbladder |
| 26 | kidney:cortex |
| 27 | kidney:medulla |
| 28 | muscle:skeletal |
| 29 | oesophagus |
| 30 | ovary |

UNITED STATES PATENT AND TRADEMARK OFFICE
CERTIFICATE OF CORRECTION

PATENT NO. : 7,339,032 B2
APPLICATION NO. : 11/486332
DATED : March 4, 2008
INVENTOR(S) : Chandra S. Ramanathan et al.

It is certified that error appears in the above-identified patent and that said Letters Patent is hereby corrected as shown below:

Column 173, Line 10 (Table) (continued)

| 31 | pancreas |
|---|---|
| 32 | pineal-gland |
| 33 | pituitary-gland |
| 34 | testis |
| 35 | thyroid-gland |
| 36 | uterus:cervix |
| 37 | uterus:myometrium |
| 38 | vas-deferens |

Column 173, Line 44 should now read:

--The expanded expression profile of the HGPRBMY5v1 polypeptide in normal tissues is provided in Fig. 5 and described elsewhere herein. The identity of each tissue presented in Fig. 5 is provided in the following table.

| Number | Tissue |
|---|---|
| 1 | adrenal-gland |
| 2 | Bladder |
| 3 | blood-vessel:renal |
| 4 | brain:amygdale |
| 5 | brain:caudate |
| 6 | brain:cerebellum |
| 7 | brain:cortex:cingulate-anterior |
| 8 | brain:cortex:cingulate-posterior |
| 9 | brain:cortex:frontal-lateral |
| 10 | brain:cortex:frontal-medial |
| 11 | brain:cortex:occipital |
| 12 | brain:cortex:parietal |
| 13 | brain:cortex:temporal |
| 14 | brain:dorsal-raphe-nucleus |
| 15 | brain:hippocampus |
| 16 | brain:hypothalamus:anterior |

UNITED STATES PATENT AND TRADEMARK OFFICE
CERTIFICATE OF CORRECTION

PATENT NO.       : 7,339,032 B2
APPLICATION NO. : 11/486332
DATED            : March 4, 2008
INVENTOR(S)      : Chandra S. Ramanathan et al.

It is certified that error appears in the above-identified patent and that said Letters Patent is hereby corrected as shown below:

Column 173, Line 44 (Continued) should read,

| 17 | brain:hypothalamus:posterior |
|----|------------------------------|
| 18 | brain:locus-coeruleus |
| 19 | brain:medulla-oblongata |
| 20 | brain:nucleus-accumbens |
| 21 | brain:substantia-nigra |
| 22 | colon |
| 23 | duodenum |
| 24 | fallopian-tube |
| 25 | gallbladder |
| 26 | kidney:cortex |
| 27 | kidney:medulla |
| 28 | muscle:skeletal |
| 29 | oesophagus |
| 30 | ovary |
| 31 | pancreas |
| 32 | pineal-gland |

UNITED STATES PATENT AND TRADEMARK OFFICE
CERTIFICATE OF CORRECTION

PATENT NO. : 7,339,032 B2
APPLICATION NO. : 11/486332
DATED : March 4, 2008
INVENTOR(S) : Chandra S. Ramanathan et al.

It is certified that error appears in the above-identified patent and that said Letters Patent is hereby corrected as shown below:

Column 173, Line 44 (Continued) should read,

| 33 | pituitary-gland | -- |
|----|-----------------|----|
| 34 | testis          |    |
| 35 | thyroid-gland   |    |
| 36 | uterus:cervix   |    |
| 37 | uterus:myometrium |  |
| 38 | vas-deferens    |    |

Column 313, line 43 (Claim 8)

Substitute "claim 2" with -- claim 7 --.

Line 46

Remove (i). In Claim 6, line 1, replace "An isolated polypeptide" by -- The isolated polypeptide of claim 1. --

Claim 8 should now read:

-- The isolated polypeptide of claim 7, wherein said heterologous polypeptide is the Fc domain of immunoglobulin. --

Signed and Sealed this

Ninth Day of September, 2008

JON W. DUDAS
*Director of the United States Patent and Trademark Office*

SEQUENCE LISTING

<160> NUMBER OF SEQ ID NOS: 102

<210> SEQ ID NO 1
<211> LENGTH: 2247
<212> TYPE: DNA
<213> ORGANISM: Homo sapiens
<220> FEATURE:
<221> NAME/KEY: CDS
<222> LOCATION: (1)..(2244)

<400> SEQUENCE: 1

```
atg cag aaa acc aag caa gat gag gac tat gaa aga gcc att gga ttt      48
Met Gln Lys Thr Lys Gln Asp Glu Asp Tyr Glu Arg Ala Ile Gly Phe
1               5                   10                  15 agt gtc aaa atg gat gac agt gat tct gat ttt gca ctg act caa ggt      96
Ser Val Lys Met Asp Asp Ser Asp Ser Asp Phe Ala Leu Thr Gln Gly
                20                  25                  30 agc atg atc act cct tca tgc caa aaa gga tat ttt ccc tgt ggg aat     144
Ser Met Ile Thr Pro Ser Cys Gln Lys Gly Tyr Phe Pro Cys Gly Asn
            35                  40                  45 ctt acc aag tgc tta ccc cga gct ttt cac tgt gat ggc aag gat gac     192
Leu Thr Lys Cys Leu Pro Arg Ala Phe His Cys Asp Gly Lys Asp Asp
        50                  55                  60 tgt ggg aac ggg gcg gac gaa gag aac tgt ggt gac act agt gga tgg     240
Cys Gly Asn Gly Ala Asp Glu Glu Asn Cys Gly Asp Thr Ser Gly Trp
65                  70                  75                  80 gcg acc ata ttt ggc aca gtg cat gga aat gct aac agc gtg gcc tta     288
Ala Thr Ile Phe Gly Thr Val His Gly Asn Ala Asn Ser Val Ala Leu
                85                  90                  95 aca cag gag tgc ttt cta aaa cag tat cca caa tgc tgt gac tgc aaa     336
Thr Gln Glu Cys Phe Leu Lys Gln Tyr Pro Gln Cys Cys Asp Cys Lys
                100                 105                 110 gaa act gaa ttg gaa tgt gta aat ggt gac tta aag tct gtg ccg atg     384
Glu Thr Glu Leu Glu Cys Val Asn Gly Asp Leu Lys Ser Val Pro Met
            115                 120                 125 att tct aac aat gtg aca tta ctg tct ctt aag aaa aac aaa atc cac     432
Ile Ser Asn Asn Val Thr Leu Leu Ser Leu Lys Lys Asn Lys Ile His
        130                 135                 140 agt ctt cca gat aaa gtt ttc atc aaa tac aca aaa ctt aaa aag ata     480
Ser Leu Pro Asp Lys Val Phe Ile Lys Tyr Thr Lys Leu Lys Lys Ile
145                 150                 155                 160
```

-continued

| | | |
|---|---|---|
| ttt ctt cag cat aat tgc att aga cac ata tcc agg aaa gca ttt ttt<br>Phe Leu Gln His Asn Cys Ile Arg His Ile Ser Arg Lys Ala Phe Phe<br>165 170 175 | 528 | |
| gga tta tgt aat ctg caa ata tta tat ctc aac cac aac tgc atc aca<br>Gly Leu Cys Asn Leu Gln Ile Leu Tyr Leu Asn His Asn Cys Ile Thr<br>180 185 190 | 576 | |
| acc ctc aga cct gga ata ttc aaa gac tta cat cag cta act tgg cta<br>Thr Leu Arg Pro Gly Ile Phe Lys Asp Leu His Gln Leu Thr Trp Leu<br>195 200 205 | 624 | |
| att cta gat gac aat cca ata acc aga att tca cag cgc ttg ttt acg<br>Ile Leu Asp Asp Asn Pro Ile Thr Arg Ile Ser Gln Arg Leu Phe Thr<br>210 215 220 | 672 | |
| gga tta aat tcc ttg ttt ttc ctg tct atg gtt aat aac tac tta gaa<br>Gly Leu Asn Ser Leu Phe Phe Leu Ser Met Val Asn Asn Tyr Leu Glu<br>225 230 235 240 | 720 | |
| gct ctt ccc aag cag atg tgt gcc caa atg cct caa ctc aac tgg gtg<br>Ala Leu Pro Lys Gln Met Cys Ala Gln Met Pro Gln Leu Asn Trp Val<br>245 250 255 | 768 | |
| gat ttg gaa ggc aat aga ata aag tat ctc aca aat tct acg ttt ctg<br>Asp Leu Glu Gly Asn Arg Ile Lys Tyr Leu Thr Asn Ser Thr Phe Leu<br>260 265 270 | 816 | |
| tcg tgc gat tcg ctc aca gtg ctg ttt ctg cct aga aat caa att ggt<br>Ser Cys Asp Ser Leu Thr Val Leu Phe Leu Pro Arg Asn Gln Ile Gly<br>275 280 285 | 864 | |
| ttt gtt cca gag aag aca ttt tct tca tta aaa aat tta gga gaa ctg<br>Phe Val Pro Glu Lys Thr Phe Ser Ser Leu Lys Asn Leu Gly Glu Leu<br>290 295 300 | 912 | |
| gat ctg tct agc aat acg ata acg gag cta tca cct cac ctt ttt aaa<br>Asp Leu Ser Ser Asn Thr Ile Thr Glu Leu Ser Pro His Leu Phe Lys<br>305 310 315 320 | 960 | |
| gac ttg aag ctt cta caa aag ctg aac ctg tca tcc aat cct ctt atg<br>Asp Leu Lys Leu Leu Gln Lys Leu Asn Leu Ser Ser Asn Pro Leu Met<br>325 330 335 | 1008 | |
| tat ctt cac aag aac cag ttt gaa agt ctt aaa caa ctt cag tct cta<br>Tyr Leu His Lys Asn Gln Phe Glu Ser Leu Lys Gln Leu Gln Ser Leu<br>340 345 350 | 1056 | |
| gac ctg gaa agg ata gag att cca aat ata aac aca cga atg ttt caa<br>Asp Leu Glu Arg Ile Glu Ile Pro Asn Ile Asn Thr Arg Met Phe Gln<br>355 360 365 | 1104 | |
| ccc atg aag aat ctt tct cac att tat ttc aaa aac ttt cga tac tgc<br>Pro Met Lys Asn Leu Ser His Ile Tyr Phe Lys Asn Phe Arg Tyr Cys<br>370 375 380 | 1152 | |
| tcc tat gct ccc cat gtc cga ata tgt atg ccc ttg acg gac ggc att<br>Ser Tyr Ala Pro His Val Arg Ile Cys Met Pro Leu Thr Asp Gly Ile<br>385 390 395 400 | 1200 | |
| tct tca ttt gag gac ctc ttg gct aac aat atc ctc aga ata ttt gtc<br>Ser Ser Phe Glu Asp Leu Leu Ala Asn Asn Ile Leu Arg Ile Phe Val<br>405 410 415 | 1248 | |
| tgg gtt ata gct ttc att acc tgc ttt gga aat ctt ttt gtc att ggc<br>Trp Val Ile Ala Phe Ile Thr Cys Phe Gly Asn Leu Phe Val Ile Gly<br>420 425 430 | 1296 | |
| atg aga tct ttc att aaa gct gaa aat aca act cac gct atg tcc atc<br>Met Arg Ser Phe Ile Lys Ala Glu Asn Thr Thr His Ala Met Ser Ile<br>435 440 445 | 1344 | |
| aaa atc ctt tgt tgt gct gat tgc ctg atg ggt gtt tac ttg ttc ttt<br>Lys Ile Leu Cys Cys Ala Asp Cys Leu Met Gly Val Tyr Leu Phe Phe<br>450 455 460 | 1392 | |
| gtt ggc att ttc gat ata aaa tac cga ggg cag tat cag aag tat gcc<br>Val Gly Ile Phe Asp Ile Lys Tyr Arg Gly Gln Tyr Gln Lys Tyr Ala<br>465 470 475 480 | 1440 | |

| | | | | | | | | | | | | | | | | |
|---|---|---|---|---|---|---|---|---|---|---|---|---|---|---|---|---|
|ttg|ctg|tgg|atg|gag|agc|gtg|cag|tgc|cgc|ctc|atg|ggg|ttc|ctg|gcc|1488|
|Leu|Leu|Trp|Met|Glu|Ser|Val|Gln|Cys|Arg|Leu|Met|Gly|Phe|Leu|Ala| |
| | | | |485| | | |490| | | |495| | | | |
|atg|ctg|tcc|acc|gaa|gtc|tct|gtt|ctg|cta|ctg|acc|tac|ttg|act|ttg|1536|
|Met|Leu|Ser|Thr|Glu|Val|Ser|Val|Leu|Leu|Leu|Thr|Tyr|Leu|Thr|Leu| |
| | | |500| | | | |505| | | | |510| | | |
|gag|aag|ttc|ctg|gtc|att|gtc|ttc|ccc|ttc|agt|aac|att|cga|cct|gga|1584|
|Glu|Lys|Phe|Leu|Val|Ile|Val|Phe|Pro|Phe|Ser|Asn|Ile|Arg|Pro|Gly| |
| | |515| | | | |520| | | | |525| | | | |
|aaa|cgg|cag|acc|tca|gtc|atc|ctc|att|tgc|atc|tgg|atg|gcg|gga|ttt|1632|
|Lys|Arg|Gln|Thr|Ser|Val|Ile|Leu|Ile|Cys|Ile|Trp|Met|Ala|Gly|Phe| |
|530| | | | |535| | | | |540| | | | | | |
|tta|ata|gct|gta|att|cca|ttt|tgg|aat|aag|gat|tat|ttt|gga|aac|ttt|1680|
|Leu|Ile|Ala|Val|Ile|Pro|Phe|Trp|Asn|Lys|Asp|Tyr|Phe|Gly|Asn|Phe| |
|545| | | | |550| | | | |555| | | | |560| |
|tat|ggg|aaa|aat|gga|gta|tgt|ttc|cca|ctt|tat|tat|gac|caa|aca|gaa|1728|
|Tyr|Gly|Lys|Asn|Gly|Val|Cys|Phe|Pro|Leu|Tyr|Tyr|Asp|Gln|Thr|Glu| |
| | | | |565| | | | |570| | | | |575| | |
|gat|att|gga|agc|aaa|ggg|tat|tct|ctt|gga|att|ttc|cta|ggt|gtg|aac|1776|
|Asp|Ile|Gly|Ser|Lys|Gly|Tyr|Ser|Leu|Gly|Ile|Phe|Leu|Gly|Val|Asn| |
| | | |580| | | | |585| | | | |590| | | |
|ttg|ctg|gct|ttt|ctc|atc|att|gtg|ttt|tcc|tat|att|act|atg|ttc|tgt|1824|
|Leu|Leu|Ala|Phe|Leu|Ile|Ile|Val|Phe|Ser|Tyr|Ile|Thr|Met|Phe|Cys| |
| | |595| | | | |600| | | | |605| | | | |
|tcc|att|caa|aaa|acc|gcc|ttg|cag|acc|aca|gaa|gta|agg|aat|tgt|ttt|1872|
|Ser|Ile|Gln|Lys|Thr|Ala|Leu|Gln|Thr|Thr|Glu|Val|Arg|Asn|Cys|Phe| |
|610| | | | |615| | | | |620| | | | | | |
|gga|aga|gag|gtg|gct|gtt|gca|aat|cgt|ttc|ttt|ttt|ata|gtg|ttc|tct|1920|
|Gly|Arg|Glu|Val|Ala|Val|Ala|Asn|Arg|Phe|Phe|Phe|Ile|Val|Phe|Ser| |
|625| | | | |630| | | | |635| | | | |640| |
|gat|gcc|atc|tgc|tgg|att|cct|gta|ttt|gta|gtt|aaa|atc|ctt|tcc|ctc|1968|
|Asp|Ala|Ile|Cys|Trp|Ile|Pro|Val|Phe|Val|Val|Lys|Ile|Leu|Ser|Leu| |
| | | |645| | | | |650| | | | |655| | | |
|ttc|cgg|gtg|gaa|ata|cca|gac|aca|atg|act|tcc|tgg|ata|gtg|att|ttt|2016|
|Phe|Arg|Val|Glu|Ile|Pro|Asp|Thr|Met|Thr|Ser|Trp|Ile|Val|Ile|Phe| |
| | |660| | | | |665| | | | |670| | | | |
|ttc|ctt|cca|gtt|aac|agt|gct|ttg|aat|cca|atc|ctc|tat|act|ctc|aca|2064|
|Phe|Leu|Pro|Val|Asn|Ser|Ala|Leu|Asn|Pro|Ile|Leu|Tyr|Thr|Leu|Thr| |
| | |675| | | | |680| | | | |685| | | | |
|acc|aac|ttt|ttt|aag|gac|aag|ttg|aaa|cag|ctg|ctg|cac|aaa|cat|cag|2112|
|Thr|Asn|Phe|Phe|Lys|Asp|Lys|Leu|Lys|Gln|Leu|Leu|His|Lys|His|Gln| |
| |690| | | | |695| | | | |700| | | | | |
|agg|aaa|tca|att|ttc|aaa|att|aaa|aaa|aaa|agt|tta|tct|aca|tcc|att|2160|
|Arg|Lys|Ser|Ile|Phe|Lys|Ile|Lys|Lys|Lys|Ser|Leu|Ser|Thr|Ser|Ile| |
|705| | | |710| | | | |715| | | | |720| | |
|gtg|tgg|ata|gag|gac|tcc|tct|tcc|ctg|aaa|ctt|ggg|gtt|ttg|aac|aaa|2208|
|Val|Trp|Ile|Glu|Asp|Ser|Ser|Ser|Leu|Lys|Leu|Gly|Val|Leu|Asn|Lys| |
| | | |725| | | | |730| | | | |735| | | |
|ata|aca|ctt|gga|gac|agt|ata|atg|aaa|cca|gtt|tcc|tag| | | |2247|
|Ile|Thr|Leu|Gly|Asp|Ser|Ile|Met|Lys|Pro|Val|Ser| | | | | |
| | | |740| | | | |745| | | | | | | | |

<210> SEQ ID NO 2
<211> LENGTH: 748
<212> TYPE: PRT
<213> ORGANISM: Homo sapiens

<400> SEQUENCE: 2

Met Gln Lys Thr Lys Gln Asp Glu Asp Tyr Glu Arg Ala Ile Gly Phe
1               5                   10                  15

-continued

```
Ser Val Lys Met Asp Asp Ser Asp Ser Asp Phe Ala Leu Thr Gln Gly
             20                  25                  30

Ser Met Ile Thr Pro Ser Cys Gln Lys Gly Tyr Phe Pro Cys Gly Asn
             35                  40                  45

Leu Thr Lys Cys Leu Pro Arg Ala Phe His Cys Asp Gly Lys Asp Asp
             50                  55                  60

Cys Gly Asn Gly Ala Asp Glu Glu Asn Cys Gly Asp Thr Ser Gly Trp
 65                  70                  75                  80

Ala Thr Ile Phe Gly Thr Val His Gly Asn Ala Asn Ser Val Ala Leu
                     85                  90                  95

Thr Gln Glu Cys Phe Leu Lys Gln Tyr Pro Gln Cys Cys Asp Cys Lys
            100                 105                 110

Glu Thr Glu Leu Glu Cys Val Asn Gly Asp Leu Lys Ser Val Pro Met
            115                 120                 125

Ile Ser Asn Asn Val Thr Leu Leu Ser Leu Lys Lys Asn Lys Ile His
            130                 135                 140

Ser Leu Pro Asp Lys Val Phe Ile Lys Tyr Thr Lys Leu Lys Lys Ile
145                 150                 155                 160

Phe Leu Gln His Asn Cys Ile Arg His Ile Ser Arg Lys Ala Phe Phe
                165                 170                 175

Gly Leu Cys Asn Leu Gln Ile Leu Tyr Leu Asn His Asn Cys Ile Thr
            180                 185                 190

Thr Leu Arg Pro Gly Ile Phe Lys Asp Leu His Gln Leu Thr Trp Leu
            195                 200                 205

Ile Leu Asp Asp Asn Pro Ile Thr Arg Ile Ser Gln Arg Leu Phe Thr
            210                 215                 220

Gly Leu Asn Ser Leu Phe Phe Leu Ser Met Val Asn Asn Tyr Leu Glu
225                 230                 235                 240

Ala Leu Pro Lys Gln Met Cys Ala Gln Met Pro Gln Leu Asn Trp Val
                245                 250                 255

Asp Leu Glu Gly Asn Arg Ile Lys Tyr Leu Thr Asn Ser Thr Phe Leu
            260                 265                 270

Ser Cys Asp Ser Leu Thr Val Leu Phe Leu Pro Arg Asn Gln Ile Gly
            275                 280                 285

Phe Val Pro Glu Lys Thr Phe Ser Ser Leu Lys Asn Leu Gly Glu Leu
            290                 295                 300

Asp Leu Ser Ser Asn Thr Ile Thr Glu Leu Ser Pro His Leu Phe Lys
305                 310                 315                 320

Asp Leu Lys Leu Leu Gln Lys Leu Asn Leu Ser Ser Asn Pro Leu Met
                325                 330                 335

Tyr Leu His Lys Asn Gln Phe Glu Ser Leu Lys Gln Leu Gln Ser Leu
            340                 345                 350

Asp Leu Glu Arg Ile Glu Ile Pro Asn Ile Asn Thr Arg Met Phe Gln
            355                 360                 365

Pro Met Lys Asn Leu Ser His Ile Tyr Phe Lys Asn Phe Arg Tyr Cys
            370                 375                 380

Ser Tyr Ala Pro His Val Arg Ile Cys Met Pro Leu Thr Asp Gly Ile
385                 390                 395                 400

Ser Ser Phe Glu Asp Leu Leu Ala Asn Asn Ile Leu Arg Ile Phe Val
                405                 410                 415

Trp Val Ile Ala Phe Ile Thr Cys Phe Gly Asn Leu Phe Val Ile Gly
            420                 425                 430
```

Met Arg Ser Phe Ile Lys Ala Glu Asn Thr Thr His Ala Met Ser Ile
            435                 440                 445

Lys Ile Leu Cys Cys Ala Asp Cys Leu Met Gly Val Tyr Leu Phe Phe
        450                 455                 460

Val Gly Ile Phe Asp Ile Lys Tyr Arg Gly Gln Tyr Gln Lys Tyr Ala
465                 470                 475                 480

Leu Leu Trp Met Glu Ser Val Gln Cys Arg Leu Met Gly Phe Leu Ala
            485                 490                 495

Met Leu Ser Thr Glu Val Ser Val Leu Leu Thr Tyr Leu Thr Leu
            500                 505                 510

Glu Lys Phe Leu Val Ile Val Phe Pro Phe Ser Asn Ile Arg Pro Gly
        515                 520                 525

Lys Arg Gln Thr Ser Val Ile Leu Ile Cys Ile Trp Met Ala Gly Phe
530                 535                 540

Leu Ile Ala Val Ile Pro Phe Trp Asn Lys Asp Tyr Phe Gly Asn Phe
545                 550                 555                 560

Tyr Gly Lys Asn Gly Val Cys Phe Pro Leu Tyr Tyr Asp Gln Thr Glu
            565                 570                 575

Asp Ile Gly Ser Lys Gly Tyr Ser Leu Gly Ile Phe Leu Gly Val Asn
            580                 585                 590

Leu Leu Ala Phe Leu Ile Ile Val Phe Ser Tyr Ile Thr Met Phe Cys
        595                 600                 605

Ser Ile Gln Lys Thr Ala Leu Gln Thr Thr Glu Val Arg Asn Cys Phe
        610                 615                 620

Gly Arg Glu Val Ala Val Ala Asn Arg Phe Phe Phe Ile Val Phe Ser
625                 630                 635                 640

Asp Ala Ile Cys Trp Ile Pro Val Phe Val Val Lys Ile Leu Ser Leu
            645                 650                 655

Phe Arg Val Glu Ile Pro Asp Thr Met Thr Ser Trp Ile Val Ile Phe
            660                 665                 670

Phe Leu Pro Val Asn Ser Ala Leu Asn Pro Ile Leu Tyr Thr Leu Thr
        675                 680                 685

Thr Asn Phe Phe Lys Asp Lys Leu Lys Gln Leu His Lys His Gln
        690                 695                 700

Arg Lys Ser Ile Phe Lys Ile Lys Lys Ser Leu Ser Thr Ser Ile
705                 710                 715                 720

Val Trp Ile Glu Asp Ser Ser Ser Leu Lys Leu Gly Val Leu Asn Lys
            725                 730                 735

Ile Thr Leu Gly Asp Ser Ile Met Lys Pro Val Ser
            740                 745

<210> SEQ ID NO 3
<211> LENGTH: 20
<212> TYPE: PRT
<213> ORGANISM: Homo sapiens

<400> SEQUENCE: 3

Ile Phe Val Trp Val Ile Ala Phe Ile Thr Cys Phe Gly Asn Leu Phe
1               5                   10                  15

Val Ile Gly Met
            20

<210> SEQ ID NO 4
<211> LENGTH: 19
<212> TYPE: PRT
<213> ORGANISM: Homo sapiens

```
<400> SEQUENCE: 4

Ile Leu Cys Cys Ala Asp Cys Leu Met Gly Val Tyr Leu Phe Phe Val
1               5                   10                  15

Gly Ile Phe

<210> SEQ ID NO 5
<211> LENGTH: 22
<212> TYPE: PRT
<213> ORGANISM: Homo sapiens

<400> SEQUENCE: 5

Leu Met Gly Phe Leu Ala Met Leu Ser Thr Glu Val Ser Val Leu Leu
1               5                   10                  15

Leu Thr Tyr Leu Thr Leu
            20

<210> SEQ ID NO 6
<211> LENGTH: 19
<212> TYPE: PRT
<213> ORGANISM: Homo sapiens

<400> SEQUENCE: 6

Val Ile Leu Ile Cys Ile Trp Met Ala Gly Phe Leu Ile Ala Val Ile
1               5                   10                  15

Pro Phe Trp

<210> SEQ ID NO 7
<211> LENGTH: 24
<212> TYPE: PRT
<213> ORGANISM: Homo sapiens

<400> SEQUENCE: 7

Leu Gly Ile Phe Leu Gly Val Asn Leu Leu Ala Phe Leu Ile Ile Val
1               5                   10                  15

Phe Ser Tyr Ile Thr Met Phe Cys
            20

<210> SEQ ID NO 8
<211> LENGTH: 24
<212> TYPE: PRT
<213> ORGANISM: Homo sapiens

<400> SEQUENCE: 8

Phe Phe Phe Ile Val Phe Ser Asp Ala Ile Cys Trp Ile Pro Val Phe
1               5                   10                  15

Val Val Lys Ile Leu Ser Leu Phe
            20

<210> SEQ ID NO 9
<211> LENGTH: 20
<212> TYPE: PRT
<213> ORGANISM: Homo sapiens

<400> SEQUENCE: 9

Ile Val Ile Phe Phe Leu Pro Val Asn Ser Ala Leu Asn Pro Ile Leu
1               5                   10                  15

Tyr Thr Leu Thr
            20

<210> SEQ ID NO 10
```

-continued

```
<211> LENGTH: 907
<212> TYPE: PRT
<213> ORGANISM: Homo sapiens

<400> SEQUENCE: 10

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
```

-continued

```
            385                 390                 395                 400
Arg Ser Leu Asn Leu Ala Trp Asn Lys Ile Ala Ile His Pro Asn
                405                 410                 415
Ala Phe Ser Thr Leu Pro Ser Leu Ile Lys Leu Asp Leu Ser Ser Asn
                420                 425                 430
Leu Leu Ser Ser Phe Pro Ile Thr Gly Leu His Gly Leu Thr His Leu
                435                 440                 445
Lys Leu Thr Gly Asn His Ala Leu Gln Ser Leu Ile Ser Ser Glu Asn
                450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
                500                 505                 510
Met Phe Gln Ala Gln Asp Glu Arg Asp Leu Glu Asp Phe Leu Leu Asp
                515                 520                 525
Phe Glu Glu Asp Leu Lys Ala Leu His Ser Val Gln Cys Ser Pro Ser
                530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
                580                 585                 590
Lys Leu Leu Ile Gly Val Ile Ala Ala Val Asn Met Leu Thr Gly Val
                595                 600                 605
Ser Ser Ala Val Leu Ala Gly Val Asp Ala Phe Thr Phe Gly Ser Phe
                610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Val Lys Tyr Ser Ala Lys Phe
                660                 665                 670
Glu Thr Lys Ala Pro Phe Ser Ser Leu Lys Val Ile Ile Leu Leu Cys
                675                 680                 685
Ala Leu Leu Ala Leu Thr Met Ala Ala Val Pro Leu Leu Gly Gly Ser
                690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
                740                 745                 750
Lys Gly Asp Leu Glu Asn Ile Trp Asp Cys Ser Met Val Lys His Ile
                755                 760                 765
Ala Leu Leu Leu Phe Thr Asn Cys Ile Leu Asn Cys Pro Val Ala Phe
                770                 775                 780
Leu Ser Phe Ser Ser Leu Ile Asn Leu Thr Phe Ile Ser Pro Glu Val
785                 790                 795                 800
Ile Lys Phe Ile Leu Leu Val Val Val Pro Leu Pro Ala Cys Leu Asn
                805                 810                 815
```

-continued

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
            835                 840                 845

Leu Met Ser Ile Asn Ser Asp Asp Val Glu Lys Gln Ser Cys Asp Ser
            850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
            885                 890                 895

His Leu Ser Ser Val Ala Phe Val Pro Cys Leu
            900                 905

<210> SEQ ID NO 11
<211> LENGTH: 907
<212> TYPE: PRT
<213> ORGANISM: Homo sapiens

<400> SEQUENCE: 11

Met Asp Thr Ser Cys Val His Met Leu Leu Ser Leu Leu Ala Leu Leu
1               5                   10                  15

Gln Leu Val Ala Ala Gly Ser Ser Pro Gly Pro Asp Ala Ile Pro Arg
            20                  25                  30

Gly Cys Pro Ser His Cys His Cys Glu Leu Asp Gly Arg Met Leu Leu
            35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Pro Ala Ser Leu Leu His Arg Leu Cys Phe Leu Glu Glu Leu Arg
            85                  90                  95

Leu Ala Gly Asn Ala Leu Thr His Ile Pro Lys Gly Ala Phe Thr Gly
            100                 105                 110

Leu His Ser Leu Lys Val Leu Met Leu Gln Asn Asn Gln Leu Arg Lys
            115                 120                 125

Val Pro Glu Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Asp
            165                 170                 175

Val Pro Val Gln Ala Phe Arg Ser Leu Ser Ala Leu Gln Ala Met Thr
            180                 185                 190

Leu Ala Leu Asn Lys Ile His His Ile Ala Asp Tyr Ala Phe Gly Asn
            195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Lys Thr Leu
            245                 250                 255

Ser Asn Leu Lys Glu Leu Gly Phe His Ser Asn Asn Ile Arg Ser Ile
            260                 265                 270

Pro Glu Arg Ala Phe Val Gly Asn Pro Ser Leu Ile Thr Ile His Phe

```
                275                 280                 285
Tyr Asp Asn Pro Ile Gln Phe Val Gly Val Ser Ala Phe Gln His Leu
                    290                 295                 300
Pro Glu Leu Arg Thr Leu Thr Leu Asn Gly Ala Ser His Ile Thr Glu
305                 310                 315                 320
Phe Pro His Leu Thr Gly Thr Ala Thr Leu Glu Ser Leu Thr Leu Thr
                    325                 330                 335
Gly Ala Lys Ile Ser Ser Leu Pro Gln Ala Val Cys Asp Gln Leu Pro
                    340                 345                 350
Asn Leu Gln Val Leu Asp Leu Ser Tyr Asn Leu Leu Glu Asp Leu Pro
                    355                 360                 365
Ser Leu Ser Gly Cys Gln Lys Leu Gln Lys Ile Asp Leu Arg His Asn
370                 375                 380
Glu Ile Tyr Glu Ile Lys Gly Ser Thr Phe Gln Gln Leu Phe Asn Leu
385                 390                 395                 400
Arg Ser Leu Asn Leu Ala Trp Asn Lys Ile Ala Ile His Pro Asn
                    405                 410                 415
Ala Phe Ser Thr Leu Pro Ser Leu Ile Lys Leu Asp Leu Ser Ser Asn
                    420                 425                 430
Leu Leu Ser Ser Phe Pro Val Thr Gly Leu His Gly Leu Thr His Leu
                    435                 440                 445
Lys Leu Thr Gly Asn Arg Ala Leu Gln Ser Leu Ile Pro Ser Ala Asn
                    450                 455                 460
Phe Pro Glu Leu Lys Ile Ile Glu Met Pro Ser Ala Tyr Gln Cys Cys
465                 470                 475                 480
Ala Phe Gly Gly Cys Glu Asn Val Tyr Lys Ile Ser Asn Gln Trp Asn
                    485                 490                 495
Lys Asp Asp Gly Asn Ser Val Asp Asp Leu His Lys Lys Asp Ala Gly
                    500                 505                 510
Leu Phe Gln Val Gln Asp Glu Arg Asp Leu Glu Asp Phe Leu Leu Asp
                    515                 520                 525
Phe Glu Glu Asp Leu Asn Ala Leu His Ser Val Gln Cys Ser Pro Ser
530                 535                 540
Pro Gly Pro Phe Lys Pro Cys Glu His Leu Phe Gly Ser Trp Leu Ile
545                 550                 555                 560
Arg Ile Gly Val Trp Thr Thr Ala Val Leu Thr Leu Ser Cys Asn Ala
                    565                 570                 575
Leu Val Ala Leu Thr Val Phe Arg Thr Pro Leu Tyr Ile Ser Ser Ile
                    580                 585                 590
Lys Leu Leu Ile Gly Val Ile Ala Val Val Asp Ile Leu Met Gly Val
                    595                 600                 605
Ser Ser Ala Val Leu Ala Ala Val Asp Ala Phe Thr Phe Gly Arg Phe
610                 615                 620
Ala Gln His Gly Ala Trp Trp Glu Asp Gly Ile Gly Cys Gln Ile Val
625                 630                 635                 640
Gly Phe Leu Ser Ile Phe Ala Ser Glu Ser Ile Phe Leu Leu Thr
                    645                 650                 655
Leu Ala Ala Leu Glu Arg Gly Phe Ser Val Lys Cys Ser Ser Lys Phe
                    660                 665                 670
Glu Val Lys Ala Pro Leu Phe Ser Leu Arg Ala Ile Val Leu Leu Cys
            675                 680                 685
Val Leu Leu Ala Leu Thr Ile Ala Thr Ile Pro Leu Leu Gly Gly Ser
        690                 695                 700
```

```
Lys Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Leu Asn Ser Leu Cys
            725                 730                 735

Phe Leu Ile Met Thr Ile Ala Tyr Thr Lys Leu Tyr Cys Ser Leu Glu
            740                 745                 750

Lys Gly Glu Leu Glu Asn Leu Trp Asp Cys Ser Met Val Lys His Ile
            755                 760                 765

Ala Leu Leu Leu Phe Ala Asn Cys Ile Leu Tyr Cys Pro Val Ala Phe
770                 775                 780

Leu Ser Phe Ser Ser Leu Leu Asn Leu Thr Phe Ile Ser Pro Asp Val
785                 790                 795                 800

Ile Lys Phe Ile Leu Leu Val Ile Val Pro Leu Pro Ser Cys Leu Asn
                805                 810                 815

Pro Leu Leu Tyr Ile Val Phe Asn Pro His Phe Lys Glu Asp Met Gly
                820                 825                 830

Ser Leu Gly Lys His Thr Arg Phe Trp Met Arg Ser Lys His Ala Ser
            835                 840                 845

Leu Leu Ser Ile Asn Ser Asp Asp Val Glu Lys Arg Ser Cys Glu Ser
850                 855                 860

Thr Gln Ala Leu Val Ser Phe Thr His Ala Ser Ile Ala Tyr Asp Leu
865                 870                 875                 880

Pro Ser Thr Ser Gly Ala Ser Pro Ala Tyr Pro Met Thr Glu Ser Cys
                885                 890                 895

His Leu Ser Ser Val Ala Phe Val Pro Cys Leu
                900                 905

<210> SEQ ID NO 12
<211> LENGTH: 757
<212> TYPE: PRT
<213> ORGANISM: Homo sapiens

<400> SEQUENCE: 12

Met Thr Ser Gly Ser Val Phe Phe Tyr Ile Leu Ile Phe Gly Lys Tyr
1               5                   10                  15

Phe Ser His Gly Gly Gln Asp Val Lys Cys Ser Leu Gly Tyr Phe
                20                  25                  30

Pro Cys Gly Asn Ile Thr Lys Cys Leu Pro Gln Leu Leu His Cys Asn
            35                  40                  45

Gly Val Asp Asp Cys Gly Asn Gln Ala Asp Glu Asn Cys Gly Asp
        50                  55                  60

Asn Asn Gly Trp Ser Met Gln Phe Asp Lys Tyr Phe Ala Ser Tyr Tyr
65                  70                  75                  80

Lys Met Thr Ser Gln Tyr Pro Phe Glu Ala Glu Thr Pro Glu Cys Leu
                85                  90                  95

Val Gly Ser Val Pro Val Gln Cys Leu Cys Gln Gly Leu Glu Leu Asp
            100                 105                 110

Cys Asp Glu Thr Asn Leu Arg Ala Val Pro Ser Val Ser Ser Asn Val
            115                 120                 125

Thr Ala Met Ser Leu Gln Trp Asn Leu Ile Arg Lys Leu Pro Pro Asp
        130                 135                 140

Cys Phe Lys Asn Tyr His Asp Leu Gln Lys Leu Tyr Leu Gln Asn Asn
145                 150                 155                 160

Lys Ile Thr Ser Ile Ser Ile Tyr Ala Phe Arg Gly Leu Asn Ser Leu
```

-continued

```
                165                 170                 175
Thr Lys Leu Tyr Leu Ser His Asn Arg Ile Thr Phe Leu Lys Pro Gly
            180                 185                 190
Val Phe Glu Asp Leu His Arg Leu Glu Trp Leu Ile Ile Glu Asp Asn
        195                 200                 205
His Leu Ser Arg Ile Ser Pro Pro Thr Phe Tyr Gly Leu Asn Ser Leu
    210                 215                 220
Ile Leu Leu Val Leu Met Asn Asn Val Leu Thr Arg Leu Pro Asp Lys
225                 230                 235                 240
Pro Leu Cys Gln His Met Pro Arg Leu His Trp Leu Asp Leu Glu Gly
            245                 250                 255
Asn His Ile His Asn Leu Arg Asn Leu Thr Phe Ile Ser Cys Ser Asn
        260                 265                 270
Leu Thr Val Leu Val Met Arg Lys Asn Lys Ile Asn His Leu Asn Glu
    275                 280                 285
Asn Thr Phe Ala Pro Leu Gln Lys Leu Asp Glu Leu Asp Leu Gly Ser
        290                 295                 300
Asn Lys Ile Glu Asn Leu Pro Pro Leu Ile Phe Lys Asp Leu Lys Glu
305                 310                 315                 320
Leu Ser Gln Leu Asn Leu Ser Tyr Asn Pro Ile Gln Lys Ile Gln Ala
            325                 330                 335
Asn Gln Phe Asp Tyr Leu Val Lys Leu Lys Ser Leu Ser Leu Glu Gly
        340                 345                 350
Ile Glu Ile Ser Asn Ile Gln Gln Arg Met Phe Arg Pro Leu Met Asn
    355                 360                 365
Leu Ser His Ile Tyr Phe Lys Lys Phe Gln Tyr Cys Gly Tyr Ala Pro
    370                 375                 380
His Val Arg Ser Cys Lys Pro Asn Thr Asp Gly Ile Ser Ser Leu Glu
385                 390                 395                 400
Asn Leu Leu Ala Ser Ile Ile Gln Arg Val Phe Val Trp Val Val Ser
            405                 410                 415
Ala Val Thr Cys Phe Gly Asn Ile Phe Val Ile Cys Met Arg Pro Tyr
        420                 425                 430
Ile Arg Ser Glu Asn Lys Leu Tyr Ala Met Ser Ile Ile Ser Leu Cys
    435                 440                 445
Cys Ala Asp Cys Leu Met Gly Ile Tyr Leu Phe Val Ile Gly Gly Phe
    450                 455                 460
Asp Leu Lys Phe Arg Gly Glu Tyr Asn Lys His Ala Gln Leu Trp Met
465                 470                 475                 480
Glu Ser Thr His Cys Gln Leu Val Gly Ser Leu Ala Ile Leu Ser Thr
            485                 490                 495
Glu Val Ser Val Leu Leu Leu Thr Phe Leu Thr Leu Glu Lys Tyr Ile
        500                 505                 510
Cys Ile Val Tyr Pro Phe Arg Cys Val Arg Pro Gly Lys Cys Arg Thr
    515                 520                 525
Ile Thr Val Leu Ile Leu Ile Trp Ile Thr Gly Phe Ile Val Ala Phe
    530                 535                 540
Ile Pro Leu Ser Asn Lys Glu Phe Phe Lys Asn Tyr Tyr Gly Thr Asn
545                 550                 555                 560
Gly Val Cys Phe Pro Leu His Ser Glu Asp Thr Glu Ser Ile Gly Ala
            565                 570                 575
Gln Ile Tyr Ser Val Ala Ile Phe Leu Gly Ile Asn Leu Ala Ala Phe
        580                 585                 590
```

```
Ile Ile Ile Val Phe Ser Tyr Gly Ser Met Phe Tyr Ser Val His Gln
            595                 600                 605

Ser Ala Ile Thr Ala Thr Glu Ile Arg Asn Gln Val Lys Lys Glu Met
            610                 615                 620

Ile Leu Ala Lys Arg Phe Phe Ile Val Phe Thr Asp Ala Leu Cys
625                 630                 635                 640

Trp Ile Pro Ile Phe Val Val Lys Phe Leu Ser Leu Leu Gln Val Glu
            645                 650                 655

Ile Pro Gly Thr Ile Thr Ser Trp Val Val Ile Phe Ile Leu Pro Ile
            660                 665                 670

Asn Ser Ala Leu Asn Pro Ile Leu Tyr Thr Leu Thr Thr Arg Pro Phe
            675                 680                 685

Lys Glu Met Ile His Arg Phe Trp Tyr Asn Tyr Arg Gln Arg Lys Ser
            690                 695                 700

Met Asp Ser Lys Gly Gln Lys Thr Tyr Ala Pro Ser Phe Ile Trp Val
705                 710                 715                 720

Glu Met Trp Pro Leu Gln Glu Met Pro Pro Glu Leu Met Lys Pro Asp
            725                 730                 735

Leu Phe Thr Tyr Pro Cys Glu Met Ser Leu Ile Ser Gln Ser Thr Arg
            740                 745                 750

Leu Asn Ser Tyr Ser
            755

<210> SEQ ID NO 13
<211> LENGTH: 754
<212> TYPE: PRT
<213> ORGANISM: Homo sapiens

<400> SEQUENCE: 13

Met Ile Val Phe Leu Val Phe Lys His Leu Phe Ser Leu Arg Leu Ile
1               5                   10                  15

Thr Met Phe Phe Leu Leu His Phe Ile Val Leu Ile Asn Val Lys Asp
            20                  25                  30

Phe Ala Leu Thr Gln Gly Ser Met Ile Thr Pro Ser Cys Gln Lys Gly
            35                  40                  45

Tyr Phe Pro Cys Gly Asn Leu Thr Lys Cys Leu Pro Arg Ala Phe His
        50                  55                  60

Cys Asp Gly Lys Asp Asp Cys Gly Asn Gly Ala Asp Glu Glu Asn Cys
65                  70                  75                  80

Gly Asp Thr Ser Gly Trp Ala Thr Ile Phe Gly Thr Val His Gly Asn
            85                  90                  95

Ala Asn Ser Val Ala Leu Thr Gln Glu Cys Phe Leu Lys Gln Tyr Pro
            100                 105                 110

Gln Cys Cys Asp Cys Lys Glu Thr Glu Leu Glu Cys Val Asn Gly Asp
            115                 120                 125

Leu Lys Ser Val Pro Met Ile Ser Asn Asn Val Thr Leu Leu Ser Leu
        130                 135                 140

Lys Lys Asn Lys Ile His Ser Leu Pro Asp Lys Val Phe Ile Lys Tyr
145                 150                 155                 160

Thr Lys Leu Lys Lys Ile Phe Leu Gln His Asn Cys Ile Arg His Ile
            165                 170                 175

Ser Arg Lys Ala Phe Phe Gly Leu Cys Asn Leu Gln Ile Leu Tyr Leu
            180                 185                 190

Asn His Asn Cys Ile Thr Thr Leu Arg Pro Gly Ile Phe Lys Asp Leu
```

-continued

```
              195                 200                 205
His Gln Leu Thr Trp Leu Ile Leu Asp Asp Asn Pro Ile Thr Arg Ile
210                 215                 220

Ser Gln Arg Leu Phe Thr Gly Leu Asn Ser Leu Phe Leu Ser Met
225                 230                 235                 240

Val Asn Asn Tyr Leu Glu Ala Leu Pro Lys Gln Met Cys Ala Gln Met
                245                 250                 255

Pro Gln Leu Asn Trp Val Asp Leu Glu Gly Asn Arg Ile Lys Tyr Leu
            260                 265                 270

Thr Asn Ser Thr Phe Leu Ser Cys Asp Ser Leu Thr Val Leu Phe Leu
        275                 280                 285

Pro Arg Asn Gln Ile Gly Phe Val Pro Glu Lys Thr Phe Ser Ser Leu
290                 295                 300

Lys Asn Leu Gly Glu Leu Asp Leu Ser Ser Asn Thr Ile Thr Glu Leu
305                 310                 315                 320

Ser Pro His Leu Phe Lys Asp Leu Lys Leu Gln Lys Leu Asn Leu
                325                 330                 335

Ser Ser Asn Pro Leu Met Tyr Leu His Lys Asn Gln Phe Glu Ser Leu
            340                 345                 350

Lys Gln Leu Gln Ser Leu Asp Leu Glu Arg Ile Glu Ile Pro Asn Ile
        355                 360                 365

Asn Thr Arg Met Phe Gln Pro Met Lys Asn Leu Ser His Ile Tyr Phe
370                 375                 380

Lys Asn Phe Arg Tyr Cys Ser Tyr Ala Pro His Val Arg Ile Cys Met
385                 390                 395                 400

Pro Leu Thr Asp Gly Ile Ser Ser Phe Glu Asp Leu Leu Ala Asn Asn
                405                 410                 415

Ile Leu Arg Ile Phe Val Trp Val Ile Ala Phe Ile Thr Cys Phe Gly
            420                 425                 430

Asn Leu Phe Val Ile Gly Met Arg Ser Phe Ile Lys Ala Glu Asn Thr
        435                 440                 445

Thr His Ala Met Ser Ile Lys Ile Leu Cys Cys Ala Asp Cys Leu Met
450                 455                 460

Gly Val Tyr Leu Phe Phe Val Gly Ile Phe Asp Ile Lys Tyr Arg Gly
465                 470                 475                 480

Gln Tyr Gln Lys Tyr Ala Leu Leu Trp Met Glu Ser Val Gln Cys Arg
                485                 490                 495

Leu Met Gly Phe Leu Ala Met Leu Ser Thr Glu Val Ser Val Leu Leu
            500                 505                 510

Leu Thr Tyr Leu Thr Leu Glu Lys Phe Leu Val Ile Val Phe Pro Phe
        515                 520                 525

Ser Asn Ile Arg Pro Gly Lys Arg Gln Thr Ser Val Ile Leu Ile Cys
530                 535                 540

Ile Trp Met Ala Gly Phe Leu Ile Ala Val Ile Pro Phe Trp Asn Lys
545                 550                 555                 560

Asp Tyr Phe Gly Asn Phe Tyr Gly Lys Asn Gly Val Cys Phe Pro Leu
                565                 570                 575

Tyr Tyr Asp Gln Thr Glu Asp Ile Gly Ser Lys Gly Tyr Ser Leu Gly
            580                 585                 590

Ile Phe Leu Gly Val Asn Leu Leu Ala Phe Leu Ile Ile Val Phe Ser
        595                 600                 605

Tyr Ile Thr Met Phe Cys Ser Ile Gln Lys Thr Ala Leu Gln Thr Thr
610                 615                 620
```

```
Glu Val Arg Asn Cys Phe Gly Arg Glu Val Ala Val Ala Asn Arg Phe
625                 630                 635                 640

Phe Phe Ile Val Phe Ser Asp Ala Ile Cys Trp Ile Pro Val Phe Val
                645                 650                 655

Val Lys Ile Leu Ser Leu Phe Arg Val Glu Ile Pro Asp Thr Met Thr
            660                 665                 670

Ser Trp Ile Val Ile Phe Phe Leu Pro Val Asn Ser Ala Leu Asn Pro
        675                 680                 685

Ile Leu Tyr Thr Leu Thr Thr Asn Phe Phe Lys Asp Lys Leu Lys Gln
    690                 695                 700

Leu Leu His Lys His Gln Arg Lys Ser Ile Phe Lys Ile Lys Lys Lys
705                 710                 715                 720

Ser Leu Ser Thr Ser Ile Val Trp Ile Glu Ser Ser Ser Leu Lys
                725                 730                 735

Leu Gly Val Leu Asn Lys Ile Thr Leu Gly Asp Ser Ile Met Lys Pro
            740                 745                 750

Val Ser

<210> SEQ ID NO 14
<211> LENGTH: 737
<212> TYPE: PRT
<213> ORGANISM: Homo sapiens

<400> SEQUENCE: 14

Met Trp Leu Leu Leu His Val Ile Leu Leu Thr Glu Val Lys Asp Phe
1               5                   10                  15

Ala Leu Ala Asp Ser Ser Met Val Ala Pro Leu Cys Pro Lys Gly Tyr
            20                  25                  30

Phe Pro Cys Gly Asn Leu Thr Lys Cys Leu Pro Arg Ala Phe His Cys
        35                  40                  45

Asp Gly Val Asp Asp Cys Gly Asn Gly Ala Asp Glu Asn Cys Gly
    50                  55                  60

Asp Thr Ser Gly Trp Thr Thr Ile Phe Gly Thr Val His Gly Asn Val
65                  70                  75                  80

Asn Lys Val Thr Leu Thr Gln Glu Cys Phe Leu Ser Gln Tyr Pro Gln
                85                  90                  95

His Cys Tyr Cys Arg Glu Asn Glu Leu Glu Cys Val Lys Ala Asp Leu
            100                 105                 110

Lys Ala Val Pro Lys Val Ser Ser Asn Val Thr Leu Leu Ser Leu Lys
        115                 120                 125

Lys Asn Lys Ile His Arg Leu Pro Val Lys Val Phe Ser Arg Tyr Thr
    130                 135                 140

Glu Leu Arg Lys Ile Tyr Leu Gln His Asn Cys Ile Thr His Ile Ser
145                 150                 155                 160

Arg Arg Ala Phe Leu Gly Leu His Asn Leu Gln Ile Leu Tyr Leu Ser
                165                 170                 175

His Asn Cys Ile Thr Ser Leu Arg Pro Gly Ile Phe Lys Asp Leu His
            180                 185                 190

Gln Leu Ala Trp Leu Ile Leu Asp Asp Asn Pro Ile Thr Arg Ile Ser
        195                 200                 205

Gln Lys Ser Phe Met Gly Leu Asn Ser Leu Phe Phe Leu Pro Met Val
    210                 215                 220

Gly Asn Arg Leu Glu Ala Leu Pro Glu Thr Leu Cys Ala Gln Met Pro
225                 230                 235                 240
```

```
Gln Leu Asn Trp Val Asp Leu Ala Asn Asn Gly Ile Lys Tyr Ile Thr
                245                 250                 255

Asn Ser Thr Phe Leu Thr Cys Asp Ser Leu Thr Val Leu Phe Leu Pro
            260                 265                 270

Arg Asn Gln Ile Gly Phe Val Pro Glu Lys Thr Phe Ser Ser Leu Lys
            275                 280                 285

Asn Leu Gly Glu Leu Asp Leu Ser Ser Asn Met Ile Thr Lys Leu Pro
290                 295                 300

Val His Leu Phe Ser Asp Leu His Leu Leu Gln Lys Leu Asn Leu Ser
305                 310                 315                 320

Ser Asn Pro Leu Leu Tyr Val His Lys Asn Gln Phe Gly Ser Leu Lys
                325                 330                 335

Gln Leu Gln Ser Leu Asp Leu Glu Arg Ile Glu Ile Pro Asn Ile Ser
            340                 345                 350

Thr Gly Met Phe Gln Pro Met Lys Asn Leu Ser His Ile Tyr Leu Lys
            355                 360                 365

Thr Phe Arg Tyr Cys Ser Tyr Val Pro His Val Arg Ile Cys Met Pro
370                 375                 380

Ser Thr Asp Gly Ile Ser Ser Glu Asp Leu Leu Ala Asn Gly Ile
385                 390                 395                 400

Leu Arg Val Ser Val Trp Val Ile Ala Phe Ile Thr Cys Val Gly Asn
                405                 410                 415

Phe Leu Val Ile Ala Val Arg Ser Leu Ile Lys Ala Glu Asn Thr Thr
            420                 425                 430

His Ala Met Ser Ile Lys Ile Leu Cys Cys Ala Asp Cys Leu Met Gly
            435                 440                 445

Val Tyr Leu Phe Ser Val Gly Val Phe Asp Ile Lys Tyr Arg Gly Gln
450                 455                 460

Tyr Gln Lys Tyr Ala Leu Leu Trp Met Glu Ser Val Pro Cys Arg Leu
465                 470                 475                 480

Leu Gly Phe Leu Ala Thr Leu Ser Thr Glu Val Ser Val Leu Leu Leu
                485                 490                 495

Thr Phe Leu Thr Leu Glu Lys Phe Leu Val Ile Val Phe Pro Phe Ser
            500                 505                 510

Asn Leu Arg Leu Gly Lys Arg Gln Thr Ala Val Ala Leu Ala Ser Ile
            515                 520                 525

Trp Val Val Gly Phe Leu Ile Ala Ala Val Pro Phe Thr Arg Glu Asp
530                 535                 540

Tyr Phe Gly Asn Phe Tyr Gly Lys Asn Gly Val Cys Phe Pro Leu His
545                 550                 555                 560

Tyr Asp Gln Ala Glu Asp Phe Gly Ser Arg Gly Tyr Ser Leu Gly Ile
                565                 570                 575

Phe Leu Gly Val Asn Leu Leu Ala Phe Leu Val Ile Val Ile Ser Tyr
            580                 585                 590

Val Thr Met Phe Cys Ser Ile His Lys Thr Ala Leu Gln Thr Ala Glu
            595                 600                 605

Val Arg Ser His Ile Gly Lys Glu Val Ala Val Ala Asn Arg Phe Phe
610                 615                 620

Phe Ile Val Phe Ser Asp Ala Ile Cys Trp Ile Pro Val Phe Val Val
625                 630                 635                 640

Lys Ile Leu Ser Leu Leu Gln Val Glu Ile Pro Gly Thr Ile Thr Ser
                645                 650                 655
```

```
Trp Ile Val Val Phe Leu Pro Val Asn Ser Ala Leu Asn Pro Ile
            660                 665                 670

Leu Tyr Thr Leu Thr Thr Ser Phe Phe Lys Asp Lys Leu Lys Gln Leu
            675                 680                 685

Leu His Lys His Arg Arg Lys Pro Ile Phe Lys Val Lys Lys Lys Ser
            690                 695                 700

Leu Ser Ala Ser Ile Val Trp Thr Asp Glu Ser Ser Leu Lys Leu Gly
705                 710                 715                 720

Val Leu Ser Lys Ile Ala Leu Gly Asp Ser Ile Met Lys Pro Val Ser
                725                 730                 735

Pro

<210> SEQ ID NO 15
<211> LENGTH: 737
<212> TYPE: PRT
<213> ORGANISM: Homo sapiens

<400> SEQUENCE: 15

Met Phe Phe Leu Leu His Phe Ile Val Leu Ile Asn Val Lys Asp Phe
1               5                   10                  15

Ala Leu Thr Gln Gly Ser Met Ile Thr Pro Ser Cys Gln Lys Gly Tyr
            20                  25                  30

Phe Pro Cys Gly Asn Leu Thr Lys Cys Leu Pro Arg Ala Phe His Cys
        35                  40                  45

Asp Gly Lys Asp Asp Cys Gly Asn Gly Ala Asp Glu Glu Asn Cys Gly
    50                  55                  60

Asp Thr Ser Gly Trp Ala Thr Ile Phe Gly Thr Val His Gly Asn Ala
65                  70                  75                  80

Asn Ser Val Ala Leu Thr Gln Glu Cys Phe Leu Lys Gln Tyr Pro Gln
                85                  90                  95

Cys Cys Asp Cys Lys Glu Thr Glu Leu Glu Cys Val Asn Gly Asp Leu
            100                 105                 110

Lys Ser Val Pro Met Ile Ser Asn Asn Val Thr Leu Leu Ser Leu Lys
        115                 120                 125

Lys Asn Lys Ile His Ser Leu Pro Asp Lys Val Phe Ile Lys Tyr Thr
    130                 135                 140

Lys Leu Lys Lys Ile Phe Leu Gln His Asn Cys Ile Arg His Ile Ser
145                 150                 155                 160

Arg Lys Ala Phe Phe Gly Leu Cys Asn Leu Gln Ile Leu Tyr Leu Asn
                165                 170                 175

His Asn Cys Ile Thr Thr Leu Arg Pro Gly Ile Phe Lys Asp Leu His
            180                 185                 190

Gln Leu Thr Trp Leu Ile Leu Asp Asp Asn Pro Ile Thr Arg Ile Ser
        195                 200                 205

Gln Arg Leu Phe Thr Gly Leu Asn Ser Leu Phe Phe Leu Ser Met Val
    210                 215                 220

Asn Asn Tyr Leu Glu Ala Leu Pro Lys Gln Met Cys Ala Gln Met Pro
225                 230                 235                 240

Gln Leu Asn Trp Val Asp Leu Glu Gly Asn Arg Ile Lys Tyr Leu Thr
                245                 250                 255

Asn Ser Thr Phe Leu Ser Cys Asp Ser Leu Thr Val Leu Phe Leu Pro
            260                 265                 270

Arg Asn Gln Ile Gly Phe Val Pro Glu Lys Thr Phe Ser Ser Leu Lys
        275                 280                 285
```

-continued

```
Asn Leu Gly Glu Leu Asp Leu Ser Ser Asn Thr Ile Thr Glu Leu Ser
    290                 295                 300
Pro His Leu Phe Lys Asp Leu Lys Leu Leu Gln Lys Leu Asn Leu Ser
305                 310                 315                 320
Ser Asn Pro Leu Met Tyr Leu His Lys Asn Gln Phe Glu Ser Leu Lys
                    325                 330                 335
Gln Leu Gln Ser Leu Asp Leu Glu Arg Ile Glu Ile Pro Asn Ile Asn
                340                 345                 350
Thr Arg Met Phe Gln Pro Met Lys Asn Leu Ser His Ile Tyr Phe Lys
            355                 360                 365
Asn Phe Arg Tyr Cys Ser Tyr Ala Pro His Val Arg Ile Cys Met Pro
370                 375                 380
Leu Thr Asp Gly Ile Ser Ser Phe Glu Asp Leu Leu Ala Asn Asn Ile
385                 390                 395                 400
Leu Arg Ile Phe Val Trp Val Ile Ala Phe Ile Thr Cys Phe Gly Asn
                    405                 410                 415
Leu Phe Val Ile Gly Met Arg Ser Phe Ile Lys Ala Glu Asn Thr Thr
                420                 425                 430
His Ala Met Ser Ile Lys Ile Leu Cys Cys Ala Asp Cys Leu Met Gly
            435                 440                 445
Val Tyr Leu Phe Phe Val Gly Ile Phe Asp Ile Lys Tyr Arg Gly Gln
450                 455                 460
Tyr Gln Lys Tyr Ala Leu Leu Trp Met Glu Ser Val Gln Cys Arg Leu
465                 470                 475                 480
Met Gly Phe Leu Ala Met Leu Ser Thr Glu Val Ser Val Leu Leu Leu
                    485                 490                 495
Thr Tyr Leu Thr Leu Glu Lys Phe Leu Val Ile Val Phe Pro Phe Ser
                500                 505                 510
Asn Ile Arg Pro Gly Lys Arg Gln Thr Ser Val Ile Leu Ile Cys Ile
            515                 520                 525
Trp Met Ala Gly Phe Leu Ile Ala Val Ile Pro Phe Trp Asn Lys Asp
530                 535                 540
Tyr Phe Gly Asn Phe Tyr Gly Lys Asn Gly Val Cys Phe Pro Leu Tyr
545                 550                 555                 560
Tyr Asp Gln Thr Glu Asp Ile Gly Ser Lys Gly Tyr Ser Leu Gly Ile
                    565                 570                 575
Phe Leu Gly Val Asn Leu Leu Ala Phe Leu Ile Ile Val Phe Ser Tyr
                580                 585                 590
Ile Thr Met Phe Cys Ser Ile Gln Lys Thr Ala Leu Gln Thr Thr Glu
            595                 600                 605
Val Arg Asn Cys Phe Gly Arg Glu Val Ala Val Ala Asn Arg Phe Phe
610                 615                 620
Phe Ile Val Phe Ser Asp Ala Ile Cys Trp Ile Pro Val Phe Val Val
625                 630                 635                 640
Lys Ile Leu Ser Leu Phe Arg Val Glu Ile Pro Asp Thr Met Thr Ser
                    645                 650                 655
Trp Ile Val Ile Phe Phe Leu Pro Val Asn Ser Ala Leu Asn Pro Ile
                660                 665                 670
Leu Tyr Thr Leu Thr Thr Asn Phe Phe Lys Asp Lys Leu Lys Gln Leu
            675                 680                 685
Leu His Lys His Gln Arg Lys Ser Ile Phe Lys Ile Lys Lys Lys Ser
690                 695                 700
Leu Ser Thr Ser Ile Val Trp Ile Glu Asp Ser Ser Ser Leu Lys Leu
```

-continued

```
            705                 710                 715                 720
Gly Val Leu Asn Lys Ile Thr Leu Gly Asp Ser Ile Met Lys Pro Val
                    725                 730                 735
Ser
```

<210> SEQ ID NO 16
<211> LENGTH: 713
<212> TYPE: PRT
<213> ORGANISM: Homo sapiens

<400> SEQUENCE: 16

```
Met Phe Phe Leu Leu His Phe Ile Val Leu Ile Asn Val Lys Asp Phe
1               5                   10                  15

Ala Leu Thr Gln Gly Ser Met Ile Thr Pro Ser Cys Gln Lys Gly Tyr
            20                  25                  30

Phe Pro Cys Gly Asn Leu Thr Lys Cys Leu Pro Arg Ala Phe His Cys
        35                  40                  45

Asp Gly Lys Asp Asp Cys Gly Asn Gly Ala Asp Glu Glu Asn Cys Gly
    50                  55                  60

Asp Thr Ser Gly Trp Ala Thr Ile Phe Gly Thr Val His Gly Asn Ala
65                  70                  75                  80

Asn Ser Val Ala Leu Thr Gln Glu Cys Phe Leu Lys Gln Tyr Pro Gln
                85                  90                  95

Cys Cys Asp Cys Lys Glu Thr Glu Leu Glu Cys Val Asn Gly Asp Leu
            100                 105                 110

Lys Ser Val Pro Met Ile Ser Asn Asn Val Thr Leu Ser Leu Lys
        115                 120                 125

Lys Asn Lys Ile His Ser Leu Pro Asp Lys Val Phe Ile Lys Tyr Thr
    130                 135                 140

Lys Leu Lys Lys Ile Phe Leu Gln His Asn Cys Ile Arg His Ile Ser
145                 150                 155                 160

Arg Lys Ala Phe Phe Gly Leu Cys Asn Leu Gln Ile Leu Ile Leu Asp
                165                 170                 175

Asp Asn Pro Ile Thr Arg Ile Ser Gln Arg Leu Phe Thr Gly Leu Asn
            180                 185                 190

Ser Leu Phe Phe Leu Ser Met Val Asn Asn Tyr Leu Glu Ala Leu Pro
        195                 200                 205

Lys Gln Met Cys Ala Gln Met Pro Gln Leu Asn Trp Val Asp Leu Glu
    210                 215                 220

Gly Asn Arg Ile Lys Tyr Leu Thr Asn Ser Thr Phe Leu Ser Cys Asp
225                 230                 235                 240

Ser Leu Thr Val Leu Phe Leu Pro Arg Asn Gln Ile Gly Phe Val Pro
                245                 250                 255

Glu Lys Thr Phe Ser Ser Leu Lys Asn Leu Gly Glu Leu Asp Leu Ser
            260                 265                 270

Ser Asn Thr Ile Thr Glu Leu Ser Pro His Leu Phe Lys Asp Leu Lys
        275                 280                 285

Leu Leu Gln Lys Leu Asn Leu Ser Asn Pro Leu Met Tyr Leu His
    290                 295                 300

Lys Asn Gln Phe Glu Ser Leu Lys Gln Leu Gln Ser Leu Asp Leu Glu
305                 310                 315                 320

Arg Ile Glu Ile Pro Asn Ile Asn Thr Arg Met Phe Gln Pro Met Lys
                325                 330                 335

Asn Leu Ser His Ile Tyr Phe Lys Asn Phe Arg Tyr Cys Ser Tyr Ala
```

-continued

```
                340                 345                 350
Pro His Val Arg Ile Cys Met Pro Leu Thr Asp Gly Ile Ser Ser Phe
            355                 360                 365

Glu Asp Leu Leu Ala Asn Asn Ile Leu Arg Ile Phe Val Trp Val Ile
        370                 375                 380

Ala Phe Ile Thr Cys Phe Gly Asn Leu Phe Val Ile Gly Met Arg Ser
385                 390                 395                 400

Phe Ile Lys Ala Glu Asn Thr Thr His Ala Met Ser Ile Lys Ile Leu
                405                 410                 415

Cys Cys Ala Asp Cys Leu Met Gly Val Tyr Leu Phe Phe Val Gly Ile
            420                 425                 430

Phe Asp Ile Lys Tyr Arg Gly Gln Tyr Gln Lys Tyr Ala Leu Leu Trp
        435                 440                 445

Met Glu Ser Val Gln Cys Arg Leu Met Gly Phe Leu Ala Met Leu Ser
    450                 455                 460

Thr Glu Val Ser Val Leu Leu Thr Tyr Leu Thr Leu Glu Lys Phe
465                 470                 475                 480

Leu Val Ile Val Phe Pro Phe Ser Asn Ile Arg Pro Gly Lys Arg Gln
                485                 490                 495

Thr Ser Val Ile Leu Ile Cys Ile Trp Met Ala Gly Phe Leu Ile Ala
            500                 505                 510

Val Ile Pro Phe Trp Asn Lys Asp Tyr Phe Gly Asn Phe Tyr Gly Lys
        515                 520                 525

Asn Gly Val Cys Phe Pro Leu Tyr Tyr Asp Gln Thr Glu Asp Ile Gly
530                 535                 540

Ser Lys Gly Tyr Ser Leu Gly Ile Phe Leu Gly Val Asn Leu Leu Ala
545                 550                 555                 560

Phe Leu Ile Ile Val Phe Ser Tyr Ile Thr Met Phe Cys Ser Ile Gln
                565                 570                 575

Lys Thr Ala Leu Gln Thr Thr Glu Val Arg Asn Cys Phe Gly Arg Glu
            580                 585                 590

Val Ala Val Ala Asn Arg Phe Phe Ile Val Phe Ser Asp Ala Ile
        595                 600                 605

Cys Trp Ile Pro Val Phe Val Val Lys Ile Leu Ser Leu Phe Arg Val
610                 615                 620

Glu Ile Pro Asp Thr Met Thr Ser Trp Ile Val Ile Phe Phe Leu Pro
625                 630                 635                 640

Val Asn Ser Ala Leu Asn Pro Ile Leu Tyr Thr Leu Thr Thr Asn Phe
                645                 650                 655

Phe Lys Asp Lys Leu Lys Gln Leu Leu His Lys His Gln Arg Lys Ser
            660                 665                 670

Ile Phe Lys Ile Lys Lys Lys Ser Leu Ser Thr Ser Ile Val Trp Ile
        675                 680                 685

Glu Asp Ser Ser Ser Leu Lys Leu Gly Val Leu Asn Lys Ile Thr Leu
690                 695                 700

Gly Asp Ser Ile Met Lys Pro Val Ser
705                 710
```

<210> SEQ ID NO 17
<211> LENGTH: 36
<212> TYPE: DNA
<213> ORGANISM: Homo sapiens

<400> SEQUENCE: 17

```
gcagcagtcg acggttgtga gagtatagag gattgg                                    36
```

```
<210> SEQ ID NO 18
<211> LENGTH: 39
<212> TYPE: DNA
<213> ORGANISM: Homo sapiens

<400> SEQUENCE: 18
gcagcagcgg ccgcatgcag aaaaccaagc aagatgagg                                 39

<210> SEQ ID NO 19
<211> LENGTH: 37
<212> TYPE: DNA
<213> ORGANISM: Homo sapiens

<400> SEQUENCE: 19
gcagcagtcg actctgagga tattgttagc caagagg                                   37

<210> SEQ ID NO 20
<211> LENGTH: 733
<212> TYPE: DNA
<213> ORGANISM: homo sapiens

<400> SEQUENCE: 20
gggatccgga gcccaaatct tctgacaaaa ctcacacatg cccaccgtgc ccagcacctg          60
aattcgaggg tgcaccgtca gtcttcctct tccccccaaa acccaaggac accctcatga         120
tctcccggac tcctgaggtc acatgcgtgg tggtggacgt aagccacgaa gaccctgagg         180
tcaagttcaa ctggtacgtg gacggcgtgg aggtgcataa tgccaagaca aagccgcggg         240
aggagcagta caacagcacg taccgtgtgg tcagcgtcct caccgtcctg caccaggact         300
ggctgaatgg caaggagtac aagtgcaagg tctccaacaa agccctccca accccatcg          360 agaaaaccat ctccaaagcc aaagggcagc ccgagaacc acaggtgtac accctgcccc          420
catcccggga tgagctgacc aagaaccagg tcagcctgac ctgcctggtc aaaggcttct         480
atccaagcga catcgccgtg gagtgggaga gcaatgggca gccggagaac aactacaaga         540
ccacgcctcc cgtgctggac tccgacggct ccttcttcct ctacagcaag ctcaccgtgg         600
acaagagcag gtggcagcag gggaacgtct tctcatgctc cgtgatgcat gaggctctgc         660
acaaccacta cacgcagaag agcctctccc tgtctccggg taaatgagtg cgacggccgc         720
gactctagag gat                                                            733

<210> SEQ ID NO 21
<211> LENGTH: 8
<212> TYPE: PRT
<213> ORGANISM: bacteriophage T7

<400> SEQUENCE: 21

Asp Tyr Lys Asp Asp Asp Asp Lys
1               5

<210> SEQ ID NO 22
<211> LENGTH: 21
<212> TYPE: DNA
<213> ORGANISM: Homo sapiens

<400> SEQUENCE: 22
aagcagatgt gtgcccaaat g                                                   21

<210> SEQ ID NO 23
```

```
<211> LENGTH: 24
<212> TYPE: DNA
<213> ORGANISM: Homo sapiens

<400> SEQUENCE: 23
ggtgaggtga tagttccgtt atcg                                              24

<210> SEQ ID NO 24
<211> LENGTH: 16
<212> TYPE: PRT
<213> ORGANISM: Homo sapiens

<400> SEQUENCE: 24

Arg Ser Phe Ile Lys Ala Glu Asn Thr Thr His Ala Met Ser Ile Lys
1               5                   10                  15

<210> SEQ ID NO 25
<211> LENGTH: 22
<212> TYPE: PRT
<213> ORGANISM: Homo sapiens

<400> SEQUENCE: 25

Asp Ile Lys Tyr Arg Gly Gln Tyr Gln Lys Tyr Ala Leu Leu Trp Met
1               5                   10                  15

Glu Ser Val Gln Cys Arg
            20

<210> SEQ ID NO 26
<211> LENGTH: 21
<212> TYPE: PRT
<213> ORGANISM: Homo sapiens

<400> SEQUENCE: 26

Glu Lys Phe Leu Val Ile Val Phe Pro Phe Ser Asn Ile Arg Pro Gly
1               5                   10                  15

Lys Arg Gln Thr Ser
            20

<210> SEQ ID NO 27
<211> LENGTH: 32
<212> TYPE: PRT
<213> ORGANISM: Homo sapiens

<400> SEQUENCE: 27

Asn Lys Asp Tyr Phe Gly Asn Phe Tyr Gly Lys Asn Gly Val Cys Phe
1               5                   10                  15

Pro Leu Tyr Tyr Asp Gln Thr Glu Asp Ile Gly Ser Lys Gly Tyr Ser
            20                  25                  30

<210> SEQ ID NO 28
<211> LENGTH: 25
<212> TYPE: PRT
<213> ORGANISM: Homo sapiens

<400> SEQUENCE: 28

Ser Ile Gln Lys Thr Ala Leu Gln Thr Thr Glu Val Arg Asn Cys Phe
1               5                   10                  15

Gly Arg Glu Val Ala Val Ala Asn Arg
            20                  25

<210> SEQ ID NO 29
<211> LENGTH: 11
<212> TYPE: PRT
```

<213> ORGANISM: Homo sapiens

<400> SEQUENCE: 29

Arg Val Glu Ile Pro Asp Thr Met Thr Ser Trp
1               5                   10

<210> SEQ ID NO 30
<211> LENGTH: 13
<212> TYPE: PRT
<213> ORGANISM: Homo sapiens

<400> SEQUENCE: 30

Arg Ala Ile Gly Phe Ser Val Lys Met Asp Asp Ser Asp
1               5                   10

<210> SEQ ID NO 31
<211> LENGTH: 13
<212> TYPE: PRT
<213> ORGANISM: Homo sapiens

<400> SEQUENCE: 31

Asn Val Thr Leu Leu Ser Leu Lys Lys Asn Lys Ile His
1               5                   10

<210> SEQ ID NO 32
<211> LENGTH: 13
<212> TYPE: PRT
<213> ORGANISM: Homo sapiens

<400> SEQUENCE: 32

Cys Ile Arg His Ile Ser Arg Lys Ala Phe Phe Gly Leu
1               5                   10

<210> SEQ ID NO 33
<211> LENGTH: 13
<212> TYPE: PRT
<213> ORGANISM: Homo sapiens

<400> SEQUENCE: 33

His Asn Cys Ile Thr Thr Leu Arg Pro Gly Ile Phe Lys
1               5                   10

<210> SEQ ID NO 34
<211> LENGTH: 13
<212> TYPE: PRT
<213> ORGANISM: Homo sapiens

<400> SEQUENCE: 34

Pro Ile Thr Arg Ile Ser Gln Arg Leu Phe Thr Gly Leu
1               5                   10

<210> SEQ ID NO 35
<211> LENGTH: 13
<212> TYPE: PRT
<213> ORGANISM: Homo sapiens

<400> SEQUENCE: 35

Glu Lys Thr Phe Ser Ser Leu Lys Asn Leu Gly Glu Leu
1               5                   10

<210> SEQ ID NO 36
<211> LENGTH: 13
<212> TYPE: PRT
<213> ORGANISM: Homo sapiens

```
<400> SEQUENCE: 36

Lys Asn Gln Phe Glu Ser Leu Lys Gln Leu Gln Ser Leu
1               5                   10

<210> SEQ ID NO 37
<211> LENGTH: 13
<212> TYPE: PRT
<213> ORGANISM: Homo sapiens

<400> SEQUENCE: 37

Thr Thr His Ala Met Ser Ile Lys Ile Leu Cys Cys Ala
1               5                   10

<210> SEQ ID NO 38
<211> LENGTH: 13
<212> TYPE: PRT
<213> ORGANISM: Homo sapiens

<400> SEQUENCE: 38

Ile Glu Asp Ser Ser Ser Leu Lys Leu Gly Val Leu Asn
1               5                   10

<210> SEQ ID NO 39
<211> LENGTH: 12
<212> TYPE: PRT
<213> ORGANISM: Homo sapiens

<400> SEQUENCE: 39

Met Gln Lys Thr Lys Gln Asp Glu Asp Tyr Glu Arg
1               5                   10

<210> SEQ ID NO 40
<211> LENGTH: 14
<212> TYPE: PRT
<213> ORGANISM: Homo sapiens

<400> SEQUENCE: 40

Val Lys Met Asp Asp Ser Asp Ser Asp Phe Ala Leu Thr Gln
1               5                   10

<210> SEQ ID NO 41
<211> LENGTH: 14
<212> TYPE: PRT
<213> ORGANISM: Homo sapiens

<400> SEQUENCE: 41

Cys Asp Cys Lys Glu Thr Glu Leu Glu Cys Val Asn Gly Asp
1               5                   10

<210> SEQ ID NO 42
<211> LENGTH: 14
<212> TYPE: PRT
<213> ORGANISM: Homo sapiens

<400> SEQUENCE: 42

Lys Asn Lys Ile His Ser Leu Pro Asp Lys Val Phe Ile Lys
1               5                   10

<210> SEQ ID NO 43
<211> LENGTH: 14
<212> TYPE: PRT
<213> ORGANISM: Homo sapiens

<400> SEQUENCE: 43
```

```
Asp Leu Ser Ser Asn Thr Ile Thr Glu Leu Ser Pro His Leu
1               5                   10
```

<210> SEQ ID NO 44
<211> LENGTH: 14
<212> TYPE: PRT
<213> ORGANISM: Homo sapiens

<400> SEQUENCE: 44

```
Leu Thr Asp Gly Ile Ser Ser Phe Glu Asp Leu Leu Ala Asn
1               5                   10
```

<210> SEQ ID NO 45
<211> LENGTH: 14
<212> TYPE: PRT
<213> ORGANISM: Homo sapiens

<400> SEQUENCE: 45

```
Thr Asp Gly Ile Ser Ser Phe Glu Asp Leu Leu Ala Asn Asn
1               5                   10
```

<210> SEQ ID NO 46
<211> LENGTH: 14
<212> TYPE: PRT
<213> ORGANISM: Homo sapiens

<400> SEQUENCE: 46

```
Val Leu Asn Lys Ile Thr Leu Gly Asp Ser Ile Met Lys Pro
1               5                   10
```

<210> SEQ ID NO 47
<211> LENGTH: 14
<212> TYPE: PRT
<213> ORGANISM: Homo sapiens

<400> SEQUENCE: 47

```
Asn Ile Arg Pro Gly Lys Arg Gln Thr Ser Val Ile Leu Ile
1               5                   10
```

<210> SEQ ID NO 48
<211> LENGTH: 14
<212> TYPE: PRT
<213> ORGANISM: Homo sapiens

<400> SEQUENCE: 48

```
Ser Ile Phe Lys Ile Lys Lys Lys Ser Leu Ser Thr Ser Ile
1               5                   10
```

<210> SEQ ID NO 49
<211> LENGTH: 15
<212> TYPE: PRT
<213> ORGANISM: Homo sapiens

<400> SEQUENCE: 49

```
Met Gln Lys Thr Lys Gln Asp Glu Asp Tyr Glu Arg Ala Ile Gly
1               5                   10                  15
```

<210> SEQ ID NO 50
<211> LENGTH: 14
<212> TYPE: PRT
<213> ORGANISM: Homo sapiens

<400> SEQUENCE: 50

```
Tyr Phe Pro Cys Gly Asn Leu Thr Lys Cys Leu Pro Arg Ala
1               5                   10
```

<210> SEQ ID NO 51
<211> LENGTH: 14
<212> TYPE: PRT
<213> ORGANISM: Homo sapiens

<400> SEQUENCE: 51

Pro Met Ile Ser Asn Asn Val Thr Leu Leu Ser Leu Lys Lys
1               5                   10

<210> SEQ ID NO 52
<211> LENGTH: 14
<212> TYPE: PRT
<213> ORGANISM: Homo sapiens

<400> SEQUENCE: 52

Ile Lys Tyr Leu Thr Asn Ser Thr Phe Leu Ser Cys Asp Ser
1               5                   10

<210> SEQ ID NO 53
<211> LENGTH: 14
<212> TYPE: PRT
<213> ORGANISM: Homo sapiens

<400> SEQUENCE: 53

Leu Leu Gln Lys Leu Asn Leu Ser Ser Asn Pro Leu Met Tyr
1               5                   10

<210> SEQ ID NO 54
<211> LENGTH: 14
<212> TYPE: PRT
<213> ORGANISM: Homo sapiens

<400> SEQUENCE: 54

Phe Gln Pro Met Lys Asn Leu Ser His Ile Tyr Phe Lys Asn
1               5                   10

<210> SEQ ID NO 55
<211> LENGTH: 14
<212> TYPE: PRT
<213> ORGANISM: Homo sapiens

<400> SEQUENCE: 55

Phe Ile Lys Ala Glu Asn Thr Thr His Ala Met Ser Ile Lys
1               5                   10

<210> SEQ ID NO 56
<211> LENGTH: 16
<212> TYPE: PRT
<213> ORGANISM: Homo sapiens

<400> SEQUENCE: 56

Trp Ala Thr Ile Phe Gly Thr Val His Gly Asn Ala Asn Ser Val Ala
1               5                   10                  15

<210> SEQ ID NO 57
<211> LENGTH: 16
<212> TYPE: PRT
<213> ORGANISM: Homo sapiens

<400> SEQUENCE: 57

Phe Gly Thr Val His Gly Asn Ala Asn Ser Val Ala Leu Thr Gln Glu
1               5                   10                  15

<210> SEQ ID NO 58
<211> LENGTH: 16
<212> TYPE: PRT
<213> ORGANISM: Homo sapiens

<400> SEQUENCE: 58

Asn Lys Asp Tyr Phe Gly Asn Phe Tyr Gly Lys Asn Gly Val Cys Phe
1               5                   10                  15

<210> SEQ ID NO 59
<211> LENGTH: 16
<212> TYPE: PRT
<213> ORGANISM: Homo sapiens

<400> SEQUENCE: 59

Lys Gly Tyr Ser Leu Gly Ile Phe Leu Gly Val Asn Leu Leu Ala Phe
1               5                   10                  15

<210> SEQ ID NO 60
<211> LENGTH: 14
<212> TYPE: PRT
<213> ORGANISM: Homo sapiens

<400> SEQUENCE: 60

Phe Ser Asn Ile Arg Pro Gly Lys Arg Gln Thr Ser Val Ile
1               5                   10

<210> SEQ ID NO 61
<211> LENGTH: 32
<212> TYPE: PRT
<213> ORGANISM: Homo sapiens

<400> SEQUENCE: 61

Ser Val Gln Cys Arg Leu Met Gly Phe Leu Ala Met Leu Ser Thr Glu
1               5                   10                  15

Val Ser Val Leu Leu Leu Thr Tyr Leu Thr Leu Glu Lys Phe Leu Val
                20                  25                  30

<210> SEQ ID NO 62
<211> LENGTH: 32
<212> TYPE: PRT
<213> ORGANISM: Homo sapiens

<400> SEQUENCE: 62

Lys Ser Leu Glu Glu Leu Asn Leu Ser His Asn Asn Leu Met Ser Leu
1               5                   10                  15

Pro His Asp Leu Phe Thr Pro Leu His Arg Leu Glu Arg Val His Leu
                20                  25                  30

<210> SEQ ID NO 63
<211> LENGTH: 24
<212> TYPE: PRT
<213> ORGANISM: Homo sapiens

<400> SEQUENCE: 63

Asn Val Thr Leu Leu Ser Leu Lys Lys Asn Lys Ile His Ser Leu Pro
1               5                   10                  15

Asp Lys Val Phe Ile Lys Tyr Thr
                20

<210> SEQ ID NO 64
<211> LENGTH: 24
<212> TYPE: PRT
<213> ORGANISM: Homo sapiens

```
<400> SEQUENCE: 64

Lys Leu Lys Lys Ile Phe Leu Gln His Asn Cys Ile Arg His Ile Ser
1               5                   10                  15

Arg Lys Ala Phe Phe Gly Leu Cys
            20

<210> SEQ ID NO 65
<211> LENGTH: 24
<212> TYPE: PRT
<213> ORGANISM: Homo sapiens

<400> SEQUENCE: 65

Asn Leu Gln Ile Leu Tyr Leu Asn His Asn Cys Ile Thr Thr Leu Arg
1               5                   10                  15

Pro Gly Ile Phe Lys Asp Leu His
            20

<210> SEQ ID NO 66
<211> LENGTH: 24
<212> TYPE: PRT
<213> ORGANISM: Homo sapiens

<400> SEQUENCE: 66

Gln Leu Thr Trp Leu Ile Leu Asp Asp Asn Pro Ile Thr Arg Ile Ser
1               5                   10                  15

Gln Arg Leu Phe Thr Gly Leu Asn
            20

<210> SEQ ID NO 67
<211> LENGTH: 24
<212> TYPE: PRT
<213> ORGANISM: Homo sapiens

<400> SEQUENCE: 67

Ser Leu Thr Val Leu Phe Leu Pro Arg Asn Gln Ile Gly Phe Val Pro
1               5                   10                  15

Glu Lys Thr Phe Ser Ser Leu Lys
            20

<210> SEQ ID NO 68
<211> LENGTH: 24
<212> TYPE: PRT
<213> ORGANISM: Homo sapiens

<400> SEQUENCE: 68

Asn Leu Gly Glu Leu Asp Leu Ser Ser Asn Thr Ile Thr Glu Leu Ser
1               5                   10                  15

Pro His Leu Phe Lys Asp Leu Lys
            20

<210> SEQ ID NO 69
<211> LENGTH: 24
<212> TYPE: PRT
<213> ORGANISM: Homo sapiens

<400> SEQUENCE: 69

Leu Leu Gln Lys Leu Asn Leu Ser Ser Asn Pro Leu Met Tyr Leu His
1               5                   10                  15

Lys Asn Gln Phe Glu Ser Leu Lys
            20
```

```
<210> SEQ ID NO 70
<211> LENGTH: 80
<212> TYPE: DNA
<213> ORGANISM: Homo sapiens

<400> SEQUENCE: 70
gtgcaaaatc agaatcactg tcatccattt tgacactaaa tccaatggct ctttcatagt    60
cctcatcttg cttggttttc                                                80

<210> SEQ ID NO 71
<211> LENGTH: 20
<212> TYPE: DNA
<213> ORGANISM: Homo sapiens

<400> SEQUENCE: 71
taatacgact cactataggg                                                20

<210> SEQ ID NO 72
<211> LENGTH: 18
<212> TYPE: DNA
<213> ORGANISM: Homo sapiens

<400> SEQUENCE: 72
atttaggtga cactatag                                                  18

<210> SEQ ID NO 73
<211> LENGTH: 21
<212> TYPE: DNA
<213> ORGANISM: Homo sapiens

<400> SEQUENCE: 73
gcagaaaacc aagcaagatg a                                              21

<210> SEQ ID NO 74
<211> LENGTH: 20
<212> TYPE: DNA
<213> ORGANISM: Homo sapiens

<400> SEQUENCE: 74
tccttgccat cacagtgaaa                                                20

<210> SEQ ID NO 75
<211> LENGTH: 39
<212> TYPE: DNA
<213> ORGANISM: Homo sapiens

<400> SEQUENCE: 75
gcagcagcgg ccgcctcaga atatttgtct gggttatag                           39

<210> SEQ ID NO 76
<211> LENGTH: 34
<212> TYPE: DNA
<213> ORGANISM: Homo sapiens

<400> SEQUENCE: 76
gcagcagtcg acggaaactg gtttcattat actg                                34

<210> SEQ ID NO 77
<211> LENGTH: 39
<212> TYPE: DNA
<213> ORGANISM: Homo sapiens

<400> SEQUENCE: 77
```

-continued

```
<210> SEQ ID NO 78
<211> LENGTH: 24
<212> TYPE: DNA
<213> ORGANISM: Homo sapiens

<400> SEQUENCE: 78
gaagatgaca tctgcaatgc tttt                                          24

<210> SEQ ID NO 79
<211> LENGTH: 22
<212> TYPE: DNA
<213> ORGANISM: Homo sapiens

<400> SEQUENCE: 79
gagccattct gctgtgctct ct                                            22

<210> SEQ ID NO 80
<211> LENGTH: 25
<212> TYPE: DNA
<213> ORGANISM: Homo sapiens

<400> SEQUENCE: 80
tttaccaacg gcaagccttt ctgca                                         25

<210> SEQ ID NO 81
<211> LENGTH: 2175
<212> TYPE: DNA
<213> ORGANISM: Homo sapiens
<220> FEATURE:
<221> NAME/KEY: CDS
<222> LOCATION: (1)..(2172)

<400> SEQUENCE: 81
```
gcagcagcgg ccgcatgcag aaaaccaagc aagatgagg                           39

| | | |
|---|---|---|
| atg cag aaa acc aag caa gat gag gac tat gaa aga gcc att gga ttt<br>Met Gln Lys Thr Lys Gln Asp Glu Asp Tyr Glu Arg Ala Ile Gly Phe<br>1               5                   10                  15 | | 48 |
| agt gtc aaa atg gat gac agt gat tct gat ttt gca ctg act caa ggt<br>Ser Val Lys Met Asp Asp Ser Asp Ser Asp Phe Ala Leu Thr Gln Gly<br>            20                  25                  30 | | 96 |
| agc atg atc act cct tca tgc caa aaa gga tat ttt ccc tgt ggg aat<br>Ser Met Ile Thr Pro Ser Cys Gln Lys Gly Tyr Phe Pro Cys Gly Asn<br>        35                  40                  45 | | 144 |
| ctt acc aag tgc tta ccc cga gct ttt cac tgt gat ggc aag gat gac<br>Leu Thr Lys Cys Leu Pro Arg Ala Phe His Cys Asp Gly Lys Asp Asp<br>    50                  55                  60 | | 192 |
| tgt ggg aac ggg gcg gac gaa gag aac tgt ggt gac act agt gga tgg<br>Cys Gly Asn Gly Ala Asp Glu Glu Asn Cys Gly Asp Thr Ser Gly Trp<br>65                  70                  75                  80 | | 240 |
| gcg acc ata ttt ggc aca gtg cat gga aat gct aac agc gtg gcc tta<br>Ala Thr Ile Phe Gly Thr Val His Gly Asn Ala Asn Ser Val Ala Leu<br>                85                  90                  95 | | 288 |
| aca cag gag tgc ttt cta aaa cag tat cca caa tgc tgt gac tgc aaa<br>Thr Gln Glu Cys Phe Leu Lys Gln Tyr Pro Gln Cys Cys Asp Cys Lys<br>            100                 105                 110 | | 336 |
| gaa act gaa ttg gaa tgt gta aat ggt gac tta aag tct gtg ccg atg<br>Glu Thr Glu Leu Glu Cys Val Asn Gly Asp Leu Lys Ser Val Pro Met<br>        115                 120                 125 | | 384 |
| att tct aac aat gtg aca tta ctg tct ctt aag aaa aac aaa atc cac<br>Ile Ser Asn Asn Val Thr Leu Leu Ser Leu Lys Lys Asn Lys Ile His<br>    130                 135                 140 | | 432 |

-continued

```
agt ctt cca gat aaa gtt ttc atc aaa tac aca aaa ctt aaa aag ata         480
Ser Leu Pro Asp Lys Val Phe Ile Lys Tyr Thr Lys Leu Lys Lys Ile
145                 150                 155                 160 ttt ctt cag cat aat tgc att aga cac ata tcc agg aaa gca ttt ttt         528
Phe Leu Gln His Asn Cys Ile Arg His Ile Ser Arg Lys Ala Phe Phe
                165                 170                 175 gga tta tgt aat ctg caa ata tta att cta gat gac aat cca ata acc         576
Gly Leu Cys Asn Leu Gln Ile Leu Ile Leu Asp Asp Asn Pro Ile Thr
        180                 185                 190 aga att tca cag cgc ttg ttt acg gga tta aat tcc ttg ttt ttc ctg         624
Arg Ile Ser Gln Arg Leu Phe Thr Gly Leu Asn Ser Leu Phe Phe Leu
    195                 200                 205 tct atg gtt aat aac tac tta gaa gct ctt ccc aag cag atg tgt gcc         672
Ser Met Val Asn Asn Tyr Leu Glu Ala Leu Pro Lys Gln Met Cys Ala
210                 215                 220 caa atg cct caa ctc aac tgg gtg gat ttg gaa ggc aat aga ata aag         720
Gln Met Pro Gln Leu Asn Trp Val Asp Leu Glu Gly Asn Arg Ile Lys
225                 230                 235                 240 tat ctc aca aat tct acg ttt ctg tcg tgc gat tcg ctc aca gtg ctg         768
Tyr Leu Thr Asn Ser Thr Phe Leu Ser Cys Asp Ser Leu Thr Val Leu
                245                 250                 255 ttt ctg cct aga aat caa att ggt ttt gtt cca gag aag aca ttt tct         816
Phe Leu Pro Arg Asn Gln Ile Gly Phe Val Pro Glu Lys Thr Phe Ser
        260                 265                 270 tca tta aaa aat tta gga gaa ctg gat ctg tct agc aat acg ata acg         864
Ser Leu Lys Asn Leu Gly Glu Leu Asp Leu Ser Ser Asn Thr Ile Thr
    275                 280                 285 gag cta tca cct cac ctt ttt aaa gac ttg aag ctt cta caa aag ctg         912
Glu Leu Ser Pro His Leu Phe Lys Asp Leu Lys Leu Leu Gln Lys Leu
290                 295                 300 aac ctg tca tcc aat cct ctt atg tat ctt cac aag aac cag ttt gaa         960
Asn Leu Ser Ser Asn Pro Leu Met Tyr Leu His Lys Asn Gln Phe Glu
305                 310                 315                 320 agt ctt aaa caa ctt cag tct cta gac ctg gaa agg ata gag att cca        1008
Ser Leu Lys Gln Leu Gln Ser Leu Asp Leu Glu Arg Ile Glu Ile Pro
                325                 330                 335 aat ata aac aca cga atg ttt caa ccc atg aag aat ctt tct cac att        1056
Asn Ile Asn Thr Arg Met Phe Gln Pro Met Lys Asn Leu Ser His Ile
        340                 345                 350 tat ttc aaa aac ttt cga tac tgc tcc tat gct ccc cat gtc cga ata        1104
Tyr Phe Lys Asn Phe Arg Tyr Cys Ser Tyr Ala Pro His Val Arg Ile
    355                 360                 365 tgt atg ccc ttg acg gac ggc att tct tca ttt gag gac ctc ttg gct        1152
Cys Met Pro Leu Thr Asp Gly Ile Ser Ser Phe Glu Asp Leu Leu Ala
370                 375                 380 aac aat atc ctc aga ata ttt gtc tgg gtt ata gct ttc att acc tgc        1200
Asn Asn Ile Leu Arg Ile Phe Val Trp Val Ile Ala Phe Ile Thr Cys
385                 390                 395                 400 ttt gga aat ctt ttt gtc att ggc atg aga tct ttc att aaa gct gaa        1248
Phe Gly Asn Leu Phe Val Ile Gly Met Arg Ser Phe Ile Lys Ala Glu
                405                 410                 415 aat aca act cac gct atg tcc atc aaa atc ctt tgt tgt gct gat tgc        1296
Asn Thr Thr His Ala Met Ser Ile Lys Ile Leu Cys Cys Ala Asp Cys
        420                 425                 430 ctg atg ggt gtt tac ttg ttc ttt gtt ggc att ttc gat ata aaa tac        1344
Leu Met Gly Val Tyr Leu Phe Phe Val Gly Ile Phe Asp Ile Lys Tyr
    435                 440                 445 cga ggg cag tat cag aag tat gcc ttg ctg tgg atg gag agc gtg cag        1392
Arg Gly Gln Tyr Gln Lys Tyr Ala Leu Leu Trp Met Glu Ser Val Gln
```

|  |  |
|---|---|
| tgc cgc ctc atg ggg ttc ctg gcc atg ctg tcc acc gaa gtc tct gtt<br>Cys Arg Leu Met Gly Phe Leu Ala Met Leu Ser Thr Glu Val Ser Val<br>465                          470                      475                      480 | 1440 |
| ctg cta ctg acc tac ttg act ttg gag aag ttc ctg gtc att gtc ttc<br>Leu Leu Leu Thr Tyr Leu Thr Leu Glu Lys Phe Leu Val Ile Val Phe<br>                          485                      490                      495 | 1488 |
| ccc ttc agt aac att cga cct gga aaa cgg cag acc tca gtc atc ctc<br>Pro Phe Ser Asn Ile Arg Pro Gly Lys Arg Gln Thr Ser Val Ile Leu<br>            500                      505                      510 | 1536 |
| att tgc atc tgg atg gcg gga ttt tta ata gct gta att cca ttt tgg<br>Ile Cys Ile Trp Met Ala Gly Phe Leu Ile Ala Val Ile Pro Phe Trp<br>                515                      520                      525 | 1584 |
| aat aag gat tat ttt gga aac ttt tat ggg aaa aat gga gta tgt ttc<br>Asn Lys Asp Tyr Phe Gly Asn Phe Tyr Gly Lys Asn Gly Val Cys Phe<br>530                          535                      540 | 1632 |
| cca ctt tat tat gac caa aca gaa gat att gga agc aaa ggg tat tct<br>Pro Leu Tyr Tyr Asp Gln Thr Glu Asp Ile Gly Ser Lys Gly Tyr Ser<br>545                          550                      555                      560 | 1680 |
| ctt gga att ttc cta ggt gtg aac ttg ctg gct ttt ctc atc att gtg<br>Leu Gly Ile Phe Leu Gly Val Asn Leu Leu Ala Phe Leu Ile Ile Val<br>                565                      570                      575 | 1728 |
| ttt tcc tat att act atg ttc tgt tcc att caa aaa acc gcc ttg cag<br>Phe Ser Tyr Ile Thr Met Phe Cys Ser Ile Gln Lys Thr Ala Leu Gln<br>            580                      585                      590 | 1776 |
| acc aca gaa gta agg aat tgt ttt gga aga gag gtg gct gtt gca aat<br>Thr Thr Glu Val Arg Asn Cys Phe Gly Arg Glu Val Ala Val Ala Asn<br>                595                      600                      605 | 1824 |
| cgt ttc ttt ttt ata gtg ttc tct gat gcc atc tgc tgg att cct gta<br>Arg Phe Phe Phe Ile Val Phe Ser Asp Ala Ile Cys Trp Ile Pro Val<br>610                          615                      620 | 1872 |
| ttt gta gtt aaa atc ctt tcc ctc ttc cgg gtg gaa ata cca gac aca<br>Phe Val Val Lys Ile Leu Ser Leu Phe Arg Val Glu Ile Pro Asp Thr<br>625                          630                      635                      640 | 1920 |
| atg act tcc tgg ata gtg att ttt ttc ctt cca gtt aac agt gct ttg<br>Met Thr Ser Trp Ile Val Ile Phe Phe Leu Pro Val Asn Ser Ala Leu<br>                645                      650                      655 | 1968 |
| aat cca atc ctc tat act ctc aca acc aac ttt ttt aag gac aag ttg<br>Asn Pro Ile Leu Tyr Thr Leu Thr Thr Asn Phe Phe Lys Asp Lys Leu<br>            660                      665                      670 | 2016 |
| aaa cag ctg ctg cac aaa cat cag agg aaa tca att ttc aaa att aaa<br>Lys Gln Leu Leu His Lys His Gln Arg Lys Ser Ile Phe Lys Ile Lys<br>                675                      680                      685 | 2064 |
| aaa aaa agt tta tct aca tcc att gtg tgg ata gag gac tcc tct tcc<br>Lys Lys Ser Leu Ser Thr Ser Ile Val Trp Ile Glu Asp Ser Ser Ser<br>690                          695                      700 | 2112 |
| ctg aaa ctt ggg gtt ttg aac aaa ata aca ctt gga gac agt ata atg<br>Leu Lys Leu Gly Val Leu Asn Lys Ile Thr Leu Gly Asp Ser Ile Met<br>705                          710                      715                      720 | 2160 |
| aaa cca gtt tcc tag<br>Lys Pro Val Ser | 2175 |

<210> SEQ ID NO 82
<211> LENGTH: 724
<212> TYPE: PRT
<213> ORGANISM: Homo sapiens

<400> SEQUENCE: 82

Met Gln Lys Thr Lys Gln Asp Glu Asp Tyr Glu Arg Ala Ile Gly Phe
1               5                  10                 15

-continued

```
Ser Val Lys Met Asp Asp Ser Asp Ser Asp Phe Ala Leu Thr Gln Gly
            20                  25                  30

Ser Met Ile Thr Pro Ser Cys Gln Lys Gly Tyr Phe Pro Cys Gly Asn
            35                  40                  45

Leu Thr Lys Cys Leu Pro Arg Ala Phe His Cys Asp Gly Lys Asp Asp
            50                  55                  60

Cys Gly Asn Gly Ala Asp Glu Glu Asn Cys Gly Asp Thr Ser Gly Trp
65                  70                  75                  80

Ala Thr Ile Phe Gly Thr Val His Gly Asn Ala Asn Ser Val Ala Leu
                    85                  90                  95

Thr Gln Glu Cys Phe Leu Lys Gln Tyr Pro Gln Cys Cys Asp Cys Lys
            100                 105                 110

Glu Thr Glu Leu Glu Cys Val Asn Gly Asp Leu Lys Ser Val Pro Met
            115                 120                 125

Ile Ser Asn Asn Val Thr Leu Leu Ser Leu Lys Lys Asn Lys Ile His
            130                 135                 140

Ser Leu Pro Asp Lys Val Phe Ile Lys Tyr Thr Lys Leu Lys Lys Ile
145                 150                 155                 160

Phe Leu Gln His Asn Cys Ile Arg His Ile Ser Arg Lys Ala Phe Phe
                    165                 170                 175

Gly Leu Cys Asn Leu Gln Ile Leu Ile Leu Asp Asp Asn Pro Ile Thr
            180                 185                 190

Arg Ile Ser Gln Arg Leu Phe Thr Gly Leu Asn Ser Leu Phe Phe Leu
            195                 200                 205

Ser Met Val Asn Asn Tyr Leu Glu Ala Leu Pro Lys Gln Met Cys Ala
            210                 215                 220

Gln Met Pro Gln Leu Asn Trp Val Asp Leu Glu Gly Asn Arg Ile Lys
225                 230                 235                 240

Tyr Leu Thr Asn Ser Thr Phe Leu Ser Cys Asp Ser Leu Thr Val Leu
                    245                 250                 255

Phe Leu Pro Arg Asn Gln Ile Gly Phe Val Pro Glu Lys Thr Phe Ser
            260                 265                 270

Ser Leu Lys Asn Leu Gly Glu Leu Asp Leu Ser Ser Asn Thr Ile Thr
            275                 280                 285

Glu Leu Ser Pro His Leu Phe Lys Asp Leu Lys Leu Leu Gln Lys Leu
            290                 295                 300

Asn Leu Ser Ser Asn Pro Leu Met Tyr Leu His Lys Asn Gln Phe Glu
305                 310                 315                 320

Ser Leu Lys Gln Leu Gln Ser Leu Asp Leu Glu Arg Ile Glu Ile Pro
                    325                 330                 335

Asn Ile Asn Thr Arg Met Phe Gln Pro Met Lys Asn Leu Ser His Ile
            340                 345                 350

Tyr Phe Lys Asn Phe Arg Tyr Cys Ser Tyr Ala Pro His Val Arg Ile
            355                 360                 365

Cys Met Pro Leu Thr Asp Gly Ile Ser Ser Phe Glu Asp Leu Leu Ala
            370                 375                 380

Asn Asn Ile Leu Arg Ile Phe Val Trp Val Ile Ala Phe Ile Thr Cys
385                 390                 395                 400

Phe Gly Asn Leu Phe Val Ile Gly Met Arg Ser Phe Ile Lys Ala Glu
                    405                 410                 415

Asn Thr Thr His Ala Met Ser Ile Lys Ile Leu Cys Cys Ala Asp Cys
            420                 425                 430
```

-continued

```
Leu Met Gly Val Tyr Leu Phe Phe Val Gly Ile Phe Asp Ile Lys Tyr
        435                 440                 445

Arg Gly Gln Tyr Gln Lys Tyr Ala Leu Leu Trp Met Glu Ser Val Gln
    450                 455                 460

Cys Arg Leu Met Gly Phe Leu Ala Met Leu Ser Thr Glu Val Ser Val
465                 470                 475                 480

Leu Leu Leu Thr Tyr Leu Thr Leu Glu Lys Phe Leu Val Ile Val Phe
                485                 490                 495

Pro Phe Ser Asn Ile Arg Pro Gly Lys Arg Gln Thr Ser Val Ile Leu
            500                 505                 510

Ile Cys Ile Trp Met Ala Gly Phe Leu Ala Val Ile Pro Phe Trp
        515                 520                 525

Asn Lys Asp Tyr Phe Gly Asn Phe Tyr Gly Lys Asn Gly Val Cys Phe
    530                 535                 540

Pro Leu Tyr Tyr Asp Gln Thr Glu Asp Ile Gly Ser Lys Gly Tyr Ser
545                 550                 555                 560

Leu Gly Ile Phe Leu Gly Val Asn Leu Leu Ala Phe Leu Ile Ile Val
                565                 570                 575

Phe Ser Tyr Ile Thr Met Phe Cys Ser Ile Gln Lys Thr Ala Leu Gln
            580                 585                 590

Thr Thr Glu Val Arg Asn Cys Phe Gly Arg Glu Val Ala Val Ala Asn
        595                 600                 605

Arg Phe Phe Phe Ile Val Phe Ser Asp Ala Ile Cys Trp Ile Pro Val
    610                 615                 620

Phe Val Val Lys Ile Leu Ser Leu Phe Arg Val Glu Ile Pro Asp Thr
625                 630                 635                 640

Met Thr Ser Trp Ile Val Ile Phe Phe Leu Pro Val Asn Ser Ala Leu
                645                 650                 655

Asn Pro Ile Leu Tyr Thr Leu Thr Thr Asn Phe Phe Lys Asp Lys Leu
            660                 665                 670

Lys Gln Leu Leu His Lys His Gln Arg Lys Ser Ile Phe Lys Ile Lys
        675                 680                 685

Lys Lys Ser Leu Ser Thr Ser Ile Val Trp Ile Glu Asp Ser Ser Ser
    690                 695                 700

Leu Lys Leu Gly Val Leu Asn Lys Ile Thr Leu Gly Asp Ser Ile Met
705                 710                 715                 720

Lys Pro Val Ser

<210> SEQ ID NO 83
<211> LENGTH: 24
<212> TYPE: DNA
<213> ORGANISM: Homo sapiens

<400> SEQUENCE: 83
ggtgaggtga tagctccgtt atcg                                            24

<210> SEQ ID NO 84
<211> LENGTH: 39
<212> TYPE: DNA
<213> ORGANISM: Homo sapiens

<400> SEQUENCE: 84
gcagcagcgg ccgcctcaga atatttgtct gggttatag                            39

<210> SEQ ID NO 85
<211> LENGTH: 36
```

```
<212> TYPE: DNA
<213> ORGANISM: Homo sapiens

<400> SEQUENCE: 85
gcagcagtcg acggaaactg gtttcattat actgtc                               36

<210> SEQ ID NO 86
<211> LENGTH: 39
<212> TYPE: DNA
<213> ORGANISM: Homo sapiens

<400> SEQUENCE: 86
gcagcagcgg ccgcatgcag aaaaccaagc aagatgagg                            39

<210> SEQ ID NO 87
<211> LENGTH: 36
<212> TYPE: DNA
<213> ORGANISM: Homo sapiens

<400> SEQUENCE: 87
gcagcagtcg acggttgtga gagtatagag gattgg                               36

<210> SEQ ID NO 88
<211> LENGTH: 39
<212> TYPE: DNA
<213> ORGANISM: Homo sapiens

<400> SEQUENCE: 88
gcagcagcgg ccgcatgcag aaaaccaagc aagatgagg                            39

<210> SEQ ID NO 89
<211> LENGTH: 37
<212> TYPE: DNA
<213> ORGANISM: Homo sapiens

<400> SEQUENCE: 89
gcagcagtcg actctgagga tattgttagc caagagg                              37

<210> SEQ ID NO 90
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 90
cacagucauc cuugccauca cagug                                           25

<210> SEQ ID NO 91
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 91
gccaaauaug gucgcccauc cacua                                           25

<210> SEQ ID NO 92
<211> LENGTH: 25
<212> TYPE: DNA
<213> ORGANISM: Artificial
<220> FEATURE:
<223> OTHER INFORMATION: Synthethized Antisense Oligonucleotide.
```

```
<400> SEQUENCE: 92
caaauccacc caguugaguu gaggc                                           25

<210> SEQ ID NO 93
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 93
ucuaggcaga aacagcacug ugagc                                           25

<210> SEQ ID NO 94
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 94
ugaucaugcu accuugaguc agugc                                           25

<210> SEQ ID NO 95
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 95
ugccaaauau ggucgcccau ccacu                                           25

<210> SEQ ID NO 96
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 96
gccuuccaaa uccacccagu ugagu                                           25

<210> SEQ ID NO 97
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 97
gaucaugcua ccuugaguca gugca                                           25

<210> SEQ ID NO 98
<211> LENGTH: 25
<212> TYPE: DNA
<213> ORGANISM: Artificial
<220> FEATURE:
<223> OTHER INFORMATION: Synthethized Antisense Oligonucleotide.

<400> SEQUENCE: 98
uaaggccacg cuguuagcau uucca                                           25

<210> SEQ ID NO 99
<211> LENGTH: 25
```

```
<212> TYPE: DNA
<213> ORGANISM: Artificial
<220> FEATURE:
<223> OTHER INFORMATION: Synthethized Antisense Oligonucleotide.

<400> SEQUENCE: 99
ucuaggcaga aacagcacug ugagc                                          25

<210> SEQ ID NO 100
<211> LENGTH: 21
<212> TYPE: DNA
<213> ORGANISM: Homo sapiens

<400> SEQUENCE: 100
ctggagactc tcagggtcga a                                              21

<210> SEQ ID NO 101
<211> LENGTH: 17
<212> TYPE: DNA
<213> ORGANISM: Homo sapiens

<400> SEQUENCE: 101
gcgcttccag gactgca                                                   17

<210> SEQ ID NO 102
<211> LENGTH: 27
<212> TYPE: DNA
<213> ORGANISM: Homo sapiens

<400> SEQUENCE: 102
acagatttct accactccaa acgccgg                                        27
```